US012404299B2

(12) United States Patent
Nomura et al.

(10) Patent No.: US 12,404,299 B2
(45) Date of Patent: Sep. 2, 2025

(54) METHOD FOR PRODUCING PEPTIDE COMPOUND COMPRISING HIGHLY STERICALLY HINDERED AMINO ACID

(71) Applicant: CHUGAI SEIYAKU KABUSHIKI KAISHA, Tokyo (JP)

(72) Inventors: Kenichi Nomura, Gotemba (JP); Yuya Morita, Kamakura (JP); Satoshi Hashimoto, Gotemba (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 635 days.

(21) Appl. No.: 17/773,734

(22) PCT Filed: Nov. 5, 2020

(86) PCT No.: PCT/JP2020/041279
§ 371 (c)(1),
(2) Date: May 2, 2022

(87) PCT Pub. No.: WO2021/090856
PCT Pub. Date: May 14, 2021

(65) Prior Publication Data
US 2023/0026641 A1 Jan. 26, 2023

(30) Foreign Application Priority Data
Nov. 7, 2019 (JP) .................................. 2019-202408

(51) Int. Cl.
*C07K 1/06* (2006.01)
*C07K 1/02* (2006.01)

(52) U.S. Cl.
CPC .............. *C07K 1/063* (2013.01); *C07K 1/026* (2013.01)

(58) Field of Classification Search
None
See application file for complete search history.

(56) References Cited

U.S. PATENT DOCUMENTS

| | | |
|---|---|---|
| 9,409,952 B2 | 8/2016 | Kariyuki et al. |
| 11,492,369 B2 | 11/2022 | Nomura et al. |
| 11,542,299 B2 | 1/2023 | Nomura et al. |
| 11,732,002 B2 | 8/2023 | Iwasaki et al. |
| 11,787,836 B2 | 10/2023 | Nomura et al. |
| 11,891,457 B2 | 2/2024 | Kariyuki et al. |
| 12,071,396 B2 | 8/2024 | Wadamoto et al. |
| 2013/0274205 A1 | 10/2013 | Guerlavais et al. |
| 2015/0080549 A1 | 3/2015 | Kariyuki et al. |
| 2016/0264627 A1 | 9/2016 | Henning et al. |
| 2016/0311858 A1 | 10/2016 | Kariyuki et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |
| 2021/0061860 A1 | 3/2021 | Kariyuki et al. |
| 2022/0017456 A1 | 1/2022 | Ishizawa |
| 2022/0024972 A1 | 1/2022 | Iwasaki et al. |
| 2022/0144762 A1 | 5/2022 | Wadamoto |
| 2022/0411462 A1 | 12/2022 | Hou et al. |
| 2023/0056969 A1 | 2/2023 | Kondo et al. |
| 2023/0096766 A1 | 3/2023 | Muraoka et al. |
| 2023/0138226 A1 | 5/2023 | Nomura et al. |
| 2023/0151060 A1 | 5/2023 | Tanada et al. |
| 2023/0295221 A1 | 9/2023 | Iwasaki et al. |
| 2023/0303619 A1 | 9/2023 | Iwasaki et al. |
| 2023/0391818 A1 | 12/2023 | Nomura et al. |
| 2023/0406879 A1 | 12/2023 | Nomura et al. |
| 2024/0067674 A1 | 2/2024 | Sekita et al. |
| 2024/0124517 A1 | 4/2024 | Morita et al. |
| 2024/0148821 A1 | 5/2024 | Tanada et al. |
| 2024/0158446 A1 | 5/2024 | Kawada et al. |
| 2024/0166689 A1 | 5/2024 | Kariyuki et al. |
| 2024/0376044 A1 | 11/2024 | Wadamoto |
| 2024/0400617 A1 | 12/2024 | Tanada et al. |
| 2025/0051394 A1 | 2/2025 | Kawada et al. |

FOREIGN PATENT DOCUMENTS

| | | |
|---|---|---|
| EP | 2813512 A1 | 12/2014 |
| EP | 3424941 A1 | 1/2019 |
| EP | 3636656 A1 | 4/2020 |
| EP | 3636807 A1 | 4/2020 |

(Continued)

OTHER PUBLICATIONS

March, Jerry; Advanced Organic Chemistry (1992) 4th ed, ISBN 0-471-60180-2, p. 425-427.*
Carpino, Louis A. et al, "Protected amino acid chlorides vs protected amino acid fluorides: reactivity comparisons." Tet. Lett. (1998) 39(3/4) p. 241-244.*
Yu, T. J. et al, "High performance liquid chromatographic mass spectrometric examination of c-methylation artifacts from teh permethylation reaction of peptides." Biomed. Mass Spect. (1983) 10(12) p. 633-640.*
Aurelio, L., et al., "Determination of the Complete Absolute Configuration of Petriellin A," Aust J Chem., 59:407-414 (2006).
Bock, J. E., et al., "Getting in Shape: Controlling Peptide Bioactivity and Bioavailability Using Conformational Constraints," ACS Chem Biol., 8(3):488-499 (2013).

(Continued)

*Primary Examiner* — Fred H Reynolds
(74) *Attorney, Agent, or Firm* — Nixon & Vanderhye P.C.

(57) ABSTRACT

It was found that a peptide compound that has an N-substituted-α,α-disubstituted amino acid residue at the N-terminus and containing a dipeptide residue in which the N-substituted-α,α-disubstituted amino acid residue and an N-substituted amino acid residue are linked together, can be efficiently produced by linking an N-unsubstituted-α,α-disubstituted amino acid whose amino group is protected with an electron-withdrawing protecting group to an N-substituted amino acid or a peptide compound having an N-substituted amino acid residue at the N-terminus, and then allowing a substituent-introducing agent to act in the presence of a specific base to selectively introduce a substituent to the amino group at the N-terminus.

27 Claims, 5 Drawing Sheets

(56) References Cited

FOREIGN PATENT DOCUMENTS

| | | | |
|---|---|---|---|
| EP | 4043478 A1 | 8/2022 | |
| EP | 4316503 A1 | 2/2024 | |
| JP | 2015509940 A | 4/2015 | |
| JP | 2020105162 A | 7/2020 | |
| WO | WO0015656 A1 | 3/2000 | |
| WO | WO2013100132 A1 | 7/2013 | |
| WO | WO2013123266 A1 | 8/2013 | |
| WO | WO2015179434 A1 | 11/2015 | |
| WO | WO2016100608 A1 | 6/2016 | |
| WO | WO2017181061 A1 | 10/2017 | |
| WO | WO2018225851 A1 | 12/2018 | |
| WO | WO2018225864 A1 | 12/2018 | |
| WO | WO2019117274 A1 | 6/2019 | |
| WO | WO2020095983 A1 | 5/2020 | |
| WO | WO2020106647 A2 | 5/2020 | |
| WO | WO2020111238 A1 | 6/2020 | |
| WO | WO2020122182 A1 | 6/2020 | |
| WO | WO2020189540 A1 | 9/2020 | |
| WO | WO2021030855 A1 | 2/2021 | |
| WO | WO2021090855 A1 | 5/2021 | |
| WO | WO2021132545 A1 | 7/2021 | |
| WO | WO2021246471 A1 | 12/2021 | |
| WO | WO2022097540 A1 | 5/2022 | |
| WO | WO2022138891 A1 | 6/2022 | |
| WO | WO2022145444 A1 | 7/2022 | |
| WO | WO2022234852 A1 | 11/2022 | |
| WO | WO2022234853 A1 | 11/2022 | |
| WO | WO2023127752 A1 | 7/2023 | |
| WO | WO2023190748 A1 | 10/2023 | |
| WO | WO2023195516 A1 | 10/2023 | |
| WO | WO2023214576 A1 | 11/2023 | |
| WO | WO2023214577 A1 | 11/2023 | |
| WO | WO2023219152 A1 | 11/2023 | |
| WO | WO2023219156 A1 | 11/2023 | |
| WO | WO2024024965 A1 | 2/2024 | |
| WO | WO2024080333 A1 | 4/2024 | |

OTHER PUBLICATIONS

Boehm, M., et al., "Discovery of Potent and Orally Bioavailable Macrocyclic Peptide-Peptoid Hybrid CXCR7 Modulators," J Med Chem., 60(23):9653-9663 (2017).
Boltromeûk, V.V., "General chemistry," Minsk, Vyšejšaâškola, 65 (2012).
Brandt, W., et al., "Systemic Conformational Investigations of Peptoids and Peptoid-Peptide Chimeras," Pept Sci., 96(5):651-668 (2011).
Brown, Z. Z. and Schafmeister, C. E., "Exploiting an Inherent Neighboring Group Effect of α-Amino Acids to Synthesize Extremely Hindered Dipeptides," J Am Chem Soc., 130(44):14382-14383 (2008).
Carpino, L.A., et al., "Protected Amnio Acid Chlorides vs Protected Amino Acid Fluorides: Reactivity Comparisons," Tetrahedron Letters, 39:241-244 (1998).
Di Gioia, M. L., et al., "'One-Pot' Methylation of N-Nosyl-α-amino Acid Methyl Esters with Diazomethane and Their Coupling to Prepare N-Methyl Dipeptides," J Org Chem., 68:7416-7421 (2003).
Di Gioia, M. L., et al., "N-Methylation of Peptides of Selected Positions during the Elongation of the Peptide Chain in Solution Phase," J Org Chem., 70:3892-3897 (2005).
Gracia, S. R., et al., "Synthesis of chemically modified bioactive peptides: recent advances, challenges and developments for medicinal chemistry," Future Medicinal Chemistry, 1(7):1289-1310 (2009).
Huang, Y., et al., "RNA Display Methods for the Discovery of Bioactive Macrocycles," Chem Rev., 119:10360-10391 (2019).
Ikawa, T., et al., "Selective N-alkylation of amines using nitriles under hydrogenation conditions: facile synthesis of secondary and tertiary amines," Org Biomol Chem., 10:293-304 (2012).
Josephson, K., et al., "mRNA Display: From Basic Principles to Macrocycle Drug Discovery," Drug Discovery Today, 19(4):388-399 (2014).
Lazo, J. S. and Sharlow, E. R., "Drugging Undruggable Molecular Cancer Targets," Annu Rev Pharmacol Toxicol., 56:23-40 (2016).
Li, P., et al., "Total synthesis and biological evaluation of ustiloxin natural products and two analogs," Bioorg Med Chem Lett. 16:4804-4807 (2006).
Miller, S. C., et al., "Site-Selective N-Methylation of Peptides on Solid Support," J Am Chem Soc., 119:2301-2302 (1997).
Nomura, K., et al., "Broadly Applicable and Comprehensive Synthetic Method for N-Alkyl-Rich Drug-like Cyclic Peptides," J Med Chem., 65:13401-13412 (2022).
Osumi, H., et al., "Cetuximab treatment for metastatic colorectal cancer with KRAS p.G13D mutations improves progression-free survival," Mol Clin Oncol., 3:1053-1057 (2015).
Paradis-Bas, M., et al., "The road to the synthesis of difficult peptides," Chem Soc Rev., 45:631-654 (2016).
Purkey, H., "Discovery of GDC 6036, a clinical stage treatment for KRAS G12C-positive cancers," AACR Annual Meeting, 11-17 (2022).
Purkey, H., "Abstract ND11: Discovery of GDC-6036, a clinical stage treatment for KRAS G12C-positive cancers," Cancer Res., 82(12_Supplement):ND11 (2022).
Räder, A. F. B., et al., "Improving oral bioavailability of cyclic peptides by N-methylation," Bioorg Med Chem., 26:2766-2773 (2018).
Sajiki, H., et al., "Reductive and Catalytic Monoalkylation of Primary Amines Using Nitriles as an Alkylating Reagent," Org Lett., 6(26):4977-4980 (2004).
Shankaramma, S. C., et al., "A family of macrocyclic antibiotics with a mixed peptide-peptoid β-hairpin backbone conformation," Chem Commun., 15:1842-1843 (2003).
Sharma, A., et al., "N-methylation in amino acids and peptides: Scope and limitations," Biopolymers, 109:e23110 (2018).
Tabernero, J., et al., "KRYSTAL-10: A randomized phase 3 study of adagrasib (MRTX849) in combination with cetuximab vs chemotherapy in patients with previously treated advanced colorectal cancer with KRASG12C mutation," Ann Oncol., 32(S3):S121 (2021).
Tanaka, M., "Design and Conformation of Peptides Containing α,α-Disubstituted α-Amino Acids," J Syn Org Chem., 60(2):125-136 (2002).
Tejpar, S., et al., "Association of KRAS G13D Tumor Mutations with Outcome in Patients with Metastatic Colorectal Cancer Treated with First-Line Chemotherapy with or without Cetuximab," J Clin Oncol., 30(29):3570-3577 (2012).
Turner, R. A., et al., "Selective, On-Resin N-Methylation of Peptide N-Trifluoroacetamides," Org Lett., 15(19):5012-5015 (2013).
White, K. N. and Konopelski, J. P., "Facile Synthesis of Highly Functionalized N-Methyl Amino Acid Esters without Side-Chain Protection," Org Lett., 7(19):4111-4112 (2005).
Xu, J., et al., "Atroposelective Negishi Coupling Optimization Guided by Multivariate Linear Regression Analysis: Asymmetric Synthesis of KRAS G12C Covalent Inhibitor GDC-6036," J Am Chem Soc., 144:20955-20963 (2022).
Zhang, Z., et al., "GTP-State-Selective Cyclic Peptide Ligands of K-Ras(G12D) Block Its Interaction with Raf," ACS Cent Sci., 6(10):1753-1761 (2020).
U.S. Appl. No. 14/368,564, filed Jun. 25, 2014, Kariyuki et al., related application.
U.S. Appl. No. 15/166,550, filed May 27, 2016, Kariyuki et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Apr. 29, 2022, Muraoka et al., related application.

(56) References Cited

OTHER PUBLICATIONS

U.S. Appl. No. 17/437,535, filed Sep. 9, 2021, Wadamoto, related application.
U.S. Appl. No. 17/738,283, filed May 6, 2022, Hou et al., related application.
U.S. Appl. No. 17/773,733, filed May 2, 2022, Tanada et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.
U.S. Appl. No. 17/976,942, filed Oct. 31, 2022, Nomura et al., related application.
U.S. Appl. No. 18/034,424, filed Apr. 28, 2023, Nomura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,451, filed Nov. 3, 2023, Tanada et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
U.S. Appl. No. 18/723,993, filed Jun. 25, 2024, Komiya et al., related application.
U.S. Appl. No. 18/724,369, filed Jun. 26, 2024, Shinoda et al., related application.
U.S. Appl. No. 18/773,066, filed Jul. 15, 2024, Tanada et al., related application.
U.S. Appl. No. 18/781,112, filed Jul. 23, 2024, Wadamoto, related application.
U.S. Appl. No. 18/829,566, filed Sep. 10, 2024, Kawada et al., related application.
U.S. Appl. No. 18/854,568, filed Oct. 7, 2024, Shinohara et al., related application.
U.S. Appl. No. 18/860,859, filed Oct. 28, 2024, Kage et al., related application.
U.S. Appl. No. 18/864,039, filed Nov. 8, 2024, Ishiyama et al., related application.
U.S. Appl. No. 18/864,049, filed Nov. 8, 2024, Ejima et al., related application.
U.S. Appl. No. 18/994,197, filed Jan. 14, 2025, Nogi, related application.
U.S. Appl. No. 19/041,438, filed Jan. 30, 2025, Iwasaki et al., related application.

* cited by examiner

METHOD FOR PRODUCING PEPTIDE COMPOUND COMPRISING HIGHLY STERICALLY HINDERED AMINO ACID

CROSS-REFERENCE TO RELATED APPLICATIONS

This application is a U.S. National Phase of PCT Application No. PCT/JP2020/041279, filed Nov. 5, 2020, which claims the benefit of Japanese Patent Application No. 2019-202408, filed Nov. 7, 2019, each of which is incorporated herein by reference in its entirety.

TECHNICAL FIELD

The present invention relates to a method for producing peptide compounds comprising amino acids with great steric hindrance.

BACKGROUND ART

Drug discovery that targets intracellular molecules or the like, drug discovery towards inhibition of protein-protein interactions, and such are exemplified as those for so-called tough targets that could not be used as drug discovery targets in conventional medicine. Reasons why such targets have not been used as drug discovery targets are that a pharmaceutical molecule cannot reach the disease target molecule, or that the action site of the target molecule has a shape on which it is difficult for a conventional pharmaceutical to act (NPL 1).

Recently, cyclic peptides attract attention as means for accessing tough targets that are difficult to access with conventional techniques (NPL 2). In order to apply cyclic peptides to pharmaceuticals, considerations have been made not only to increase their target-binding ability, but also to make them into being drug-like cyclic peptides (druglikeness: preferably, exhibiting both membrane permeability and metabolic stability) as well as to efficiently screen for them (NPL 3 and NPL 4). Conditions required for drug-like unnatural cyclic peptides containing unnatural amino acids have been revealed, and thus the importance and recognition of the peptides in drug discovery are increasing (PTL 1). Unnatural amino acids are important elements of such unnatural peptides, and it is widely recognized that synthesis of peptides containing unnatural amino acids such as N-methyl (or N-alkyl) amino acids or, in some cases, peptides containing a unit having a series of N-methyl (or N-alkyl) amino acids is more difficult due to their bulkiness as compared with synthesis of natural peptides (NPL 5 and NPL 6).

When shifting the perspective to unnatural amino acids having amino acid side chains that are different from those of natural amino acids, it has been reported that α,α-disubstituted amino acids, in which the α-position of the amino acid is substituted with two substituents, contribute to increased lipophilicity, limited conformational freedom of peptides containing them due to their steric hindrance, and in vivo stabilization (NPL 7). Thus, α,α-disubstituted amino acids can be expected to exert a major positive effect on both medicinal effects and druglikeness.

The Fmoc method, which is most commonly used in peptide synthesis, is known to be unsuitable as a method for producing peptides containing such unnatural amino acids due to the structural bulkiness of the unnatural amino acids (NPL 8).

Accordingly, it is easily inferred that peptide synthesis by a condensation reaction of the carboxyl group of an α,α-disubstituted amino acid to the amino group of an amino acid or, in particular, peptide synthesis by a condensation reaction of the carboxyl group of an N-alkylated α,α-disubstituted amino acid to the amino group of an N-alkylated amino acid, is difficult due to the steric bulkiness of one or both of the amino acids.

As a method for continuously introducing N-alkyl amino acids, a method is known in which a peptide is synthesized by condensing N—H amino acids, which have a smaller steric hindrance than N-alkyl amino acids, and then NH groups of interest, among the multiple NH groups present in the resulting peptide, are selectively N-alkylated (NPL 9 and NPL 10). However, this is a method for linking an α-monosubstituted amino acid to an N-alkyl amino acid, and thus no practical method is known for synthesizing peptides having a sequence in which an N-alkyl-α,α-disubstituted amino acid and an N-alkyl amino acid are linked together.

CITATION LIST

Patent Literature

[PTL 1] International Publication No. WO 2018/225864

Non-Patent Literature

[NPL 1] Annu. Rev. Pharmacol. Toxicol., 2016, 56, 23-40
[NPL 2] Future Med. Chem. 2009, 1, 1289-1310
[NPL 3] ACS Chem. Biol., 2013, 8, 488-499
[NPL 4] Drug Discovery Today, 2014, 19, 388-399
[NPL 5] J. Peptide Res., 2005, 65, 153-166
[NPL 6] Biopolymers, 109; e23110 (DOI:10.1002/bip.23110)
[NPL 7] Journal of Synthetic Organic Chemistry, Japan, 2002, vol. 60, No. 2, 125-136
[NPL 8] Chem. Soc. Rev., 2016, 45, 631-654
[NPL 9] Org. Lett., 2013, 15, 5012-5015
[NPL 10] J. Am. Chem. Soc., 1997, 119, 2301-2302

SUMMARY OF INVENTION

Technical Problem

As an example of a method for producing peptides containing bulky amino acids, NPL describes a method for producing peptides containing N-alkyl amino acids. However, this literature provides no more than a discussion on the mechanism of side reactions in the condensation reaction of amino acids as well as description about condensing reagents, and is silent on the condensation reaction of bulkier α,α-disubstituted amino acids.

NPL 6 provides an example of a method for producing N-alkyl amino acids and an example of a method for producing peptides containing N-alkyl amino acids. This literature provides an exemplary production method that focuses on amino acid condensing agents, but is silent on the condensation reaction of bulkier α,α-disubstituted amino acids.

NPL 7 describes a method for producing α,α-disubstituted amino acids, usefulness of peptides containing α,α-disubstituted amino acids, examples of α,α-disubstituted amino acids, and a production method therefor; however, production of peptides containing sterically bulky amino acids is not described.

NPL 8 provides an example of a method for producing peptides that are difficult to be synthesized. This literature describes production of peptides that have poor solubility or readily aggregate; however, it is silent on a solution of the problem by using a condensation reaction.

NPL 9 provides an example of a method for forming a peptide bond for N-alkyl amino acids using a trifluoroacetyl group which is removable under mild conditions, and an example of a method for producing peptides containing N-alkyl amino acids. However, no condensation reaction with bulkier α,α-disubstituted amino acids is described. In addition, it is known that an alkyl group cannot be selectively introduced only to the nitrogen atom to which the trifluoroacetyl group is bonded, and that the method produces isomeric by-products in which an alkyl group is also introduced to the oxygen atom of the trifluoroacetyl group.

NPL 10 describes a method for producing peptides containing N-alkyl amino acids by introducing an alkyl group to a nosyl group-protected nitrogen atom of an amino acid. However, it is known that side reactions occur in the step of deprotecting the nosyl group, which makes production of the intended product problematic (NPL 9).

As described above, it is difficult to conduct a reaction for forming a bond between an N-substituted-α,α-disubstituted amino acid such as an N-alkyl-ax-disubstituted amino acid and an N-substituted amino acid such as an N-alkyl amino acid, and no effective means for solving the problem is known. The present invention was achieved in view of the above circumstances, and an objective is to provide a method for producing peptide compounds comprising N-substituted-α,α-disubstituted amino acid residues and/or N-substituted amino acid residues. More specifically, an objective is to provide a method for introducing an N-substituted-α,α-disubstituted amino acid to an N-substituted amino acid. Another objective is to provide a method for highly selectively N-functionalizing the amino group of an N-unsubstituted-α,α-disubstituted amino acid residue.

Solution to Problem

The present inventors found a method for connecting an N-substituted amino acid and an N-substituted-α,α-disubstituted amino acid. Specifically, the present inventors found that an amino acid of interest can be efficiently introduced by using an N-unsubstituted-α,α-disubstituted amino acid which is less sterically bulky as compared with N-substituted amino acids and in which the reactivity of the carboxyl group has been increased by protecting the amino group with an electron-withdrawing protecting group. Moreover, the present inventors found that in the subsequent functionalization of the amino group, an N-functionalizing reaction such as an N-alkylating reaction selectively proceeds on the NH group, the acidity of which has increased due to the electron-withdrawing protecting group. Furthermore, the present inventors, having focused on the increased acidity of the NH group due to the electron-withdrawing protecting group, found a specific base for use in the N-functionalizing reaction, and accomplished the present invention.

Specifically, the present invention encompasses the following in one non-limiting specific embodiment:

[1] a method for producing a peptide compound having an N-substituted-α,α-disubstituted amino acid residue at the N-terminus and comprising a dipeptide residue in which the N-substituted-α,α-disubstituted amino acid residue is linked to an N-substituted amino acid residue, a salt thereof, or a solvate of these, the method comprising the following steps of:

Step A: reacting an N-substituted amino acid, a salt thereof, or a solvate of these, or a peptide compound having an N-substituted amino acid residue at the N-terminus, a salt thereof, or a solvate of these, with an N-unsubstituted-α,α-disubstituted amino acid having an amino group protected with an electron-withdrawing protecting group, a salt thereof, a dehydrated product thereof, or a solvate of these in the presence or absence of a condensing reagent to obtain a peptide compound having an N-unsubstituted-α,α-disubstituted amino acid residue having an amino group protected with an electron-withdrawing protecting group at the N-terminus and comprising a dipeptide residue in which the N-unsubstituted-α,α-disubstituted amino acid residue is linked to an N-substituted amino acid residue, a salt thereof, or a solvate of these; and Step B: introducing a substituent to the amino group of the N-unsubstituted-α,α-disubstituted amino acid residue having an amino group protected with an electron-withdrawing protecting group at the N-terminus in the presence of a base and a substituent-introducing agent to obtain a peptide compound having an N-substituted-α,α-disubstituted amino acid residue having an amino group protected with an electron-withdrawing protecting group at the N-terminus and comprising a dipeptide residue in which the N-substituted-α,α-disubstituted amino acid residue is linked to an N-substituted amino acid residue, a salt thereof, or a solvate of these;

[2] the method of [1], wherein the electron-withdrawing protecting group is a protecting group with which the pKa (in water) of the NH group to which the protecting group is bonded is 6 to 11;

[3] the method of [1] or [2], wherein the pKa (in acetonitrile) of the conjugate acid of the base is 18 to 31;

[4] the method of any of [1] to [3], wherein the N-substituted amino acid or the peptide compound having an N-substituted amino acid residue at the N-terminus is loaded on a resin for solid-phase synthesis;

[5] the method of any of [1] to [4], wherein the N-substituted amino acid or the peptide compound having an N-substituted amino acid residue at the N-terminus is represented by formula (2):

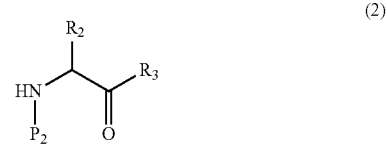

(2)

wherein
P$_2$ is C$_1$-C$_6$ alkyl, C$_2$-C$_6$ alkenyl, or C$_7$-C$_{14}$ aralkyl;
R$_2$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_2$-C$_6$ alkynyl, C$_1$-C$_6$ alkoxyC$_1$-C$_6$ alkyl optionally substituted with one or more halogens, C$_3$-C$_8$ cycloalkyl, C$_3$-C$_8$ cycloalkylC$_1$-C$_6$ alkyl, C$_3$-C$_8$ cycloalkoxyC$_1$-C$_6$ alkyl, or C$_7$-C$_{14}$ aralkyl;
R$_3$ is hydroxy, 0-PG$_2$, an arbitrary amino acid residue, or an arbitrary peptide residue;
PG$_2$ is a protecting group for a carboxyl group; and

[6] the method of any of [1] to [5], wherein the N-unsubstituted-α,α-disubstituted amino acid having an amino group protected with an electron-withdrawing protecting group is represented by formula (3):

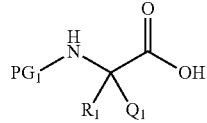
(3)

wherein

PG$_1$ is an electron-withdrawing protecting group; and

R$_1$ and Q$_1$ are independently selected from C$_1$-C$_6$ alkyl, C$_2$-C$_6$ alkenyl, C$_1$-C$_6$ alkoxyC$_1$-C$_6$ alkyl, C$_3$-C$_8$ cycloalkylC$_1$-C$_6$ alkyl, and optionally substituted C$_7$-C$_{14}$ aralkyl, or R$_1$ and Q$_1$ together with the carbon atom to which they are bonded form a 3- to 8-membered alicyclic ring or a 4- to 7-membered saturated heterocyclic ring;

[7] the method of any of [1] to [6], wherein the peptide compound obtained in step A is represented by formula (4):

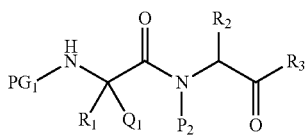
(4)

wherein

PG$_1$, R$_1$, and Q$_1$ are the same as PG$_1$, R$_1$, and Q$_1$ in formula (3), respectively; and P$_2$, R$_2$, and R$_3$ are the same as P$_2$, R$_2$, and R$_3$ in formula (2), respectively;

[8] the method of any of [1] to [7], wherein the substituent-introducing agent in step B is P$_1$X (wherein P$_1$ is the same as P$_1$ in formula (1), and X is a leaving group), and the peptide compound obtained in step B is represented by formula (1):

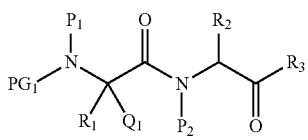
(1)

wherein

P$_1$ is C$_1$-C$_6$ alkyl, C$_2$-C$_6$ alkenyl, or C$_7$-C$_{14}$ aralkyl;

PG$_1$, R$_1$, and Q$_1$ are the same as PG$_1$, R$_1$, and Q$_1$ in formula (3), respectively; and P$_2$, R$_2$, and R$_3$ are the same as P$_2$, R$_2$, and R$_3$ in formula (2), respectively;

[9] a method for producing a peptide compound comprising a structure in which two amino acid residues are connected as represented by formula (1), a salt thereof, or a solvate of these:

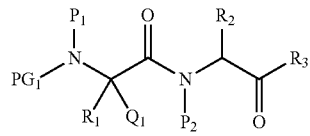
(1)

wherein

PG$_1$ is a protecting group for an amino group;

P$_1$ is C$_1$-C$_6$ alkyl, C$_2$-C$_6$ alkenyl, or C$_7$-C$_{14}$ aralkyl;

R$_1$ and Q$_1$ are independently selected from C$_1$-C$_6$ alkyl, C$_2$-C$_6$ alkenyl, C$_1$-C$_6$ alkoxyC$_1$-C$_6$ alkyl, C$_3$-C$_8$ cycloalkylC$_1$-C$_6$ alkyl, and optionally substituted C$_7$-C$_{14}$ aralkyl, or R$_1$ and Q$_1$ together with the carbon atom to which they are bonded form a 3- to 8-membered alicyclic ring or a 4- to 7-membered saturated heterocyclic ring;

P$_2$ is C$_1$-C$_6$ alkyl, C$_2$-C$_6$ alkenyl, or C$_7$-C$_{14}$ aralkyl;

R$_2$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_2$-C$_6$ alkynyl, C$_1$-C$_6$ alkoxyC$_1$-C$_6$ alkyl optionally substituted with one or more halogens, C$_3$-C$_8$ cycloalkyl, C$_3$-C$_8$ cycloalkylC$_1$-C$_6$ alkyl, C$_3$-C$_8$ cycloalkoxyC$_1$-C$_6$ alkyl, or C$_7$-C$_{14}$ aralkyl;

R$_3$ is hydroxy, 0-PG$_2$, an arbitrary amino acid residue, or an arbitrary peptide residue; and PG$_2$ is a protecting group for a carboxyl group, the method comprising the following steps of:

Step A: reacting a compound represented by formula (2):

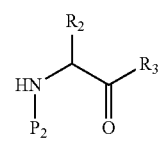
(2)

[wherein P$_2$, R$_2$, and R$_3$ are the same as P$_2$. R$_2$, and R$_3$ in formula (I), respectively], a salt thereof, or a solvate of these and a compound represented by formula (3):

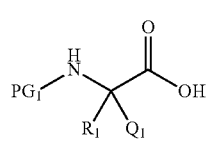
(3)

[wherein PG$_1$, Q$_1$, and R$_1$ are the same as PG$_1$, Q$_1$, and R$_1$ in formula (1), respectively], a salt thereof, a dehydrated product thereof, or a solvate of these with a condensing reagent, or reacting the compound represented by formula (2), a salt thereof, or a solvate of these with a dehydrated product of the compound represented by formula (3), a salt thereof, or a solvate of these to obtain a compound represented by formula (4):

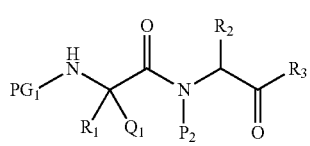

[wherein $PG_1$, $P_2$, $Q_1$, and $R_1$ to $R_3$ are the same as $PG_1$, $P_2$, $Q_1$, and $R_1$ to $R_3$ in formula (1), respectively],
a salt thereof, or a solvate of these; and
  Step B: reacting the compound represented by formula (4), a salt thereof, or a solvate of these with a $P_1$-introducing reagent to obtain the peptide compound represented by formula (1), a salt thereof, or a solvate of these;

[10] the method of any of [6] to [9], wherein
  $R_1$ and $Q_1$ together with the carbon atom to which they are bonded form a cyclopropane ring, a cyclobutane ring, a cyclopentane ring, a cyclohexane ring, or a tetrahydropyran ring; or
  $R_1$ and $Q_1$ are independently selected from methyl, ethyl, 2-methylpropyl, allyl, methoxymethyl, cyclohexylmethyl, optionally substituted benzyl, or optionally substituted phenethyl;

[11] the method of any of [6] to [10], wherein the pKa (in water) of the NH group to which $PG_1$ is bonded in formula (3) and/or formula (4) is 6 to 11;

[12] the method of any of [6] to [11], wherein $PG_1$ is $C_2$-$C_6$ haloacyl;

[13] the method of [12], wherein $C_2$-$C_6$ haloacyl is trifluoroacetyl, trichloroacetyl, pentafluoropropionyl, 2,3,3,3-tetrafluoro-2-(trifluoromethyl)propionyl, or 3,3,3-trifluoro-2-(trifluoromethyl)propionyl;

[14] the method of any of [1] to [13], wherein the dehydrated product is represented by the following formula:

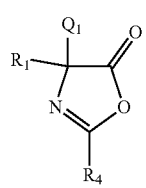

wherein $Q_1$ and $R_1$ are the same as $Q_1$ and $R_1$ in formula (1), respectively, and $R_4$ is $C_1$-$C_5$ haloalkyl;

[15] the method of [14], wherein $R_1$ and $Q_1$ together with the carbon atom to which they are bonded form a 3- to 8-membered alicyclic ring;

[16] the method of [14] or [15], wherein $R_4$ is trifluoromethyl, trichloromethyl, pentafluoroethyl, 1,2,2,2-tetrafluoro-1-(trifluoromethyl)ethyl, or 2,2,2-trifluoro-1-(trifluoromethyl)ethyl;

[17] the method of any of [8] to [16], wherein $P_1$ is methyl, ethyl, n-propyl, i-propyl, allyl, benzyl, or phenethyl;

to [18] the method of any of [5] to [17], wherein $P_2$ is methyl, ethyl, n-propyl, i-propyl, allyl, benzyl, or phenethyl;

[19] the method of any of [5] to [18], wherein $R_3$ is an arbitrary amino acid residue or an arbitrary peptide residue loaded on a resin for solid-phase synthesis;

[20] the method of any of [4] to [8] and [19], wherein the resin for solid-phase synthesis is CTC resin, Wang resin, or SASRIN resin;

[21] the method of any of [1] to [20], wherein the condensing reagent is either DIC or EDCI·HCl, or a combination of DIC and Oxyma;

[22] the method of any of [9] to [21], wherein the $P_1$-introducing reagent is a combination of $P_1X$ (wherein $P_1$ is the same as $P_1$ in formula (1), and X is a leaving group) and a base;

[23] the method of [22], wherein pKa (in acetonitrile) of a conjugate acid of the base is 18 to 31;

[24] the method of any of [3] to [8] and [22] to [23], wherein the base is selected from the group consisting of:

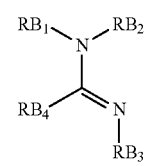

wherein
  $RB_1$ and $RB_4$ are each independently $C_1$-$C_4$ alkyl, or $RB_1$ and $RB_4$ together with the nitrogen atom to which $RB_1$ is bonded and the carbon atom to which $RB_4$ is bonded form a 5- to 8-membered ring; and
  $RB_2$ and $RB_3$ are each independently $C_1$-$C_4$ alkyl, or $RB_2$ and $RB_3$ together with the nitrogen atom to which $RB_2$ is bonded, the nitrogen atom to which $RB_3$ is bonded, and the carbon atom to which the nitrogen atoms are bonded form a 5- to 8-membered ring;

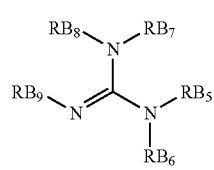

wherein
  $RB_6$ is $C_1$-$C_4$ alkyl;
  $RB_3$ and $RB_7$ are each independently $C_1$-$C_4$ alkyl or, together with the respective nitrogen atoms to which they are bonded and the carbon atom to which the respective nitrogen atoms are bonded, form a 5- to 8-membered ring;
  $RB_8$ is $C_1$-$C_4$ alkyl and $RB_9$ is $C_1$-$C_4$ alkyl or phenyl, or $RB_8$ and $RB_9$ together with the respective nitrogen atoms to which they are bonded and the carbon atom to which the respective nitrogen atoms are bonded, form a 5- to 8-membered ring; and
  wherein, when $RB_9$ is phenyl, two benzene rings of the phenyl groups in two B2 may be condensed to form naphthalene;

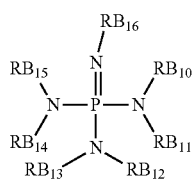

(B3)

wherein
  $RB_{10}$ is $C_1$-$C_4$ alkyl, or $RB_{10}$ and $RB_{11}$ together with the nitrogen atom to which they are bonded form a 5- to 8-membered ring;
  $RB_{11}$ except when $RB_{10}$ and $RB_{11}$ form a 5- to 8-membered ring is $C_1$-$C_4$ alkyl, or $RB_{11}$ and $RB_{12}$ together with the respective nitrogen atoms to which they are bonded and the phosphorus atom to which the respective nitrogen atoms are bonded form a 5- to 8-membered ring;
  $RB_{12}$ except when $RB_{11}$ and $RB_{12}$ form a 5- to 8-membered ring is $C_1$-$C_4$ alkyl, or $RB_{12}$ and $RB_{13}$ together with the nitrogen atom to which they are bonded form a 5- to 8-membered ring;
  $RB_{13}$ except when $RB_{12}$ and $RB_{13}$ form a 5- to 8-membered ring is $C_1$-$C_4$ alkyl, or $RB_{13}$ and $RB_{14}$ together with the respective nitrogen atoms to which they are bonded and the phosphorus atom to which the respective nitrogen atoms are bonded form a 5- to 8-membered ring;
  $RB_{14}$ except when $RB_{13}$ and $RB_{14}$ form a 5- to 8-membered ring is $C_1$-$C_4$ alkyl, or $RB_{14}$ and $RB_{15}$ together with the nitrogen atom to which they are bonded form a 5- to 8-membered ring;
  $RB_{15}$ except when $RB_{14}$ and $RB_{15}$ form a 5- to 8-membered ring is $C_1$-$C_4$ alkyl; and
  $RB_{16}$ is hydrogen, $C_1$-$C_8$ alkyl, or $C_6$-$C_{10}$ aryl; and

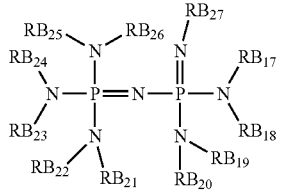

(B4)

wherein
  $RB_{17}$ is independently $C_1$-$C_4$ alkyl, or $RB_{17}$ and $RB_1a$ together with the nitrogen atom to which they are bonded form a 5- to 8-membered ring;
  $RB_{18}$ except when $RB_{17}$ and $RB_{15}$ form a 5- to 8-membered ring is $C_1$-$C_4$ alkyl, or RBIs and $RB_{19}$ together with the respective nitrogen atoms to which they are bonded and the phosphorus atom to which the respective nitrogen atoms are bonded form a 5- to 8-membered ring;
  $RB_{19}$ except when $RB_{18}$ and $RB_{19}$ form a 5- to 8-membered ring is $C_1$-$C_4$ alkyl, or $RB_{19}$ and $RB_{20}$ together with the nitrogen atom to which they are bonded form a 5- to 8-membered ring;
  $RB_{20}$ except when $RB_{19}$ and $RB_{20}$ form a 5- to 8-membered ring is $C_1$-$C_4$ alkyl;
  $RB_{21}$ is $C_1$-$C_4$ alkyl, or $RB_{21}$ and $RB_{22}$ together with the nitrogen atom to which they are bonded form a 5- to 8-membered ring;
  $RB_{22}$ except when $RB_{21}$ and $RB_2$ form a 5- to 8-membered ring is $C_1$-$C_4$ alkyl, or $RB_{22}$ and $RB_3$ together with the respective nitrogen atoms to which they are bonded and the phosphorus atom to which the respective nitrogen atoms are bonded form a 5- to 8-membered ring;
  $RB_{23}$ except when $RB_{22}$ and $RB_2$ form a 5- to 8-membered ring is $C_1$-$C_4$ alkyl, or $RB_3$ and $RB_{24}$ together with the nitrogen atom to which they are bonded form a 5- to 8-membered ring;
  $RB_{24}$ except when $RB_2$ and $RB_{24}$ form a 5- to 8-membered ring is $C_1$-$C_4$ alkyl, or $RB_{24}$ and $RB_{25}$ together with the respective nitrogen atoms to which they are bonded and the phosphorus atom to which the respective nitrogen atoms are bonded form a 5- to 8-membered ring;
  $RB_{25}$ except when $RB_{24}$ and $RB_{25}$ form a 5- to 8-membered ring is $C_1$-$C_4$ alkyl, or $RB_{25}$ and $RB_{26}$ together with the nitrogen atom to which they are bonded form a 5- to 8-membered ring;
  $RB_6$ except when $RB_{25}$ and $RB_6$ form a 5- to 8-membered ring is $C_1$-$C_4$ alkyl; and
  $RB_{27}$ is $C_1$-$C_4$ alkyl or $C_6$-$C_{10}$ aryl;

[25] the method of any of [3] to [8] and [22] to [24], wherein the base is selected from the group consisting of 1,8-diazabicyclo[5.4.0]undec-7-ene (DBU), 1,5-diazabicyclo[4.3.0]non-5-ene (DBN), 1,8-bis(tetramethylguanidino)naphthalene (TMGN), 7-methyl-1,5,7-triazabicyclo[4.4.0]dec-5-ene (MTBD), 2-tert-butyl-1,1,3,3-tetramethylguanidine (BTMG), 1,5,7-triazabicyclo[4.4.0]dec-5-ene (TBD), tert-butylimino-tris(dimethylamino)phosphorane ($P_1$-tBu), tert-butylimino-tri(pyrrolidino)phosphorane ($P_1$-t-Bu-tris(tetramethylene), BTPP), 2-tert-butylimino-2-diethylamino-1,3-dimethylperhydro-1,3,2-diazaphosphorine (BEMP), tert-octylimino-tris(dimethylamino)phosphorane (P1-t-Oct), imino-tris(dimethylamino)phosphorane (HP1(dma)), 1-tert-butyl-2,2,4,4,4-pentakis(dimethylamino)-$2\lambda^5,4\lambda^5$-catenadi(phosphazene) ($P_2$-t-Bu), and 1-ethyl-2,2,4,4,4-pentakis(dimethylamino)-$2\lambda^5,4\lambda^5$-catenadi(phosphazene) ($P_2$-Et);

[26] the method of any of [1] to [25], wherein step B is carried out in a solvent selected from the group consisting of DMF, NMP, DMI, tetrahydrofuran, 2-methyltetrahydrofuran, and acetonitrile;

[27] a method for producing a peptide compound comprising a dipeptide residue in which an N-substituted-α,α-disubstituted amino acid residue is linked to an N-substituted amino acid residue, a salt thereof, or a solvate of these, the method comprising the method of any of [1] to [26]; and

[28] a method for producing a cyclic peptide compound, a salt thereof, or a solvate of these, the method comprising the steps of:
  deprotecting an N-terminal protecting group from a peptide compound, a salt thereof, or a solvate of these produced by the method of any of [1] to [27];
  optionally, elongating a peptide chain; and
  cyclizing a group on the C-terminal side and a group on the N-terminal side to form a cyclic moiety,
  wherein the cyclic peptide compound comprises 8 to 15 amino acid residues, at least 3 N-substituted amino acid residues, and at least 1 N-unsubstituted amino acid residue, and the cyclic moiety comprises at least 8 amino acid residues.

Effects of the Invention

According to the present invention, it is possible to efficiently produce peptide compounds that comprise a dipeptide residue in which an N-substituted-α,α-disubstituted amino acid residue is linked to an N-substituted amino acid residue, and that are useful in peptide pharmaceuticals, in searching for peptide pharmaceuticals, and/or in being supplied as active ingredients of pharmaceuticals. Moreover, since it is possible to also produce peptide compounds in which various unnatural amino acid residues are bonded together, peptide compounds having various structures can be provided.

DESCRIPTION OF EMBODIMENTS

Figure 1:
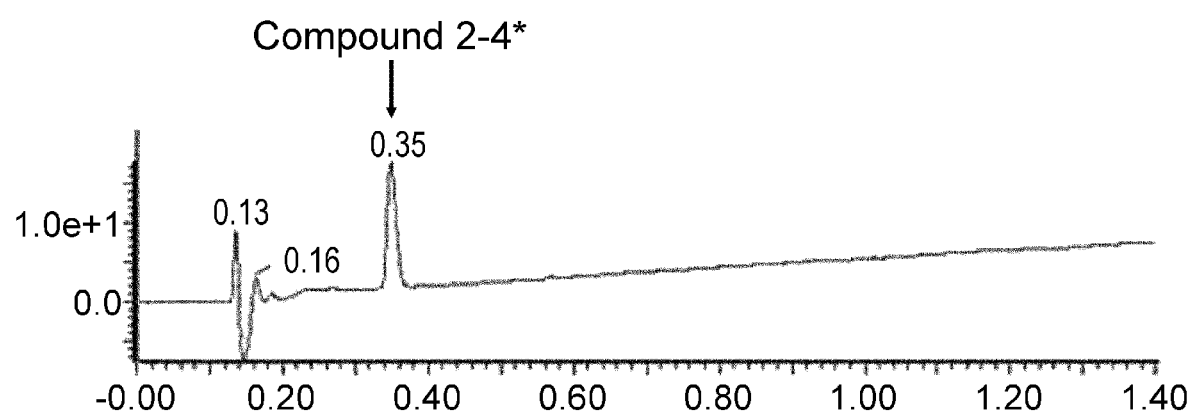
FIG. 1 shows the results of LCMS analysis (analysis condition: SQDFA05) on the reaction mixture of Example 2-4 detected at the maximum absorption wavelength using a photodiode array detector.

The abbreviations used herein are as follows.
AA: Ammonium acetate
CSA: (+)-10-Camphorsulfonic acid
DBU: 1,8-Diazabicyclo[5.4.0]-7-undecene
DCC: N,N'-Dicyclohexylcarbodiimide
DCM: Dichloromethane
DCE: 1,2-Dichloroethane
DEAD: Diethyl azodicarboxylate
DMA: Dimethylacetamide
DMF: N,N-Dimethylformamide
DIAD: Diisopropyl azodicarboxylate
DIC: N,N'-Diisopropylcarbodiimide
DIPEA: N,N-Diisopropylethylamine
DMAP: N,N-Dimethyl-4-aminopyridine
dtbbpy: 4,4'-Di-tert-butyl-2,2'-bipyridyl
EDTA: Ethylenediaminetetraacetic acid
FA: Formic acid
Fmoc: 9-Fluorenylmethyloxycarbonyl group
NMP: N-Methyl-2-pyrrolidone
TBME: t-Butyl methyl ether
TES: Triethylsilane
TFA: Trifluoroacetic acid
TFE: 2,2,2-Trifluoroethanol
THF: Tetrahydrofuran
THP: Tetrahydropyranyl group
TMSCI: Chlorotrimethylsilane
HFIP: 1,1,1,3,3,3-Hexafluoroisopropyl alcohol
HOAt: 1-Hydroxy-7-azabenzotriazole
HOBt: 1-Hydroxybenzotriazole
HOOBt: 3,4-Dihydro-3-hydroxy-4-oxo-1,2,3-benzotriazine
IPAC: Isopropyl acetate
oxyma: Ethyl cyano(hydroxyimino)acetate
PPTS: Pyridinium p-toluenesulfonate
EDCI·HCl: 1-Ethyl-3-(3-dimethylaminopropyl)carbodiimide hydrochloride
TIPS: Triisopropylsilane
TfOH: Trifluoromethanesulfonic acid
HATU: 0-(7-Aza-1H-benzotriazole-1-yl)-N,N,N',N'-tetramethyluronium hexafluorophosphate
DMSO: Dimethylsulfoxide
Fmoc-Cl: (9H-Fluoren-9-yl)methyl carbonochloridate
Fmoc-OSu: 9-Fluorenylmethyl N-succinimidyl carbonate
Ns: o-Nitrobenzenesulfonyl group
Trt: Triphenylmethyl group or trityl group
Tfa: Trifluoroacetyl group
MTBD: 7-Methyl-1,5,7-triazabicyclo[4.4.0]dec-5-ene
TMGN: 1,8-Bis(tetramethylguanidino)naphthalene
P1-tBu: tert-Butylimino-tris(dimethylamino)phosphorane (Definitions of Functional Groups and the Like)

Examples of "halogen atoms" herein include F, Cl, Br, and I.

"Alkyl" herein means a monovalent group derived by removing any one hydrogen atom from an aliphatic hydrocarbon, and has a subset of hydrocarbyl or hydrocarbon group structures not containing either a heteroatom (which refers to an atom other than carbon and hydrogen atoms) or an unsaturated carbon-carbon bond but containing hydrogen and carbon atoms in its backbone. The alkyl includes linear and branched alkyls. Specifically, the alkyl has 1 to 20 carbon atoms ($C_1$-$C_{20}$, hereinafter "$C_p$-$C_q$" means that the number of carbon atoms is p to q), and is preferably $C_1$-$C_{10}$ alkyl, and more preferably $C_1$-$C_6$ alkyl. Specific examples of alkyl include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

"Alkenyl" herein means a monovalent group having at least one double bond (two adjacent $SP^2$ carbon atoms). Depending on the configuration of a double bond and a substituent (if present), the geometrical form of the double bond can be entgegen (E) or zusammen (Z) as well as cis or trans configuration. The alkenyl includes linear and branched alkenyls. The alkenyl is preferably $C_2$-$C_{10}$ alkenyl, and more preferably $C_2$-$C_6$ alkenyl, and specific examples include vinyl, allyl, 1-propenyl, 2-propenyl, 1-butenyl, 2-butenyl (including cis and trans forms), 3-butenyl, pentenyl, 3-methyl-2-butenyl, and hexenyl.

"Alkynyl" herein means a monovalent group having at least one triple bond (two adjacent SP carbon atoms). The alkynyl includes linear and branched alkynyls. The alkynyl is preferably $C_2$-$C_{10}$ alkynyl, and more preferably $C_2$-$C_6$ alkynyl, and specific examples include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

"Cycloalkyl" herein means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl, and specific examples include cyclopropyl, cyclobutyl, cyclopentyl, cyclohexyl, cycloheptyl, cyclooctyl, bicyclo[2.2.1]heptyl, and spiro[3.3]heptyl.

"Aryl" herein means a monovalent aromatic hydrocarbon ring, and is preferably $C_6$-C10 aryl. Specific examples of the aryl include phenyl and naphthyl (e.g., 1-naphthyl and 2-naphthyl).

"Heterocyclyl" herein means a non-aromatic cyclic monovalent group containing 1 to hetero atoms in addition to carbon atoms. The heterocyclyl may have a double and/or triple bond within the ring, a carbon atom within the ring may be oxidized to form carbonyl, and heterocyclyl may be a monocyclic ring or a condensed ring. The number of atoms constituting the ring is preferably 4 to 10 (4- to 10-membered heterocyclyl), and more preferably 4 to 7 (4- to 7-membered heterocyclyl). Specific examples of the heterocyclyl include azetidinyl, oxetanyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, sultam, and 2-oxaspiro[3.3]heptyl.

"Heteroaryl" herein means an aromatic cyclic monovalent group containing 1 to 5 heteroatoms in addition to carbon atoms. The ring may be a monocyclic ring, may be a condensed ring formed with another ring, or may be partially saturated. The number of atoms constituting the ring is preferably 5 to 10 (5- to 10-membered heteroaryl) and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

"Alkoxy" herein means an oxy group to which the above-defined "alkyl" is bonded, and is preferably $C_1$-$C_6$ alkoxy. Specific examples of the alkoxy include methoxy, ethoxy, 1-propoxy, 2-propoxy, n-butoxy, i-butoxy, s-butoxy, t-butoxy, pentyloxy, and 3-methylbutoxy.

"Acyl (alkanoyl)" herein means a group in which a carbonyl group is bonded to hydrogen or the "alkyl", and is preferably $C_1$-$C_6$ acyl, and more preferably $C_2$-$C_4$ acyl. Specific examples of acyl include formyl, acetyl, propionyl, and butanoyl.

"Cycloalkoxy" herein means an oxy group to which the above-defined "cycloalkyl" is bonded, and is preferably $C_3$-$C_8$ cycloalkoxy. Specific examples of the cycloalkoxy include cyclopropoxy, cyclobutoxy, and cyclopentyloxy.

"Alkylsulfonyl" herein means a sulfonyl group to which the above-defined "alkyl" is bonded, and is preferably $C_1$-$C_6$ alkylsulfonyl. Specific examples of the alkylsulfonyl include methylsulfonyl.

"Hydroxyalkyl" herein means a group in which one or more hydrogens of the above-defined "alkyl" are replaced with hydroxyl groups, and is preferably $C_1$-$C_6$ hydroxyalkyl. Specific examples of the hydroxyalkyl include hydroxymethyl, 1-hydroxyethyl, 2-hydroxyethyl, 2-hydroxy-2-methylpropyl, and 5-hydroxypentyl.

"Haloalkyl" herein means a group in which one or more hydrogens of the above-defined "alkyl" are replaced with halogen, and is preferably $C_1$-$C_6$ haloalkyl, and more preferably $C_1$-$C_6$ fluoroalkyl. Specific examples of the haloalkyl include difluoromethyl, trifluoromethyl, 2,2-difluoroethyl, 2,2,2-trifluoroethyl, 3,3-difluoropropyl, 4,4-difluorobutyl, and 5,5-difluoropentyl.

"Haloalkoxy" herein means a group in which one or more hydrogens of the above-defined "alkoxy" are replaced with halogen, and is preferably $C_1$-$C_6$ haloalkoxy. Specific examples of the haloalkoxy include difluoromethoxy, trifluoromethoxy, 2,2-difluoroethoxy, and 2,2,2-trifluoroethoxy.

"Haloacyl (haloalkanoyl)" herein means a group in which a carbonyl group is bonded to the "haloalkyl", and is preferably $C_2$-$C_6$ haloacyl, and more preferably $C_2$-$C_4$ haloacyl. Specific examples of haloacyl include trifluoroacetyl, trichloroacetyl, pentafluoropropionyl, 2,3,3,3-tetrafluoro-2-(trifluoromethyl)propionyl, and 3,3,3-trifluoro-2-(trifluoromethyl)propionyl.

"Alkoxyalkyl" herein means a group in which one or more hydrogens of the above-defined "alkyl" are replaced with the above-defined "alkoxy", and is preferably $C_1$-$C_6$ alkoxy $C_1$-$C_6$ alkyl, and more preferably $C_1$-$C_6$ alkoxy $C_1$-$C_2$ alkyl. Specific examples of the alkoxyalkyl include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, and 2-ethoxyethyl.

"Cycloalkylalkyl" herein means a group in which one or more hydrogens of the above-defined "alkyl" are replaced with the above-defined "cycloalkyl", and is preferably $C_3$-$C_8$ cycloalkyl $C_1$-$C_6$ alkyl, and more preferably $C_3$-$C_6$ cycloalkyl $C_1$-$C_2$ alkyl. Specific examples of the cycloalkylalkyl include cyclopropylmethyl, cyclobutylmethyl, cyclopentylmethyl, and cyclohexylmethyl.

"Cycloalkoxyalkyl" herein means a group in which one or more hydrogens of the above-defined "alkyl" are replaced with the above-defined "cycloalkoxy", and is preferably $C_3$-$C_8$ cycloalkoxy $C_1$-$C_6$ alkyl, and more preferably $C_3$-$C_6$ cycloalkoxy $C_1$-$C_2$ alkyl. Specific examples of the cycloalkoxyalkyl include cyclopropoxymethyl and cyclobutoxymethyl.

"Alkylsulfonylalkyl" herein means a group in which one or more hydrogens of the above-defined "alkyl" are replaced with the above-defined "alkylsulfonyl", and is preferably $C_1$-$C_6$ alkylsulfonyl $C_1$-$C_6$ alkyl, and more preferably $C_1$-$C_6$ alkylsulfonyl $C_1$-$C_2$ alkyl. Specific examples of the alkylsulfonylalkyl include methylsulfonylmethyl and 2-(methylsulfonyl)ethyl.

"Aralkyl (arylalkyl)" herein means a group in which one or more hydrogen atoms of the above-defined "alkyl" are replaced with the above-defined "aryl", and is preferably $C_7$-$C_{14}$ aralkyl, and more preferably $C_7$-$C_{10}$ aralkyl. Specific examples of the aralkyl include benzyl, phenethyl, and 3-phenylpropyl.

"Heteroaralkyl (heteroarylalkyl)" herein means a group in which one or more hydrogen atoms of the above-defined "alkyl" are replaced with the above-defined "heteroaryl", and is preferably 5- to 10-membered heteroaryl $C_1$-$C_6$ alkyl, and more preferably 5- to 10-membered heteroaryl $C_1$-$C_2$ alkyl. Specific examples of the heteroarylalkyl include 3-thienylmethyl, 4-thiazolylmethyl, 2-pyridylmethyl, 3-pyridylmethyl, 4-pyridylmethyl, 2-(2-pyridyl)ethyl, 2-(3- pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

Examples of the "protecting group for a carboxyl group" herein include an alkyl ester-type protecting group, a benzyl ester-type protecting group, and a substituted alkyl ester-type protecting group. Specific examples of the protecting group for a carboxyl group include a methyl group, an ethyl group, a t-Bu group, a benzyl group, a trityl group, a cumyl group, a methoxytrityl group, a 2-(trimethylsilyl)ethyl group, a 2,2,2-trichloroethyl group, and an allyl group.

Examples of the "protecting group for an amino group" herein include a carbamate-type protecting group, an amide-type protecting group, an imide-type protecting group, and a sulfonamide-type protecting group. Specific examples of the protecting group for an amino group include Fmoc, Boc, Cbz, Alloc, trifluoroacetyl, pentafluoropropionyl, phthaloyl, tosyl, 2-nitrobenzenesulfonyl, 4-nitrobenzenesulfonyl, and 2,4-dinitrobenzenesulfonyl.

"Alicyclic ring" herein means a non-aromatic hydrocarbon ring. The alicyclic ring may have an unsaturated bond within the ring, and may be a polycyclic ring having two or more rings. A carbon atom constituting the ring may be oxidized to form carbonyl. The alicyclic ring is preferably a 3- to 8-membered alicyclic ring, and specific examples include a cyclopropane ring, a cyclobutane ring, a cyclopentane ring, a cyclohexane ring, a cycloheptane ring, a cyclooctane ring, and a bicyclo[2.2.1]heptane ring.

"Heterocyclic ring" herein means a non-aromatic heterocyclic ring containing 1 to 5 heteroatoms in addition to carbon atoms. The heterocyclic ring may have a double and/or triple bond within the ring, a carbon atom within the ring may be oxidized to form carbonyl, and the heterocyclic ring may be a monocyclic ring, a condensed ring, or a spiro ring. The number of atoms constituting the ring is not limited, and is preferably 3 to 12 (3- to 12-membered heterocyclic ring) and more preferably 4 to 7 (4- to 7-membered heterocyclic ring). Specific examples of the heterocyclic ring include piperazine, pyrrolidine, piperidine, morpholine, homomorpholine, hexahydropyrazine, 3-oxopiperazine, 2-oxopyrrolidine, azetidine, 2-oxoimidazolidine, oxetane, dihydrofuran, tetrahydrofuran, dihydropyran, tetrahydropyran, tetrahydropyridine, thiomorpholine, pyrazolidine, imidazoline, oxazolidine, isooxazolidine, thiazolidine, imidazolidine, isothiazolidine, thiadiazolidine, oxazolidone, benzodioxane, dioxolane, dioxane, and tetrahydrothiopyran.

"Saturated heterocyclic ring" herein means a non-aromatic heterocyclic ring containing 1 to 5 hetero atoms in addition to carbon atoms and not containing a double bond and/or a triple bond within the ring. The saturated heterocyclic ring may be a monocyclic ring, or may form a condensed ring with another ring, e.g., an aromatic ring such as a benzene ring. When the saturated heterocyclic ring forms a condensed ring, the saturated heterocyclic ring is preferably a 4- to 7-membered saturated heterocyclic ring, and specific examples include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, and an indoline ring.

"Peptide chain" herein refers to a peptide chain in which one or more natural amino acids and/or unnatural amino acids are connected by an amide bond and/or an ester bond. The peptide chain is preferably a peptide chain comprising 1 to 15 amino acid residues, and more preferably a peptide chain consisting of 5 to 12 amino acid residues.

"Peptide compound" in the present invention is not particularly limited as long as it is a peptide compound in which natural amino acids and/or unnatural amino acids are linked by way of an amide bond or an ester bond, and is a peptide compound preferably having, as number of amino acid residues, 5 to 30 residues, more preferably 8 to 15 residues, and even more preferably 9 to 13 residues. The peptide compound also encompasses peptide compounds that are loaded on a resin for solid-phase synthesis. The peptide compound synthesized in the present invention preferably contains at least 3 N-substituted amino acids, and more preferably contains at least 5 or more N-substituted amino acids, per peptide. These N-substituted amino acids may be present consecutively or nonconsecutively in the peptide compound. Herein, an "amino acid" constituting the peptide compound may be referred to as an "amino acid residue", and a "peptide" constituting the entire or partial peptide compound may be referred to as a "peptide residue". The peptide compound in the present invention may be linear or cyclic, and is preferably a cyclic peptide compound.

"Cyclic peptide compound" in the present invention is a cyclic peptide compound that can be obtained by cyclizing the group on the N-terminal side and the group on the C-terminal side of a linear peptide compound. Cyclization may be performed in any manner, such as cyclization by a carbon-nitrogen bond as in an amide bond, cyclization by a carbon-oxygen bond as in an ester bond and an ether bond, cyclization by a carbon-sulfur bond as in a thioether bond, cyclization by a carbon-carbon bond, or cyclization by heterocyclic ring construction. Among these, cyclization via a covalent bond such as an amide bond or a carbon-carbon bond is preferable, and cyclization via an amide bond formed between a side-chain carboxylic acid group and a main-chain amino group at the N-terminus is more preferable. The positions of the carboxylic acid group, amino group, and the like used in cyclization may be a position on the main chain or on a side chain, and are not particularly limited as long as cyclization is possible.

"One or more" herein means one or two or more. When "one or more" is used in a context relating to the substituent of a group, the phrase means a number encompassing one to the maximum number of substituents permitted by that group. Specific examples of "one or more" include 1, 2, 3, 4, 5, 6, 7, 8, 9, 10, and/or a greater number.

Herein, the "resin for solid-phase synthesis" is not particularly limited as long as it can be used in the synthesis of a peptide compound by a solid-phase method. Specific examples of such a resin for solid-phase synthesis include those that enable removal under acidic conditions, such as CTC resin, Wang resin, SASRIN resin, trityl chloride resin (Trt resin), 4-methyltrityl chloride resin (Mtt resin), and 4-methoxytrityl chloride resin (Mmt). The resin can be suitably selected according to the functional group used on the amino acid side. For example, when a carboxylic acid (a main-chain carboxylic acid, or a side-chain carboxylic acid represented by Asp or Glu) or a hydroxy group on an aromatic ring (a phenol group represented by Tyr) is used as the functional group on the amino acid side, a trityl chloride resin (Trt resin) or a 2-chlorotrityl chloride resin (CTC resin) is preferably used as the resin. When an aliphatic hydroxy group (an aliphatic alcohol group represented by Ser or Thr) is used as the functional group on the amino acid side, a trityl chloride resin (Trt resin), a 2-chlorotrityl chloride resin (CTC resin), or a 4-methyltrityl chloride resin (Mtt resin) is preferably used as the resin. Herein, the resin may be referred to as resin. The resin for solid-phase synthesis can be linked to an amino acid at any position, which is not limited to the amino acid at the C-terminus in the peptide. The carboxyl group of the amino acid at the C-terminus is preferably linked to the resin for solid-phase synthesis, and the carboxyl group may be a carboxyl group of the main chain or a carboxyl group of a side chain.

The type of the polymer constituting the resin is also not particularly limited. In the case of a resin composed of polystyrene, polystyrene having either 100 to 200 mesh or 200 to 400 mesh may be used. The extent of crosslinking is also not particularly limited, and a resin crosslinked with 1% DVB (divinylbenzene) is preferable. Examples of the type of the polymer constituting the resin include Tentagel and Chemmatrix.

In the production of the compound described herein, when the defined group undergoes undesired chemical conversion under the conditions of the performed method, the compound can be produced by means of, for example, protection and deprotection of a functional group. Selection and introduction/removal procedures of a protecting group can be performed according to, for example, the methods described in Greene's "Protective Groups in Organic Synthesis" (5th Ed., John Wiley & Sons, 2014), which may be suitably used depending on the reaction conditions. Further, the order of reaction steps such as introduction of a substituent can be changed as necessary.

Herein, when the modifier "optionally substituted" is used, examples of substituents therefor include alkyl, alkoxy, fluoroalkyl, fluoroalkoxy, oxo, aminocarbonyl, alkylsulfonyl, alkylsulfonylamino, cycloalkyl, aryl, heteroaryl, heterocyclyl, arylalkyl, heteroarylalkyl, halogen, nitro, amino, monoalkylamino, dialkylamino, cyano, carboxyl, alkoxycarbonyl, and formyl.

Moreover, each of these substituents may be substituted, the substituents not being limited, and one or two or more may be freely and independently selected from, for example, any substituents including a halogen atom, an oxygen atom, a sulfur atom, a nitrogen atom, a boron atom, a silicon atom, or a phosphorus atom. That is, examples include optionally substituted alkyl, alkenyl, alkynyl, aryl, heteroaryl, aralkyl, and cycloalkyl.

The compound of the present invention can be a salt thereof or a solvate thereof. Examples of salts of the compound of the present invention include hydrochloride; hydrobromide; hydroiodide; phosphate; phosphonate; sulfate; sulfonates such as methanesulfonate and p-toluenesulfonate; carboxylates such as acetate, citrate, malate, tartrate, succinate, and salicylate; alkali metal salts such as a sodium salt and a potassium salt; alkaline earth metal salts such as a magnesium salt and a calcium salt; and ammonium salts such as an ammonium salt, an alkylammonium salt, a dialkylammonium salt, a trialkylammonium salt, and a tetraalkylammonium salt. These salts are produced by, for example, bringing the compound into contact with an acid or a base. The solvate of the compound of the present invention refers to a phenomenon in which solute molecules strongly attract solvent molecules in a solution and form one molecular group, and is called a hydrate when the solvent is water. The compound of the present invention may not only be a solvate formed of a single solvent selected from water, organic solvents such as alcohol (e.g., methanol, ethanol, 1-propanol, or 2-propanol), dimethylformamide, or diglyme, and the like, but may also be a solvate formed of a plurality of solvents.

The term "amino acid" as used herein includes natural amino acids and unnatural amino acids (sometimes referred to as amino acid derivatives). The term "natural amino acid" as used herein refers to Gly, Ala, Ser, Thr, Val, Leu, Ile, Phe, Tyr, Trp, His, Glu, Asp, Gln, Asn, Cys, Met, Lys, Arg, and Pro. The unnatural amino acids (amino acid derivatives) are not particularly limited, and examples include n-amino acids, D-amino acids, N-substituted amino acids, α,α-disubstituted amino acids, amino acids having side chains that are different from those of natural amino acids, and hydroxycarboxylic acids. Amino acids herein may have any conformation; however, L-amino acids are preferable. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, a heteroaralkyl group, a cycloalkyl group, and a spiro-bonded cycloalkyl group. Each group may have a substituent, and there are no limitations on the substituent. For example, one or two or more substituents may be freely and independently selected from any substituents including a halogen atom, an O atom, an S atom, an N atom, a B atom, an Si atom, or a P atom. That is, examples include an optionally substituted alkyl group, alkoxy group, alkenyl group, alkynyl group, aryl group, heteroaryl group, aralkyl group, and cycloalkyl group, as well as oxo, aminocarbonyl, and a halogen atom. In a non-limiting embodiment, amino acids herein may be compounds having a carboxy group and an amino group in the same molecule (even in this case, imino acids such as proline and hydroxyproline are also included in amino acids).

Substituents containing a halogen atom as used herein include a halogen-substituted alkyl group, cycloalkyl group, alkenyl group, alkynyl group, aryl group, heteroaryl group, or aralkyl group. More specific examples include fluoroalkyl, difluoroalkyl, and trifluoroalkyl.

Substituents containing an O atom include groups such as hydroxy (—OH), oxy (—OR), carbonyl (—C=O—R), carboxy (—CO$_2$H), oxycarbonyl (—C=O-OR), carbonyloxy (—O—C=O—R), thiocarbonyl (—C=O-SR), carbonylthio (—S—C=O—R), aminocarbonyl (—C=O—NHR), carbonylamino (—NH—C=O—R), oxycarbonylamino (—NH—C=O—OR), sulfonylamino (—NH—SO$_2$—R), aminosulfonyl (—SO$_2$—NHR), sulfamoylamino (—NH—SO$_2$—NHR), thiocarboxyl (—C=O-SH), and carboxylcarbonyl (—C=O-CO$_2$H).

Examples of oxy (—OR) include alkoxy, cycloalkoxy, alkenyloxy, alkynyloxy, aryloxy, heteroaryloxy, and aralkyloxy. The alkoxy is preferably C$_1$-C$_4$ alkoxy and C$_1$-C$_2$ alkoxy, and particularly preferably methoxy or ethoxy.

Examples of carbonyl (—C=O—R) include formyl (—C=O-H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O-OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O-SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl (examples of which include $C_1$-$C_6$ or $C_1$-$C_4$ alkylaminocarbonyl, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Additional examples include groups in which the H atom bonded to the N atom in —C=O—NHR is further replaced with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include groups in which the H atom bonded to the N atom in —NH—C=O—R is further replaced with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include groups in which the H atom bonded to the N atom in —NH—C=O—OR is further replaced with alkyl, cycloalkyl, alkenyl, alkynyl, aryl, heteroaryl, or aralkyl.

Examples of sulfonylamino (—NH—SO$_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include groups in which the H atom attached to the N atom in —NH—SO$_2$—R is further replaced with alkyl, cycloalkyl, alkenyl, alkynyl, aryl, heteroaryl, or aralkyl.

Examples of aminosulfonyl (—SO$_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include groups in which the H atom attached to the N atom in —SO$_2$—NHR is further replaced with alkyl, cycloalkyl, alkenyl, alkynyl, aryl, heteroaryl, or aralkyl.

Examples of sulfamoylamino (—NH—SO$_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—SO$_2$—NHR may be further replaced with substituents independently selected from the group consisting of alkyl, cycloalkyl, alkenyl, alkynyl, aryl, heteroaryl, and aralkyl, and these two substituents may form a ring.

Substituents containing an S atom include thiol (—SH), thio (—S—R), sulfinyl (—S=O—R), sulfonyl (—SO$_2$—R), sulfo (—SO$_3$H) and pentafluorosulfanyl (—SF$_5$).

Examples of thio (—S—R) include alkylthio, cycloalkylthio, alkenylthio, alkynylthio, arylthio, heteroarylthio, and aralkylthio.

Examples of sulfinyl (—S=O—R) include alkylsulfinyl, cycloalkylsulfinyl, alkenylsulfinyl, alkynylsulfinyl, arylsulfinyl, heteroarylsulfinyl, and aralkylsulfinyl.

Examples of sulfonyl (—SO$_2$-R) include alkylsulfonyl, cycloalkylsulfonyl, alkenylsulfonyl, alkynylsulfonyl, arylsulfonyl, heteroarylsulfonyl, and aralkylsulfonyl.

Substituents containing an N atom include groups such as azido (—N$_3$, also called "azido group"), cyano (—CN), primary amino (—NH$_2$), secondary amino (—NH—R; also called monosubstituted amino), tertiary amino (—NR(R'); also called disubstituted amino), amidino (—C(=NH)—NH$_2$), substituted amidino (—C(=NR)—NR'R"), guanidino (—NH—C(=NH)—NH$_2$), substituted guanidino (—NR—C(=NR')-NR'R"), aminocarbonylamino (—NR—CO—NR'R"), pyridyl, piperidino, morpholino, and azetidinyl.

Examples of secondary amino (—NH—R) include alkylamino, cycloalkylamino, alkenylamino, alkynylamino, arylamino, heteroarylamino, and aralkylamino.

Examples of tertiary amino (—NR(R'); disubstituted amino) include amino groups having any two substituents each independently selected from alkyl, cycloalkyl, alkenyl, alkynyl, aryl, heteroaryl, and aralkyl, such as alkyl(aralkyl)amino, where any two such substituents may form a ring. Specific examples include dialkylamino, in particular, $C_1$-$C_6$ dialkylamino, $C_1$-$C_4$ dialkylamino, dimethylamino, and diethylamino. The term "$C_p$-$C_q$ dialkylamino group" as used herein refers to an amino group substituted with two $C_p$-$C_q$ alkyl groups, where the two $C_p$-$C_q$ alkyl groups may be the same or different.

Examples of substituted amidino (—C(=NR)—NR'R") include groups in which three substituents R, R', and R" on the N atom are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')-NR'R") include groups in which R, R', R", and R''' are each independently selected from alkyl, cycloalkyl, alkenyl, alkynyl, aryl, heteroaryl, and aralkyl, and groups in which these form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, and groups in which these form a ring.

Examples of a substituent containing a B atom include boryl (—BR(R')) and dioxyboryl (—B(OR)(OR')). These two substituents R and R' are each independently selected from alkyl, cycloalkyl, alkenyl, alkynyl, aryl, heteroaryl, aralkyl, and the like, or these may form a ring. Specific examples include a cyclic boryl group, and more specific examples include a pinacholatoboryl group, a neopentanediolatoboryl group, and a catecholatoboryl group.

Specific examples of the substituent on the nitrogen atom of the N-substituted amino acid herein include alkyl, $C_1$-$C_6$ alkyl, $C_1$-$C_4$ alkyl, methyl, $C_7$-$C_{14}$ aralkyl, benzyl, and phenethyl.

The main-chain amino group of the amino acid may be unsubstituted (—NH$_2$) or substituted (i.e., —NHR, wherein R represents optionally substituted alkyl, alkenyl, alkynyl, aryl, heteroaryl, aralkyl, or cycloalkyl, and the carbon chain bonded to the N atom and the carbon atom at the α-position may form a ring as in proline). Such an amino acid in which a hydrogen atom of the main-chain amino group is substituted may be referred to as an "N-substituted amino acid" herein. Preferable examples of the "N-substituted amino acid" herein include, but are not limited to, N-alkyl amino acid, N-$C_1$-$C_6$ alkyl amino acid, N-$C_1$-$C_4$ alkyl amino acid, N-methyl amino acid, N-$C_2$-$C_6$ alkenyl amino acid, N-allyl amino acid, N—$C_7$-$C_{14}$ aralkyl amino acid, N-benzyl amino acid, and N-phenethyl amino acid.

The "amino acids" as used herein include all isotopes corresponding to the respective amino acids. In an isotope of an "amino acid", at least one atom is replaced with an atom having the same atomic number (number of protons) but a different mass number (sum of protons and neutrons). Examples of isotopes contained in the "amino acids" herein include a hydrogen atom, a carbon atom, a nitrogen atom, an oxygen atom, a phosphorus atom, a sulfur atom, a fluorine atom, and a chlorine atom, such as $^{2}$H, $^{3}$H, $^{13}$C, 14C, $^{15}$N, $^{17}$O, $^{18}$O, $^{32}$P, $^{35}$S, $^{18}$F, and $^{36}$Cl, respectively.

(Production Method)

In an embodiment, the present invention relates to a method for producing a peptide compound having an N-substituted-α,α-disubstituted amino acid residue at the N-terminus and comprising a dipeptide residue in which the N-substituted-α,α-disubstituted amino acid residue is linked to an N-substituted amino acid residue, a salt thereof, or a solvate of these, the method including step A and step B described below.

Step A

Step A is a step of reacting an N-substituted amino acid, a salt of the amino acid, or a solvate of the amino acid or the salt, or a peptide compound having an N-substituted amino acid residue at the N-terminus, a salt of the peptide compound, or a solvate of the peptide compound or the salt, with an N-unsubstituted-α,α-disubstituted amino acid having an amino group protected with an electron-withdrawing protecting group, a salt of the amino acid, a dehydrated product of the amino acid, or a solvate of the amino acid, the salt, or the dehydrated product in the presence or absence of a condensing reagent to obtain a peptide compound having an N-unsubstituted-α,α-disubstituted amino acid residue at the N-terminus and comprising a dipeptide residue in which the N-unsubstituted-α,α-disubstituted amino acid residue is linked to an N-substituted amino acid residue, a salt of the peptide compound, or a solvate of the peptide compound or the salt. A peptide compound contains a dipeptide means herein that the dipeptide is contained in the amino acid sequence constituting the peptide compound.

In an embodiment, the "N-substituted amino acid" used in step A is any natural or unnatural amino acid in which the main-chain amino group is —NHR, wherein R is any group other than hydrogen. Specific examples of R include optionally substituted alkyl, optionally substituted alkenyl, optionally substituted alkynyl, optionally substituted aryl, optionally substituted heteroaryl, optionally substituted aralkyl, and optionally substituted cycloalkyl, and moreover, concerning R, the carbon chain bonded to the N atom and the carbon atom at the α-position may form a ring as in proline, and the ring may be further substituted with any substituent. The N-substituted amino acid may be in a salt form or a solvate form.

In an embodiment, the type and number of the other amino acids contained in the "peptide compound having an N-substituted amino acid residue at the N-terminus" used in step A are not limited as long as the peptide compound has the N-substituted amino acid residue at the N-terminus. The peptide compound may be in a salt form or a solvate form.

The N-substituted amino acid or the peptide compound having an N-substituted amino acid residue at the N-terminus used in step A may be purchased from a commercial supplier, or may be prepared by modifying a material purchased from a commercial supplier.

Specific examples of the N-substituted amino acid or the peptide compound having an N-substituted amino acid residue at the N-terminus include compounds represented by the following formula (2), salts thereof, or solvates of these:

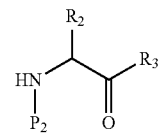

(2)

wherein $P_2$ is $C_1$-$C_6$ alkyl, $C_2$-$C_6$ alkenyl, or $C_7$-$C_{14}$ aralkyl;

$R_2$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_5$ cycloalkyl, $C_3$-$C_8$ cycloalkyl$C_1$-$C_6$ alkyl, $C_3$-$C_5$ cycloalkoxy$C_1$-$C_6$ alkyl, or $C_7$-$C_{14}$ aralkyl;

$R_3$ is hydroxy, 0-$PG_2$, an arbitrary amino acid residue, or an arbitrary peptide residue; and $PG_2$ is a protecting group for a carboxyl group.

In an embodiment, the "N-unsubstituted-α,α-disubstituted amino acid having an amino group protected with an electron-withdrawing protecting group" used in step A means an amino acid that has any two substituents other than hydrogen at the α-carbon of the amino acid and in which the amino group on the main chain of the amino acid is unsubstituted and the amino group is protected with an electron-withdrawing protecting group (i.e., "protecting group-NH-"). The amino acid may be in a salt form or a solvate form. The two substituents bonded to the α-carbon may be the same or different. Specific examples of the substituents include optionally substituted alkyl, optionally substituted alkoxyalkyl, optionally substituted alkenyl, optionally substituted alkynyl, optionally substituted aryl, optionally substituted heteroaryl, optionally substituted aralkyl, optionally substituted heteroaralkyl, optionally substituted cycloalkyl, and optionally substituted cycloalkylalkyl. The two substituents bonded to the α-carbon, together with the carbon atom to which they are bonded, may form an optionally substituted alicyclic ring or an optionally substituted heterocyclic ring.

The N-unsubstituted-α,α-disubstituted amino acid having an amino group protected with an electron-withdrawing protecting group used in step A may be purchased from a commercial supplier, or may be prepared by modifying a material purchased from a commercial supplier.

In an embodiment, the reaction of step A can be carried out in the presence of a condensing reagent. On the other hand, the reaction of step A may be carried out in the absence of a condensing reagent as long as the condensation reaction proceeds, for example, when a dehydrated product of the N-unsubstituted-α,α-disubstituted amino acid is used.

Specific examples of the N-unsubstituted-α,α-disubstituted amino acid having an amino group protected with an electron-withdrawing protecting group include compounds represented by the following formula (3), salts thereof, or solvates of these:

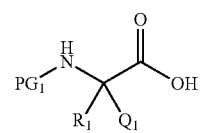

(3)

wherein

PG$_1$ is an electron-withdrawing protecting group; and

R$_1$ and Q$_1$ are independently selected from C$_1$-C$_6$ alkyl, C$_2$-C$_6$ alkenyl, C$_1$-C$_6$ alkoxyC$_1$-C$_6$ alkyl, C$_3$-C$_8$ cycloalkylC$_1$-C$_6$ alkyl, and optionally substituted C$_7$-C$_{14}$ aralkyl, or R$_1$ and Q$_1$ together with the carbon atom to which they are bonded form a 3- to 8-membered alicyclic ring or a 4- to 7-membered saturated heterocyclic ring.

In an embodiment, the electron-withdrawing protecting group bonded to the N-unsubstituted-α,α-disubstituted amino acid is a protecting group with which the pKa (in water) of the NH group to which the protecting group is bonded becomes 6 to 11, and is preferably a protecting group with which the pKa (in water) of the NH group becomes 8 to 11. Specific examples of such protecting groups include C$_2$-C$_6$ haloacyl, and more specific examples include trifluoroacetyl, trichloroacetyl, pentafluoropropionyl, 2,3,3,3-tetrafluoro-2-(trifluoromethyl)propionyl, and 3,3,3-trifluoro-2-(trifluoromethyl)propionyl.

In an embodiment, specific examples of the peptide compound having an N-unsubstituted-α,α-disubstituted amino acid residue at the N-terminus and comprising a dipeptide residue in which the N-unsubstituted-α,α-disubstituted amino acid residue is linked to an N-substituted amino acid residue obtained in step A include compounds represented by the following formula (4), salts thereof, or solvates of these:

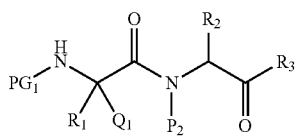

(4)

wherein

PG$_1$, R$_1$, and Q$_1$ are the same as PG$_1$, R$_1$, and Q$_1$ in formula (3), respectively; and P$_2$, R$_2$, and R$_3$ are the same as P$_2$, R$_2$, and R$_3$ in formula (2), respectively.

Step B

Step B is a step of introducing, in the presence of a base and a substituent-introducing agent, a substituent to the amino group of the N-unsubstituted-α,α-disubstituted amino acid residue having an amino group protected with an electron-withdrawing protecting group present at the N-terminus of the peptide compound obtained in step A to obtain a peptide compound having an N-substituted-α,α-disubstituted amino acid residue having an amino group protected with an electron-withdrawing protecting group at the N-terminus and comprising a dipeptide residue in which the N-substituted-α,α-disubstituted amino acid residue is linked to an N-substituted amino acid residue, a salt of the peptide compound, or a solvate of the peptide compound or the salt.

Specific examples of the substituent introduced in this step include optionally substituted alkyl, optionally substituted alkenyl, optionally substituted alkynyl, optionally substituted aralkyl, and optionally substituted cycloalkyl.

In an embodiment, the base used in step B is preferably a base whose conjugate acid has a pKa (in acetonitrile) of 23 to 30. Specific examples of such a base include a base having an amidine skeleton, a base having a guanidine skeleton, and a base having a phosphazene skeleton described below.

In an embodiment, the substituent-introducing agent used in step B is used to introduce a substituent to the amino group of the N-unsubstituted-α,α-disubstituted amino acid residue in which the amino group is protected with an electron-withdrawing protecting group at the N-terminus (i.e., "protecting group-NH-"). An electrophilic reagent can be used as the substituent-introducing agent. Specifically, a compound can be used in which a substituent to be introduced and a leaving group (such as halogen, a sulfonic acid group such as a trifluoromethanesulfonyl group, a methanesulfonyl group or a tosyl group, or a phosphoric acid group) are bonded.

In an embodiment, specific examples of the peptide compound having an N-substituted-α,α-disubstituted amino acid residue having an amino group protected with an electron-withdrawing protecting group at the N-terminus and comprising a dipeptide residue in which the N-substituted-α,α-disubstituted amino acid residue is linked to an N-substituted amino acid residue obtained in step B include compounds represented by the following formula (1), salts thereof, or solvates of these:

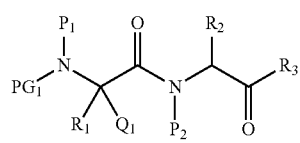

(1)

wherein

P$_1$ is C$_1$-C$_6$ alkyl, C$_2$-C$_6$ alkenyl, or C$_7$-C$_{14}$ aralkyl; PG$_1$, R$_1$, and Q$_1$ are the same as PG$_1$, R$_1$, and Q$_1$ in formula (3), respectively; and P$_2$, R$_2$, and R$_3$ are the same as P$_2$, R$_2$, and R$_3$ in formula (2), respectively.

The "peptide compound having an N-substituted-α,α-disubstituted amino acid residue at the N-terminus and comprising a dipeptide residue in which the N-substituted-α,α-disubstituted amino acid residue is linked to an N-substituted amino acid residue" produced by the method of the present invention may be a peptide compound in which the amino group at the N-terminus is protected with a protecting group or a peptide compound in which the protecting group is removed to give a free amino group (NHR—). When the amino group at the N-terminus is protected with a protecting group, the protecting group may be an electron-withdrawing protecting group resulting from the "N-unsubstituted-α,α-disubstituted amino acid having an amino group protected with an electron-withdrawing protecting group" used in step A, or a different protecting group (such as an Fmoc group) introduced after the electron-withdrawing protecting group is deprotected. The present invention may include, in addition to steps A and B, a step of removing the electron-withdrawing protecting group and a step of introducing another arbitrary protecting group different from the electron-withdrawing protecting group. For attachment and removal of the protecting group, a method described in, for example, Greene's, "Protective Groups in Organic Synthesis" (5th edition, John Wiley & Sons 2014) can be used.

In an embodiment, the present invention relates to a method for producing a peptide compound having a structure depicted in formula (1) in which two amino acid residues are connected, a salt of the compound, or a solvate of the compound or the salt, the method comprising step A and step B as shown in the following scheme.

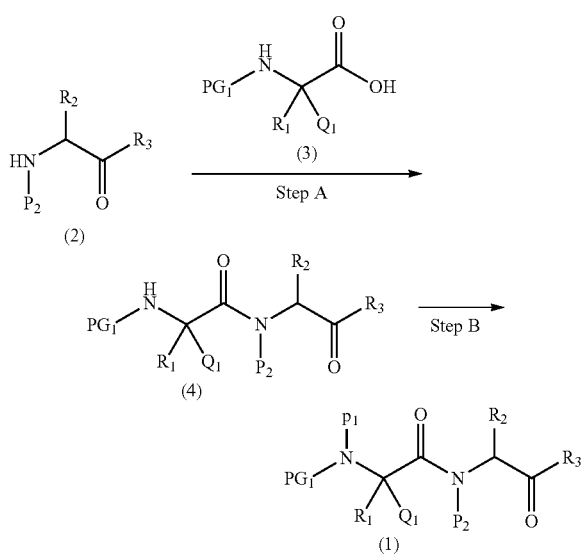

In the above formulae, $PG_1$ is a protecting group for an amino group, and preferably used is a protecting group with which the pKa of the NH group to which $PG_1$ is bonded in formula (4) becomes 11 or less. When the pKa of the NH group to which $PG_1$ is bonded is 11 or less, preferably 6 to 11, and more preferably 8 to 11, a $P_1$ group can be selectively introduced to the NH group of formula (4) to which $PG_1$ is bonded. As for the pKa, a calculated value calculated using Advanced Chemistry Development (ACD/Labs) Software V 11.02 ((C) 1994-2019 ACD/Labs) can be used. For example, the pka of the NH group of tert-butyl (2,2,2-trifluoroacetyl) alaninate is 9.71, and the pka of the NH group of tert-butyl 2-methyl-2-(2,2,2-trifluoroacetamido)propanoate is 9.21, both in which trifluoroacetyl is bonded to the nitrogen atom. Moreover, the pka of the NH group of methyl 2-methyl-2-(2,2,3,3,3-pentafluoropropanamide)propanoate in which pentafluoropropionyl is bonded to the nitrogen atom is 9.27, and the pka of the NH group of methyl 2-methyl-2-(2,2,2-trichloroacetamide)propanoate in which trichloroacetyl is bonded to the nitrogen atom is 9.72. On the other hand, the pka of the NH group of methyl 2-acetamido-2-methylpropanoate in which an acetyl group having a weaker electron-withdrawing force than these haloacyl groups is bonded to the nitrogen atom is 14.36, and the acidity of the NH group is weaker than that of the haloacyl groups. In the present invention, PG is preferably an electron-withdrawing protecting group with which the acidity of the proton of the NH group is increased, and an example of such a protecting group is $C_2$-$C_6$ haloacyl. $C_2$-$C_6$ haloacyl is preferably trifluoroacetyl, trichloroacetyl, pentafluoropropionyl, 2,3,3,3-tetrafluoro-2-(trifluoromethyl)propionyl, 3,3,3-trifluoro-2-(trifluoromethyl)propionyl, or the like.

In formula (1), $P_1$ is $C_1$-$C_6$ alkyl, $C_2$-$C_6$ alkenyl, or $C_7$-$C_{14}$ aralkyl. When $P_1$ is $C_1$-$C_6$ alkyl, $C_1$-$C_6$ alkyl is preferably methyl, ethyl, n-propyl, or i-propyl; when $P_1$ is $C_2$-$C_6$ alkenyl, $C_2$-$C_6$ alkenyl is preferably allyl; and when $P_1$ is $C_7$-$C_{14}$ aralkyl, $C_7$-$C_{14}$ aralkyl is preferably benzyl or phenethyl.

In each formula above, $R_1$ and $Q_1$ are independently selected from $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, and optionally substituted $C_7$-$C_{14}$ aralkyl, or $R_1$ and $Q_1$, together with the carbon atom to which they are bonded, form a 3- to 8-membered alicyclic ring or a 4- to 7-membered saturated heterocyclic ring.

When $R_1$ and/or $Q_1$ are $C_1$-$C_6$ alkyl, $C_1$-$C_6$ alkyl is preferably methyl, ethyl, i-propyl, or 2-methylpropyl. When $R_1$ and/or $Q_1$ are $C_2$-$C_6$ alkenyl, $C_2$-$C_6$ alkenyl is preferably allyl. When $R_1$ and/or $Q_1$ are $C_1$-$C_6$ alkoxy$C_1$-$C_6$ alkyl, $C_1$-$C_6$ alkoxy$C_1$-$C_6$ alkyl is preferably methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, I-methoxyethyl, 2-methoxyethyl, or 2-ethoxyethyl. When $R_1$ and/or $Q_1$ are $C_3$-$C_8$ cycloalkyl$C_1$-$C_6$ alkyl, $C_3$-$C_9$ cycloalkyl$C_1$-$C_6$ alkyl is preferably cyclopropylmethyl, cyclobutylmethyl, cyclopentylmethyl, cyclohexylmethyl, cycloheptylmethyl, 2-cyclopropylethyl, 2-cyclobutylethyl, 2-cyclopentylethyl, or 2-cyclohexylethyl. When $R_1$ and/or $Q_1$ are optionally substituted $C_7$-$C_{14}$ aralkyl, $C_7$-$C_{14}$ aralkyl is preferably benzyl or phenethyl, and the substituent for aryl of $C_7$-$C_{14}$ aralkyl is preferably one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, and cyano.

When $R_1$ and $Q_1$ together with the carbon atom to which they are bonded form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydropyran ring.

In each formula above, $P_2$ is $C_1$-$C_6$ alkyl, $C_2$-$C_6$ alkenyl, or $C_7$-$C_{14}$ aralkyl. When $P_2$ is $C_1$-$C_6$ alkyl, $C_1$-$C_6$ alkyl is preferably methyl, ethyl, n-propyl, or i-propyl; when $P_2$ is $C_2$-$C_6$ alkenyl, $C_2$-$C_6$ alkenyl is preferably allyl; and when $P_2$ is $C_7$-$C_{14}$ aralkyl, $C_7$-$C_{14}$ aralkyl is preferably benzyl or phenethyl.

In each formula above, $R_2$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-Calkyl optionally substituted with one or more halogen atoms, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl.

$R_2$ is preferably $C_1$-$C_6$ alkyl, $C_1$-$C_6$ fluoroalkyl, $C_1$-$C_4$ hydroxyalkyl, methylsulfonyl$C_1$-$C_2$ alkyl, $C_2$-$C_3$ alkynyl, $C_1$-$C_4$ alkoxy$C_1$-$C_2$ alkyl optionally substituted with one or more fluorine atoms, $C_3$-$C_6$ cycloalkyl, $C_3$-$C_6$ cycloalkyl$C_1$-$C_2$ alkyl, $C_3$-$C_6$ cycloalkoxy$C_1$-$C_2$ alkyl, benzyl, or phenethyl.

Specific examples of $R_2$ include methyl, ethyl, n-propyl, i-propyl, 1-methylpropyl, 2-methylpropyl, n-butyl, 2-methylbutyl, 3-methylbutyl, n-pentyl, propargyl, 3,3-difluorobutyl, 5,5-difluoropentyl, methoxymethyl, 1-methoxyethyl, 2-methoxyethyl, n-propoxymethyl, 1-hydroxyethyl, cyclopropoxymethyl, cyclobutoxymethyl, (2,2,2-trifluoroethoxy)methyl, 2-methylsulfonylethyl, cyclopropyl, cyclobutyl, cyclopentyl, cyclohexyl, cyclopropylmethyl, cyclobutylmethyl, cyclopentylmethyl, cyclohexylmethyl, benzyl, and phenethyl.

In each formula above, $R_3$ is hydroxy, O-$PG_2$, an arbitrary amino acid residue, or an arbitrary peptide residue, wherein $PG_2$ is a protecting group for a carboxyl group. When $R_3$ is O-$PG_2$, specific examples of $PG_2$ include alkyl such as t-butyl, as well as trityl, cumyl, allyl, and benzyl. When $R_3$ is an arbitrary amino acid residue or an arbitrary peptide residue, the amino acid residue or the peptide residue may be loaded on a resin for solid-phase synthesis. When the peptide residue is loaded on a resin for solid-phase synthesis, the resin may be loaded on the amino acid residue at the C-terminus of the peptide residue, or loaded on an amino acid residue at another arbitrary position. The resin for solid-phase synthesis is preferably CTC resin, Wang resin, or SASRIN resin, and is more preferably CTC resin. When $R_3$ is an arbitrary peptide residue, the peptide residue is composed of any kind and number of amino acid residues. The number of amino acid residues constituting the peptide residue is preferably 2 to 13, and more preferably 2 to 9.

In formula (1), specific examples of the amino acid residue represented by the following formula:

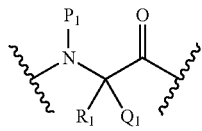

include MeAib, MecLeu, Me(Me)Phe, Me(Me)Abu, Me(Me)Leu, Me(Me)Ser(Me), Me(Me)Phe, Me(Me)Cha, Me(Me)Val, EtAib, nPrAib, AllylAib, and BnAib.

In formula (1), specific examples of the amino acid residue represented by the following formula:

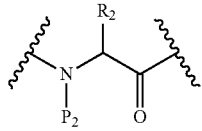

include McAla, McLeu, MeCha, MeVal, MeAla(cPent), McAla(cBu), MeAla(cPr), MeChg, MeGly(cPent), MeGly (cBu), MeGly(cPr), MeAbu, MeNva, McNle, McNva(5-F2), MeHie, MeIle, MeSer(nPr), MeSer(cPr), MeHnl, MeHnl(7-F2), MePRA, MeSer(Me), MeThr, MeSer(cBu), MeSer (Tfe), MeThr(Me), MeHse(Me), MeMet(02), EtVal, and nPrVal.

In formula (1), when $R_3$ is an arbitrary amino acid residue, specific examples of the amino acid residue include MeSer (tBuOH), bAla, bMeAla, MeGly, MePhe, MePhe(3-F), MePhe(4-F), D-MePhe, 2-ACHxC, 2-ACPnC, 3-CF3-bAla, Asp-mor, Asp-mor(26-bicyc), Asp-mor(S02), Asp-NMe2, Asp-oxz, Asp-pip, Asp-pip(345-F6), Asp-pip(4-Me), Asp-pip-tBu, Asp-piz(oxe), Asp-pyrro, Asp-pyrro(34-F4), Asp-pyrro(3-Me2), D-(Propargyl)Gly-(C#CH2), D-3-Abu, D-3-McAbu, D-Gly(Allyl)-(C#CH2), D-Hph-(C#CH2), D-Leu-(C#CH2), D-McAsp-pyrro, D-McLeu-(C#CH2), D-Pic(2)-(C#CH2), D-Pro-(C#CH2), D-Ser(iPen)-(C#CH2), D-Ser (NtBu-Aca)-(C#CH2), EtAsp-pip, MeAsp-aze, McAsp-mor, MeAsp-mor(26-bicyc), MeAsp-mor(S02), McAsp-NMe2, McAsp-oxz, MeAsp-pip, McAsp-pip(345-F6), MeAsp-pip (3-F2), MeAsp-pip(4-F2), MeAsp-pip(4-Me), MeAsp-piz (oxe), MeAsp-pyrro, MeAsp-pyrro(34-F4), MeAsp-pyrro (3-Me2), and nPrAsp-pip.

Step A is a step of reacting a compound represented by formula (2), a salt thereof, or a solvate of these with a compound represented by formula (3), a salt thereof, a dehydrated product thereof, or a solvate of these in the presence of a condensing reagent to obtain a compound represented by formula (4), a salt thereof, or a solvate of these; or is a step of reacting a compound represented by formula (2), a salt thereof, or a solvate of these with a dehydrated product of a compound represented by formula (3) (i.e., a compound represented by formula (3')), a salt thereof, or a solvate of these in the absence of a condensing reagent to obtain a compound represented by formula (4), a salt thereof, or a solvate of these.

The compound represented by the following formula (2) can be purchased from a commercial supplier or, as necessary, a material purchased from a commercial supplier can be modified and used. Specifically, for example, the compound represented by formula (2) can be produced by introducing $P_2$ to a material purchased from a commercial supplier.

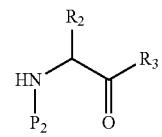

$P_2$, $R_2$, and $R_3$ in formula (2) are the same as $P_2$, $R_2$, and $R_3$ in formula (1), respectively.

The compound represented by the following formula (3) can be purchased from a commercial supplier or, as necessary, a material purchased from a commercial supplier can be modified and used. Specifically, for example, the compound represented by formula (3) can be produced by introducing PG to a material purchased from a commercial supplier using a base and a $PG_1$-introducting reagent in a solvent. Specific examples of the $PG_1$-introducing reagent include ethyl trifluoroacetate, ethyl pentafluoropropionate, ethyl trichloroacetate, trifluoroacetic anhydride, pentafluoropropionic anhydride, and trichloroacetic anhydride, and specific examples of the base include N,N-diisopropylethylamine, triethylamine, sodium methoxide, and sodium ethoxide. Specific examples of the solvent used when introducing $PG_1$ include methanol and ethanol in the case of using ethyl trifluoroacetate, ethyl pentafluoropropionate, or ethyl trichloroacetate as the introducing reagent. In the case of using trifluoroacetic anhydride, pentafluoropropionic anhydride, or trichloroacetic anhydride as the introducing reagent, examples include dichloromethane, tetrahydrofuran, and pyridine.

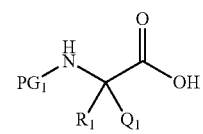

In the formula, $PG_1$, $Q_1$, and $R_1$ are the same as $PG_1$, $Q_1$, and $R_1$ in formula (1), respectively.

Step A can be carried out by applying reaction conditions that are known through the literature. Examples include methods described in, for example, the Solid-Phase Synthesis Handbook published by Merck on May 1, 2002, and such methods may be suitably used according to the reaction conditions. As condensing reagent used in step A, the following can be used: carbodiimide-based condensing agents represented by DCC (N,N'-dicyclohexylcarbodiimide), DIC (N,N'-diisopropylcarbodiimide), and EDCI·HCl (1-ethyl-3-(3-dimethylaminopropyl)carbodiimide hydrochloride); combinations of carbodiimide-based condensing agents and additives represented by HOAt, HOBt, and oxyma; uronium salt-based condensing agents represented by HATU (0-(7-aza-1H-benzotriazol-1-yl)-N,N,N',N'-tetramethyluronium hexafluorophosphate), HBTU (0-(1H-benzotriazol-1-yl)-N,N,N',N'-tetramethyluronium hexafluorophosphate), HCTU (0-(6-chloro-1H-benzotriazol-1-yl)-N,N,N',N'-tetramethyluronium hexafluorophosphate), and COMU ((l-cyano-2-ethoxy-2-oxoethylideneaminooxy) dimcthylaminomorpholinocarbenium hexafluorophosphate); phosphonium salt-based condensing agents represented by PyAOP ((7-azabenzotriazol-1-yloxy)trispyrrolidinophosphonium hexafluorophosphate), PyBOP (1H-benzotriazol-1-yloxy-tri(pyrrolidino)phosphonium hcxafluorophosphate), and PyOxim ([ethylcyano(hydroxyimino)acetato-02]tri-1-pyrrolidinylphosphonium hexafluorophosphate); 1-chloro-N,N-2-trimethyl-1-propenylamine (Ghosez reagent); formamidinium salt-based condensing agents represented by TCFH (chloro-N,N,N',N'-tetramethylformamidinium hexafluorophosphate), PyCIU (N,N,N',N'-bis(tetramethylene)chloroformamidinium hexafluorophosphate), BTFFH (fluoro-N,N,N',N'-bis(tetramethylene)formamidinium hexafluorophosphate), and TFFH (fluoro-N,N,N',N'-tetramethylamidinium hexafluorophosphate); and the like. Either DIC or EDCI·HCl, or a combination of DIC and Oxyma, is preferable.

When $PG_1$ is $C_2$-$C_6$ haloacyl, oxazolone represented by formula (3'), which is prepared from the compound represented by formula (3) and is a dehydrated product of the compound, can also be used in step A. The oxygen atom, and the carbon atom between the oxygen atom and the nitrogen atom, constituting the oxazolone ring are derived from the carbonyl group of $C_2$-$C_e$ haloacyl of $PG_1$, and $R_4$ is $C_1$-$C_5$ haloalkyl derived from the haloalkyl group of $C_2$-$C_6$ haloacyl of $PG_1$. Specific examples of reactants for preparing oxazolone include N,N'-diisopropylcarbodiimide, 1-(3-dimethylaminopropyl)-3-ethylcarbodiimide hydrochloride, and thionyl chloride.

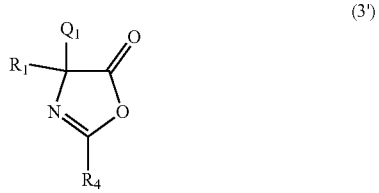

(3')

In the compound represented by formula (3'), $R_1$ and $Q_1$ are the same as $R_1$ and $Q_1$ in formula (3). $R_1$ and $Q_1$ together with the carbon atom to which they are bonded may form a 3- to 8-membered alicyclic ring, and specific examples of such 3- to 8-membered alicyclic ring include a cyclopropane ring, a cyclobutane ring, a cyclopentane ring, and a cyclohexane ring.

In the compound represented by formula (3'), $R_4$ is $C_1$-$C_5$ haloalkyl, and specific examples of $C_1$-$C_5$ haloalkyl include trifluoromethyl, trichloromethyl, pentafluoroethyl, 1,2,2,2-tetrafluoro-1-(trifluoromethyl)ethyl, and 2,2,2-trifluoro-1-(trifluoromethyl)ethyl. Among these, trifluoromethyl is preferable.

Step B is the step of reacting a compound represented by formula (4), a salt thereof, or a solvate of these with a $P_1$-introducing reagent to obtain a peptide compound represented by formula (1), a salt thereof, or a solvate of these.

In the present invention, a combination of $P_1X$ (wherein $P_1$ is the same as $P_1$ in formula (1), and X is a leaving group) and a base can be used as the $P_1$-introducing reagent. In step B, $P_1$ can be selectively introduced to the nitrogen atom to which $PG_1$ is bonded by causing $P_1X$ to act on the compound represented by formula (4) in the presence of a base having a suitable pKa.

Specific examples of $P_1X$ include alkyl iodide, alkyl bromide, alkyl trifluoromethanesulfonate, alkyl p-toluenesulfonate, alkenyl iodide, alkenyl bromide, alkenyl trifluoromethanesulfonate, alkenyl p-toluenesulfonate, aralkyl iodide, aralkyl bromide, aralkyl trifluoromethanesulfonate, and aralkyl p-toluenesulfonate. When the $P_1$-introducing reagent is a methylating reagent, specific examples of the methylating reagent include methyl iodide, dimethyl sulfate, methyl trifluoromethanesulfonate, methyl p-toluenesulfonate, and methyl methanesulfonate. When the $P_1$-introducing reagent is an ethylating reagent, specific examples of the ethylating reagent include ethyl iodide, ethyl bromide, diethyl sulfate, ethyl trifluoromethanesulfonate, ethyl p-toluenesulfonate, and ethyl methanesulfonate. When the $P_1$-introducing reagent is an allylating reagent, specific examples of the allylating reagent include allyl chloride and allyl bromide. When the $P_1$-introducing reagent is a benzylating reagent, specific examples of the benzylating reagent include benzyl chloride and benzyl bromide. When the $P_1$-introducing reagent is a phenethylating reagent, specific examples of the phenethylating reagent include (2-iodoethyl)benzene and (2-bromoethyl)benzene.

When using a combination of $P_1X$ and a base as the $P_1$-introducing reagent, a base that has a basicity that is suitable for introducing $P_1$ to the nitrogen atom of interest can be used. The basicity of a base is expressed as the pKa of the conjugate acid of the base. The pKa of the conjugate acid of the base may be referred to as the pKa of the base.

Specifically, a base having a pKa that is sufficient to dehydrogenate the hydrogen of the NH group to which $P_1$ is bonded can be used.

As for the pKa of the conjugate acid of the base, a calculated value calculated using Advanced Chemistry Development (ACD/Labs) Software V 11.02 ((c) 1994-2019 ACD/Labs), a value provided in Chem. Eur. J. 2002, 8, 1682-1693, J. Org. Chem. 2005, 70, 3, 1019-1028, Eur. J. Org. Chem., 2019, 40, 6735-6748, or catalogues of Sigma-Aldrich, and the like can be suitably referred to.

The pKa varies according to the solvent. The pKa of conjugated acids of DBU, DBN, TMGN, MTBD, and BTMG in water are 13.28, 13.42, 12.26, 14.37, and 13.81, respectively (calculated values calculated using Advanced Chemistry Development (ACD/Labs) Software V11.02 (c) 1994-2019 ACD/Labs).

On the other hand, the pKa of conjugate acids of DBU, TMGN, MTBD, P1-tBu, BTPP, and BEMP in acetonitrile are 24.32, 25.1, 25.43, 26.9, 28.4, and 27.6 (values provided in Chem. Eur. J. 2002, 8, 1682-1693, and catalogues of Sigma-Aldrich). The pKa value of the conjugate acid of DBN in acetonitrile is 23.89 (Eur. J. Org. Chem., 2019, 40, 6735-6748).

TABLE 1

| | DBU | DBN | TMGN | MTBD | BTMG | P1-tBu | BTPP | BEMP |
|---|---|---|---|---|---|---|---|---|
| pKa in database (Calculated value (water)) | 13.28 | 13.42 | 12.26 | 14.37 | 13.81 | | | |

TABLE 1-continued

|  | DBU | DBN | TMGN | MTBD | BTMG | P1-tBu | BTPP | BEMP |
|---|---|---|---|---|---|---|---|---|
| pKa (Value in literature (acetonitrile)) | 24.32 | 23.89 | 25.1 | 25.43 |  | 26.9 | 28.4 | 27.6 |

The pKa value of the conjugate acid of a base in acetonitrile is roughly 10 to 14 greater than the pKa value in water (a calculated value calculated by Advanced Chemistry Development (ACD/Labs) Software V 11.02 (C) 1994-2019 ACD/Labs).

In the present invention, a protecting group with which the pKa (in water) of the NH group to which $PG_1$ is bonded becomes 11 or less is preferably used. The pKa (in water) of the NH group to which $PG_1$ is bonded is preferably 6 to 11, and more preferably 8 to 11.

The pKa of the conjugate acid of the base required to deprotonate the proton of the NH group needs to be different from the pKa of the NH group by at least 2 or more, preferably 2 to 3, and more preferably 2 to 6.

Accordingly, when the pKa of the NH group to which PG is bonded is 6 to 11, preferably, the pKa of the conjugate acid of the base to be used is (1) greater than the pKa of the NH group, (2) moreover the pKa values are different by at least 2 or more and preferably by 6 or more, and (3) furthermore the base has a pKa in acetonitrile that is greater by a converted value (10 to 14) than the pKa in water. When the specific pKa value (in acetonitrile) of the conjugate acid of the base is 18 to 31, 22 to 29, 22 to 30, 22 to 31, 23 to 29, 23 to 30, or 23 to 31, the base can be used as the base of the present reaction. The range of the pKa (in acetonitrile) of the conjugate acid of the base to be used is preferably 22 to 31.

In the case where the pKa (in acetonitrile) of the NH group to which $PG_1$ is bonded is 8 to 11, when the pKa (in acetonitrile) of the conjugate acid of the base to be used is 20 to 31, 20 to 30, 20 to 29, 21 to 31, 21 to 30, 21 to 29, 22 to 31, 22 to 30, 22 to 29, 23 to 31, 23 to 30, or 23 to 29, the base can be used as the base of the present reaction. The range of the pKa (in acetonitrile) of the conjugate acid of the base to be used is preferably 23 to 30.

In an embodiment, the base is represented by the following formula B1 having an amidine skeleton:

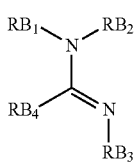

(B1)

$RB_1$ and $RB_4$ are each independently $C_1$-$C_4$ alkyl, or $RB_1$ and $RB_4$ together with the nitrogen atom to which $RB_1$ is bonded and the carbon atom to which $RB_4$ is bonded form a 5- to 8-membered ring; and $RB_2$ and $RB_3$ are each independently $C_1$-$C_4$ alkyl, or $RB_2$ and $RB_3$ together with the nitrogen atom to which $RB_2$ is bonded, the nitrogen atom to which $RB_3$ is bonded, and the carbon atom to which the nitrogen atoms are bonded form a 5- to 8-membered ring.

When $RB_1$ to $RB_4$ are $C_1$-$C_4$ alkyl, the $C_1$-$C_4$ alkyl is preferably methyl or ethyl.

When $RB_1$ and $RB_4$ form a 5- to 8-membered ring, the 5- to 8-membered ring is preferably a pyrrolidine ring, a piperidine ring, an azepane ring, or the like.

When $RB_2$ and $RB_3$ form a 5- to 8-membered ring, the 5- to 8-membered ring is preferably a 1,4,5,6-tetrahydropyrimidine ring or the like.

Specific examples of the base represented by formula B1 include 1,8-diazabicyclo[5.4.0]undec-7-ene (DBU) and 1,5-diazabicyclo[4.3.0]non-5-ene (DBN).

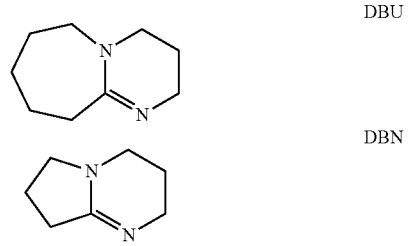

DBU

DBN

In an embodiment, the base is represented by the following formula B2 having a guanidine skeleton:

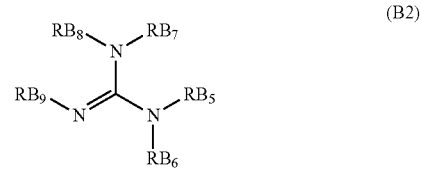

(B2)

wherein
  $RB_6$ is hydrogen or $C_1$-$C_4$ alkyl;
  $RB_5$ and $RB_7$ are each independently $C_1$-$C_4$ alkyl or, together with the respective nitrogen atoms to which they are bonded and the carbon atom to which the respective nitrogen atoms are bonded, form a 5- to 8-membered ring;
  $RB_8$ is $C_1$-$C_4$ alkyl and $RB_9$ is $C_1$-$C_4$ alkyl or phenyl, or RB, and $RB_9$ together with the respective nitrogen atoms to which they are bonded and the carbon atom to which the respective nitrogen atoms are bonded, form a 5- to 8-membered ring; and
  wherein when $RB_9$ is phenyl, two benzene rings of the phenyl groups of two B2 may be condensed to form naphthalene.

When $RB_5$ to $RB_5$ are $C_1$-$C_4$ alkyl, the $C_1$-$C_4$ alkyl is preferably methyl, and when $RB_9$ is $C_1$-$C_4$ alkyl, the $C_1$-$C_4$ alkyl is preferably t-butyl.

When $RB_8$ and $RB_9$ form a 5- to 8-membered ring, the 5- to 8-membered ring is preferably an imidazolidine ring, a hexahydropyrimidine ring, a 1,3-diazepane ring, or the like.

When $RB_5$ and $RB_9$ form a 5- to 8-membered ring, the 5- to 8-membered ring is preferably a 1,4,5,6-tetrahydropyrimidine ring or the like.

Specific examples of the base represented by formula B2 include 1,8-bis(tetramethylguanidino)naphthalene (TMGN), 7-methyl-1,5,7-triazabicyclo[4.4.0]dec-5-ene (MTBD), 2-tert-butyl-1,1,3,3-tetramethylguanidine (BTMG), and 1,5,7-triazabicyclo[4.4.0]dec-5-ene (TBD).

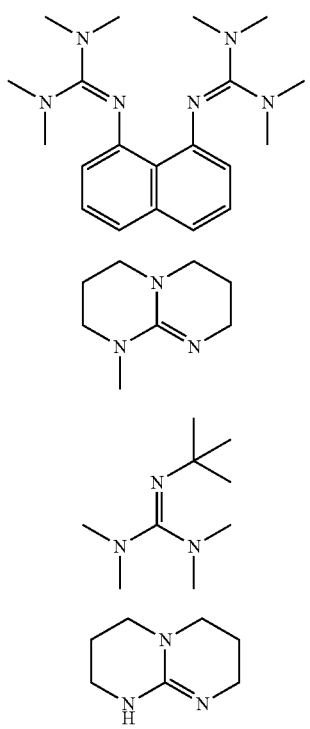

In an embodiment, the base is represented by the following formula B3 having a phosphazene skeleton:

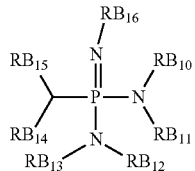

(B3)

wherein
RB$_{10}$ is C$_1$-C$_4$ alkyl, or RB$_{10}$ and RB$_{11}$ together with the nitrogen atom to which they are bonded form a 5- to 8-membered ring;
RB$_{11}$ except when RB$_{10}$ and RB$_{11}$ form a 5- to 8-membered ring is C$_1$-C$_4$ alkyl, or RB$_{11}$ and RB$_{12}$ together with the respective nitrogen atoms to which they are bonded and the phosphorus atom to which the respective nitrogen atoms are bonded form a 5- to 8-membered ring;
RB$_{12}$ except when RB$_{11}$ and RB$_{12}$ form a 5- to 8-membered ring is C$_1$-C$_4$ alkyl, or RB$_{12}$ and RB$_{13}$ together with the nitrogen atom to which they are bonded form a 5- to 8-membered ring;
RB$_{13}$ except when RB$_{12}$ and RB$_{13}$ form a 5- to 8-membered ring is C$_1$-C$_4$ alkyl, or RB$_{13}$ and RB$_{14}$ together with the respective nitrogen atoms to which they are bonded and the phosphorus atom to which the respective nitrogen atoms are bonded form a 5- to 8-membered ring;
RB$_{14}$ except when RB$_{13}$ and RB$_{14}$ form a 5- to 8-membered ring is C$_1$-C$_4$ alkyl, or RB$_{14}$ and RB$_{15}$ together with the nitrogen atom to which they are bonded form a 5- to 8-membered ring;
RB$_{15}$ except when RB$_{14}$ and RB$_{15}$ form a 5- to 8-membered ring is C$_1$-C$_4$ alkyl; and
RB$_{16}$ is hydrogen, C$_1$-C$_5$ alkyl, or C$_6$-C$_{10}$ aryl.

When RB$_{10}$ to RB$_{15}$ are C$_1$-C$_4$ alkyl, the C$_1$-C$_4$ alkyl is preferably methyl or ethyl, and when RB$_{16}$ is C$_1$-C$_5$ alkyl, the C$_1$-C$_5$ alkyl is preferably t-butyl or t-octyl.

When RB$_{10}$ and RB$_{11}$, RB$_{12}$ and RB$_{13}$, and/or RB$_{14}$ and RB$_{15}$ form a 5- to 8-membered ring, the 5- to 8-membered ring is preferably a pyrrolidine ring, a piperidine ring, an azepane ring, or the like.

When RB$_{11}$ and RB$_{12}$, and/or RB$_{13}$ and RB$_{14}$, form a 5- to 8-membered ring, the 5- to 8-membered ring is preferably a 5- to 8-membered saturated ring that does not contain a heteroatom other than the respective nitrogen atoms to which RB$_{11}$, RB$_{12}$, RB$_{13}$, and RB$_{14}$ are bonded and the phosphorus atom to which the respective nitrogen atoms are bonded.

Specific examples of the base represented by formula B3 include tert-butylimino-tris(dimethylamino)phosphorane (P1-tBu), tert-octylimino-tris(dimethylamino)phosphorane (P1-t-Oct), tert-butylimino-tri(pyrrolidino)phosphorane (P1-t-Bu-tris(tetramethylene), BTPP), 2-tert-butylimino-2-diethylamino-1,3-dimethylperhydro-1,3,2-diazaphosphorine (BEMP), and imino-tris(dimethylamino)phosphorane (HP1(dma)).

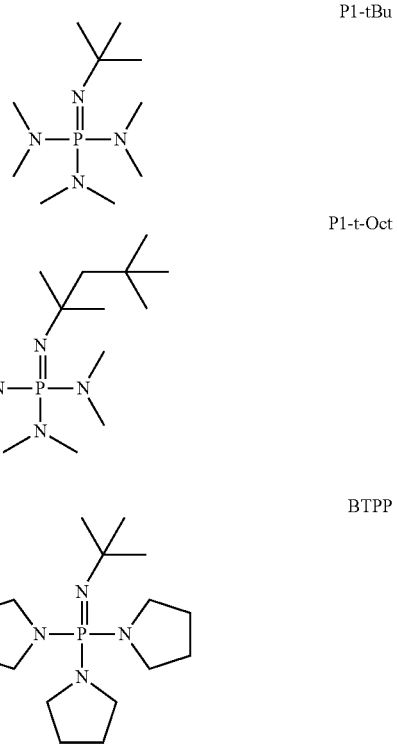

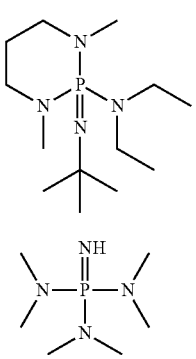

BEMP

HP1(dma)

In an embodiment, the base is represented by the following formula B4 having a phosphazene skeleton that contains two phosphorus atoms via a nitrogen atom:

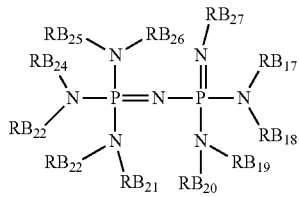

(B4)

wherein
- $RB_{17}$ is independently $C_1$-$C_4$ alkyl, or $RB_{17}$ and $RB_{1a}$ together with the nitrogen atom to which they are bonded form a 5- to 8-membered ring;
- $RB_{18}$ except when $RB_{17}$ and $RB_{15}$ form a 5- to 8-membered ring is $C_1$-$C_4$ alkyl, or $RB_{18}$ to and $RB_{19}$ together with the respective nitrogen atoms to which they are bonded and the phosphorus atom to which the respective nitrogen atoms are bonded form a 5- to 8-membered ring;
- $RB_{18}$ except when $RB_{15}$ and $RB_{18}$ form a 5- to 8-membered ring is $C_1$-$C_4$ alkyl, or $RB_{19}$ and $RB_{20}$ together with the nitrogen atom to which they are bonded form a 5- to 8-membered ring;
- $RB_{20}$ except when $RB_{19}$ and $RB_{20}$ form a 5- to 8-membered ring is $C_1$-$C_4$ alkyl;
- $RB_{21}$ is $C_1$-$C_4$ alkyl, or $RB_{21}$ and $RB_{22}$ together with the nitrogen atom to which they are bonded form a 5- to 8-membered ring;
- $RB_{22}$ except when $RB_2$, and $RB_{22}$ form a 5- to 8-membered ring is $C_1$-$C_4$ alkyl, or $RB_{22}$ and $RB_3$ together with the respective nitrogen atoms to which they are bonded and the phosphorus atom to which the respective nitrogen atoms are bonded form a 5- to 8-membered ring;
- $RB_{23}$ except when $RB_{22}$ and $RB_{23}$ form a 5- to 8-membered ring is $C_1$-$C_4$ alkyl, or $RB_{23}$ and $RB_2$ together with the nitrogen atom to which they are bonded form a 5- to 8-membered ring;
- $RB_{24}$ except when $RB_{23}$ and $RB_{24}$ form a 5- to 8-membered ring is $C_1$-$C_4$ alkyl, or $RB_{24}$ and $RB_{25}$ together with the respective nitrogen atoms to which they are bonded and the phosphorus atom to which the respective nitrogen atoms are bonded form a 5- to 8-membered ring;
- $RB_{25}$ except when $RB_{24}$ and $RB_{25}$ form a 5- to 8-membered ring is $C_1$-$C_4$ alkyl, or $RB_{25}$ and $RB_{26}$ together with the nitrogen atom to which they are bonded form a 5- to 8-membered ring;
- $RB_{26}$ except when $RB_{25}$ and $RB_{26}$ form a 5- to 8-membered ring is $C_1$-$C_4$ alkyl; and
- $RB_{27}$ is $C_1$-$C_4$ alkyl or $C_6$-$C_{10}$ aryl.

When $RB_{17}$ to $RB_{26}$ are $C_1$-$C_4$ alkyl, $C_1$-$C_4$ alkyl is preferably methyl or ethyl, and when $RB_{27}$ is $C_1$-$C_4$ alkyl, $C_1$-$C_4$ alkyl is preferably t-butyl.

When $RB_{17}$ and $RB_{18}$, $RB_{19}$ and $RB_{20}$, $RB_{21}$ and $RB_{22}$, $RB_{23}$ and $RB_{24}$, and $RB_{25}$ and $RB_6$ form a 5- to 8-membered ring, the 5- to 8-membered ring is preferably a pyrrolidine ring, a piperidine ring, an azepane ring, or the like.

When $RB_{17}$ and $RB_{18}$ are both $C_1$-$C_4$ alkyl, $RB_1$ and $RB_2O$ are also both preferably $C_1$-$C_4$ alkyl, and, preferably, $RB_1$ and $RB_{15}$ form a 5- to 8-membered ring, and $RB_{11}$ and $RB_{20}$ also form a 5- to 8-membered ring.

When $RB_{21}$ and $RB_{22}$ are both $C_1$-$C_4$ alkyl, $RB_{23}$ and $RB_{24}$ as well as $RB_{25}$ and $RB_2$ are also preferably $C_1$-$C_4$ alkyl, and, preferably, $RB_{21}$ and $RB_{22}$ form a 5- to 8-membered ring, and $RB_{23}$ and $RB_{24}$ as well as $RB_{25}$ and $RB_{26}$ also form a 5- to 8-membered ring.

When $RB_{15}$ and $RB_{19}$, and/or $RB_{22}$ and $RB_{23}$, form a 5- to 8-membered ring, the 5- to 8-membered ring is preferably a 5- to 8-membered saturated ring that does not contain a heteroatom other than the respective nitrogen atoms to which $RB_{11}$, $RB_{12}$, $RB_{13}$, and $RB_{14}$ are bonded and the phosphorus atoms to which the respective nitrogen atoms are bonded.

Specific examples of the base represented by formula B4 include 1-tert-butyl-2,2,4,4,4-pentakis(dimethylamino)-$2\lambda^5$, $4\lambda^5$-catenadi(phosphazene) (P2-t-Bu) and 1-ethyl-2,2,4,4,4-pentakis(dimethylamino)-$2\lambda^5,4\lambda^5$-catenadi(phosphazene) (P2-Et).

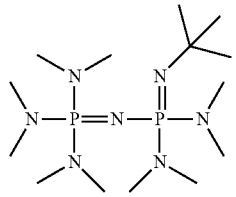

P2-t-Bu

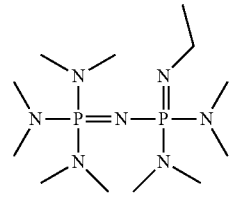

P2-Et

In the present invention, when a combination of $P_1X$ and a base is used as the $P_1$-introducting reagent, examples of the solvent to be used in the reaction include amide-based solvents represented by DMF and NMP, urea-based solvents represented by DMI, ether-based solvents represented by tetrahydrofuran and 2-methyltetrahydrofuran, and acetonitrile. Among these, amide-based solvents are preferable.

When using $P_1X$ and a base as the $P_1$-introducing reagent, the combination of $PG_1$ and the base is preferably one in which the pKa (in water) of the $PG_1$-protected amino group is 6 to 11 and the pKa (in acetonitrile) of the conjugate acid of the base is 23 to 30. The combination of $PG_1$ and the base is more preferably one in which the pKa (in water) of the $PG_1$-protected amino group is 8 to 11 and the pKa (in acetonitrile) of the conjugate acid of the base is 23 to 27. As for the combination of $PG_1$, $P_1X$, and the base, preferably, $PG_1$ is trifluoroacetyl, $P_1X$ is methyl iodide, dimethyl sulfate, ethyl iodide, allyl bromide, n-propyl iodide, or benzyl bromide, and the base is P1-tBu, TMGN, or MTBD. Specific examples of the combination of $PG_1$ and the base include trifluoroacetyl and TMGN, trifluoroacetyl and P1-tBu, and trifluoroacetyl and MTBD.

In an embodiment, the present invention relates to a method for producing a peptide compound comprising a dipeptide residue in which an N-substituted-α,α-disubstituted amino acid residue is linked to an N-substituted amino acid residue, a salt thereof, or a solvate of these, including the above-described method for producing a peptide compound having an N-substituted-α,α-disubstituted amino acid residue at the N-terminus and comprising a dipeptide residue in which the N-substituted-α,α-disubstituted amino acid residue is linked to an N-substituted amino acid residue, a salt thereof, or a solvate of these. The method may further include a step of condensing one or more amino acid residues and/or peptide residues to the N-terminus and/or the C-terminus of the peptide compound having an N-substituted-α,α-disubstituted amino acid residue at the N-terminus and comprising a dipeptide residue in which the N-substituted-α,α-disubstituted amino acid residue is linked to an N-substituted amino acid residue produced by the method described herein. The peptide compound produced by this method is an arbitrary peptide compound containing a dipeptide residue in which an N-substituted-α,α-disubstituted amino acid residue and an N-substituted amino acid residue are connected, and encompasses peptide compounds in which any number and kind of amino acids are linked to the N-terminal side and C-terminal side of the dipeptide residue.

In an embodiment, the present invention also relates to a method for producing a cyclic peptide compound, further comprising a step of deprotecting a protecting group (e.g., $PG_1$) at the N-terminus from a peptide compound represented by formula (1), a salt thereof, or a solvate of these produced by the method of the present invention and, optionally a step of elongating the peptide chain and a step of cyclizing the group at the C-terminal side and the group at the N-terminal side to form a cyclic moiety.

The cyclic peptide compound comprises 8 to 15 amino acid residues and preferably 10 to 13 amino acid residues, at least 3 and preferably at least 3 to (the number of amino acid residues constituting the cyclic peptide compound—1)N-substituted amino acid residues, and at least 1 and preferably at least 3 N-unsubstituted amino acid residues, and the cyclic moiety comprises at least 8 amino acid residues and preferably at least 10 amino acid residues.

In the step of deprotecting $PG_1$ from the peptide compound represented by formula (1), for example, the method described in Greene's, "Protective Groups in Organic Synthesis" (5th edition, John Wiley & Sons 2014) can be used.

In the step of elongating the peptide chain and the step of forming a cyclic moiety, known methods such as the methods described in WO 2013/100132 or WO 2018/225864 can be used. When the peptide chain is elongated by solid-phase synthesis, the method may include a step of cleaving the peptide compound from the resin before the elongating step and the step of forming a cyclic moiety.

All prior art documents cited herein are incorporated herein by reference.

Example

The content of the present invention will be further described with reference to Examples, Comparative Examples, and Reference Examples below, but it is not to be construed as being limited thereto. All starting materials and reagents were obtained from commercial suppliers or synthesized by known methods. The LCMS analysis conditions are described in Table 2.

TABLE 2

| Analysis condition | Equipment | Column (ID. × Length) (mm) | Mobile phase | Gradient (A/B) | Flow rate (mL/min) | Column temperature (° C.) | Wavelength | Remarks |
|---|---|---|---|---|---|---|---|---|
| SQDAA05 | Acquity UPLC/SQD2 | Ascentis Express C18 (2.1 × 50) | A) 10 mM $AcONH_4$, water B) methanol | 95/5 (initial) => 0/100 (1.0 min) => 0/100 (0.4 min) | 1.0 | 35 | 210-400 nm PDA total | |
| SQDFA05 | Acquity UPLC/SQD2 | Ascentis Express C18 (2.1 × 50) | A) 0.1% FA, water B) 0.1% FA, acetonitrite | 95/5 (initial) => 0/100 (1.0 min) => 0/100 (0.4 min) | 1.0 | 35 | 210-400 nm PDA total | |
| SQDFA05long | Acquity UPLC/SQD2 | Ascentis Express C18 (2.1 × 50) | A) 0.1% FA, water B) 0.1% FA, acetonitrile | 95/5 (initial) => 0/100 (4.5 min) => 0/100 (0.5 min) | 1.0 | 35 | 210-400 nm PDA total | |
| SMDmethod_16 | Shimadzu LCMS-2020 | Accucore C18 (2.1 × 50) | A) 0.1'% FA, water B) 0.1% FA, acetonitrile | 90/10 (initial) => 0/100 (1.1 min) => 0/100 (0.5 min) | 1.0 | 40 | 190-400nm PDA total | |
| SMDmethod_17 | Shimadzu LCMS-2020 | Ascentis Express C18 (3.0 × 50) | A) 0.05% TFA, water B) 0.05% TFA, acetonitrile | 95/5 (initial) => 5/95 (2.7 min) => 5/95 (1.0 min) | 1.0 | 40 | 190-400 nm PDA total | |
| SMDmethod_21 | Shimadzu LCMS-2010EV | Shim-Pack XR-ODS (3.0 × 50) | A) 0.05% TFA, water B) 0.05% TFA, acetonitrile | 95/5 (initial) => 5/95 (2.0 min) => 5/95 (0.7 min) | 1.2 | 40 | 190-400 nm PDA total | |
| SSC-A-AF-01 | Nexera UC/2020 | Ascentis Express C18 (2.1 × 50) | A) 10 mM $NH_4HCO_2$, water B) methanol | 70/30 (initial) => 0/100 (8.75 min) => 0/100 (1.25 min) | 0.5 | 50 | 210-400 nm PDA total | Injection in loop-wise manner |
| SSC-A-FA-01 | Nexera UC/2020 | XSelect CSH C18 (2.1 × 50) | A) 0.1% FA, water B) 0.1% FA, acetonitrile | 70/30 (initial) => 10/90 (7.5 min) => 0/100 (0.01 min) => 0/100 (2.49 min) | 0.5 | 50 | 210-400 nm PDA total | Injection in loop-wise manner |

Example 1: Preparation of Amino Acids, Resin-Loaded Peptides. And the Like Used in the Present Example

Example 1-1: Fmoc-Amino Acids Used in Peptide Synthesis by a Peptide Synthesizer In peptide synthesis described herein, Fmoc-amino acids listed in Table 3 to Table 5 were used in synthesis by a peptide synthesizer.

Fmoc-amino acids listed in Table 3 and Table 5 were purchased from a commercial supplier.

Fmoc-amino acids listed in Table 4 were synthesized according to the scheme shown below.

TABLE 3

| Amino acid number | Abbreviation | Structural formula | Name | CAS number |
|---|---|---|---|---|
| AA1-001 | Fmoc-MeAla-OH | | (2S)-2-[9H-Fluoren-9-ylmethoxycarbonyl (methyl)amino] propanoic acid | 84000-07-7 |
| AA1-002 | Fmoc-MeIle-OH | | (2S,3S)-2-[9H-Fluoren-9-ylmethoxycarbonyl (methyl)amino]-3-methylpentanoic acid | 138775-22-1 |
| AA1-003 | Fmoc-Ile-OH | | (2S,3S)-2-(9H-Fluoren-9-ylmethoxycarbonylamino)-3-methylpentanoic acid | 71989-23-6 |
| AA1-004 | Fmoc-Aze(2)-OH | | (2S)-1-(9H-Fluoren-9-ylmethoxycarbonyl) azetidine-2-carboxylic acid | 136552-06-2 |

TABLE 3-continued

| Amino acid number | Abbreviation | Structural formula | Name | CAS number |
|---|---|---|---|---|
| AA1-005 | Fmoc-MeCha-OH | | (2S)-3-Cyclohexy-2-[9H-fluoren-9-ylmethoxycarbonyl(methyl)amino]propanoic acid | 148983-03-3 |
| AA1-006 | Fmoc-MeGly-OH | | 2-[9H-Fluoren-9-ylmethoxycarbonyl(methyl)amino]acetic acid | 77128-70-2 |
| AA1-007 | Fmoc-Pro-OH | | (2S)-1-(9H-Fluoren-9-ylmethoxycarbonyl)pyrrolidine-2-carboxylic acid | 71989-31-6 |
| AA1-008 | Fmoc-MeAib-OH | | 2-[9H-Fluoren-9-ylmethoxycarbonyl(methyl)amino]-2-methylpropanoic acid | 400779-65-9 |
| AA1-009 | Fmoc-MeAbu-OH | | (2S)-2-[9H-Fluoren-9-ylmethoxycarbonyl(methyl)amino]butanoic acid | 1310575-53-1 |
| AA1-010 | Fmoc-MeChg-OH | | (2S)-2-Cyclohexyl-2-[9H-fluoren-9-ylmethoxycarbonyl(methyl)aminoacetic acid | 925240-97-7 |

TABLE 3-continued

| Amino acid number | Abbreviation | Structural formula | Name | CAS number |
|---|---|---|---|---|
| AA1-011 | Fmoc-MeVal-OH | | (2S)-2-[9H-Fluoren-9-ylmethoxycarbonyl (methyl)amino]-3-methylbutanoic acid | 84000-11-3 |
| AA1-012 | Fmoc-MeLeu-OH | | (2S)-2-[9H-Fluoren-9-ylmethoxycarbonyl (methyl)amino]-4-methylpentanoic acid | 103478-62-2 |
| AA1-013 | Fmoc-Gly-OH | | 2-(9H-Fluoren-9-ylmethoxycarbonylamino) acetic acid | 29022-11-5 |
| AA1-014 | Fmoc-MePhe-OH | | (2S)-2-[9H-Fluoren-9-ylmethoxycarbonyl (methyl)amino]-3-phenylpropanoic acid | 77128-73-5 |

TABLE 4

| Amino acid number | Abbreviation | Structure | Name |
|---|---|---|---|
| AA2-001 | Fmoc-Hph(4-CF3-3-Cl)-OH | 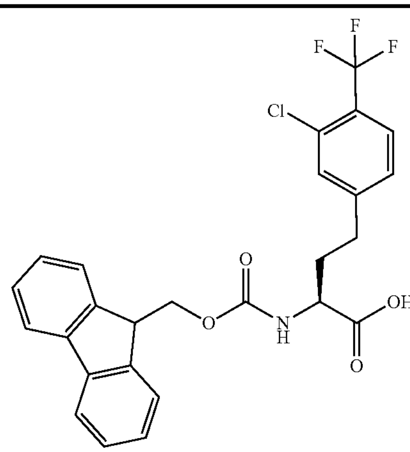 | (2S)-4-[3-Chloro-4-(trifluoromethyl)phenyl]-2-(9H-fluoren-9-ylmethaxycarbonylamino) butanoic acid |

TABLE 4-continued

| Amino acid number | Abbreviation | Structure | Name |
|---|---|---|---|
| AA2-002 | Fmoc-MeAla(cBu)-OH | 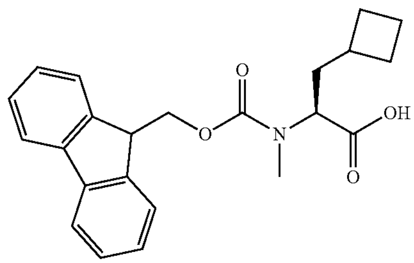 [SMILES: CN(C(=O)OCC1c2ccccc2-c2ccccc21)[C@@H](CC1CCC1)C(=O)O] | (2S)-3-Cyclobutyl-2-[9H-fluoren-9-ylmethoxycarbonyl(methyl)amino]propanoic acid |
| AA2-003 | Fmoc-MeGly(cPent)-OH | 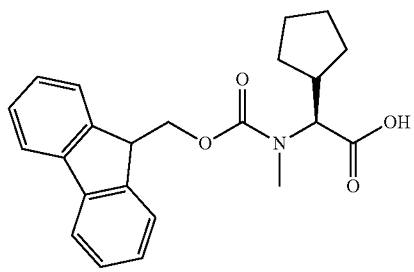 [SMILES: CN(C(=O)OCC1c2ccccc2-c2ccccc21)[C@H](C(=O)O)C1CCCC1] | (2S)-2-Cyclopentyl-2-[9H-fluoren-9-ylmethoxycarbonyl(methyl)amino]acetic acid |
| AA2-004 | Fmoc-MeGly(cBu)-OH | 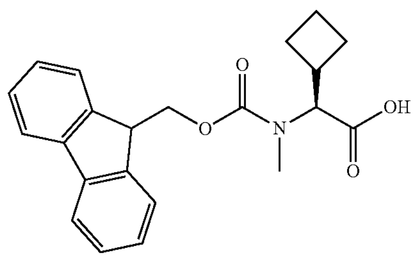 [SMILES: CN(C(=O)OCC1c2ccccc2-c2ccccc21)[C@H](C(=O)O)C1CCC1] | (2S)-2-Cyclobutyl-2-[9H-fluoren-9-ylmethoxycarbonyl(methyl)amino]acetic acid |
| AA2-005 | Fmoc-MeAla(cPent)-OH | 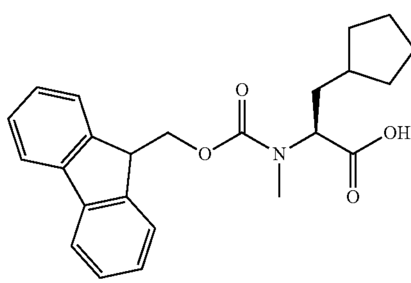 | (2S)-3-Cyclopentyl-2-[9H-fluoren-9-ylmethoxycarbonyl(methyl)amino]propanoic acid |

TABLE 5

| Amino acid number | Abbreviation | Structure | Name | CAS number |
|---|---|---|---|---|
| AA3-001 | Fmoc-D-3-MeAbu-OH | 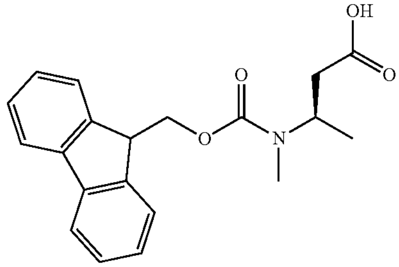 [SMILES: C[C@H](CC(=O)O)N(C)C(=O)OCC1c2ccccc2-c2ccccc21] | (3R)-3-[9H-Fluoren-9-ylmethoxycarbonyl(methyl)amino]butanoic acid | 1460306-60-8 |

Example 1-1-1: Synthesis of Compound AA2-001. (2S)-4-[3-chloro-4-(trifluoromethyl)phenyl]-2-(9H-fluoren-9-ylmethoxycarbonylamino)butanoic acid, (Fmoc-Hph(4-CF3-3-Cl)-OH

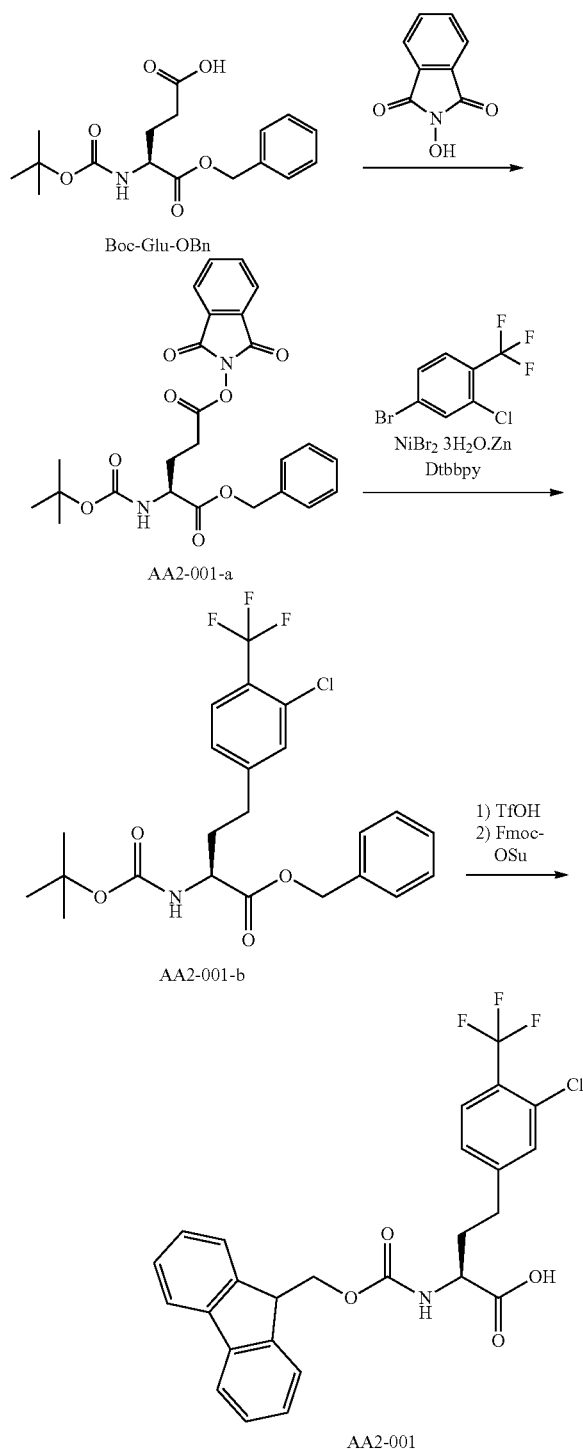

DIC (138 mL, 1.54 eq) was added dropwise at 0° C. in a nitrogen atmosphere to a THF (2 L) solution of (4S)-4-[(2-methylpropan-2-yl)oxycarbonylamino]-5-oxo-5-phenyl-methoxypentanoic acid (Boc-Glu-OBn, CAS number 30924-93-7) (200 g, 592.82 mmol), N-hydroxyphthalimide (106 g. 649.78 mmol, 1.10 eq), and DMAP (3.6 g, 29.47 mmol, 0.05 eq). The reaction solution was stirred at 25° C. for 16 hours, solid was removed by filtration, and the solvent was removed under reduced pressure. The residue was diluted with toluene, the resulting solids were removed by filtration, and the solvent was removed under reduced pressure. The residue was purified by recrystallization (acetone/heptane) to give Compound AA2-001-a (1-O-benzyl 5-O-(1,3-dioxoisoindol-2-yl) (2S)-2-[(2-methylpropan-2-yl)oxycarbonylamino]pentanedioate). (230 g, 80%)

LCMS (ESI) m/z=505.2 (M+Na)+

Retention time: 0.992 min (Analysis condition SMD method_16)

Nickel bromide trihydrate (NiBr2-3H$_2$O) (4 g, 0.07 eq) and 4,4'-di-tert-butyl-2,2'-bipyridyl (dtbbpy) (3.9 g, 14.55 mmol, 0.07 eq) were added to DMA (500 mL), and the mixture was stirred at 50° C. for 2 hours in a nitrogen atmosphere to prepare a Ni solution.

The Ni solution prepared above was added to a DMA (500 mL) mixed solution of Compound AA2-001-a (100 g, 207.3 mmol), zinc powder (70 g, 5 eq), and 4-bromo-2-chloro-1-(trifluoromethyl)benzene (160 g, 617 mmol, 3 eq), and the mixture was stirred at 25° C. for 16 hours. An aqueous EDTA-2Na solution (10%) was added to the reaction solution, and the mixture was extracted with ethyl acetate. The combined organic layer was washed with a saturated aqueous sodium chloride solution and dried over anhydrous sodium sulfate, and the solvent was removed under reduced pressure. The resulting residue was purified by silica gel column chromatography (ethyl acetate/petrolium ether) to give Compound AA2-001-b. (75 g, 77%)

LCMS (ESI) m/z=494 (M+Na)+

Retention time: 2.863 min (Analysis condition SMD method_17)

A toluene solution (900 mL) of Compound AA2-001-b (75 g, 158.93 mmol) was cooled to 0° C., and trifluoromethanesulfonic acid (TfOH) (42 mL, 3.00 eq) was added dropwise. After 1 hour of stirring at room temperature, water (75 mL) was added. The mixed solution was extracted with water, and the combined aqueous layer was extracted with ethyl acetate. The combined organic layer was washed with water and dried over anhydrous sodium sulfate, and the solvent was removed under reduced pressure. Acetonitrile/water (900/900 mL) was added to the residue, and the pH was adjusted to 7 with an aqueous sodium hydroxide solution (48%). Fmoc-OSu (51.2 g, 151.93 mmol, 0.95 eq) was added to the solution, and the mixture was stirred at room temperature for 16 hours while maintaining the pH at 7.8 to 8.0. The reaction solution was filtered, and the pH of the filtrate was adjusted to 2 with a 6 mol/L hydrochloric acid solution. Precipitated solids were collected and dried at 50° C. to give Compound AA2-001 ((2S)-4-[3-chloro-4-(trifluoromethyl)phenyl]-2-(9H-fluoren-9-ylmethoxycarbonylamino)butanoic acid, Fmoc-Hph(4-CF3-3-Cl)-OH). (70 g, 87%)

LCMS (ESI) m/z=525.8 (M+Na)+

Retention time: 2.180 min (Analysis condition SMD method_21) 1H-NMR (300-MHz, DMSO-d6) δ 12.70 (s, 1H), 7.91 (d, J=7.5 Hz, 2H), 7.79-7.59 (m, 5H), 7.45-7.28 (m, 5H), 4.40-4.19 (m, 3H), 3.96-3.88 (m, 1H), 2.82-2.60 (m, 2H), 2.11-1.77 (m, 2H)

Example 1-1-2: Synthesis of Compound AA2-002. (2S)-3-cyclobutyl-2-[9H-fluoren-9-ylmethoxycarbonyl(mnethyl)amino]propanoic acid (Fmoc-McAla(cBu)—OH)

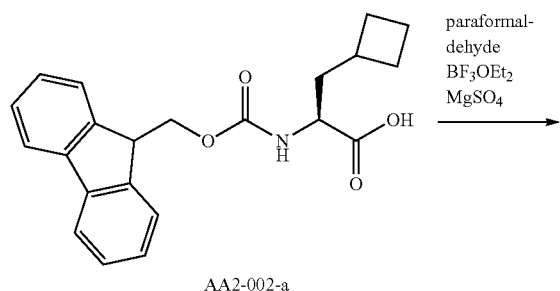

AA2-002-a

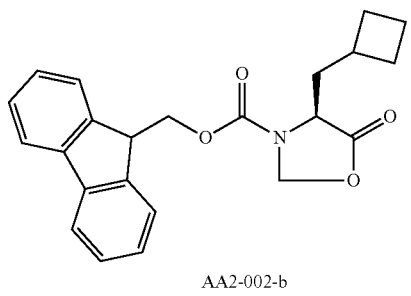

AA2-002-b

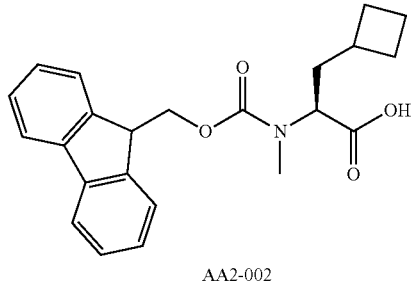

AA2-002

Paraformaldehyde (0.828 g, 27.6 mmol), anhydrous magnesium sulfate (2.77 g, 22.99 mmol), a boron trifluoride diethyl ether complex (BF$_3$·OEt$_2$) (1.398 mL, 11.03 mmol) were added to a DCM (46 mL) solution of Compound AA2-002-a ((2S)-3-cyclobutyl-2-[9H-fluoren-9-ylmethoxycarbonylamino]propanoic acid, Fmoc-Ala(cBu)—OH) (3.36 g, 9.19 mmol) in a nitrogen atmosphere, and the mixture was stirred at room temperature for 2 hours. An aqueous solution obtained by diluting a saturated aqueous sodium chloride solution with water to half the concentration was added to the reaction solution, and DCM was added for further dilution. The separated organic layer was washed with a saturated aqueous sodium chloride solution and filtered. The solvent was removed from the resulting organic layer under reduced pressure to give Compound AA2-002-b as a crude product (3.63 g).

LCMS (ESI) m/z=378 (M+H)+
Retention time: 1.01 min (Analysis condition SQDFA05)

Triethylsilane (4.39 mL, 27.6 mmol), water (0.166 g, 9.19 mmol), a boron trifluoride diethyl ether complex (BF$_3$·OEt$_2$) (3.50 mL, 27.6 mmol) were added to a DCM (30.6 mL) solution of the resulting Compound AA2-002-b (3.47 g) in a nitrogen atmosphere, and the mixture was stirred for 2 hours. An aqueous solution obtained by diluting a saturated aqueous sodium chloride solution with water to half the concentration was added to the reaction solution, and the mixture was stirred at room temperature for 15 minutes. The solvent was removed under reduced pressure from the organic layer separated from the resulting mixture. The resulting residue was purified by reverse phase column chromatography (0.1% formic acid-water/0.1% formic acid—acetonitrile) to give Compound AA2-002 ((2S)-3-cyclobutyl-2-[9H-fluoren-9-ylmethoxycarbonyl(methyl) amino]propanoic acid, Fmoc-MeAla(cBu)—OH). (3.18 g, 91% in 2 steps)

LCMS (ESI) m/z=380 (M+H)+
Retention time: 0.94 min (Analysis condition SQDFA05)

Example 1-1-3: Synthesis of Compound AA2-003. (2S)-2-cyclopentyl-2-[9H-fluoren-9-ylmethoxycarbonyl(methyl)amino]acetic acid (Fmoc-MeGly(cPent)—OH)

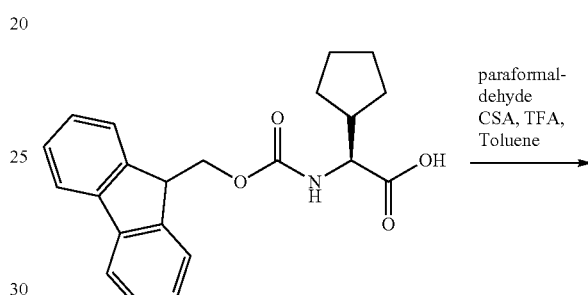

AA2-003-a

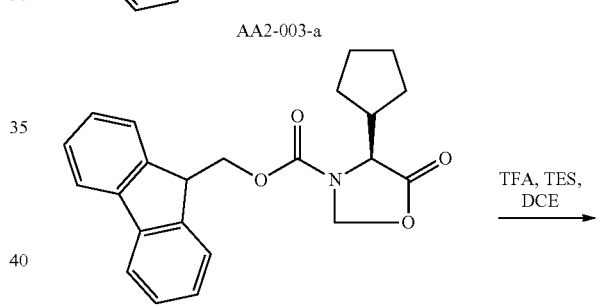

AA2-003-b

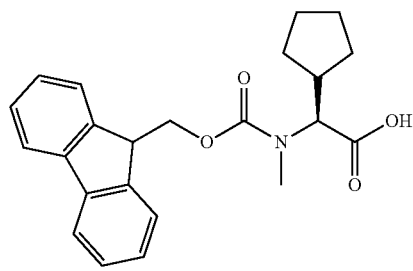

AA2-03

After trifluoroacetic acid (TFA) (9.0 mL) was added to a toluene (160 mL) mixture of Compound AA2-003-a ((2S)-2-cyclopentyl-2-[9H-fluoren-9-ylmethoxycarbonylamino] acetic acid, Fmoc-Gly(cPent)—OH) (30.0 g, 82 mmol), paraformaldehyde (7.39 g, 246 mmol), and CSA (0.954 g, 4.10 mmol), the mixture was stirred at 60° C. for 4 hours. After the reaction solution was cooled to room temperature, solids were removed by filtration. The filtrate was diluted with ethyl acetate (220 mL), and then washed with a saturated aqueous sodium hydrogen carbonate solution and a saturated aqueous sodium chloride solution sequentially. The organic layer was dried over anhydrous sodium sulfate, filtered, and then concentrated under reduced pressure to give Compound AA2-003-b as a crude product. The next reaction was performed without further purification.

LCMS (ESI) m/z=378 (M+H)+
Retention time: 1.01 min (Analysis condition SQDFA05)

Trifluoroacetic acid (TFA) (76 mL, 984 mmol) was added to a mixture of the resulting Compound AA2-003-b (31 g, 82 mmol), triethylsilane (TES) (65.5 mL, 410 mmol), and dichloroethane (DCE) (90 mL), and the mixture was stirred at 60° C. for 16 hours. The reaction solution was cooled to room temperature and then concentrated under reduced pressure, and the resulting solids were washed with n-hexane/ethyl acetate (95/5) and dried under reduced pressure to give Compound AA2-003 ((2S)-2-cyclopentyl-2-[9H-fluoren-9-ylmethoxycarbonyl(methyl)amino]acetic acid, Fmoc-MeGly(cPent)-OH) (29.1 g, 93%).

LCMS (ESI) m/z=380 (M+H)+
Retention time: 0.92 min (Analysis condition SQDFA05)

Example 1-1-4: Synthesis of Compound AA2-004, (2S)-2-cyclobutyl-2-[9H-fluoren-9-ylmethoxycarbonyl(methyl)amino]acetic acid (Fmoc-MeGly(cBu)-OH)

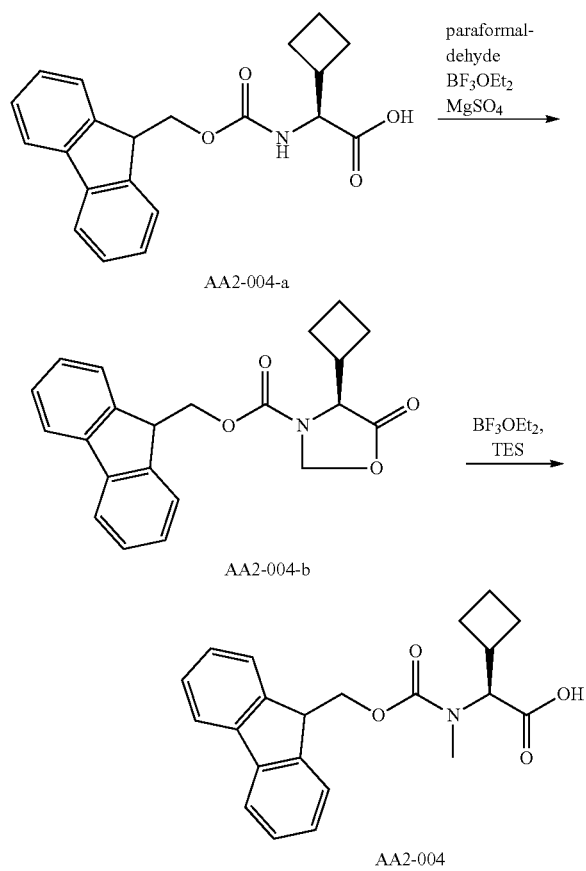 [SMILES: O=C(N[C@H](C(=O)O)C1CCC1)OCC1c2ccccc2-c2ccccc21 ; O=C1OCN(C(=O)OCC2c3ccccc3-c3ccccc32)[C@H]1C1CCC1 ; CN(C(=O)OCC1c2ccccc2-c2ccccc21)[C@H](C(=O)O)C1CCC1]

Using Compound AA2-004-a ((2S)-2-cyclobutyl-2-[9H-fluoren-9-ylmethoxycarbonylamino]acetic acid, Fmoc-Gly(cBu)-OH) (2.5 g, 7.11 mmol) as a starting material, Compound AA2-004-b was obtained as a crude product in the same manner as in the synthesis of Compound AA2-002-b.

LCMS (ESI) m/z=364 (M+H)+
Retention time: 0.97 min (Analysis condition SQDFA05)

The entire amount of Compound AA2-004-b obtained above was used in a reaction in the same manner as in the synthesis of Compound AA2-002 and then purified by reverse phase column chromatography (0.1% aqueous formic acid solution/0.1% formic acid acetonitrile solution) to give Compound AA2-004 ((2S)-2-cyclobutyl-2-[9H-fluoren-9-ylmethoxycarbonyl(methyl)amino]acetic acid, Fmoc-MeGly(cBu)-OH). (2.32 g, 89% in 2 steps)

LCMS (ESI) m/z=366 (M+H)+
Retention time: 0.88 min (Analysis condition SQDFA05)

Example 1-1-5: Synthesis of Compound AA2-005. (2S)-3-cyclopentyl-2-[9H-fluoren-9-ylmethoxycarbonyl(methyl)amino]propanoic acid (Fmoc-MeAla(cPent)-OH)

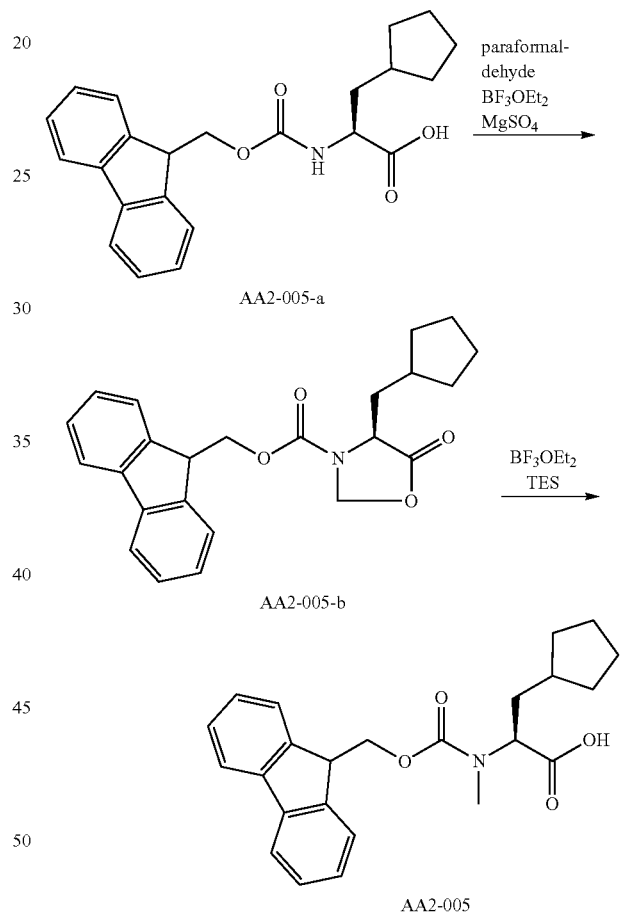

Using Compound AA2-005-a ((2S)-3-cyclopentyl-2-[9H-fluoren-9-ylmethoxycarbonylamino]propanoic acid, Fmoc-Ala(cPent)-OH) (10 g, 26.4 mmol) as a starting material, Compound AA2-005-b (10.5 g) was obtained as a crude product in the same manner as in the synthesis of Compound AA2-002-b.

LCMS (ESI) m/z=392 (M+H)+
Retention time: 1.05 min (Analysis condition SQDFA05)

The resulting Compound AA2-005-b (10.5 g) was used in a reaction in the same manner as in the synthesis of Compound AA2-002 and then purified by reverse phase column chromatography (0.1% aqueous formic acid solution/0.1% formic acid acetonitrile solution) to give Compound AA2-005 ((2S)-3-cyclopentyl-2-[9H-fluoren-9-yl-methoxycarbonyl(methyl)amino]propanoic acid, Fmoc-MeAla(cPent)-OH). (10.11 g, 96% in 2 steps)

LCMS (ESI) m/z=394 (M+H)+

Retention time: 0.98 min (Analysis condition SQDFA05)

Example 1-2: Preparation of Resin-Loaded Amino Acids, Peptides, and the Like Used in the Present Example Example 1-2-1: Synthesis of Compound 1-2-1. (3S)-3-(9H-fluoren-9-ylmethoxycarbonylamino)-4-oxo-4-pyrrolidin-1-ylbutanoic acid-2-chlorotrityl resin (Fmoc-Asp(O-Trt(2-Cl)-resin)-pyrro)

Compound 1-2-1

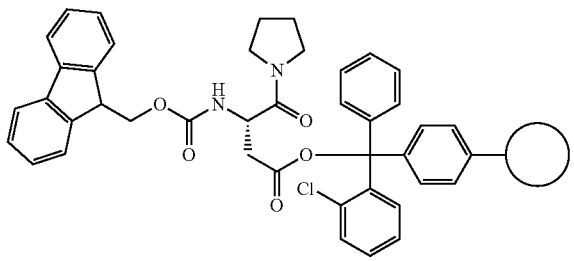

Herein, when a compound is bonded to a polymer or a resin, the polymer or resin moiety may be indicated as o. Also, to clarify the reaction point of the resin moiety, the chemical structure of the reaction moiety connected to o may be indicated. For example, in the above structure (Fmoc-Asp(O-Trt(2-Cl)-resin)-pyrro (Compound 1-2-1)), the 2-chlorotrityl group of the resin is bonded to the side-chain carboxylic acid of Asp via an ester bond. It is noted that pyrro means pyrrolidine and, in the above structure, the C-terminal carboxylic acid group forms an amide bond with pyrrolidine.

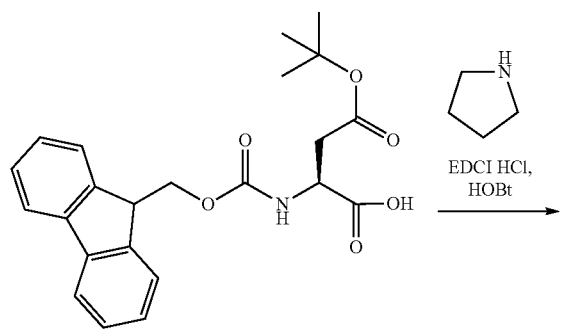

Fmoc-Asp(OtBu)—OH
CAS 71989-14-5

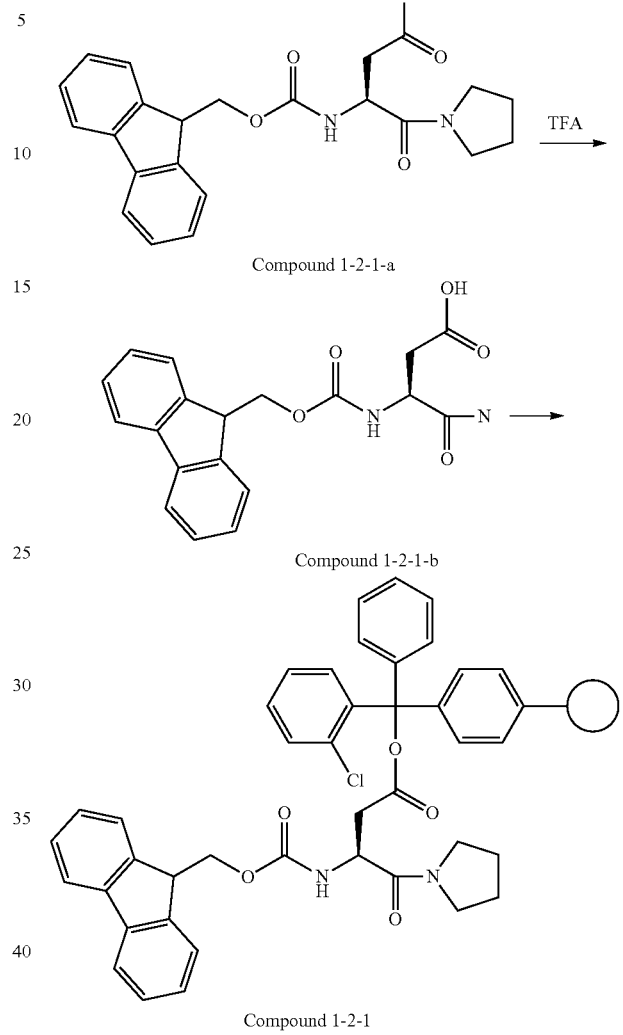

Compound 1-2-1-a

Compound 1-2-1-b

Compound 1-2-1

EDCI·HCl (67.1 g, 350 mmol), HOBt (43.4 g, 321 mmol), and Fmoc-Asp(OtBu)-OH (120 g, 292 mmol) were sequentially added to DMF (600 mL) at 0° C. in a nitrogen atmosphere, and the mixture was stirred at 0° C. for 1 hour. Pyrrolidine (26.3 mL, 321 mmol) was slowly added to this reaction solution, and the mixture was stirred at 0° C. for one and a half hours. Ethyl acetate (10 v) and a 0.5 mol/L hydrochloric acid solution (2 v) were added to the reaction solution at 0° C. to separate the organic layer. The resulting organic layer was washed with a 0.5 mol/L hydrochloric acid solution, water, a saturated aqueous sodium hydrogen carbonate solution/water (1/1 (v/v)), and a saturated aqueous sodium chloride solution/water (1/1 (v/v)) sequentially, and dried over anhydrous sodium sulfate, and then the solvent was removed under reduced pressure to give Compound 1-2-1-a as a crude product. (137.1 g, quant.)

LCMS (ESI) m/z=465 (M+H)+

Retention time: 1.05 min (Analysis condition SQD compound AA05)

TFA (271 mL) was slowly added to an ice-cooled DCM (137 mL) solution of Compound 1-2-1-a (137 g, 395 mmol) so as not to exceed the internal temperature of 10° C. After 1 hour of stirring at room temperature, diisopropyl ether (3.4 L) was added in 4 divided portions, and the precipitated solids were collected by filtration and dried to give Compound 1-2-1-b ((3S)-3-(9H-fluoren-9-ylmethoxycarbonylamino)-4-oxo-4-pyrrolidin-1-ylbutanoic acid, Fmoc-Asp-pyrro). (108.4 g, 90%)

LCMS (ESI) m/z=409 (M+H)+

Retention time: 0.83 min (Analysis condition SQD compound AA05)

The reaction for loading the Fmoc amino acid on a resin was performed according to the method described in WO2013/100132 or WO2018/225864. 2-Chlorotrityl chloride resin (1.60 mmol/g, 100-200 mesh, 1% DVB, 48.7 g) and dehydrated dichloromethane (500 mL) were placed in a filter-equipped reaction vessel, and shaken at room temperature for 20 minutes. After dichloromethane was removed by applying nitrogen pressure. Compound 1-2-1-b (15.91 g) and a mixed solution obtained by adding dehydrated methanol (12.63 mL) and diisopropylethylamine (DIPEA) (32.6 mL) to dehydrated dichloromethane (350 mL) were added to the reaction vessel, and shaken for 60 minutes. After the reaction solution was removed by applying nitrogen pressure, a mixed solution obtained by adding dehydrated methanol (97.3 mL) and diisopropylethylamine (DIPEA) (32.6 mL) to dehydrated dichloromethane (350 mL) was added to the reaction vessel, and shaken for 1 hour and 30 minutes. After the reaction solution was removed by applying nitrogen pressure, dichloromethane (350 mL) was added and shaken for 5 minutes, and then the reaction solution was removed by applying nitrogen pressure. This washing of the resin with dichloromethane was repeated 5 times, and the resulting resin was dried under reduced pressure overnight to give (3S)-3-(9H-fluoren-9-ylmethoxycarbonylamino)-4-oxo-4-pyrrolidin-1-ylbutanoic acid-2-chlorotrityl resin (Fmoc-Asp(O-Trt(2-Cl)-resin)-pyrro, Compound 1-2-1, 59.79 g).

To check the loading rate, the resulting Compound 1-2-1 (12.6 mg) was placed in the reaction vessel, DMF (2 mL) was added, and the mixture was shaken at room temperature for 1 hour. Then, DBU (40 µL) was added, and the mixture was shaken at 30° C. for 30 minutes. Then, DMF (8 mL) was added to the reaction mixture, and 1 mL of the solution was diluted with DMF (11.5 mL). The absorbance (294 nm) of the resulting diluted solution was measured (using Shimadzu UV-1600PC (cell length 1.0 cm)). By measuring dibenzofulvene derived from Fmoc of the Fmoc amino acid loaded on the resin, the amount of loaded Compound 1-2-1 was calculated to be 0.464 mmol/g.

Other similarly synthesized lots having different loaded amounts were also used in peptide syntheses, investigations, and the like.

Example 1-2-2: Preparation of Fmoc-MeVal-Asp(O-Trt(2-Cl)-resin)-pyrro (Compound 1-2-2)

Fmoc-MeVal-Asp(O-Trt(2-Cl)-resin)-pyrro (Compound 1-2-2) used in the present Example was prepared by the Fmoc method using a peptide synthesizer (Multipep RS; manufactured by Intavis). For the detailed operational procedure, the manual appended to the synthesizer was followed.

An NMP solution of Fmoc-Asp(O-Trt(2-Cl)-resin)-pyrro (Compound 1-2-1, 0.464 mmol/g) (100 mg per column) prepared in Example 1-2-1, Fmoc-MeVal-OH (0.6 mol/L), and 1-hydroxy-7-azabenzotriazole (HOAt, 0.375 mol/L) as well as an N,N-dimethylformamide (DMF) (10% v/v) solution of diisopropylcarbodiimide (DIC) were placed in a synthesizer.

Before starting synthesis, 1 mL of dichloromethane (DCM) was added per column to the placed Fmoc-Asp(O-Trt(2-Cl)-resin)-pyrro (Compound 1-2-1, 0.464 mmol/g) (100 mg per column), and the mixture was left to stand still for about 30 minutes to swell the resin. Subsequently, the resin was washed with DMF.

De-Fmoc Step

A DMF solution (2% v/v) of 1,8-diazabicyclo[5.4.0]-7-undecene (DBU) was added in an amount of 0.7 mL per column, and the mixture was left to stand still for 5 to 10 minutes to remove Fmoc. Subsequently, the resin was washed with DMF (0.7 mL per column, repeated 4 times).

Elongation Step

A solution obtained by mixing the placed Fmoc-amino acid solution (0.30 mL per column) and a DIC/DMF solution (0.36 mL per column) was added to the resin that had undergone the de-Fmoc step, and the mixture was left to stand still at 40° C. After completion of the reaction, the resin was washed with DMF (0.7 mL per column, repeated 4 times).

Fmoc-MeVal was elongated in the above-described step. After elongation, the de-Fmoc step was not performed, and the resin was further washed with DCM, dried, and then used in the subsequent investigations.

To check whether Compound 1-2-2 was obtained, peptide cleavage was conducted with a TFE/DCM solution (1/1 (v/v)) on a part of the obtained resin. LCMS analysis of the cleaved solution confirmed the production of the peptide of interest Fmoc-MeVal-Asp-pyrro (Compound 1-2-2*). In the present Example, * added to a compound number indicates a compound that was confirmed by cleaving a peptide from the resin to verify the reaction. Compound 1-2-2*indicates a peptide compound obtained by cutting the bond between the carboxylic acid of the peptide contained in Compound 1-2-2 and the 2-chlorotrityl group of the resin.

Compound 1-2-2

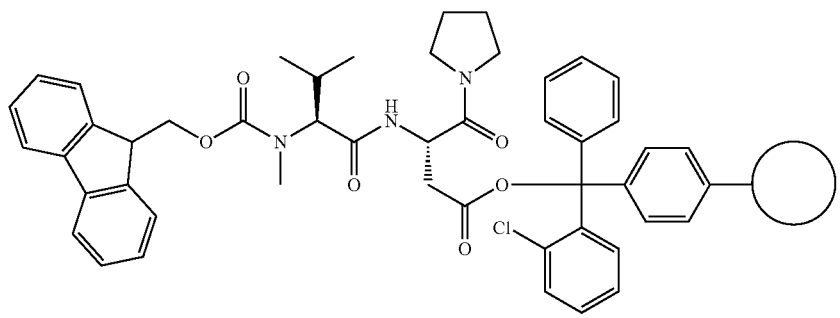

Compound 1-2-2*

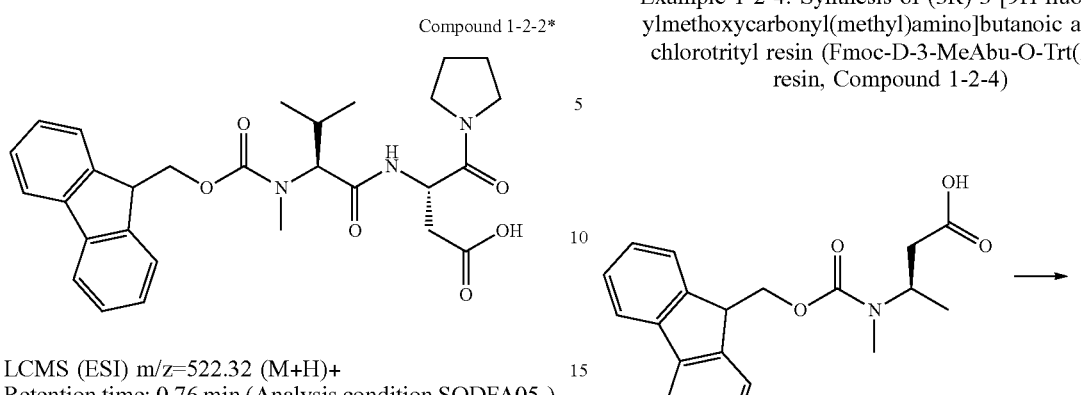

LCMS (ESI) m/z=522.32 (M+H)+
Retention time: 0.76 min (Analysis condition SQDFA05-)

Example 1-2-3: Preparation of Fmoc-MePhe-Asp (O-Trt(2-Cl)-resin)-pyrro (Compound 1-2-3)

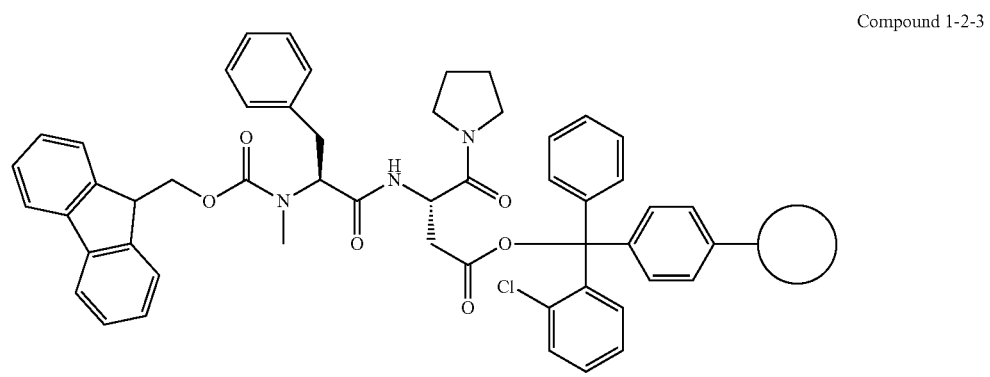 [SMILES: Cc1ccc(C(OC(=O)C[C@H](NC(=O)[C@H](Cc2ccccc2)N(C)C(=O)OCC2c3ccccc3-c3ccccc32)C(=O)N2CCCC2)(c2ccccc2)c2ccccc2Cl)cc1]

Preparation was performed on Fmoc-Asp(O-Trt(2-Cl)-resin)-pyrro (Compound 1-2-1, 0.464 mmol/g) by elongating Fmoc-MePhe-OH similarly as in Example 1-2-2.

To check whether Compound 1-2-3 was obtained, peptide cleavage was conducted with a TFE/DCM solution (1/1 (v/v)) on a part of the obtained resin. LCMS analysis of the cleaved solution confirmed the production of the peptide of interest Fmoc-MePhe-Asp-pyrro (Compound 1-2-3*).

Compound 1-2-3*

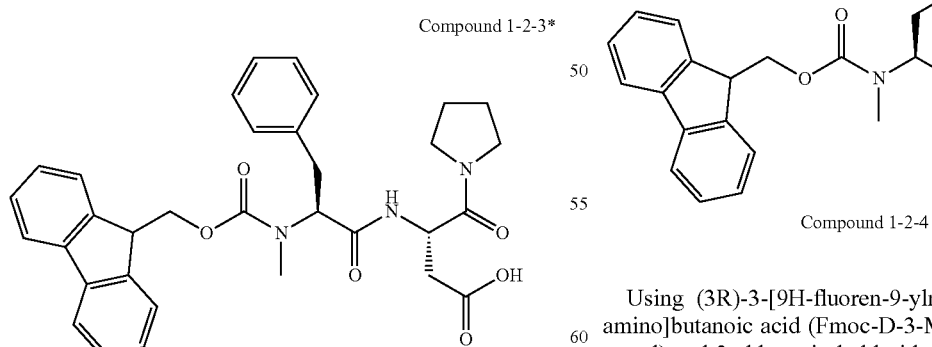

LCMS (ESI) m/z=570.31 (M+H)+
Retention time: 0.80 min (Analysis condition SQDFA05)

Example 1-2-4: Synthesis of (3R)-3-[9H-fluoren-9-ylmethoxycarbonyl(methyl)amino]butanoic acid-2-chlorotrityl resin (Fmoc-D-3-MeAbu-O-Trt(2-Cl) resin, Compound 1-2-4)

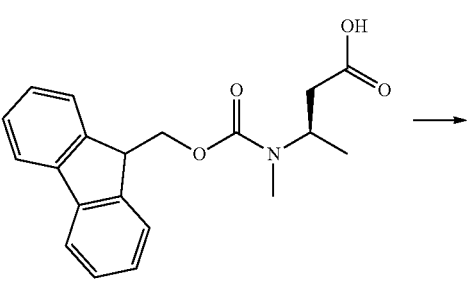

Fmoc-D-3-MeAbu—OH

Compound 1-2-3

-continued

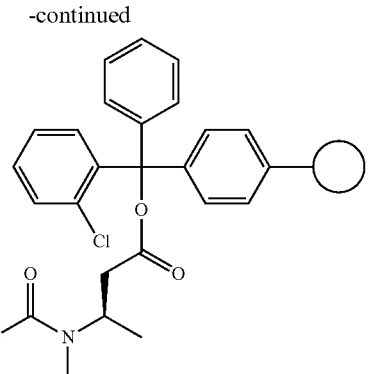

Compound 1-2-4

Using (3R)-3-[9H-fluoren-9-ylmethoxycarbonyl(methyl) amino]butanoic acid (Fmoc-D-3-MeAbu-OH) (11.5 g, 33.9 mmol) and 2-chlorotrityl chloride resin (1.69 mmol/g, 100-200 mesh, 1% DVB, 50 g, 84.5 mmol) purchased from a commercial supplier, (3R)-3-[9H-fluoren-9-ylmethoxycarbonyl(methyl)amino]butanoic acid-2-chlorotrityl resin (Fmoc-D-3-MeAbu-O-Trt(2-Cl) resin, Compound 1-2-4) was obtained in the same manner as in the synthesis of Compound 1-2-1. (58.95 g, loaded amount 0.343 mmol/g)

Other similarly synthesized lots having different loaded amounts were also used in peptide syntheses in the present Example.

Example 1-3: Amino Acids Protected with Protecting Group Other than Fmoc and Dehydrated Products Thereof Used in Peptide Synthesis Amino acids protected with a protecting group other than Fmoc and dehydrated products thereof used in the peptide synthesis described herein were synthesized as follows.

Example 1-3-1: Preparation of 2-methyl-2-[(2,2,2-trifluoroacetyl)amino]propanoic acid (Tfa-Aib-OH) (Compound 1-3-1)

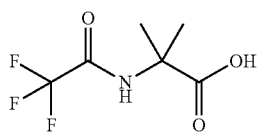

Compound 1-3-1

Methanol (242 mL), DIPEA (63.5 mL, 1.5 eq), and ethyl trifluoroacetate ((CAS number 383-63-1), 37.6 mL, 1.3 eq) were added to 2-amino-2-methylpropanoic acid (25.0 g), and the the mixture was stirred at 50° C. for 18 hours. Then, the solvent was removed under reduced pressure, and a 1 N aqueous hydrochloric acid solution and ethyl acetate were added to the resulting residue to separate the organic layer and the aqueous layer. The resulting organic layer was washed with a saturated aqueous sodium chloride solution and dried over anhydrous sodium sulfate, and the solvent was removed under reduced pressure to give 18.2 g of a crude product.

After the crude product (16.0 g) was dissolved in TBME (80 mL), heptane (320 mL) was added dropwise for 1 hour or longer while stirring the solution. The mixture was stirred for one more hour while being ice-cooled, and then filtered. The resulting powder was washed with a TBME/heptane solution (¼, 32 mL), and dried under reduced pressure to give 13.5 g of 2-methyl-2-[(2,2,2-trifluoroacetyl)amino]propanoic acid (Tfa-Aib-OH) (Compound 1-3-1).

LCMS (ESI) m/z=197.93 (M−H)−
Retention time: 0.40 min (Analysis condition SQDFA05)

Example 1-3-2. Synthesis of Tfa-(Me)Abu-OH ((S)-2-methyl-2-(2,2,2-trifluoroacetamide)butanoic acid, Compound 1-3-2-b)

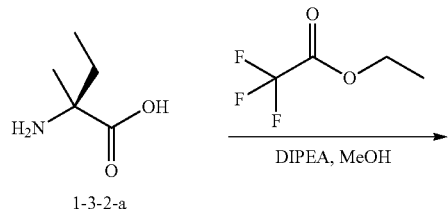

1-3-2-a

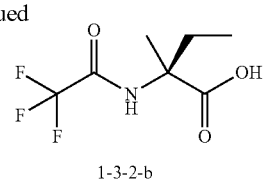

1-3-2-b

After diisopropylethylamine (82.7 g, 640 mmol) and ethyl trifluoroacetate (54.6 g, 384 mmol) were added to a methanol (150 mL) solution of Compound 1-3-2-a ((S)-2-amino-2-methylbutanoic acid, isovaline, H—(Me)Abu-OH) (15.0 g, 128 mmol), the mixture was stirred at 50° C. for 16 hours. The reaction solution after being cooled to room temperature was concentrated under reduced pressure, and the resulting residue was dissolved in TBME and then washed twice with a 1 N aqueous hydrochloric acid solution. The organic layer was dried over anhydrous sodium sulfate, filtered, and then concentrated under reduced pressure to give a crude product. The resulting crude product was recrystallized from TBME/hexane (1:7) to give Compound 1-3-2-b ((S)-2-methyl-2-(2,2,2-trifluoroacetamide)butanoic acid) (12 g, 44%).

LCMS (ESI) m/z=214.0 (M+H)+
Retention time: 0.32 min (Analysis condition SQDFA05)

Example 1-3-3. Synthesis of Tfa-(Me)Leu-OH ((S)-2,4-dimethyl-2-(2,2,2-trifluoroacetamide)pentanoic acid. Compound 1-3-3-b)

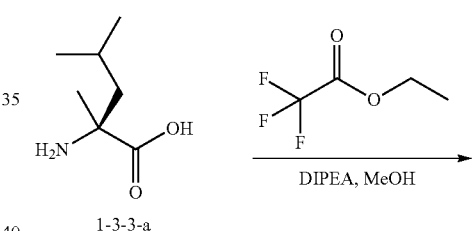

1-3-3-a

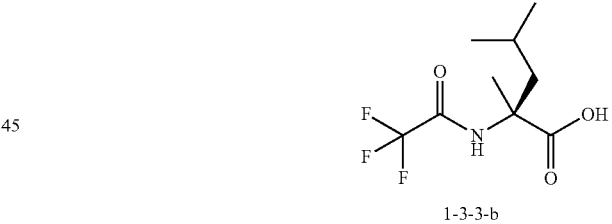

1-3-3-b

After diisopropylethylamine (40.1 g, 310 mmol) and ethyl trifluoroacetate (44.0 g, 310 mmol) were added to a methanol (50 mL) solution of Compound 1-3-3-a (2-methylleucine, (S)-2-amino-2,4-dimethylpentanoic acid, H—(Me)Leu-OH) (15.0 g, 103 mmol), the mixture was stirred at 50° C. for 16 hours. The reaction solution after being cooled to room temperature was concentrated under reduced pressure, and the resulting residue was dissolved in TBME and then washed twice with a 1 N aqueous hydrochloric acid solution. The organic layer was dried over anhydrous sodium sulfate, filtered, and then concentrated under reduced pressure to give a crude product. The resulting crude product was recrystallized from TBME/hexane (1:7) to give Compound 1-3-3-b ((S)-2,4-dimethyl-2-(2,2,2-trifluoroacetamide)pentanoic acid) (10 g, 40%).

LCMS (ESI) m/z=242.1 (M+H)+
Retention time: 0.66 min (Analysis condition SQDFA05)

Example 1-3-4. Synthesis of Tfa-(Me)Ser(Me)-OH ((S)-3-methoxy-2-methyl-2-(2.2,2-trifluoroacetamide)propanoic acid. Compound 1-3-4-b)

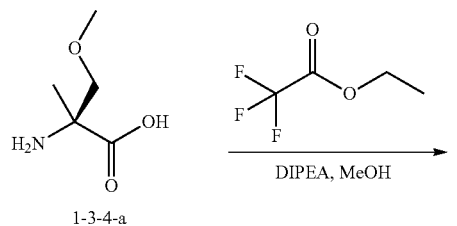

1-3-4-a

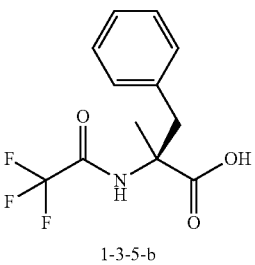

1-3-4-b

After diisopropylethylamine (5.9 mL, 34 mmol) and ethyl trifluoroacetate (4.0 mL were added to a methanol (19 mL) solution of Compound 1-3-4-a (3-methoxy-2-methyl-L-alanine, (S)-2-amino-3-methoxy-2-methylpropanoic acid, H—(Me)Ser(Me)-OH) (1.5 g, 11 mmol), the mixture was stirred at 50° C. for 21 hours. The reaction solution after being cooled to room temperature was concentrated under reduced pressure, and the resulting residue was dissolved in TBME (45 mL) and then washed twice with a 1 N aqueous hydrochloric acid solution (45 mL) and once with a saturated aqueous sodium chloride solution (45 mL). The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound 1-3-4-b ((S)-3-methoxy-2-methyl-2-(2,2,2-trifluoroacetamide)propanoic acid) (2.07 g, 72%).

LCMS (ESI) m/z=228.2 (M–H)–

Retention time: 0.41 min (Analysis condition SQDFA05)

Example 1-3-5. Synthesis of Tfa-(Me)Phe-OH ((S)-2-methyl-3-phenyl-2-(2.2,2-trifluoroacetamide)propanoic acid, Compound 1-3-5-b)

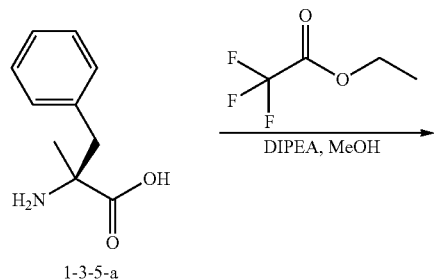

1-3-5-a 1-3-5-b

After diisopropylethylamine (21.63 g, 167.4 mmol) and ethyl trifluoroacetate (23.78 g, 167.4 mmol) were added to a methanol (500 mL) solution of Compound 1-3-5-a ((2S)-2-amino-2-methyl-3-phenylpropanoic acid, H—(Me)Phe-OH) (10.0 g, 55.8 mmol), the mixture was stirred at 50° C. for 16 hours. The reaction solution after being cooled to room temperature was concentrated under reduced pressure, and the resulting residue was dissolved in TBME and then washed twice with a 1 N aqueous hydrochloric acid solution and once with a saturated aqueous sodium chloride solution. The organic layer was dried over anhydrous sodium sulfate, filtered, and then concentrated under reduced pressure to give a crude product. The resulting crude product was recrystallized from TBME/hexane (1:15) to give Compound 1-3-5-b ((S)-2-methyl-3-phenyl-2-(2,2,2-trifluoroacetamide)propanoic acid) (8 g, 52%).

LCMS (ESI) m/z=274.0 (M–H)–

Retention time: 0.68 min (Analysis condition SQDFA05)

Example 1-3-6. Synthesis of Tfa-(Me)Cha-OH ((S)-3-cyclohexyl-2-methyl-2-(2.2,2-trifluoroacetamide)propanoic acid. Compound 1-3-6-c)

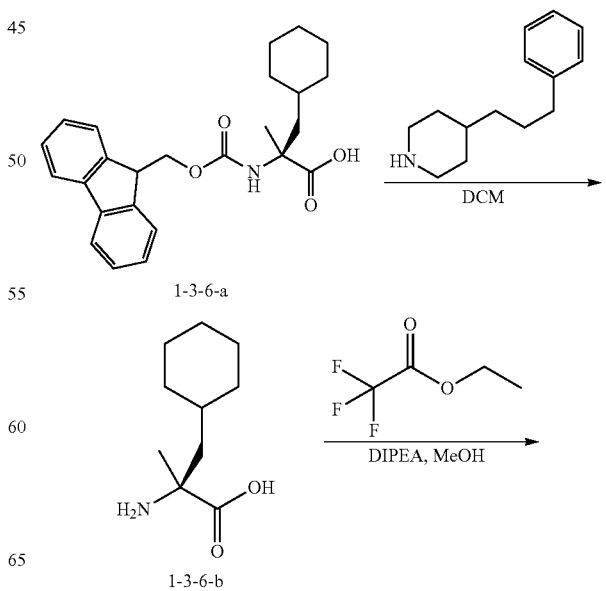

1-3-6-a 1-3-6-b

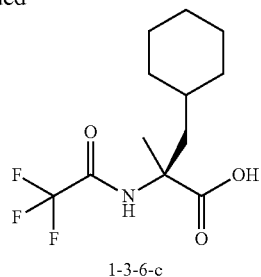

1-3-6-c 4-(3-Phenylpropyl)piperidine (4.7 mL, 22 mmol) was added to a dichloromethane (18.4 mL) solution of Compound 1-3-6a (2-(9H-fluoren-9-ylmethoxycarbonylamino)-3-cyclohexyl-2-methylpropanoic acid, Fmoc-(Me)Cha-OH), and the mixture was stirred at room temperature for 16 hours in a nitrogen atmosphere. Water (8 mL) was added to the reaction solution to extract the product, and the aqueous layer was purified by reverse phase column chromatography (0.1% formic acid-water/0.1% formic acid-acetonitrile). After water (5 mL) and 2 N hydrochloric acid (5 mL) were added to the organic phase to extract the remaining crude product into the aqueous layer, the aqueous layer was purified by reverse phase column chromatography (0.1% formic acid-water/0.1% formic acid-acetonitrile). The column-purified products were combined to give Compound 1-3-6-b ((S)-2-amino-3-cyclohexyl-2-methylpropanoic acid, H—(Mc)Cha-OH) (1.1 g, 81%), which was used in the next reaction.

LCMS (ESI) m/z=186.1 (M+H)+

Retention time: 0.32 min (Analysis condition SQDFA05)

After diisopropylethylamine (3.1 mL, 18 mmol) and ethyl trifluoroacetate (2.1 mL) were added to a methanol (20 mL) solution of Compound 1-3-6-b ((S)-2-amino-3-cyclohexyl-2-methylpropanoic acid, H—(Me)Cha-OH) (1.1 g, 6.0 mmol), the mixture was stirred at 50° C. for 2 hours. After the reaction solution was cooled to room temperature, diisopropylethylamine (3.1 mL, 18 mmol) and ethyl trifluoroacetate (2.1 mL) were added, and then the mixture was stirred at 50° C. for 20 hours. The reaction solution was concentrated under reduced pressure, and the resulting residue was dissolved in TBME (30 mL) and then washed twice with a 1 N aqueous hydrochloric acid solution (30 mL) and once with a saturated aqueous sodium chloride solution (40 mL). The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound 1-3-6-c ((S)-3-cyclohexyl-2-methyl-2-(2,2,2-trifluoroacetamide)propanoic acid) (1.22 g, 72%).

LCMS (ESI) m/z=280.2 (M–H)–

Retention time: 0.75 min (Analysis condition SQDFA05)

Example 1-3-7. Synthesis of Tfa-(Me)Val-OH ((S)-2,3-dimethyl-2-(2,2,2-trifluoroacetamide)butanoic acid, Compound 1-3-7-b)

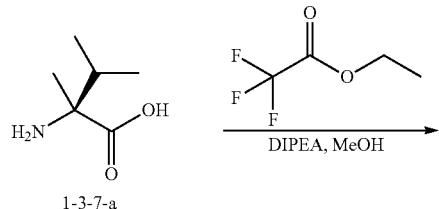

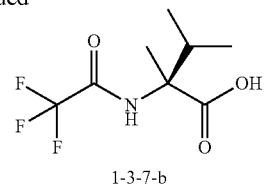

1-3-7-b

After diisopropylethylamine (8.0 mL, 46 mmol) and ethyl trifluoroacetate (5.5 mL) were added to a methanol (25 mL) solution of Compound 1-3-7-a ((S)-2-amino-2,3-dimethylbutanoic acid, H—(Me)Val-OH) (2.0 g, 15 mmol), the mixture was stirred at 50° C. for 3 hours. After the reaction solution was cooled to room temperature, diisopropylethylamine (4.0 mL, 23 mmol) and ethyl trifluoroacetate (2.7 mL) were added, and the mixture was stirred at 50° C. for 16 hours. The reaction solution was concentrated under reduced pressure, and the resulting residue was dissolved in TBME (40 mL) and then washed with a 1 N aqueous hydrochloric acid solution (40 mL) and a saturated aqueous sodium chloride solution (40 mL) sequentially. The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound 1-3-7-b ((S)-2,3-dimethyl-2-(2,2,2-trifluoroacetamide)butanoic acid) (1.17 g, 34%).

LCMS (ESI) m/z=226.1 (M–H)–

Retention time: 0.54 min (Analysis condition SQDFA05)

Example 1-3-8. Synthesis of Tfa-cLeu-OH (1-(2,2,2-trifluoroacetamide)cyclopentane-1-carboxylic acid, Compound 1-3-8-b)

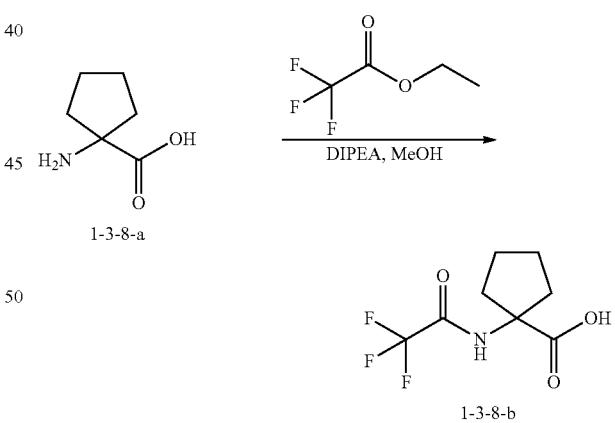

After diisopropylethylamine (37.5 g, 290 mmol) and ethyl trifluoroacetate (41.3 g, 290 mmol) were added to a methanol (100 mL) solution of Compound 1-3-8-a (1-aminocyclopentanecarboxylic acid, H-cLeu-OH) (25 g, 194 mmol), the mixture was stirred at 50° C. for 2 days. After the reaction solution was cooled to room temperature, diisopropylethylamine (4.0 mL, 23 mmol) and ethyl trifluoroacetate (2.7 mL) were added, the mixture was stirred at 50° C. for 16 hours. The reaction solution was concentrated under reduced pressure, and the resulting residue was dissolved in TBME and then washed with a 1 N aqueous hydrochloric acid solution and a saturated aqueous sodium chloride solution sequentially. The organic layer was dried over anhydrous sodium sulfate, filtered, and then concentrated under reduced pressure to give a crude product. The resulting crude product was recrystallized from TBME/hexane (3:20) to give Compound 1-3-8-b (1-(2,2,2-trifluoroacetamide)cyclopentane-1-carboxylic acid) (20 g, 46%).

LCMS (ESI) m/z=224.0 (M−H)−

Retention time: 0.49 min (Analysis condition SQDFA05)

Example 1-3-9. Synthesis of 2-(trifluoromethyl)-3-oxa-1-azaspiro[4.4]non-1-en-4-one (Compound 1-3-9)

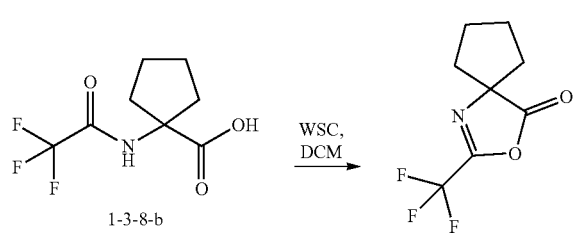

1-Ethyl-3-(3-dimethylaminopropyl)carbodiimide hydrochloride (27.7 g, 144 mmol) was added to a dichloromethane (225 mL) solution of Compound 1-3-8-b (Tfa-cLeu-OH, 1-(2,2,2-trifluoroacetamide)cyclopentane-1-carboxylic acid) (25 g, 111 mmol), and the mixture was stirred at room temperature for 2 days. After reaction, the reaction solution was concentrated under reduced pressure to give a crude product. The resulting crude product was purified by silica gel column chromatography (ethyl acetate/petroleum ether) to give Compound 1-3-9 (2-(trifluoromethyl)-3-oxa-1-azaspiro[4.4]non-1-en-4-one) (11.9 g, 52%).

LCMS (ESI) m/z=208.1 (M+H)+

Retention time: 0.86 min (Analysis condition SQDAA05)

Example 2: Experiment Attempting to Introduce an N-Substituted-α,α-Disubstituted Amino Acid Residue. Which was Obtained Through Elongating an N-Unsubstituted-α,α-Disubstituted Amino Acid Having Tfa-Protected N-Terminus and N-Functionalization on a Solid Phase. To an Amino Acid Residue Having an N-Substituted N-Terminus in a Peptide in Solid-Phase Synthesis

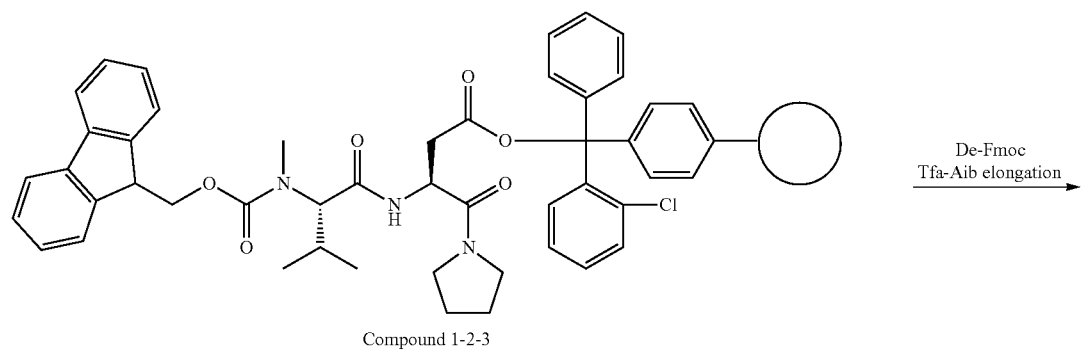

Compound 1-2-3

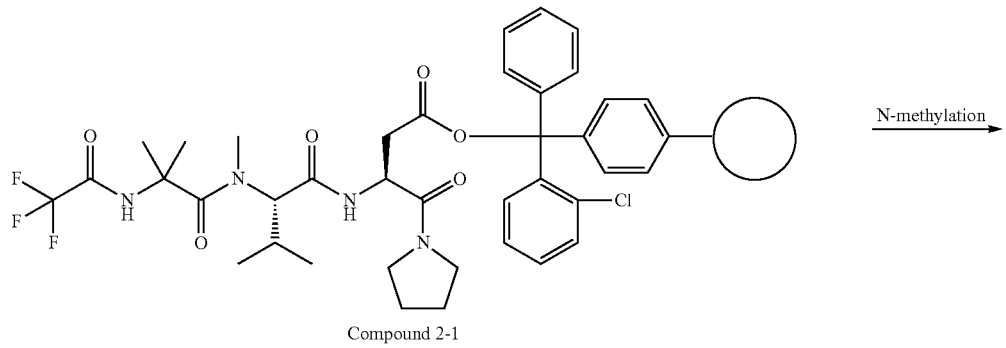

Compound 2-1

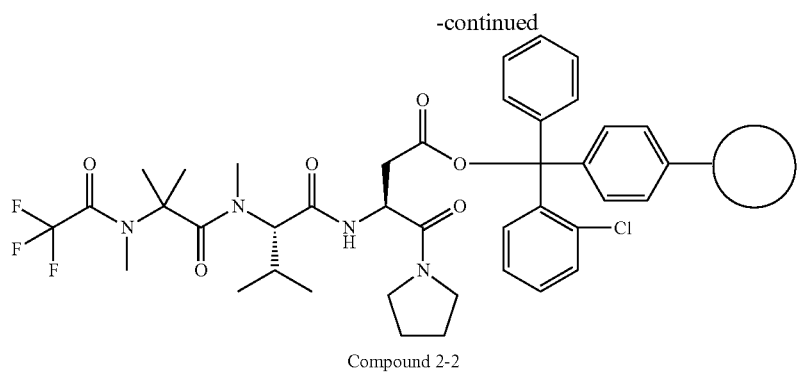

Compound 2-2

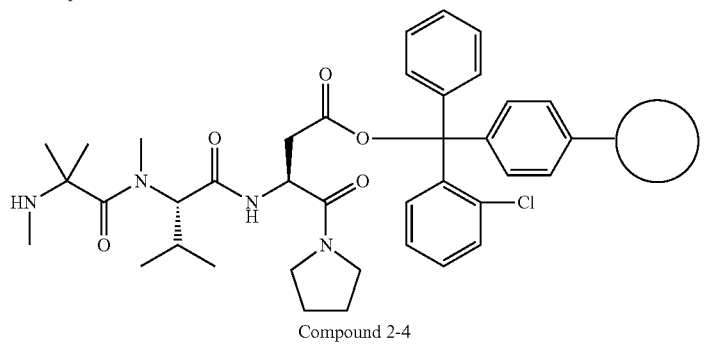

Compound 2-4

Example 2-1: Elongation of Tfa-Aib-OH after De-Fmoc-MeVal-Asp(O-Trt(2-Cl)-Resin)-Pyrro (Compound 1-2-2)

Example 2-1-1: Elongation of Tfa-Aib-OH using DIC after De-Fmoc-MeVal-Asp(O-Trt(2-Cl)-Resin)-Pyrro (Compound 1-2-2)

Fmoc-MeVal-Asp(O-Trt(2-Cl)-resin)-pyrro (Compound 1-2-2) (0.473 mmol/g, 100 mg) prepared in Example 1-2-2 was placed in a filter-equipped reaction vessel, dichloromethane (0 mL) was added, and the mixture was shaken at room temperature for 1 hour to swell the resin. After dichloromethane was removed through a filter, the resin was washed 3 times with DMF (0.7 mL). Subsequently, a 2% DBU/DMF solution (de-Fmoc solution: 0.7 mL) was added to the resin, and the mixture was shaken at room temperature for 5 minutes to remove Fmoc. After the de-Fmoc solution was removed, the resin was washed 4 times with DMF (0.7 mL).

A Tfa-Aib-OH elongation reaction was performed on the resulting resin.

The elongation reaction was performed by adding a solution obtained by mixing a 0.6 M Tfa-Aib-OH/NMP solution (0.3 mL) and a 10% DIC/DMF solution (0.36 mL) to the resin and shaking the mixture at 40° C. for 20 hours.

After the liquid phase of the elongation reaction was removed through a filter, the resin was washed 4 times with DMF (0.7 mL) and 4 times with dichloromethane (0.7 mL) to give Lot 1 (hereinafter referred to as Compound 2-1-1) of Compound 2-1 (Tfa-Aib-MeVal-Asp(O-Trt(2-Cl)-resin)-pyrro).

To check the progress of the reaction, peptide cleavage was conducted with a TFF/DCM solution (1/1 (v/v)) on the resulting resin (Compound 2-1-1), and LCMS analysis of the cleaved solution confirmed production of the peptide of interest Tfa-Aib-MeVal-Asp-pyrro (Compound 2-1*). No other peptide components were detected. This resin (Compound 2-1-1) was used in Example 2-3.

Compound 2-1*

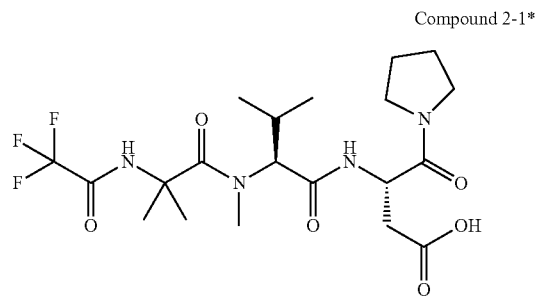 [SMILES: CC(C)[C@@H](C(=O)N[C@@H](CC(=O)O)C(=O)N1CCCC1)N(C)C(=O)C(C)(C)NC(=O)C(F)(F)F]

LCMS (ESI) m/z=481.21 (M+H)+
Retention time: 0.53 min (Analysis condition SQDFA05)

Example 2-1-2: Elongation of Tfa-Aib-OH by using DIC and adding Oxyma as an additive after de-Fmoc of Fmoc-MeVal-Asp(O-Trt(2-Cl)-resin)-pyrro (Compound 1-2-2)

Fmoc-MeVal-Asp(O-Trt(2-Cl)-resin)-pyrro (Compound 1-2-2) (0.473 mmol/g, 100 mg) prepared in Example 1-2-2 was placed in a filter-equipped reaction vessel, and elongation of Tfa-Aib was performed in the same manner as in Example 2-1-1 except for the elongation reagent. As for the elongation reagent, a solution obtained by mixing a 0.6 M Tfa-Aib-OH/0.375 M oxyma/NMP solution (0.3 mL) and a 10% DIC/DMF solution (0.36 mL) was used. As a result of cleaving the peptide from the resin and performing LCMS analysis as in Example 2-1-1, 2.2% (UV area) of unreacted H-MeVal-Asp-pyrro and two unidentified peaks (8.85% and 1.43% (UV area), respectively) were confirmed in addition to 87.50% (UV area) of the peptide of interest Tfa-Aib- MeVal-Asp-pyrro (Compound 2-1*). This resin (Lot 2 of Compound 2-1, hereinafter referred to as Compound 2-1-2) was used in Comparative Example 1.

Example 2-1-3: Elongation of Tfa-Aib-OH using EDCI·HCl after de-Fmoc of Fmoc-MeVal-Asp(O-Trt(2-Cl)-resin)-pyrro (Compound 1-2-2)

Fmoc-MeVal-Asp(O-Trt(2-Cl)-resin)-pyrro (Compound 1-2-2) (0.473 mmol/g, 100 mg) prepared in Example 1-2-2 was placed in a filter-equipped reaction vessel, and elongation of Tfa-Aib was performed in the same manner as in Example 2-1-1 except for the elongation reagent. As for the elongation reagent, a solution obtained by mixing a 0.6 M Tfa-Aib-OH/NMP solution (0.3 mL) and an EDCI·HCl (48 mg, 0.250 mmol)/DMF solution (0.36 mL) was used. As a result of cleaving the peptide from the resin and performing LCMS analysis as in Example 2-1-1, 3.0% (UV area) of unreacted H-MeVal-Asp-pyrro and 3.9% (UV area) of an unidentified peak were confirmed in addition to 93.1% (UV area) of the peptide of interest Tfa-Aib-MeVal-Asp-pyrro (Compound 2-1*). This resin (Lot 3 of Compound 2-1, hereinafter referred to as Compound 2-1-3) was used in Example 2-2 and Example 2-3.

Example 2-2: N-Methylation by nucleophilic substitution reaction (methyl iodide as methylating agent, DBU as base) on the Tfa amide moiety of Tfa-Aib-MeVal-Asp(0-Trt(2-Cl)-resin)-pyrro (Compound 2-1)

In a filter-equipped reaction vessel, dichloromethane (1 mL) was added to Tfa-Aib-MeVal-Asp(O-Trt(2-Cl)-resin)-pyrro (Compound 2-1-3) (25 mg) prepared in Example 2-1, and the mixture was shaken at room temperature for 15 minutes to swell the resin. After dichloromethane was removed through a filter, the resin was washed 4 times with NMP (0.7 mL).

A DBU (23 µL)/NMP (0.35 mL) solution was added to the resulting resin, then a methyl iodide (63 µL)/NMP (0.35 mL) solution was added, and the mixture was shaken at 40° C. for 30 minutes. After the liquid phase was removed through a filter, washing was performed 4 times with NMP (0.7 mL) and 4 times with dichloromethane. A small amount of the resulting resin was sampled, peptide cleavage was conducted with a TFE/DCM solution (1/1 (v/v)), and the cleaved solution was analyzed by LCMS.

To increase the reaction conversion ratio, the same operation was performed again on the resin that has been methylated once. The second methylation was performed by shaking the resin at 40° C. for 20 hours. The resin was washed to give Compound 2-2. A small amount of the resulting resin was sampled, peptide cleavage was conducted with a TFE/DCM solution (1/1 (v/v)), and LCMS analysis of the cleaved solution confirmed the product on interest (Compound to 2-2*) and an unreacted product (Compound 2-1*). The result was as shown in Table 6.

TABLE 6

| | Product of interest (Compound 2-2*) (UV area %) | Unreacted product (Compound 2-1*) (UV area %) |
|---|---|---|
| First run (40° C., 0.5 h) | 13.8 | 86.2 |
| Second run (40° C., 20 h) | 25.6 | 74.4 |

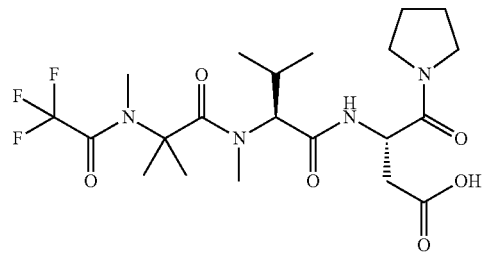

Compound 2-2*

LCMS (ESI) m/z=495.23 (M+H)+

Retention time: 0.57 min (Analysis condition SQDFA05)

It was found from this result that N-methylation proceeds in a Tfa-protected N-terminus-selective manner in a nucleophilic substitution reaction which uses methyl iodide as a methylating agent and DBU (pKa of conjugate acid in acetonitrile=24.34 (J. Org. Chem. 2005, 70, 1019-1028)) as a base. It was shown that the conversion ratio of the reaction can be increased by replacing the reagents and repeating the reaction.

Example 2-3: N-Methylation by Nucleophilic Substitution Reaction (Methyl Iodide as Methylating Agent, Various Bases) on the Tfa Amide Moiety of Tfa-Aib-MeVal-Asp (0-Trt(2-Cl)-Resin)-Pyrro (Compound 2-1)

In a filter-equipped reaction vessel, dichloromethane (1 mL) was added to Tfa-Aib-MeVal-Asp(O-Trt(2-Cl)-resin)-pyrro (Compound 2-1-1 or 2-1-3) (25 mg) prepared in Example 2-1, and the mixture was shaken at room temperature for 15 minutes to swell the resin. After dichloromethane was removed through a filter, the resin was washed 4 times with DMF (0.7 mL).

A base (the added amount is shown in Table 7)/DMF (0.35 mL) solution was added to the resulting resin, then a methyl iodide (63 µL)/DMF (0.35 mL) solution was added, and the mixture was shaken at 40° C. for 15 hours. After the liquid phase was removed through a filter, washing was performed 4 times with DMF (0.7 mL) and 4 times with dichloromethane to give Compound 2-2. A small amount of the resulting resin was sampled, peptide cleavage was conducted with a TFE/DCM solution (1/1 (v/v)), and the cleaved solution was analyzed by LCMS.

The result of confirming the reaction after cleaving was as shown in Table 7. When $P_1$-tBu was used as a base, production of an excessively methylated product (Compound 2-3*) was also slightly observed.

TABLE 7

| run | Base | Resin used | Product of interest (Compound 2-2*) (UV area %) | Unreacted product (Compound 2-1*) (UV area %) | Excessively methylated product (Compound 2-3*) (UV area %) |
|---|---|---|---|---|---|
| 1 | DIPEA (87 µL) | Compound 2-1-3 | 0 | 100 | 0 |
| 2 | MTBD (21 µL) | Compound 2-1-1 | 49.0 | 51.0 | 0 |
| 3 | TMGN (53 mg) | Compound 2-1-1 | 96.3 | 3.7 | 0 |

TABLE 7-continued

| run | Base | Resin used | Product of interest (Compound 2-2*) (UV area %) | Unreacted product (Compound 2-1*) (UV area %) | Excessively methylated product (Compound 2-3*) (UV area %) |
|---|---|---|---|---|---|
| 4 | P1-tBu (35 μL) | Compound 2-1-1 | 92.6 | 3.6 | 3.8 |

Compound 2-3*

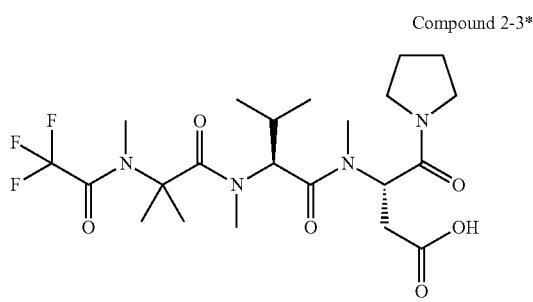 [SMILES: CC(C)[C@@H](C(=O)N(C)[C@@H](CC(=O)O)C(=O)N1CCCC1)N(C)C(=O)C(C)(C)N(C)C(=O)C(F)(F)F]

LCMS (ESI) m/z=509.25 (M+H)+

Retention time: 0.59 min (Analysis condition SQDFA05)

From this result, it was shown that the N-methylation of interest proceeds in nucleophilic substitution reactions using MTBD (pKa of conjugate acid in acetonitrile=25.43 (Chem. Eur. J. 2002, 8, 1682-1693)), TMGN (pKa of conjugate acid in acetonitrile=25.1 (Chem. Eur. J. 2002, 8, 1682-1693)), and $P_1$-tBu (pKa of conjugate acid in acetonitrile=26.9 (website of Aldrich concerning phosphazene bases: https://www.sigmaaldrich.com/chemistry/chemical-synthesis/technology-spotlights/phosphazenes.html (viewed on Oct. 10, 2019)) having a stronger basicity than DBU as bases. When P1-tBu was used, a small amount (3.8%) of a product excessively methylated at a secondary amide moiety (an amide moiety composed of the amino group of Asp and the carboxyl group of MeVal) different from the Tfa amide moiety of interest was confirmed. It is inferred from this result that it is more preferable to use a base, the pKa value of the conjugate acid of which is 27 or less, to selectively attain N-methylation at the Tfa amide moiety.

Example 2-4: Deprotection of Tfa protection of Tfa-MeAib-MeVal-Asp(O-Trt(2-Cl)-resin)-pyrro (Compound 2-2) after N-alkylation In a nitrogen atmosphere, triglyme (triethylene glycol dimethyl ether) (6.6 mL) was added to sodium borohydride (0.5 g), and the mixture was stirred at room temperature for 10 minutes to give a 2.0 M sodium borohydride/triglyme solution.

A resin that was N-methylated using TMGN as a base and prepared in run 3 of Table 7 in Example 2-3 (Compound 2-2) was added to a filter-equipped reaction vessel, then dichloromethane (1 mL) was added, and the mixture was shaken at room temperature for 30 minutes to swell the resin. After dichloromethane was removed through a filter, the resin was washed 4 times with THF (0.7 mL).

THF (125 μL), methanol (63 μL), and the 2.0 M sodium borohydride/triglyme solution (63 μL) prepared above were added to the resulting resin, and the mixture was shaken at room temperature for 30 minutes. After the liquid phase was removed through a filter, washing was performed 4 times with methanol (0.7 mL) (the time of each washing was 1 minute) and then 4 times with dichloromethane (0.7 mL) to give Compound 2-4. A small amount of the resulting resin was sampled, peptide cleavage was conducted with a TFE/DCM solution (1/1 (v/v)), and the cleaved solution was analyzed by LCMS.

The Tfa-protected raw material peptide Tfa-MeAib-MeVal-Asp-pyrro (Compound 2-2*) was completely consumed, and the peptide of interest H-MeAib-MeVal-Asp-pyrro (Compound 2-4*) was observed. The LC chart is as provided in FIG. 1, and it was confirmed that high-purity synthesis is possible.

Compound 2-4*

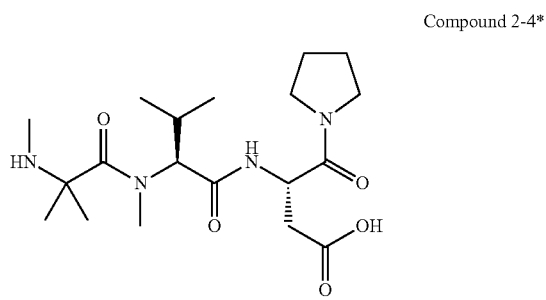 [SMILES: CNC(C)(C)C(=O)N(C)[C@H](C(=O)N[C@@H](CC(=O)O)C(=O)N1CCCC1)C(C)C]

Peptide of interest H-MeAib-MeVal-Asp-pyrro (Compound 2-4*)

LCMS (ESI) m/z=399.23 (M+H)+

Retention time: 0.35 min (Analysis condition SQDFA05)

As such, it was shown that, with the present invention, an N-methyl-α,α-dialkyl amino acid can be introduced with high purity subsequent to a bulky N-alkyl amino acid. Moreover, it was confirmed that the subsequent de-Tfa step also proceeds favorably, so that conventional peptide elongation from the N-terminus and the like can be subsequently carried out.

Example 2-5. Experiment in which various N-methyl-α,α-dialkyl amino acids were introduced subsequent to a bulky N-methylamino acid (MeVal) on a solid phase According to the following general scheme, Compound 2-5-1-1 to Compound 2-5-7-1 and Compound 2-5-1-2 to Compound 2-5-7-2 were synthesized using various Tfa-amino acids.

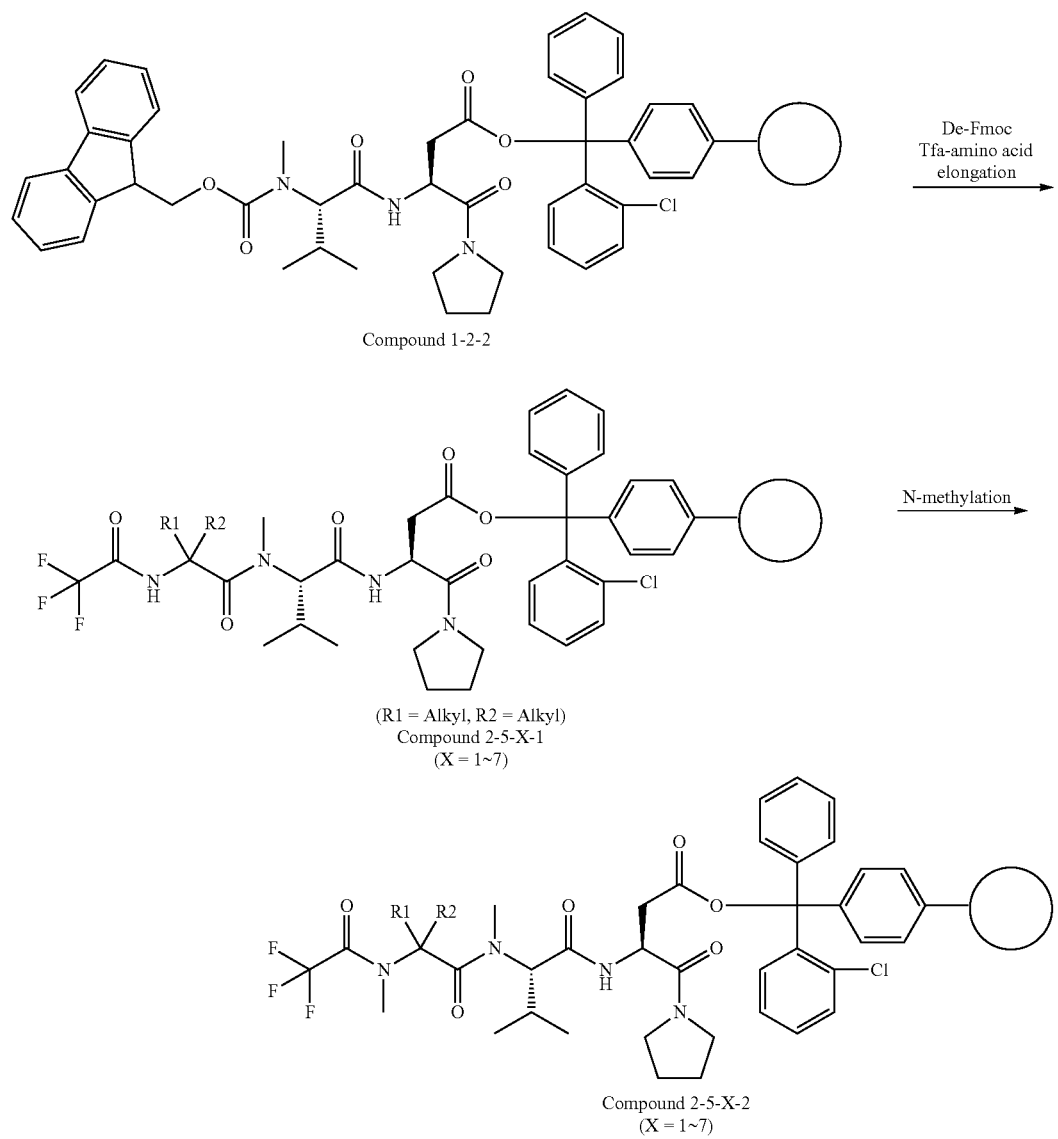
Compound 1-2-2
De-Fmoc
Tfa-amino acid elongation
(R1 = Alkyl, R2 = Alkyl)
Compound 2-5-X-1
(X = 1~7)
N-methylation
Compound 2-5-X-2
(X = 1~7)
TABLE 8
| Compound number | Structural formula | Abbreviation |
|---|---|---|
| Compound 2-5-1-1 | 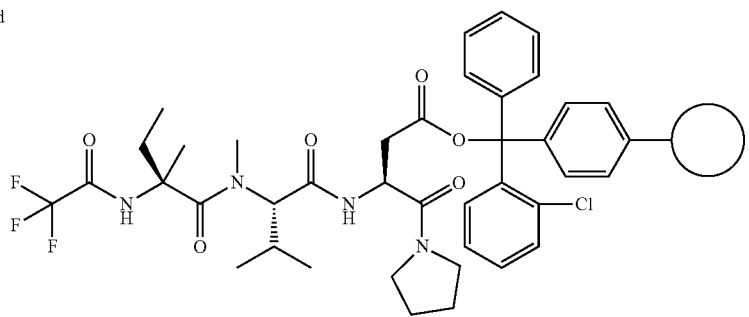 | Tfa-(Me)Abu-MeVal-Asp(O-Trt(2-Cl)-resin)-pyrro |

TABLE 8-continued
| Compound number | Structural formula | Abbreviation |
|---|---|---|
| Compound 2-5-2-1 | 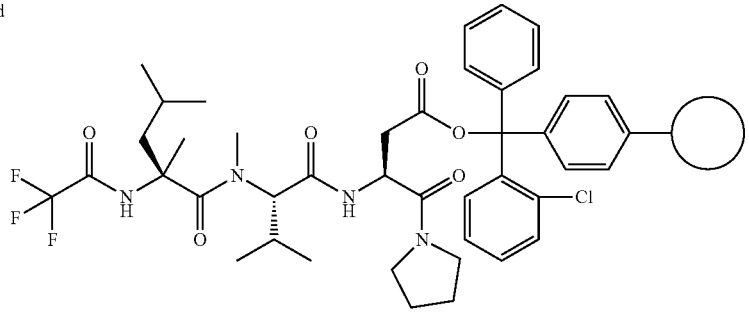 | Tfa-(Me)Leu-MeVal-Asp(O-Trt(2-Cl)-resin)-pyrro |
| Compound 2-5-3-1 | 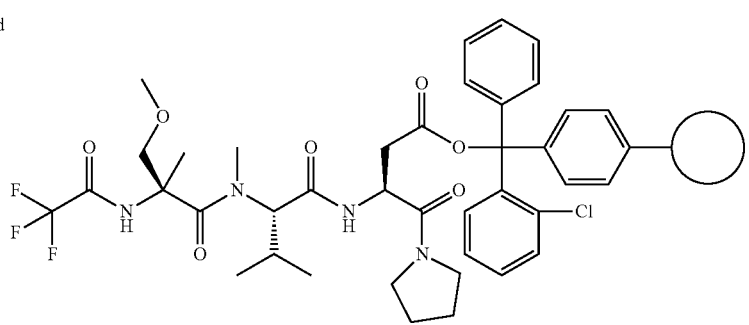 | Tfa-(Me)Ser(Me)-MeVal-Asp(O-Trt(2-Cl)-resin)-pyrro |
| Compound 2-5-4-1 | 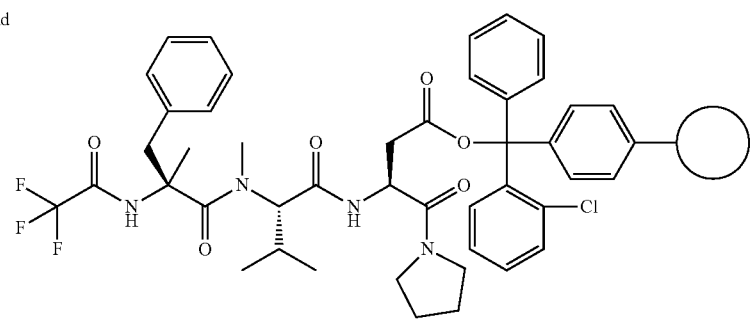 | Tfa-(Me)Phe-MeVal-Asp(O-Trt(2-Cl)-resin)-pyrro |
| Compound 2-5-5-1 | 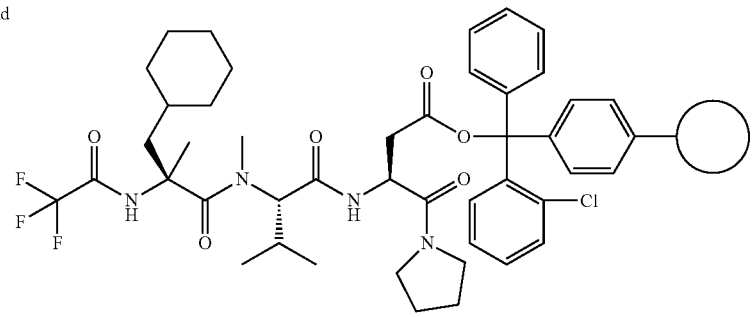 | Tfa-(Me)Cha-MeVal-Asp(O-Trt(2-Cl)-resin)-pyrro |

TABLE 8-continued
| Compound number | Structural formula | Abbreviation |
|---|---|---|
| Compound 2-5-6-1 | | Tfa-(Me)Val-MeVal-Asp(O-Trt(2-Cl)-resin)-pyrro |
| Compound 2-5-7-1 | | Tfa-cLeu-MeVal-Asp(O-Trt(2-Cl)-resin)-pyrro |
| Compound 2-5-1-2 | | Tfa-Me(Me)Abu-MeVal-Asp(O-Trt(2-Cl)-resin)-pyrro |
| Compound 2-5-2-2 | | Tfa-Me(Me)Leu-MeVal-Asp(O-Trt(2-Cl)-resin)-pyrro |
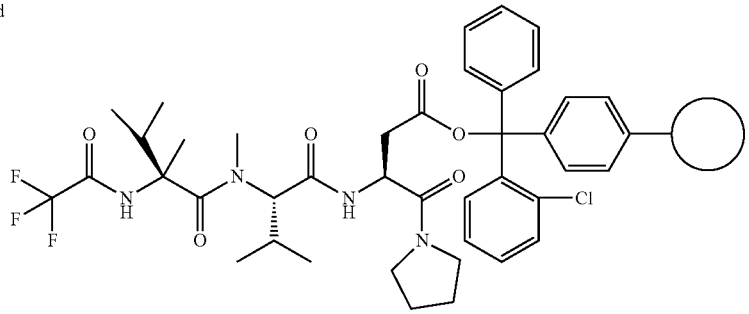
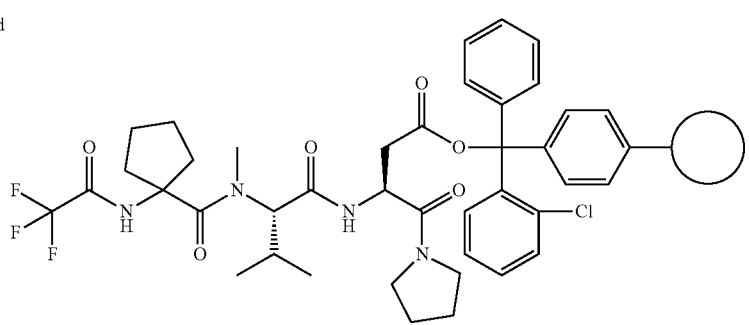
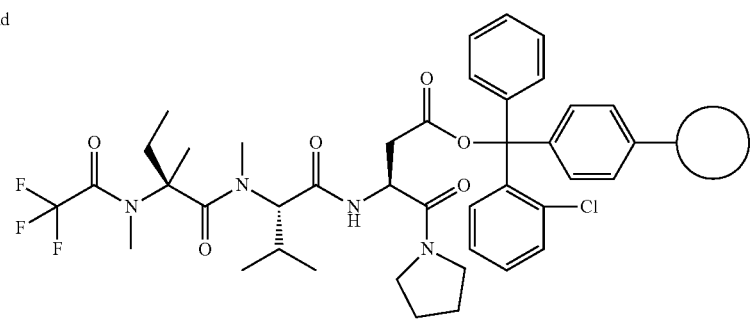
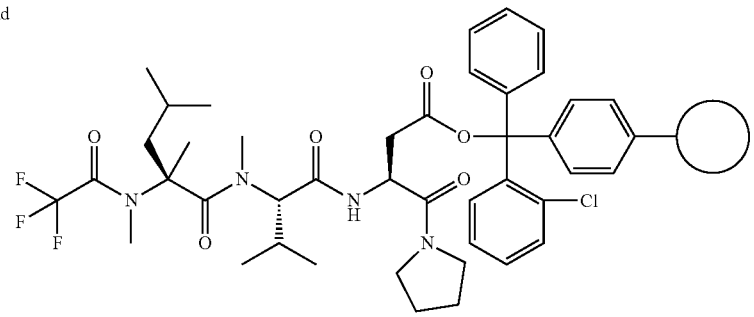

TABLE 8-continued
| Compound number | Structural formula | Abbreviation |
|---|---|---|
| Compound 2-5-3-2 | 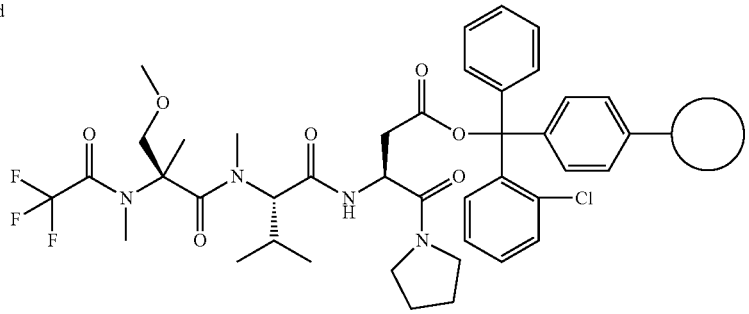 | Tfa-Me(Me)Ser(Me)-MeVal-Asp(O-Trt(2-Cl)-resin)-pyrro |
| Compound 2-5-4-2 | 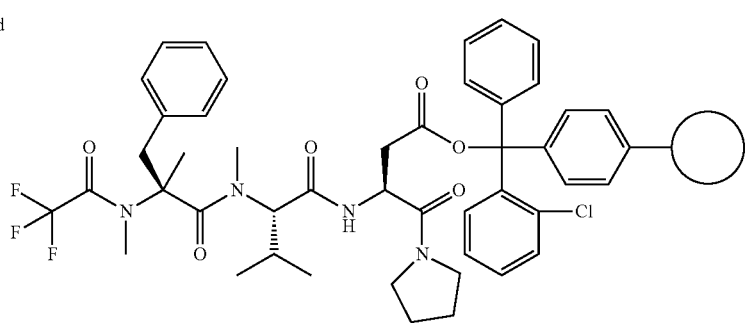 | Tfa-Me(Me)Phe-MeVal-Asp(O-Trt(2-Cl)-resin)-pyrro |
| Compound 2-5-5-2 | 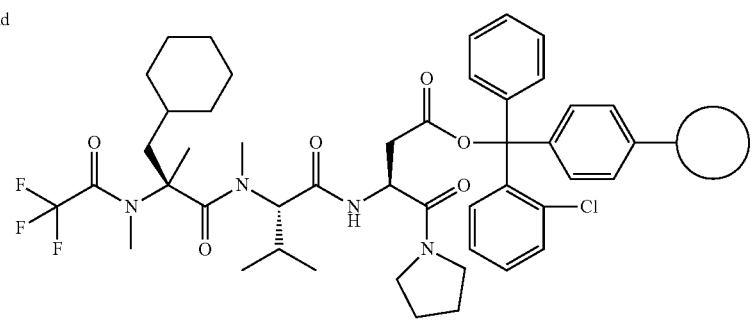 | Tfa-Me(Me)Cha-MeVal-Asp(O-Trt(2-Cl)-resin)pyrro |
| Compound 2-5-6-2 | 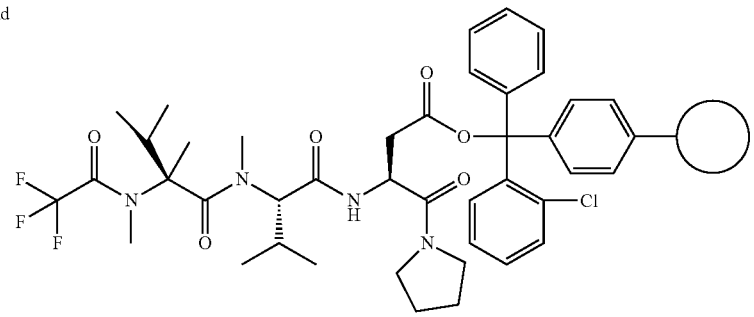 | Tfa-Me(Me)Val-MeVal-Asp(O-Trt(2-Cl)-resin)-pyrro |

TABLE 8-continued

| Compound number | Structural formula | Abbreviation |
|---|---|---|
| Compound 2-5-7-2 | 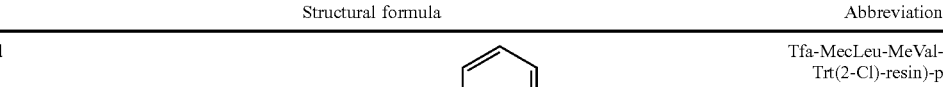 | Tfa-MecLeu-MeVal-Asp(O-Trt(2-Cl)-resin)-pyrro |

Example 2-5-1. Synthesis of Tfa-Me(Me)Abu-Me-Val-Asp(O-Trt(2-Cl)-resin)-pyrro (Compound 2-5-1-2)

Example 2-5-1-1. Elongation of Tfa-(Me)Abu-OH after de-Fmoc of Fmoc-MeVal-Asp(O-Trt(2-C)-resin)-pyrro (Compound 1-2-2)

Fmoc-MeVal-Asp(O-Trt(2-Cl)-resin)-pyrro (Compound 1-2-2) (0.552 mmol/g, 100 mg) prepared by the same method as in Example 1-2-2 was placed in a filter-equipped reaction vessel, dichloromethane (I mL) was added, and the mixture was shaken at room temperature for 45 minutes to swell the resin. After dichloromethane was removed through a filter, the resin was washed 3 times with DMF (0.7 mL). Subsequently, a 2% DBU/DMF solution (de-Fmoc solution: 0.7 mL) was added to the resin, and the mixture was shaken at room temperature for 5 minutes to remove Fmoc. After the de-Fmoc solution was removed, the resin was washed 4 times with DMF (0.7 mL).

A Tfa-(Me)Abu-OH (Compound 1-3-2-b) elongation reaction was performed on the resulting resin.

The elongation reaction was performed by adding a solution obtained by mixing a 0.6 M Tfa-(Me)Abu-OH (Compound 1-3-2-b)/NMP solution (0.3 mL) and a 10% DIC/DMF solution (0.36 mL) to the resin and shaking the mixture at 60° C. for 48 hours.

After the liquid phase of the elongation reaction was removed through a filter, the resin was washed 4 times with DMF (0.7 mL) and 4 times with dichloromethane (0.7 mL) to give Compound 2-5-1-1 (Tfa-(Me)Abu-MeVal-Asp(O-Trt(2-Cl)-resin)-pyrro).

To confirm the progression of the reaction, a part of the resulting resin (Compound 2-5-1-1) was removed, peptide cleavage was conducted with a TFE/DCM/DIPEA solution (1:1:0.015), and LCMS analysis of the cleaved solution confirmed production of the peptide of interest Tfa-(Me)Abu-MeVal-Asp-pyrro (Compound 2-5-1-1*). No other peptide components were detected. After elongation, the peptide was washed with DCM, dried, and then used in the subsequent investigations.

Compound 2-5-1-1*

LCMS (ESI) m/z=495.4 (M+H)+
Retention time: 0.56 min (Analysis condition SQDFA05)

Example 2-5-1-2. N-Methylation by nucleophilic substitution reaction on the Tfa amide moiety of Tfa-(Me)Abu-MeVal-Asp(O-Trt(2-Cl)-resin)-pyrro (Compound 2-5-1-1)

Tfa-(Me)Abu-MeVal-Asp(O-Trt(2-Cl)-resin)-pyrro (Compound 2-5-1-1) (45 mg) prepared in Example 2-5-1-1 was placed in a filter-equipped reaction vessel, dichloromethane (1 mL) was added, and the mixture was shaken at room temperature for 45 minutes to swell the resin. After dichloromethane was removed through a filter, the resin was washed 4 times with DMF (0.7 mL).

A TMGN (27 mg)/DMF (0.175 mL) solution was added to the resulting resin, then a methyl iodide (31 μL)/DMF (0.175 mL) solution was added, and the mixture was shaken at 40° C. for 1 hour. After the liquid phase was removed through a filter, washing was performed twice with DMF (0.7 mL). A small amount of the resulting resin was sampled, peptide cleavage was conducted with a TFE/DCM/DIPEA solution (1:1:0.015), and the cleaved solution was analyzed by LCMS.

To increase the reaction conversion ratio, the same operation was performed 3 more times on the resin that has been methylated once. The second methylation was performed by shaking the resin at 40° C. for 1.5 hours. The third and fourth methylations were performed by shaking the resin at 40° C. for 1 hour. After the fourth methylation, the resin was washed 4 times with DMF and 4 more times with DCM to give Compound 2-5-1-2. A part of the resulting resin was removed, peptide cleavage was conducted with a TFE/DCM/DIPEA solution (1:1:0.015), and LCMS analysis of the cleaved solution confirmed 6.0% (UV area) of an O-methylated product of the Tfa amide moiety (Compound 2-5-1-2a*) in addition to 94.0% (UV area) of the peptide of interest Tfa-Me(Me)Abu-MeVal-Asp-pyrro (Compound 2-5-1-2*).

Compound 2-5-1-2*

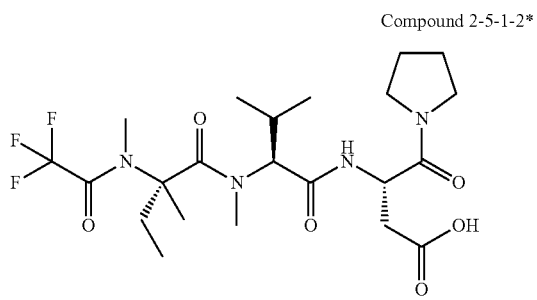 [SMILES: CC[C@@](C)(C(=O)N(C)[C@H](C(=O)N[C@@H](CC(=O)O)C(=O)N1CCCC1)C(C)C)N(C)C(=O)C(F)(F)F]

LCMS (ESI) m/z=509.5 (M+H)+
Retention time: 0.60 min (Analysis condition SQDFA05)

Compound 2-5-1-2a*

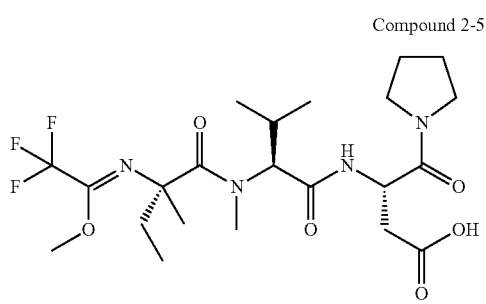

LCMS (ESI) m/z=509.5 (M+H)+
Retention time: 0.69 min (Analysis condition SQDFA05)

Example 2-5-2. Synthesis of Tfa-Me(Me)Leu-MeVal-Asp(O-Trt(2-Cl)-resin)-pyrro (Compound 2-5-2-2)

Example 2-5-2-1. Elongation of Tfa-(Me)Leu-OH after de-Fmoc of Fmoc-MeVal-Asp(O-Trt(2-Cl)-resin)-pyrro (Compound 1-2-2)

Compound 2-5-2-1 (Tfa-(Me)Leu-MeVal-Asp(O-Trt(2-Cl)-resin)-pyrro) was similarly synthesized by the method shown in Example 2-5-1-1 using Compound 1-2-2 (0.552 mmol/g, 100 mg) and a 0.6 M Tfa-(Me)Leu-OH (Compound 1-3-3-b)/DMF solution (0.3 mL). A part of the resulting resin was removed, peptide cleavage was conducted with a TFE/DCM/DIPEA solution (1:1:0.015), and LCMS analysis of the cleaved solution confirmed 6.8% (UV area) of an excessively elongated product of MeVal-Asp-pyrro (Compound 2-5-2-1a*) as a main impurity in addition to the peptide of interest Tfa-(Me)Leu-MeVal-Asp-pyrro (Compound 2-5-2-1*) (84.5% UV area) (the conversion efficiency after de-Fmoc was >99%).

Compound 2-5-2-1*

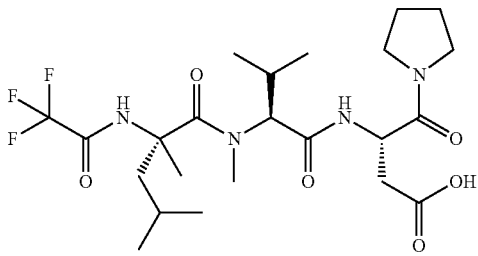

LCMS (ESI) m/z=523.5 (M+H)+
Retention time: 0.67 min (Analysis condition SQDFA05)

Compound 2-5-2-1a*

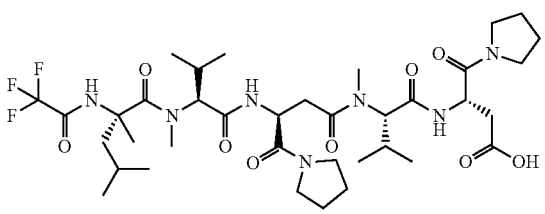

LCMS (ESI) m/z=804.7 (M+H)+
Retention time: 0.73 min (Analysis condition SQDFA05)

Example 2-5-2-2. N-Methylation by Nucleophilic Substitution Reaction on the Tfa Amide Moiety of Tfa-(Me)Leu-MeVal-Asp(O-Trt(2-Cl)-resin)-pyrro (Compound 2-5-2-1)

Compound 2-5-2-2 (Tfa-Me(Me)Leu-MeVal-Asp(O-Trt (2-Cl)-resin)-pyrro) was similarly synthesized by the method shown in Example 2-5-1-2 using Compound 2-5-2-1 (45 mg). A part of the resulting resin was removed, peptide cleavage was conducted with a TFE/DCM/DIPEA solution (1:1:0.015), and LCMS analysis of the cleaved solution confirmed 17.0% (UV area) of an O-methylated product of the Tfa amide moiety (Compound 2-5-2-2a*) and the starting material Compound 2-5-2-1*(14.5%, UV area) in addition to the peptide of interest Tfa-Me(Me)Leu-MeVal-Asp-pyrro (Compound 2-5-2-2*) (68.5% UV area).

Compound 2-5-2-2*

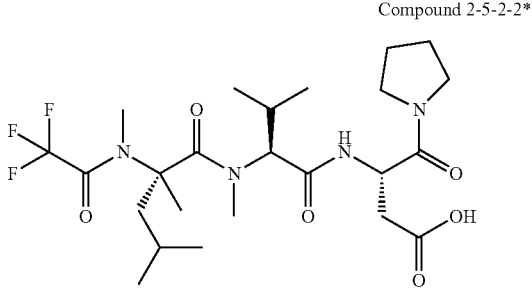 [SMILES: CC(C)C[C@@](C)(C(=O)N(C)[C@H](C(=O)N[C@@H](CC(=O)O)C(=O)N1CCCC1)C(C)C)N(C)C(=O)C(F)(F)F]

LCMS (ESI) m/z=537.5 (M+H)+
Retention time: 0.70 min (Analysis condition SQDFA05)

Compound 2-5-2-2a*

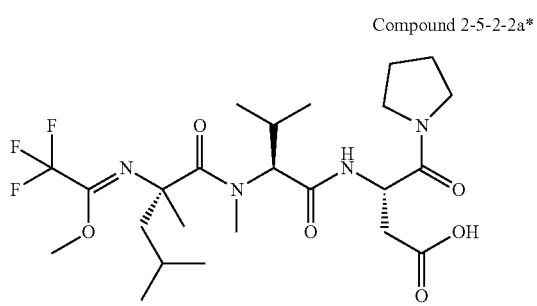 [SMILES: CO/C(=N\[C@@](C)(CC(C)C)C(=O)N(C)[C@H](C(=O)N[C@@H](CC(=O)O)C(=O)N1CCCC1)C(C)C)C(F)(F)F]

LCMS (ESI) m/z=537.5 (M+H)+
Retention time: 0.81 min (Analysis condition SQDFA05)

Example 2-5-3. Synthesis of Tfa-Me(Me)Ser(Me)-MeVal-Asp(O-Trt(2-Cl)-resin)-pyrro (Compound 2-5-3-2)

Example 2-5-3-1. Elongation of Tfa-(Me)Ser(Me)-OH after de-Fmoc of Fmoc-MeVal-Asp(O-Trt(2-Cl)-resin)-pyrro (Compound 1-2-2)

Compound 2-5-3-1 (Tfa-(Me)Ser(Me)-MeVal-Asp(O-Trt(2-Cl)-resin)-pyrro) was similarly synthesized by the method shown in Example 2-5-1-1 using Compound 1-2-2 (0.552 mmol/g, 100 mg) and a 0.6 M Tfa-(Me)Ser(Me)-OH (Compound 1-3-4-b)/DMF solution (0.3 mL). A part of the resulting resin was removed, peptide cleavage was conducted with a TFE/DCM/DIPEA solution (1:1:0.015), and LCMS analysis of the cleaved solution confirmed production of the peptide of interest Tfa-(Me)Ser(Me)-MeVal-Asp-pyrro (Compound 2-5-3-1*). No other peptide components were detected.

Compound 2-5-3-1*

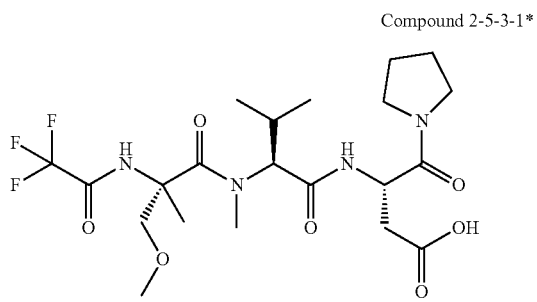 [SMILES: COC[C@](C)(NC(=O)C(F)(F)F)C(=O)N(C)[C@H](C(=O)N[C@@H](CC(=O)O)C(=O)N1CCCC1)C(C)C]

LCMS (ESI) m/z=511.4 (M+H)+
Retention time: 0.55 min (Analysis condition SQDFA05)

Example 2-5-3-2. N-Methylation by nucleophilic substitution reaction on the Tfa amide moiety of Tfa-(Me)Ser(Me)-MeVal-Asp(O-Trt(2-Cl)-resin)-pyrro (Compound 2-5-3-1)

Compound 2-5-3-2 (Tfa-Me(Me)Ser(Me)-MeVal-Asp(O-Trt(2-Cl)-resin)-pyrro) was similarly synthesized by the method shown in Example 2-5-1-2 using Compound 2-5-3-1 (45 mg). A part of the resulting resin was removed, peptide cleavage was conducted with a TFE/DCM/DIPEA solution (1:1:0.015), and LCMS analysis of the cleaved solution confirmed production of the peptide of interest Tfa-Me(Me)Ser(Me)-MeVal-Asp-pyrro (Compound 2-5-3-2*)(94.0% UV area).

Compound 2-5-3-2*

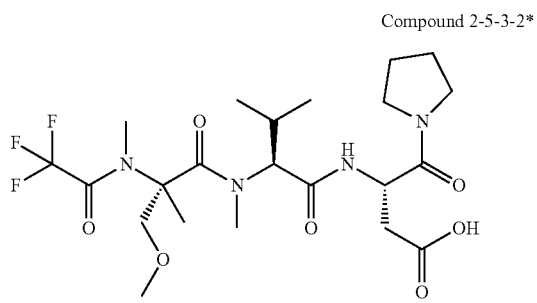 [SMILES: COC[C@@](C)(C(=O)N(C)[C@H](C(=O)N[C@@H](CC(=O)O)C(=O)N1CCCC1)C(C)C)N(C)C(=O)C(F)(F)F]

LCMS (ESI) m/z=525.5 (M+H)+
Retention time: 0.61 min (Analysis condition SQDFA05)

Example 2-5-4. Synthesis of Tfa-Me(Me)Phe-MeVal-Asp(O-Trt(2-Cl)-resin)-pyrro (Compound 2-5-4-2)

Example 2-5-4-1. Elongation of Tfa-(Me)Phe-OH after de-Fmoc of Fmoc-MeVal-Asp(O-Trt(2-Cl)-resin)-pyrro (Compound 1-2-2)

Compound 2-5-4-1 (Tfa-(Me)Phe-MeVal-Asp(O-Trt(2-Cl)-resin)-pyrro) was similarly synthesized by the same method as in Example 2-5-1-1 using Compound 1-2-2 (0.552 mmol/g, 100 mg) and a 0.6 M Tfa-(Me)Phe-OH (Compound 1-3-5-b)/DMF solution (0.3 mL) by setting the reaction time to 72 hours. A part of the resulting resin was removed, peptide cleavage was conducted with a TFF/DCM/DIPEA solution (1:1:0.015), and LCMS analysis of the cleaved solution confirmed production of the peptide of interest Tfa-(Me)Phe-MeVal-Asp-pyrro (Compound 2-5-4-1*) (81.4% UV area). The conversion efficiency after de-Fmoc was >99% and, other than a 4.1% (UV area) excessively elongated product of MeVal-Asp-pyrro (Compound 2-5-4-1a*) as a main impurity, peaks of unknown structures were detected.

Compound 2-5-4-1*

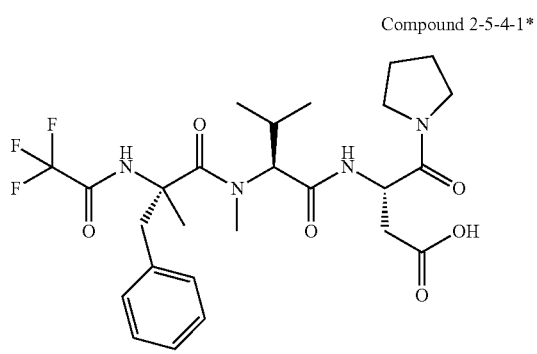 [SMILES: CC(C)[C@@H](C(=O)N[C@@H](CC(=O)O)C(=O)N1CCCC1)N(C)C(=O)[C@](C)(Cc1ccccc1)NC(=O)C(F)(F)F]

LCMS (ESI) m/z=557.5 (M+H)+
Retention time: 0.68 min (Analysis condition

Compound 2-5-4-1a*

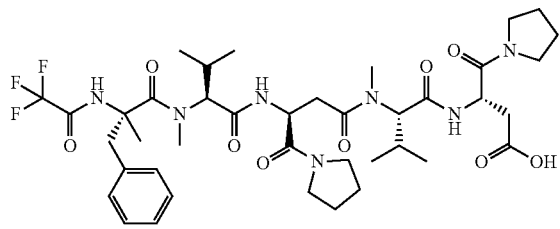

LCMS (ESI) m/z=838.7 (M+H)+
Retention time: 0.73 min (Analysis condition SQDFA05)

Example 2-5-4-2. N-Methylation by nucleophilic substitution reaction on the Tfa amide moiety of Tfa-(Me)Phe-MeVal-Asp(O-Trt(2-Cl)-resin)-pyrro (Compound 2-5-4-1)

Compound 2-5-4-2 (Tfa-Me(Me)Phe-MeVal-Asp(O-Trt (2-Cl)-resin)-pyrro) was similarly synthesized by the method shown in Example 2-5-1-2 using Compound 2-5-4-1(45 mg). At this time, the second N-methylation was also performed for 1 hour. A part of the resulting resin was removed, peptide cleavage was conducted with a TFE/DCM/DIPEA solution (1:1:0.015), and LCMS analysis of the cleaved solution confirmed production of the peptide of interest Tfa-Me(Me)Phe-MeVal-Asp-pyrro (Compound 2-5-4-2*) (79.7% UV area) and, in addition, detected an excessively elongated product of MeVal-Asp-pyrro (Compound 2-5-4-2a*) and an O-methylated product of the Tfa amide moiety (Compound 2-5-4-2b*) (11.8% UV area together) as impurities (the conversion efficiency of the starting material was 100%).

Compound 2-5-4-2*

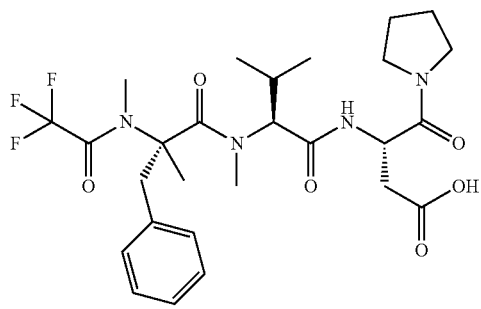

LCMS (ESI) m/z=571.5 (M+H)+
Retention time: 0.74 min (Analysis condition DFA

Compound 2-5-4-2a*

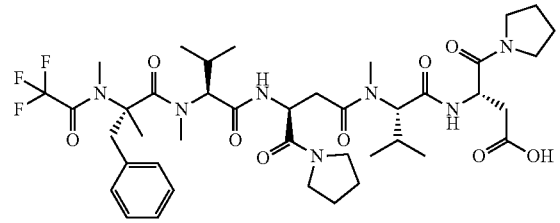

LCMS (ESI) m/z=852.7 (M+H)+
Retention time: 0.79 min (Analysis condition SQDFA05)

Compound 2-5-5-1*

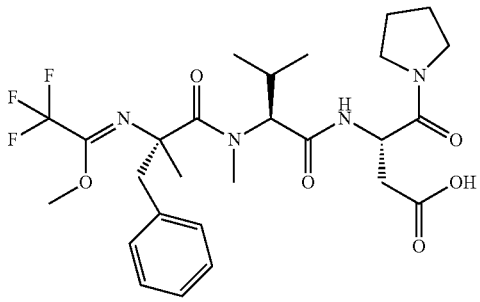

LCMS (ESI) m/z=571.5 (M+H)+
Retention time: 0.79 min (Analysis condition SQDFA05)

Example 2-5-5. Synthesis of Tfa-Me(Me)Cha-MeVal-Asp(O-Trt(2-Cl)-resin)-pyrro (Compound 2-5-5-2)

Example 2-5-5-1. Elongation of Tfa-(Me)Cha-OH after de-Fmoc of Fmoc-MeVal-Ap(0-Trt(2-Cl)-resin)-pyrro (Compound 1-2-2)

Compound 2-5-5-1 (Tfa-(Me)Cha-MeVal-Asp(O-Trt(2-Cl)-resin)-pyrro) was similarly to synthesized by the same method as in Example 2-5-1-1 using Compound 1-2-2 (0.552 mmol/g, 100 mg) and a 0.6 M Tfa-(Me)Cha-OH (Compound 1-3-6-c)/DMF solution (0.3 mL) by setting the reaction time to 72 hours. A part of the resulting resin was removed, peptide cleavage was conducted with a TFE/DCM/DIPEA solution (1:1:0.015), and LCMS analysis of the cleaved solution confirmed production of the peptide of interest Tfa-(Me)Cha-MeVal-Asp-pyrro (Compound 2-5-5-1*) (81.1% UV area). A plurality of peaks of unknown structures, including an excessively elongated product of MeVal-Asp-pyrro (Compound 2-5-5-1a*) as a main impurity, were detected (the conversion efficiency after de-Fmoc was 100%).

Compound 2-5-5-1*

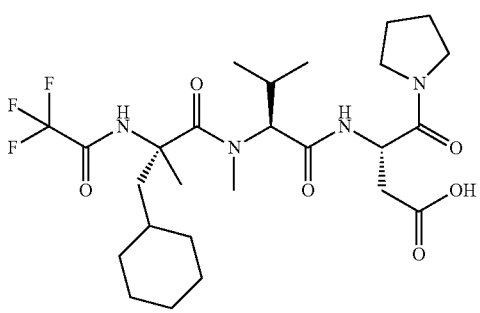

LCMS (ESI) m/z=563.6 (M+H)+
Retention time: 0.76 min (Analysis condition SQDFA05)

Compound 2-5-5-1a*

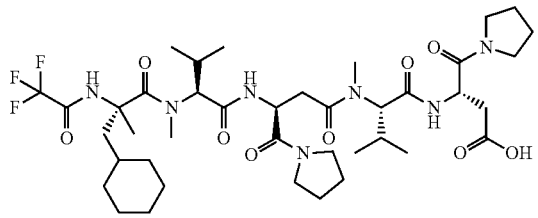

LCMS (ESI) m/z=844.8 (M+H)+
Retention time: 0.80 min (Analysis condition SQDFA05)

Example 2-5-5-2. N-Methylation by nucleophilic substitution reaction on the Tfa amide moiety of Tfa-(Me)Phe-MeVal-Asp(O-Trt(2-Cl)-resin)-pyrro (Compound 2-5-5-1)

Compound 2-5-5-2 (Tfa-Me(Me)Cha-MeVal-Asp(O-Trt(2-Cl)-resin)-pyrro) was to similarly synthesized by the method shown in Example 2-5-1-2 using Compound 2-5-5-1 (45 mg). At this time, the second N-methylation was also performed for 1 hour. A part of the resulting resin was removed, peptide cleavage was conducted with a TFE/DCM/DIPEA solution (1:1:0.015), and LCMS analysis of the cleaved solution confirmed 12.1% (UV area) of an O-methylated product of the Tfa amide moiety (Compound 2-5-5-2a*) and the starting material Compound 2-5-5-1* (13.5%, UV area) in addition to the peptide of interest Tfa-Me(Me)Cha-MeVal-Asp-pyrro (Compound 2-5-5-2*) (74.4% UV area).

Compound 2-5-5-2*

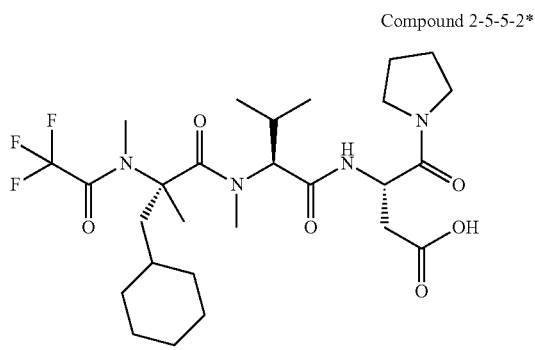 [SMILES: CC(C)[C@@H](C(=O)N[C@@H](CC(=O)O)C(=O)N1CCCC1)N(C)C(=O)[C@](C)(CC1CCCCC1)N(C)C(=O)C(F)(F)F]

LCMS (ESI) m/z=577.5 (M+H)+
Retention time: 0.80 min (Analysis condition SQDFA05)

Compound 2-5-5-2a*

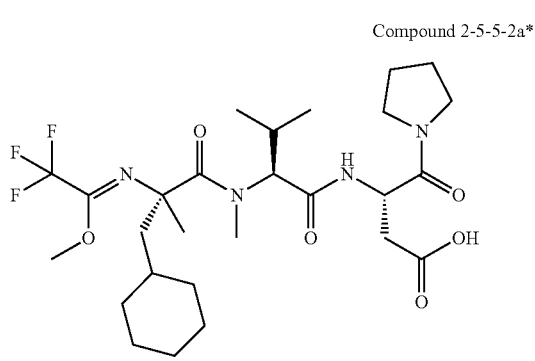 [SMILES: CO/C(=N\[C@@](C)(CC1CCCCC1)C(=O)N(C)[C@H](C(=O)N[C@@H](CC(=O)O)C(=O)N1CCCC1)C(C)C)C(F)(F)F]

LCMS (ESI) m/z=577.5 (M+H)+
Retention time: 0.92 min (Analysis condition SQDFA05)

Example 2-5-6. Synthesis of Tfa-Me(Me)Val-MeVal-Asp(O-Trt(2-Cl)-resin)-pyrro (Compound 2-5-6-2)

Example 2-5-6-1. Elongation of Tfa-(Me)Val-OH after de-Fmoc of Fmoc-MeVal-Asp(O-Trt(2-Cl)-resin)-pyrro (Compound 1-2-2)

Compound 2-5-6-1 (Tfa-(Me)Val-MeVal-Asp(O-Trt(2-Cl)-resin)-pyrro) was similarly synthesized by the same method as in Example 2-5-1-1 using Compound 1-2-2 (0.552 mmol/g, 100 mg) and a 0.6 M Tfa-(Me)Val-OH (Compound 1-3-7-b)/DMF solution (0.3 mL) by setting the reaction time to 72 hours. A part of the resulting resin was removed, peptide cleavage was conducted with a TFE/DCM/DIPEA solution (1:1:0.015), and LCMS analysis of the cleaved solution confirmed production of the peptide of interest Tfa-(Me)Val-MeVal-Asp-pyrro (Compound 2-5-6-1*) (66.6% UV area). A plurality of peaks of unknown structures, including an excessively elongated product of MeVal-Asp-pyrro (Compound 2-5-6-1a*), were detected as impurities (the conversion efficiency after de-Fmoc was 98%).

Compound 2-5-6-1*

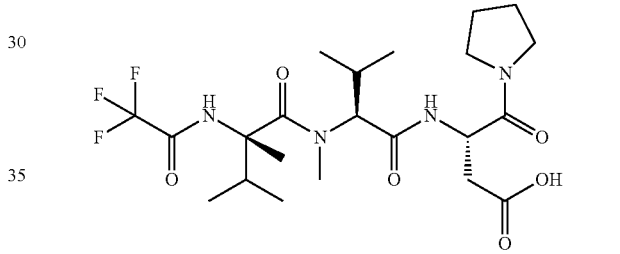

LCMS (ESI) m/z=509.5 (M+H)+
Retention time: 0.59 min (Analysis condition SQDFA05)

Compound 2-5-6-1a*

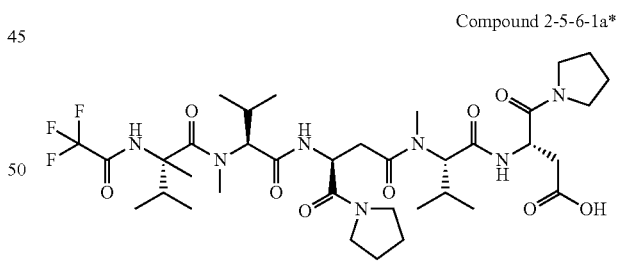

LCMS (ESI) m/z=790.7 (M+H)+
Retention time: 0.67 min (Analysis condition SQDFA05)

Example 2-5-6-2. N-Methylation by nucleophilic substitution reaction on the Tfa amide moiety of Tfa-(Me)Val-MeVal-Asp(O-Trt(2-Cl)-resin)-pyrro (Compound 2-5-6-1)

Compound 2-5-6-2 (Tfa-Me(Me)Val-MeVal-Asp(0-Trt (2-Cl)-resin)-pyrro) was similarly synthesized by the method shown in Example 2-5-1-2 at a reaction temperature of 60° C. using Compound 2-5-6-1 (40 mg). At this time, the second N-methylation was also performed for 1 hour. A part of the resulting resin was removed, peptide cleavage was conducted with a TFE/DCM/DIPEA solution (1:1:0.015), and LCMS analysis of the cleaved solution confirmed 17.1% (UV area) of an O-methylated product of the Tfa amide moiety (Compound 2-5-6-2a*) and starting material Compound 2-5-6-1* (39.6%, UV area) in addition to the peptide of interest Tfa-Me(Me)Val-MeVal-Asp-pyrro (Compound 2-5-6-2*) (21.2% UV area). Also, multiple peaks of unknown structures were detected.

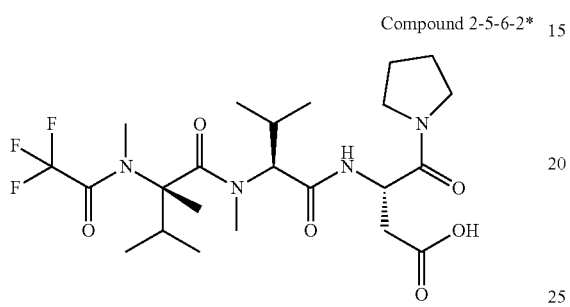

Compound 2-5-6-2*

LCMS (ESI) m/z=523.5 (M+H)+
Retention time: 0.65 min (Analysis condition SQDFA05)

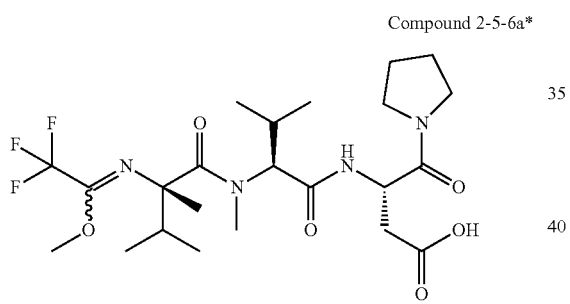

Compound 2-5-6a*

LCMS (ESI) m/z=523.5 (M+H)+
Retention time: 0.77 min (Analysis condition SQDFA05)

Example 2-5-7. Synthesis of Tfa-MecLeu-MeVal-Asp(O-Trt(2-Cl)-resin)-pyrro (Compound 2-5-7-2)

Example 2-5-7-1. Elongation of Tfa-cLeu-OH after de-Fmoc of Fmoc-MeVal-Asp(O-Trt(2-Cl)-resin)-pyrro (Compound 1-2-2)

Compound 2-5-7-1 (Tfa-cLeu-MeVal-Asp(O-Trt(2-Cl)-resin)-pyrro) was similarly synthesized by the method shown in Example 2-5-1-1 using Compound 1-2-2 (0.552 mmol/g, 100 mg) and a 0.6 M Tfa-cLeu-OH (Compound 1-3-8-b)/DMF solution (0.3 mL). A part of the resulting resin was removed, peptide cleavage was conducted with a TFE/DCM/DIPEA solution (1:1:0.015), and LCMS analysis of the cleaved solution confirmed production of the peptide of interest Tfa-cLeu-MeVal-Asp-pyrro (Compound 2-5-7-1*). No other peptide components were detected.

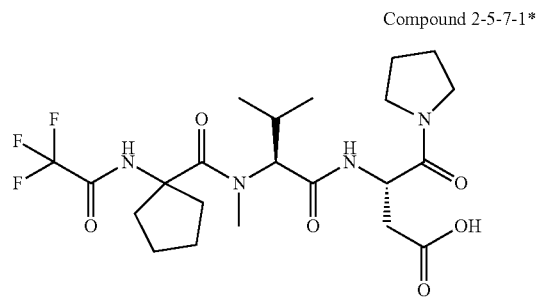 [SMILES: CC(C)[C@@H](C(=O)N[C@@H](CC(=O)O)C(=O)N1CCCC1)N(C)C(=O)C1(NC(=O)C(F)(F)F)CCCC1]

Compound 2-5-7-1*

LCMS (ESI) m/z=507.4 (M+H)+
Retention time: 0.56 min (Analysis condition SQDFA05)

Example 2-5-7-2. N-Methylation by Nucleophilic Substitution Reaction on the Tfa Amide Moiety Of Tfa-cLeu-MeVal-Asp(O-Trt(2-Cl)-Resin)-Pyrro (Compound 2-5-7-1)

Compound 2-5-7-2 (Tfa-MecLeu-MeVal-Asp(O-Trt(2-Cl)-resin)-pyrro) was similarly synthesized by the method shown in Example 2-5-1-2 using Compound 2-5-7-1 (45 mg). A part of the resulting resin was removed, peptide cleavage was conducted with a TFE/DCM/DIPEA solution (1:1:0.015), and LCMS analysis of the cleaved solution confirmed production of the peptide of interest Tfa-MecLeu-MeVal-Asp-pyrro (Compound 2-5-7-2*) (92.1% UV area) and, in addition, detected 7.9% (UV area) of an O-methylated product of the Tfa amide moiety (Compound 2-5-7-2a*) as an impurity (the conversion efficiency of the starting material was 100%).

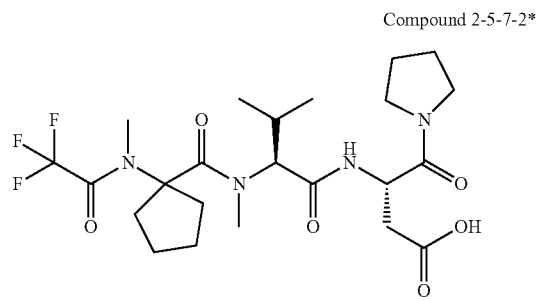 [SMILES: CC(C)[C@@H](C(=O)N[C@@H](CC(=O)O)C(=O)N1CCCC1)N(C)C(=O)C1(N(C)C(=O)C(F)(F)F)CCCC1]

Compound 2-5-7-2*

LCMS (ESI) m/z=521.4 (M+H)+
Retention time: 0.61 min (Analysis condition SQDFA05)

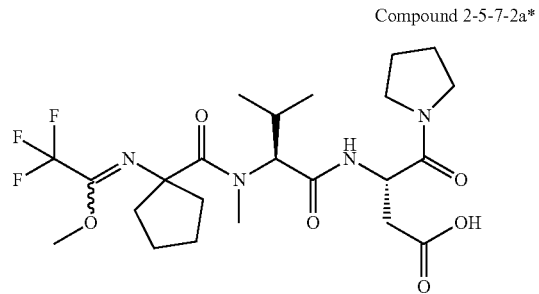 [SMILES: COC(=NC1(C(=O)N(C)[C@H](C(=O)N[C@@H](CC(=O)O)C(=O)N2CCCC2)C(C)C)CCCC1)C(F)(F)F]

Compound 2-5-7-2a*

LCMS (ESI) m/z=521.4 (M+H)+
Retention time: 0.70 min (Analysis condition SQDFA05)

Thus, it was shown from the results of Example 2-5 that, subsequent to bulky N-methylamino acids, various N-methyl-α,α-dialkylamino acids other than MeAib can be introduced at a practical level in solid-phase synthesis by the method of the present invention.

Example 2-6. Experiment in which Various N-Substituted-α,α-Dialkyl Amino Acids were Introduced Subsequent to a Bulky N-Methylamino Acid (MeVal) on a Solid Phase According to the following general scheme, Compound 2-6-1 to Compound 2-6-4 were synthesized using various Tfa-amino acids.

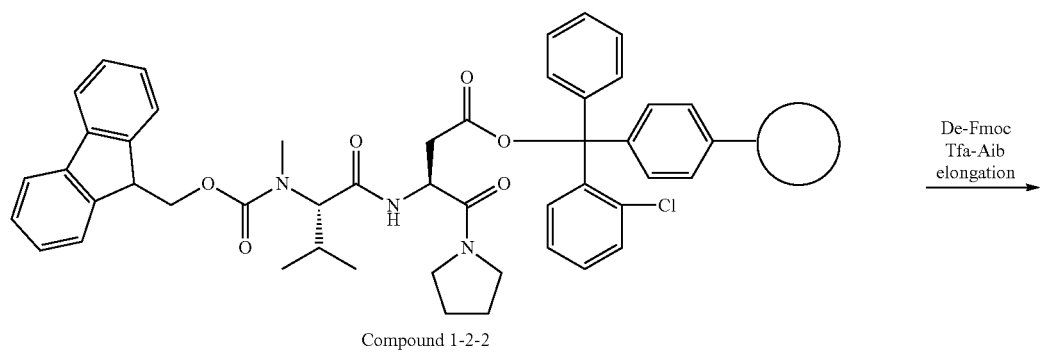

Compound 1-2-2

De-Fmoc
Tfa-Aib
elongation

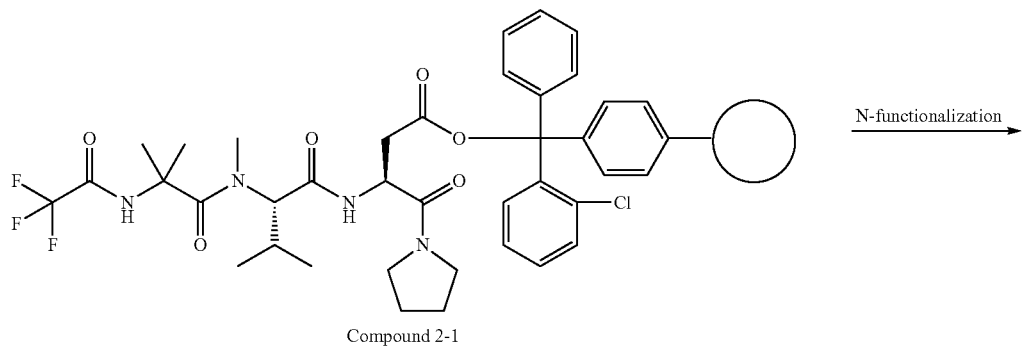

Compound 2-1

N-functionalization

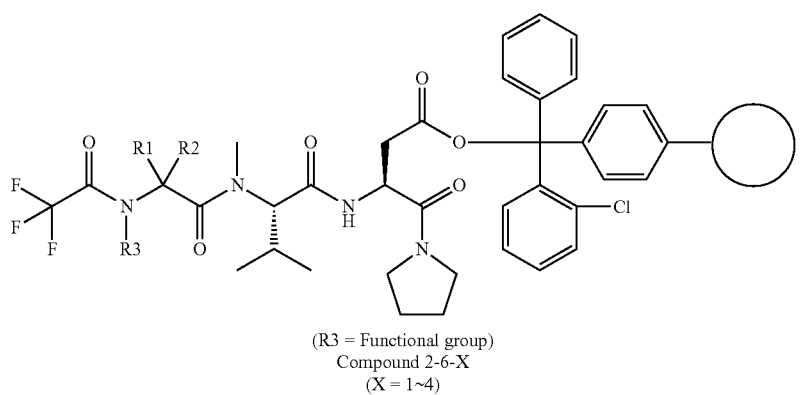

(R3 = Functional group)
Compound 2-6-X
(X = 1~4)

TABLE 9

| Compound number | Structural formula | Abbreviation |
|---|---|---|
| Compound 2-6-1 | 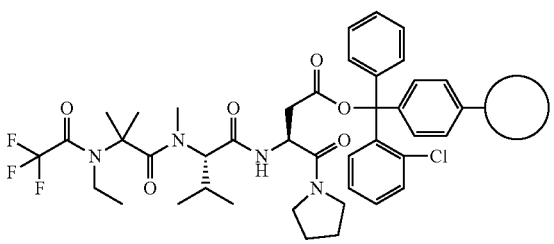 [SMILES: CCN(C(=O)C(F)(F)F)C(C)(C)C(=O)N(C)[C@H](C(=O)N[C@@H](CC(=O)OC(c1ccccc1)(c1ccc(C)cc1)c1ccccc1Cl)C(=O)N1CCCC1)C(C)C] | Tfa-EtAib-MeVal-Asp(O-Trt(2-Cl)-resin)-pyrro |
| Compound 2-6-2 | 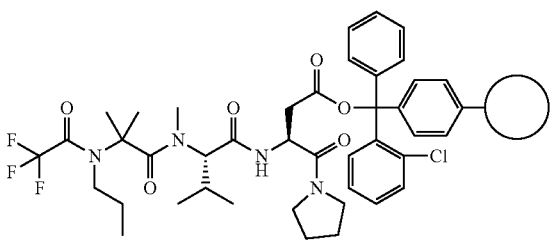 | Tfa-nPrAib-MeVal-Asp(O-Trt(2-Cl)-resin)-pyrro |
| Compound 2-6-3 | 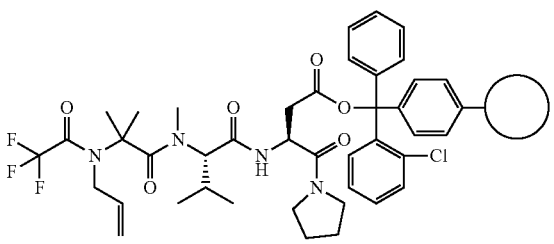 [SMILES: C=CCN(C(=O)C(F)(F)F)C(C)(C)C(=O)N(C)[C@H](C(=O)N[C@@H](CC(=O)OC(c1ccccc1)(c1ccc(C)cc1)c1ccccc1Cl)C(=O)N1CCCC1)C(C)C] | Tfa-AllylAib-MeVal-Asp(O-Trt(2-Cl)-resin)-pyrro |
| Compound 2-6-4 | 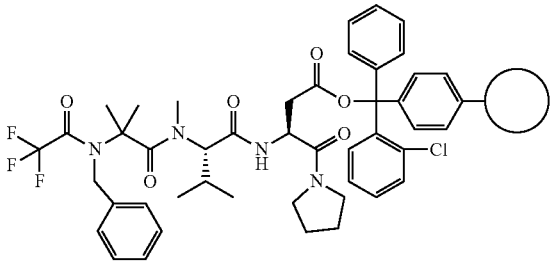 [SMILES: Cc1ccc(C(OC(=O)C[C@H](NC(=O)[C@H](C(C)C)N(C)C(=O)C(C)(C)N(Cc2ccccc2)C(=O)C(F)(F)F)C(=O)N2CCCC2)(c2ccccc2)c2ccccc2Cl)cc1] | Tfa-BnAib-MeVal-Asp(O-Trt(2-Cl)-resin)-pyrro |

Example 2-6-1. N-Ethylation of Tfa amide moiety of Tfa-Aib-MeVal-Asp(O-Trt(2-Cl)-resin)-pyrro (Compound 2-1)

Tfa-Aib-MeVal-Asp(O-Trt(2-Cl)-resin)-pyrro (Compound 2-1) (0.552 mmollg, 50 mug) prepared by the same method as in Example 2-1-1 was placed in a filter-equipped reaction vessel, dichloromethane (I mL) was added, and the mixture was shaken at room temperature for 45 minutes to swell the resin. After dichloromethane was removed through a filter, the resin was washed 4 times with DMF (0.7 mL).

A TMGN (29 mg)/DMF (0.175 mL) solution was added to the resulting resin, then an ethyl iodide (44 μL)/DMF (0.175 mL) solution was added, and the mixture was shaken at 60° C. for 1 hour. After the liquid phase was removed through a filter, washing was performed twice with DMF (0.7 mL). A small amount of the resulting resin was sampled, peptide cleavage was conducted with a TFE/DCM/DIPEA solution (1:1:0.015), and the cleaved solution was analyzed by LCMS.

To increase the reaction conversion ratio, the same operation was performed 4 more times on the resin that has been ethylated once. After the fifth ethylation, the resin was washed 4 times with DMF and 4 more times with DCM to give Compound 2-6-1 (Tfa-EtAib-MeVal-Asp(O-Trt(2-Cl)-resin)-pyrro). A part of the resulting resin was removed, peptide cleavage was conducted with a TFE/DCM/DIPEA solution (1:1:0.015), and LCMS analysis of the cleaved solution confirmed 15.4% (UV area) of an O-ethylated product of the Tfa amide moiety (Compound 2-6-1a*), starting-material Compound 2-1* (54.8%, UV area), and the like in addition to the peptide of interest Tfa-EtAib-MeVal-Asp-pyrro (Compound 2-6-1*) (26.1% UV area).

Compound 2-6-1*

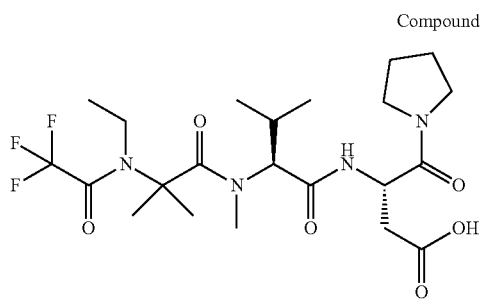

LCMS (ESI) m/z=509.4 (M+H)+
Retention time: 0.60 min (Analysis condition SQDFA05)

Compound 2-6-1a*

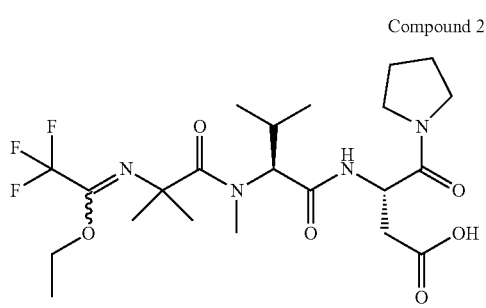

LCMS (ESI) m/z=509.4 (M+H)+
Retention time: 0.67 min (Analysis condition SQDFA05)

Example 2-6-2. N-n-Propylation of the Tfa amide moiety of Tfa-Aib-MeVal-Asp(O-Trt(2-Cl)-resin)-pyrro (Compound 2-1)

Compound 2-6-2 (Tfa-nPrAib-MeVal-Asp(O-Trt(2-Cl)-resin)-pyrro) was similarly synthesized by the method shown in Example 2-6-1 using Compound 2-1 (0.552 mmol/g, 50 mg) and n-propyl iodide (54 μL×5). A part of the resulting resin was removed, peptide cleavage was conducted with a TFE/DCM/DIPEA solution (1:1:0.015), and LCMS analysis of the cleaved solution confirmed 6.3% (UV area) of an O-n-propylated product of the Tfa amide moiety (Compound 2-6-2a*), starting material Compound 2-1* (82.7%, UV area), and the like in addition to the peptide of interest Tfa-nPrAib-MeVal-Asp-pyrro (Compound 2-6-2*) (10.0% UV area).

Compound 2-6-2*

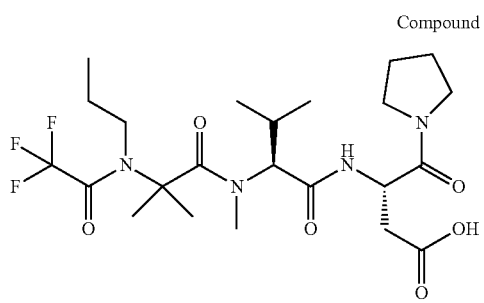

LCMS (ESI) m/z=523.5 (M+H)+
Retention time: 0.66 min (Analysis condition SQDFA05)

Compound 2-6-2a*

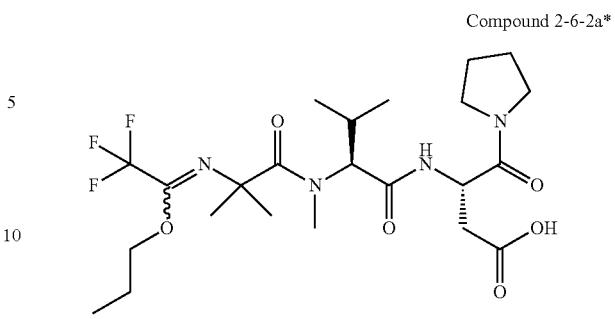

LCMS (ESI) m/z=523.5 (M+H)+
Retention time: 0.73 min (Analysis condition SQDFA05)

Example 2-6-3. N-Allylation of the Tfa amide moiety of Tfa-Aib-MeVal-Asp(O-Trt(2-Cl)-resin)-pyrro (Compound 2-1)

Compound 2-6-3 (Tfa-AllylAib-MeVal-Asp(O-Trt(2-Cl)-resin)-pyrro) was similarly synthesized by the method shown in Example 2-6-1 using Compound 2-1 (0.552 mmol/g, 50 mg) and allyl bromide (48 μL×5). A part of the resulting resin was removed, peptide cleavage was conducted with a TFE/DCM/DIPEA solution (1:1:0.015), and LCMS analysis of the cleaved solution confirmed 6.9% (UV area) of an O-allylated product of the Tfa amide moiety (Compound 2-6-3a*) and starting material Compound 2-1* (72.8%, UV area) in addition to the peptide of interest Tfa-AllylAib-MeVal-Asp-pyrro (Compound 2-6-3*) (20.3% UV area).

Compound 2-6-3*

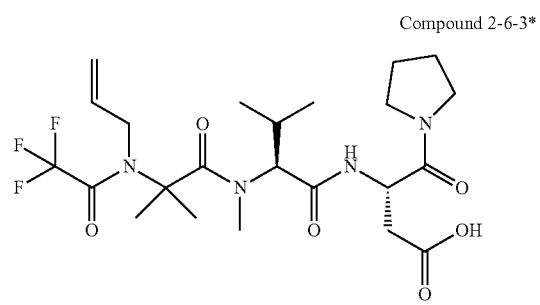 [SMILES: C=CCN(C(=O)C(F)(F)F)C(C)(C)C(=O)N(C)[C@H](C(=O)N[C@@H](CC(=O)O)C(=O)N1CCCC1)C(C)C]

LCMS (ESI) m/z=521.4 (M+H)+
Retention time: 0.64 min (Analysis condition SQDFA05)

Compound 2-6-3a*

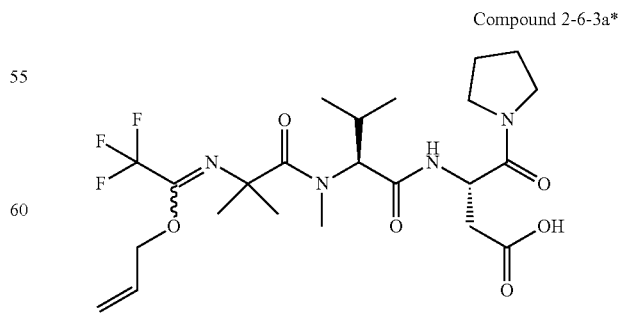

LCMS (ESI) m/z=521.5 (M+H)+
Retention time: 0.71 min (Analysis condition SQDFA05)

Example 2-6-4. N-Benzylation of the Tfa amide moiety of Tfa-Aib-MeVal-Asp(O-Trt(2-Cl)-resin)-pyrro (Compound 2-1)

Compound 2-6-4 (Tfa-BnAib-MeVal-Asp(O-Trt(2-Cl)-resin)-pyrro) was similarly synthesized by the method shown in Example 2-6-1 using Compound 2-1 (0.552 mmol/g, 50 mg) and benzyl bromide (66 L×5). A part of the resulting resin was removed, peptide cleavage was conducted with a TFE/DCM/DIPEA solution (1:1:0.015), and LCMS analysis of the cleaved solution confirmed 7.7% (UV area) of an O-benzylated product of the Tfa amide moiety (Compound 2-6-4a*) and starting material Compound 2-1* (79.5%, UV area) in addition to the peptide of interest Tfa-BnAib-MeVal-Asp-pyrro (Compound 2-6-4*) (6.2% UV area).

Compound 2-6-4*

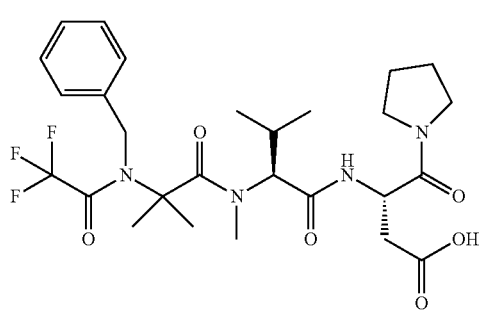

LCMS (ESI) m/z=571.5 (M+H)+
Retention time: 0.72 min (Analysis condition SQDF05)

Compound 2-6-4a*

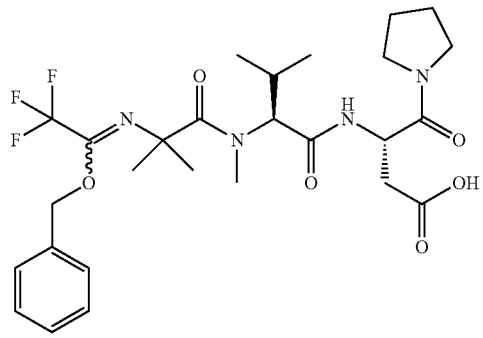

LCMS (ESI) m/z=571.5 (M+H)+
Retention time: 0.79 min (Analysis condition SQDFA05)

Thus, it was shown from the results of Example 2-6 that, subsequent to bulky N-methylamino acids, not only N-methyl-α,α-dialkylamino acids but also N-substituted-α,α-dialkylamino acids can be introduced at a practical level in solid-phase synthesis by the method of the present invention.

Example 2-7. Experiment in which N-methyl-α,α-dialkyl amino acid (MecLeu) was introduced subsequent to a bulky N-alkylamino acid (EtVal/nPrVal) on a solid phase According to the following general scheme, Compound 2-7-1 to Compound 2-7-2, Compound 2-7-3-1 to Compound 2-7-3-4, and Compound 2-7-4-1 to Compound 2-7-4-4 were synthesized.

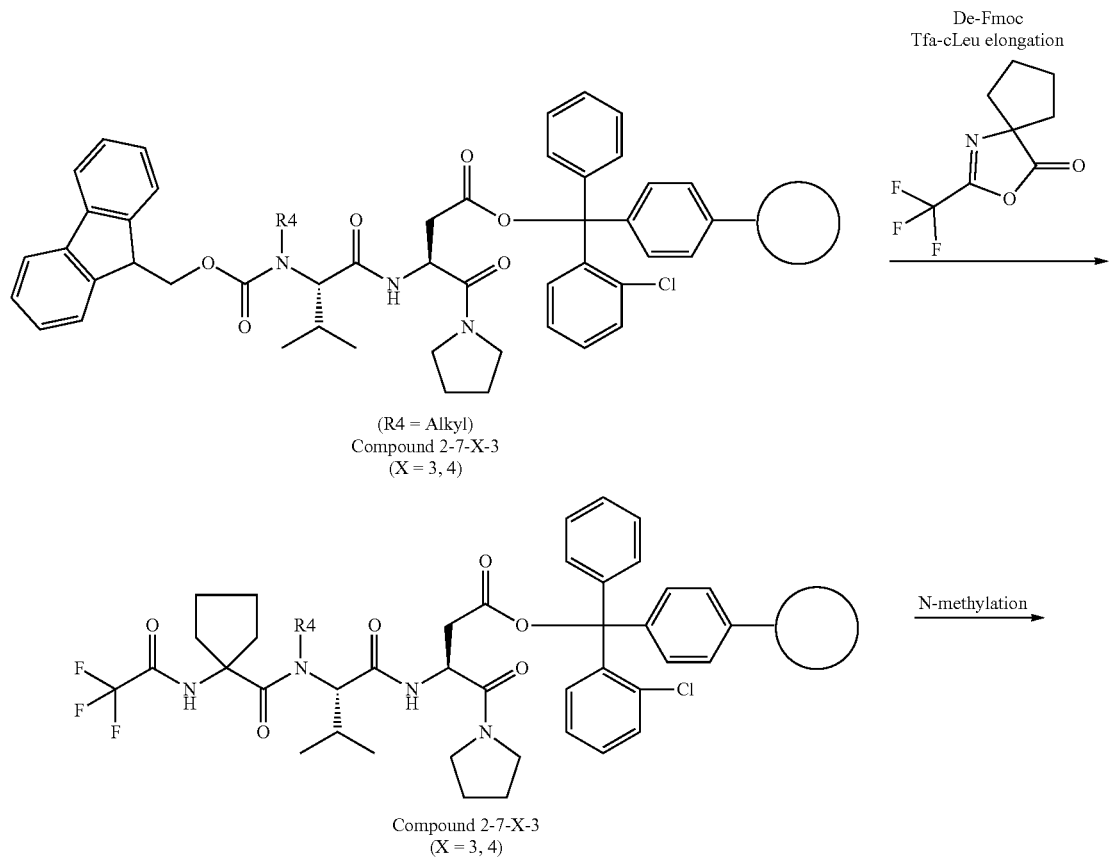

-continued
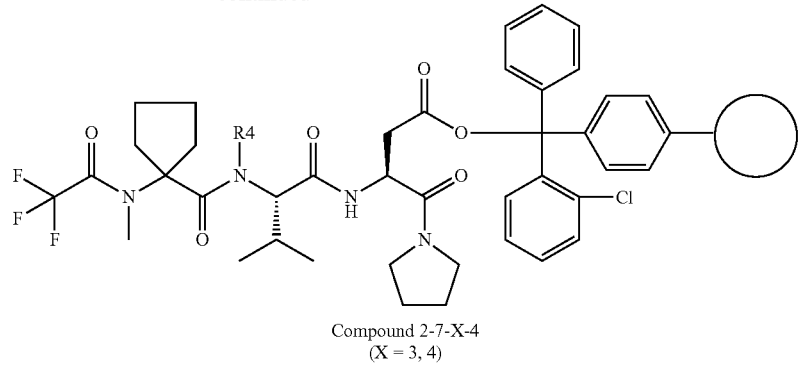
Compound 2-7-X-4
(X = 3, 4)
TABLE 10
| Compound number | Structural formula | Abbreviation |
|---|---|---|
| Compound 2-7-1 | | Fmoc-Val-Asp(O-Trt(2-Cl)-resin)-pyrro |
| Compound 2-7-2 | | Ns-Val-Asp(O-Trt(2-Cl)-resin)-pyrro |
| Compound 2-7-3-1 | | Ns-EtVal-Asp(O-Trt(2-Cl)-resin)-pyrro |

TABLE 10-continued

| Compound number | Structural formula | Abbreviation |
|---|---|---|
| Compound 2-7-3-2 | | H-EtVal-Asp(O-Trt(2-Cl)-resin)-pyrro |
| Compound 2-7-3-3 | | Tfa-cLeu-EtVal-Asp(O-Trt(2-Cl)-resin)-pyrro |
| Compound 2-7-3-4 | | Tfa-MecLeu-EtVal-Asp(O-Trt(2-Cl)-resin)-pyrro |
| Compound 2-7-4-1 | | Ns-nPrVal-Asp(O-Trt(2-Cl)-resin)-pyrro |

TABLE 10-continued

| Compound number | Structural formula | Abbreviation |
|---|---|---|
| Compound 2-7-4-2 | 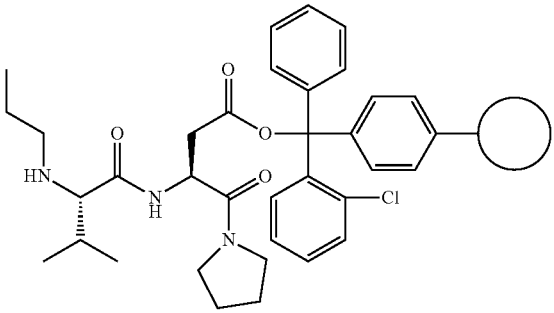 [SMILES: CCCN[C@H](C(=O)N[C@@H](CC(=O)OC(c1ccccc1)(c1ccc(C)cc1)c1ccccc1Cl)C(=O)N1CCCC1)C(C)C] | H-nPrVal-Asp(O-Trt(2-Cl)-resin)-pyrro |
| Compound 2-7-4-3 | 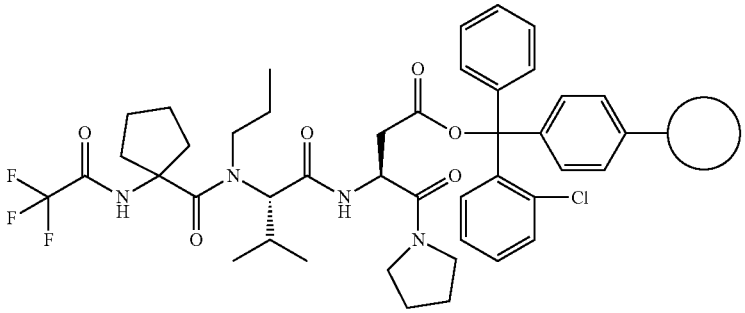 [SMILES: CCCN(C(=O)C1(NC(=O)C(F)(F)F)CCCC1)[C@H](C(=O)N[C@@H](CC(=O)OC(c1ccccc1)(c1ccc(C)cc1)c1ccccc1Cl)C(=O)N1CCCC1)C(C)C] | Tfa-cLeu-nPrVal-Asp(O-Trt(2-Cl)-resin)-pyrro |
| Compound 2-7-4-4 | 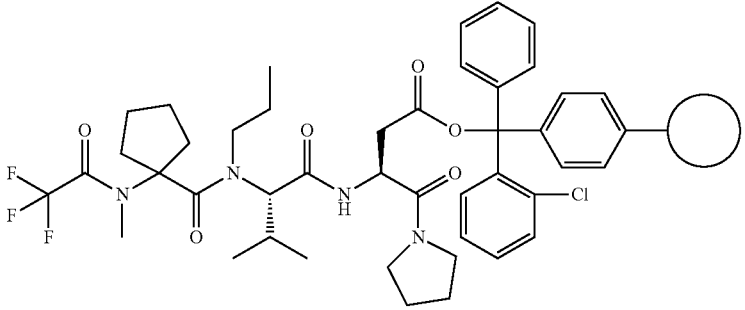 [SMILES: CCCN(C(=O)C1(N(C)C(=O)C(F)(F)F)CCCC1)[C@H](C(=O)N[C@@H](CC(=O)OC(c1ccccc1)(c1ccc(C)cc1)c1ccccc1Cl)C(=O)N1CCCC1)C(C)C] | Tfa-MecLeu-nPrVal-Asp(O-Trt(2-Cl)-resin)-pyrro |

Example 2-7-1. Preparation of Fmoc-Val-Asp(O-Trt (2-Cl)-resin)-pyrro (Compound 2-7-1)

Fmoc-Asp(O-Trt(2-Cl)-resin)-pyrro (Compound 1-2-1) (0.552 mmol/g, 100 mg) prepared by the same method as in Example 1-2-1 was placed in a filter-equipped reaction vessel, dichloromethane (I mL) was added, and the mixture was shaken at room temperature for 45 minutes to swell the resin. After dichloromethane was removed through a filter, the resin was washed 3 times with DMF (0.7 mL). Subsequently, a 2% DBU/DMF solution (de-Fmoc solution: 0.7 mL) was added to the resin, and the mixture was shaken at room temperature for 5 minutes to remove Fmoc. After the de-Fmoc solution was removed, the resin was washed 4 times with DMF (0.7 mL).

An Fmoc-Val-OH elongating reaction was performed on the resulting resin.

The elongation reaction was performed by adding a solution obtained by mixing an NMP solution (0.3 mL) of Fmoc-Val-OH (0.6 mol/L) and 1-hydroxy-7-azabenzotriazole (HOAt, 0.375 mol/L) with a 10% DIC/DMF solution (0.36 mL) to the resin and shaking the mixture at 40° C. for 3 hours.

After the liquid phase of the elongation reaction was removed through a filter, the resin was washed 4 times with DMF (0.7 mL) and 4 times with dichloromethane (0.7 mL) to give Compound 2-7-1 (Fmoc-Val-Asp(O-Trt(2-Cl)-resin)-pyrro).

To confirm the progression of the reaction, a part (about 5 mg) of the resulting resin (Compound 2-7-1) was taken, peptide cleavage was conducted with a TFE/DCM/DIPEA solution (1:1:0.015), and LCMS analysis of the cleaved solution confirmed production of the peptide of interest Fmoc-Val-Asp-pyrro (Compound 2-7-1*) (97.3% UV area). 2.7% (UV area) of an excessively elongated product of Val (Compound 2-7-1a*) was also detected at the same time. After elongation, the peptide was washed with DCM, dried, and then used in the subsequent investigations.

Compound 2-7-1*

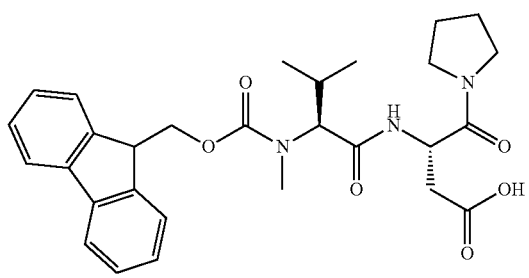

LCMS (ESI) m/z=508.4 (M+H)+
Retention time: 0.72 min (Analysis condition SQDFA05)

Compound 2-7-1a*

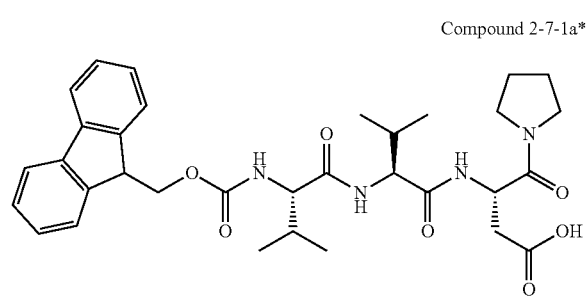 [SMILES: CC(C)[C@H](NC(=O)OCC1c2ccccc2-c2ccccc21)C(=O)N[C@H](C(=O)N[C@@H](CC(=O)O)C(=O)N1CCCC1)C(C)C]

LCMS (ESI) m/z=607.5 (M+H)+
Retention time: 0.74 min (Analysis condition SQDFA05)

Example 2-7-2. De-Fmoc and N-terminal nosylation of Fmoc-Val-Asp(O-Trt(2-Cl)-resin)-pyrro (Compound 2-7-1)

Fmoc-Val-Asp(O-Trt(2-Cl)-resin)-pyrro (Compound 2-7-1) (0.552 mmol/g, 100 mg per column) prepared in Example 2-7-1 was placed in a filter-equipped reaction vessel, dichloromethane (1 mL) was added, and the mixture was shaken at room temperature for 45 minutes to swell the resin. After dichloromethane was removed through a filter, the resin was washed twice with DMF (0.7 mL). Subsequently, a 2% DBU/DMF solution (de-Fmoc solution: 0.7 mL) was added to the resin, and the mixture was shaken at room temperature for 10 minutes to remove Fmoc. After the de-Fmoc solution was removed, the resin was sequentially washed with DMF (0.7 mL), a DMF solution (0.7 mL) of 1-hydroxy-7-azabenzotriazole (HOAt, 0.157 mol/L) and DIPEA (0.157 mol/L), and DMF (0.7 mL), and subsequently washed 3 times with THF (0.7 mL).
A THF solution (0.35 mL) of 2,4,6-trimethylpyridine (0.074 mL, 0.552 mmol) and a THF solution (0.35 mL) of 2-nitrobenzenesulfonyl chloride (0.049 g, 0.221 mmol) were added to the resulting resin, and the mixture was shaken at 40° C. for 3 hours.
After the liquid phase was removed through a filter, the resin was washed 5 times with THF (1 mL) and 5 times with dichloromethane (1 mL) to give Compound 2-7-2 (Ns-Val-Asp(O-Trt(2-Cl)-resin)-pyrro).
To confirm the progression of elongation, a part (about 5 mg) of the resulting resin was removed, peptide cleavage was conducted with a TFE/DCM/DIPEA solution (1:1:0.015), and LCMS analysis of the cleaved solution confirmed production of 94.3% (UV area) of the peptide of interest Ns-Val-Asp-pyrro (Compound 2-7-2*). After nosylation, the peptide was washed with DCM, dried, and then used in the subsequent investigations.

Compound 2-7-2*

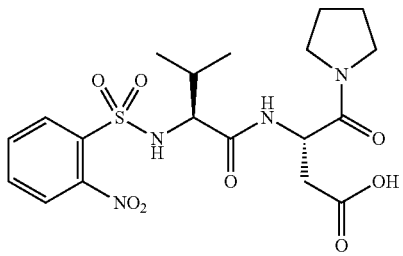

LCMS (ESI) m/z=471.3 (M+H)+
Retention time: 0.55 min (Analysis condition SQDFA05)

Example 2-7-3-1. N-Ethylation by Mitsunobu reaction on the Ns amide moiety of Ns-Val-Asp (O-Trt (2-Cl)-resin)-pyrro (Compound 2-7-2)

Ns-Val-Asp(O-Trt(2-Cl)-resin)-pyrro (Compound 2-7-2) (0.552 mmol/g, 100 mg) prepared in Example 2-7-2 was placed in a filter-equipped reaction vessel, dichloromethane (1 mL) was added, and the mixture was shaken at room temperature for 45 minutes to swell the resin. After dichloromethane was removed through a filter, the resin was washed twice with THF (1 mL).
Separately, a THF (0.35 mL) solution of triphenylphosphine (72.0 mg, 0.276 mmol) and a THF (0.35 mL) solution of DIAD (54 µL, 0.276 mmol) were added to a 1.5 mL vial, mixed through light shaking, and left to stand still at room temperature for 15 minutes, then ethanol (32 µL, 0.552 mmol) was added and mixed, and then the mixture was left to stand still for 5 minutes. The resulting solution was added to the swollen resin and shaken at 35° C. for 1 hour. After the liquid phase was removed through a filter, the resin was washed 4 times with THF (0.7 mL) and 4 times with dichloromethane (0.7 mL) to give Compound 2-7-3-1 (Ns-EtVal-Asp(O-Trt(2-Cl)-resin)-pyrro).
Peptide cleavage was conducted with a TFE/DCM/DIPEA solution (1:1:0.015) on a part (about 5 mg) of the resulting resin, and LCMS analysis of the cleaved solution confirmed production of the peptide of interest Ns-EtVal-Asp-pyrro (Compound 2-7-3-1*) (the conversion ratio from Compound 2-7-2 was 100%). The resulting resin after being dried was used in the subsequent investigations.

Compound 2-7-3-1*

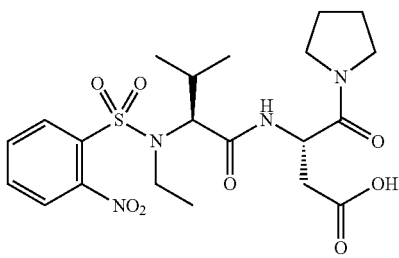

LCMS (ESI) m/z=499.4 (M+H)+
Retention time: 0.64 min (Analysis condition SQDFA05)

Example 2-7-3-2. Denosylation of Ns-EtVal-Asp(O-Trt(2-Cl)-resin)-pyrro (Compound 2-7-3-1)

Ns-Val-Asp(O-Trt(2-Cl)-resin)-pyrro (Compound 2-7-3-1) (0.552 mmol/g, 100 mg) prepared in Example 2-7-3-1 was placed in a filter-equipped reaction vessel, dichloromethane (1 mL) was added, and the mixture was shaken at room temperature for 45 minutes to swell the resin. After dichloromethane was removed through a filter, the resin was washed twice with NMP (0.7 mL).

A DBU (42 μL, 0.276 mmol)/NMP solution (0.35 mL) and a 1-dodecanethiol (126 μL, 0.552 mmol)/NMP solution (0.35 mL) were added to the resulting resin, and the mixture was shaken at 60° C. for 4 hours. After the liquid phase was removed through a filter, washing was performed twice with NMP (0.7 mL). A part of the resulting resin was removed, peptide cleavage was conducted with a TFE/DCM/DIPEA solution (1:1:0.015), and the cleaved solution was analyzed by LCMS.

To increase the reaction conversion ratio, the same operation was performed again on the resin that has been denosylated once. The second denosylation was performed by shaking the resin at 60° C. for 12 hours. After the second denosylation, the resin was washed 4 times with NMP and 4 more times with DCM to give Compound 2-7-3-2 (H-EtVal-Asp(O-Trt(2-Cl)-resin)-pyrro). A part of the resulting resin was removed, peptide cleavage was conducted with a TFE/DCM/DIPEA solution (1:1:0.015), and LCMS analysis of the cleaved solution detected an impurity presumed to be obtained by ipso-substitution of 1-dodecanethiol for the Ns-protected nitro group (Compound 2-7-3-2a*) (12.6% UV area) in addition to 84.6% (UV area) of the peptide of interest H-EtVal-Asp-pyrro (Compound 2-7-3-2*).

Compound 2-7-3-2*

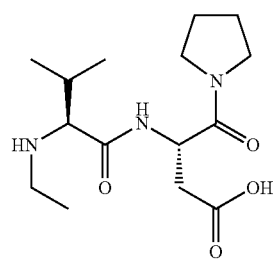

LCMS (ESI) m/z=314.3 (M+H)+
Retention time: 0.26 min (Analysis condition SQDFA05)

Compound 2-7-3-2a*

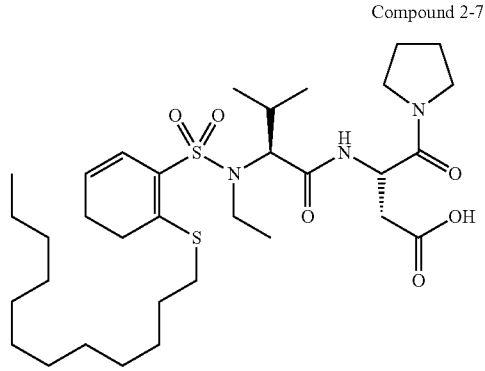

LCMS (ESI) m/z=654.5 (M+H)+
Retention time: 1.25 min (Analysis condition SQDFA05)

Example 2-7-3-3. Tfa-cLeu-OH elongation reaction on H-EtVal-Asp(O-Trt(2-Cl)-resin)-pyrro (Compound 2-7-3-2) is elongation of Tfa-cLeu using 2-(trifluoromethyl)-3-oxa-1-azaspiro[4.4]non-1-en-4-one (Compound 1-3-9) as resin H-EtVal-Asp(O-Trt(2-Cl)-resin)-pyrro (Compound 2-7-3-2) (0.552 mmol/g, 100 mg) prepared in Example 2-7-3-2 was placed in a filter-equipped reaction vessel, dichloromethane (1 to mL) was added, and the mixture was shaken at room temperature for 45 minutes to swell the resin. After dichloromethane was removed through a filter, the resin was washed 3 times with DMF (0.7 mL). The elongation reaction of Tfa-cLeu-OH was performed by adding neat 2-(trifluoromethyl)-3-oxa-1-azaspiro[4.4]non-1-en-4-one (Compound 1-3-9) (0.582 g, 2.81 mmol) to the resin, and shaking the mixture at 60° C. for 48 hours. To confirm the progression of the reaction, a small amount of the resulting resin was sampled after 24 hours, peptide cleavage was conducted with a TFE/DCM/DIPEA solution (1:1:0.015), and LCMS analysis of the cleaved solution confirmed production of the peptide of interest. The liquid phase after the elongation reaction was removed through a filter, and then the resin was washed 4 times with DMF (1 mL) and 4 times with dichloromethane (1 mL) to give Compound 2-7-3-3 (Tfa-cLeu-EtVal-Asp(O-Trt(2-C)-resin)-pyrro).

To confirm the progression of the reaction, a part of the resulting resin (Compound 2-7-3-3) was removed, peptide cleavage was conducted with a TFE/DCM/DIPEA solution (1:1:0.015), and LCMS analysis of the cleaved solution detected an excessively elongated product of EtVal-Asp-pyrro (Compound 2-7-3-3a*) (18.0% UV area), an impurity presumed to be obtained by ipso-substitution of I-dodecanethiol for the Ns-protected nitro group (Compound 2-7-3-2a*) (11.8% UV area), and the like in addition to confirming production of the peptide of interest Tfa-cLeu-EtVal-Asp-pyrro (Compound 2-7-3-3*) (55.5% UV area). A peak which seemed like Tfa-cLeu-OH loaded on the resin was also detected. After elongation, the peptide was washed with DCM, dried, and then used in the subsequent investigations.

Compound 2-7-3-3*

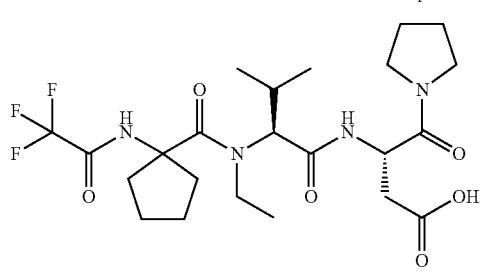

LCMS (ESI) m/z=521.5 (M+H)+
Retention time: 0.60 min (Analysis condition SQDFA05)

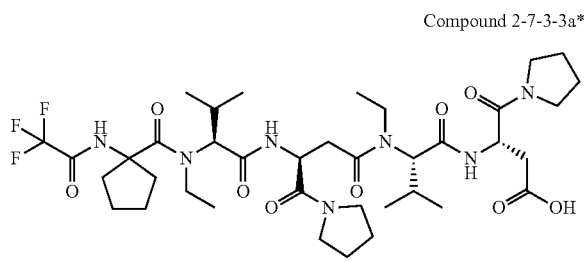 [SMILES: CCN(C(=O)C[C@H](NC(=O)[C@H](C(C)C)N(CC)C(=O)C1(NC(=O)C(F)(F)F)CCCC1)C(=O)N1CCCC1)[C@H](C(=O)N[C@@H](CC(=O)O)C(=O)N1CCCC1)C(C)C]

Compound 2-7-3-3a*

LCMS (ESI) m/z=816.7 (M+H)+
Retention time: 0.69 min (Analysis condition SQDFA05)

Example 2-7-3-4. N-Methylation by Nucleophilic Substitution Reaction on the Tfa Amide Moiety Of Tfa-cLeu-EtVal-Asp(O-Trt(2-Cl)-Resin)-Pyrro (Compound 2-7-3-3)

Tfa-cLeu-EtVal-Asp(O-Trt(2-Cl)-resin)-pyrro (Compound 2-7-3-3) (66 mg) prepared in Example 2-7-3-3 was placed in a filter-equipped reaction vessel, dichloromethane (1 mL) was added, and the mixture was shaken at room temperature for 1 hour to swell the resin. After dichloromethane was removed through a filter, the resin was washed 4 times with DMF (0.7 mL).

A TMGN (59 mg)/DMF (0.35 mL) solution was added to the resulting resin, then a methyl iodide (69 µL)/DMF (0.35 mL) solution was added, and the mixture was shaken at 40° C. for 1 hour. After the liquid phase was removed through a filter, washing was performed twice with DMF (0.7 mL). A part of the resulting resin was removed, peptide cleavage was conducted with a TFE/DCM/DIPEA solution (1:1:0.015), and the cleaved solution was analyzed by LCMS.

To increase the reaction conversion ratio, the same operation was performed 2 more times on the resin that has been methylated once. After the third methylation, the resin was washed 4 times with DMF and 4 more times with DCM to give Compound 2-7-3-4 (Tfa-MecLeu-EtVal-Asp(O-Trt(2-Cl)-resin)-pyrro). A part of the resulting resin was removed, peptide cleavage was conducted with a TFE/DCM/DIPEA solution (1:1:0.015), and LCMS analysis of the cleaved solution confirmed a compound obtained by excessive elongation and then methylation of EtVal-Asp-pyrro (Compound 2-7-3-4a*) (29.8% UV area), an impurity presumed to be obtained by ipso-substitution of 1-dodecanethiol for the Ns-protected nitro group (Compound 2-7-3-2a*) (11.9% UV area), and the like in addition to the peptide of interest Tfa-MecLeu-EtVal-Asp-pyrro (Compound 2-7-3-4*) (53.2% UV area). A peak which seemed like Tfa-cLeu-OH loaded on the resin and methylated was also detected.

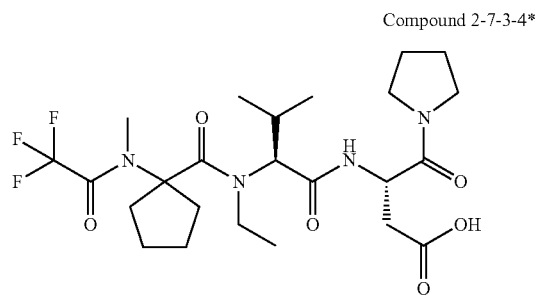 [SMILES: CCN(C(=O)C1(N(C)C(=O)C(F)(F)F)CCCC1)[C@H](C(=O)N[C@@H](CC(=O)O)C(=O)N1CCCC1)C(C)C]

Compound 2-7-3-4*

LCMS (ESI) m/z=535.4 (M+H)+
Retention time: 0.66 min (Analysis condition SQDFA05)

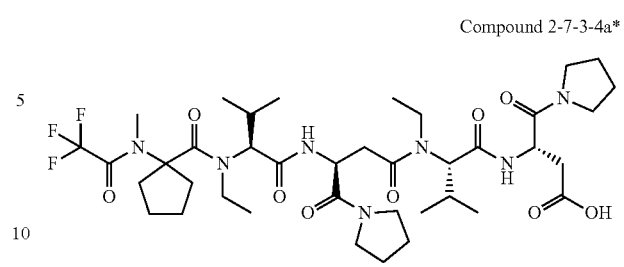

Compound 2-7-3-4a*

LCMS (ESI) m/z=830.7 (M+H)+
Retention time: 0.75 min (Analysis condition SQDFA05)

Example 2-7-4-1. N-n-Propylation by Mitsunobu reaction on the Ns amide moiety of Ns-Val-Asp(O-Trt(2-Cl)-resin)-pyrro (Compound 2-7-2)

Compound 2-7-4-1 (Ns-nPrVal-Asp(O-Trt(2-Cl)-resin)-pyrro) was similarly synthesized by the method shown in Example 2-7-3-1 using Compound 2-7-2 (0.552 mmol/g, 100 mg) and 1-propanol (41 L, 0.552 mmol). A part of the resulting resin was removed, peptide cleavage was conducted with a TFE/DCM/DIPEA solution (1:1:0.015), and LCMS analysis of the cleaved solution confirmed production of 94.7% (UV area) of the peptide of interest Ns-nPrVal-Asp-pyrro (Compound 2-7-4-1*) (the conversion ratio from Compound 2-7-2 was 100%).

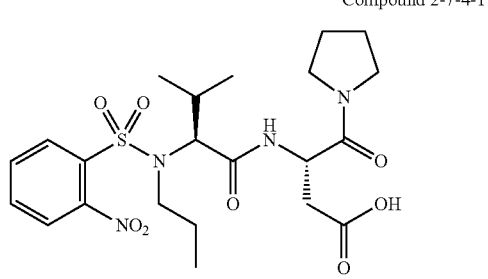

Compound 2-7-4-1*

LCMS (ESI) m/z=513.4 (M+H)+
Retention time: 0.69 min (Analysis condition SQDFA05)

Example 2-7-4-2. Denosylation of Ns-nPrVal-Asp(O-Trt(2-Cl)-resin)-pyrro (Compound 2-7-4-1)

Compound 2-7-4-2 (H-nPrVal-Asp(O-Trt(2-Cl)-resin)-pyrro) was similarly synthesized by the method shown in Example 2-7-3-2 using Compound 2-7-4-1 (0.552 mmol/g, 100 mg). A part of the resulting resin was removed, peptide cleavage was conducted with a TFE/DCM/DIPEA solution (1:1:0.015), and LCMS analysis of the cleaved solution detected an impurity presumed to be obtained by ipso-substitution of I-dodecanethiol for the Ns-protected nitro group (Compound 2-7-4-2*) (15.1% UV area) in addition to 81.1% (UV area) of the peptide of interest H-nPrVal-Asp-pyrro (Compound 2-7-4-2*).

Compound 2-7-4-2*

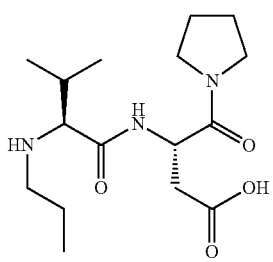

LCMS (ESI) m/z=328.3 (M+H)+
Retention time: 0.28 min (Analysis condition S DFA05)

Compound 2-7-4-3*

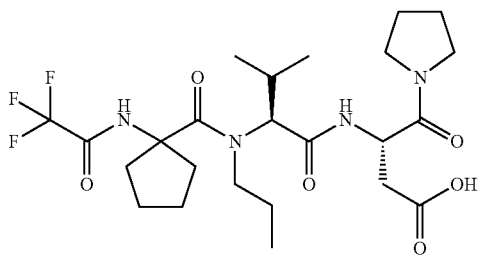

LCMS (ESI) m/z=535.5 (M+H)+
Retention time: 0.65 min (Analysis condition SQDFA05)

Compund 2-7-4-2*

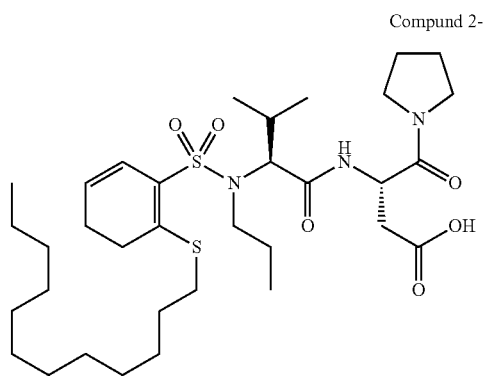

LCMS (ESI) m/z=668.6 (M+H)+
Retention time: 1.28 min (Analysis condition SQDFA05)

Example 2-7-4-3. Tfa-cLeu elongation on H-nPr-Val-Asp(O-Trt(2-Cl)-resin)-pyrro (Compound 2-7-4-2) using 2-(trifluoromethyl)-3-oxa-1-azaspiro[4.4]non-1-en-4-one (Compound 1-3-9)

Compound 2-7-4-3 (Tfa-cLeu-nPrVal-Asp(O-Trt(2-Cl)-resin)-pyrro) was similarly synthesized by the method shown in Example 2-7-3-3 using Compound 2-7-4-2 (0.552 mmol/g, 100 mg). A part of the resulting resin was removed, peptide cleavage was conducted with a TFE/DCM/DIPEA solution (1:1:0.015), and LCMS analysis of the cleaved solution detected an excessively elongated product of nPr-Val-Asp-pyrro (Compound 2-7-4-3a*) (31.0% UV area), an impurity presumed to be obtained by ipso-substitution of 1-dodecanethiol for the Ns-protected nitro group (Compound 2-74-2a*) (13.3% UV area), and the like in addition to confirming production of the peptide of interest Tfa-cLeu-nPrVal-Asp-pyrro (Compound 2-7-4-3*) (53.1% UV area). A peak which seemed like Tfa-cLeu-OH loaded on the resin was also detected.

Compound 2-7-4-3a*

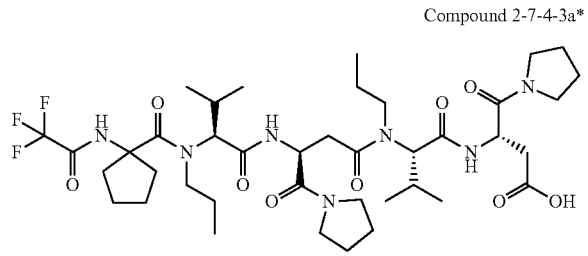 [SMILES: CCCN(C(=O)C[C@H](NC(=O)[C@H](C(C)C)N(CCC)C(=O)C1(NC(=O)C(F)(F)F)CCCC1)C(=O)N1CCCC1)[C@H](C(=O)N[C@@H](CC(=O)O)C(=O)N1CCCC1)C(C)C]

LCMS (ESI) m/z=844.8 (M+H)+
Retention time: 0.77 min (Analysis condition SQDFA05)

Example 2-7-4-4. N-Methylation by nucleophilic substitution reaction on the Tfa amide moiety of Tfa-cLeu-nPrVal-Asp(OTrt(2-Cl)-resin)-pyrro (Compound 2-7-4-3)

Compound 2-74-4 (Tfa-MecLeu-nPrVal-Asp(O-Trt(2-Cl)-resin)-pyrro) was similarly synthesized by the method shown in Example 2-7-3-4 using Compound 2-7-4-3 (0.552 mmol/g, 60 mg). A part of the resulting resin was removed, peptide cleavage was conducted with a TFE/DCM/DIPEA solution (1:1:0.015), and LCMS analysis of the cleaved solution confirmed a compound obtained by excessive elongation and then methylation of nPrVal-Asp-pyrro (Compound 2-7-4-4a*) (38.3% UV area), an impurity presumed to be obtained by ipso-substitution of 1-dodecanethiol for the Ns-protected nitro group (Compound 2-7-4-2a*) (12.6% UV area), and the like in addition to the peptide of interest Tfa-MecLeu-nPrVal-Asp-pyrro (Compound 2-7-4-4*) (46.1% UV area). A peak which seemed like Tfa-cLeu-OH loaded on the resin and methylated was also detected.

Compound 2-7-4-4*

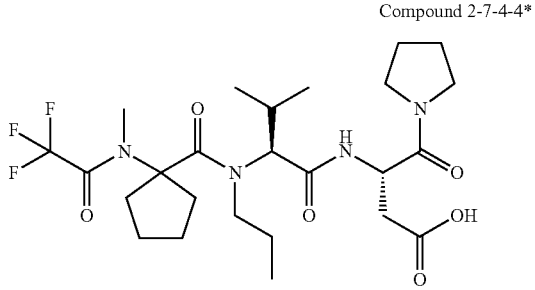 [SMILES: CCCN(C(=O)C1(N(C)C(=O)C(F)(F)F)CCCC1)[C@H](C(=O)N[C@@H](CC(=O)O)C(=O)N1CCCC1)C(C)C]

LCMS (ESI) m/z=549.5 (M+H)+
Retention time: 0.71 min (Analysis condition SQDFA05)

Compound 2 - 7 - 4 - 4a*

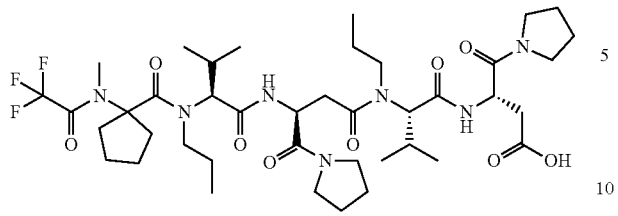

LCMS (ESI) m/z=858.7 (M+H)+

Retention time: 0.83 min (Analysis condition SQDFA05)

Thus, it was shown from the results of Example 2-7 that, subsequent to bulky N-alkylamino acids, N-methyl-α,α-dialkylamino acids can be introduced at a practical level in solid-phase synthesis by the method of the present invention.

Figure 5:
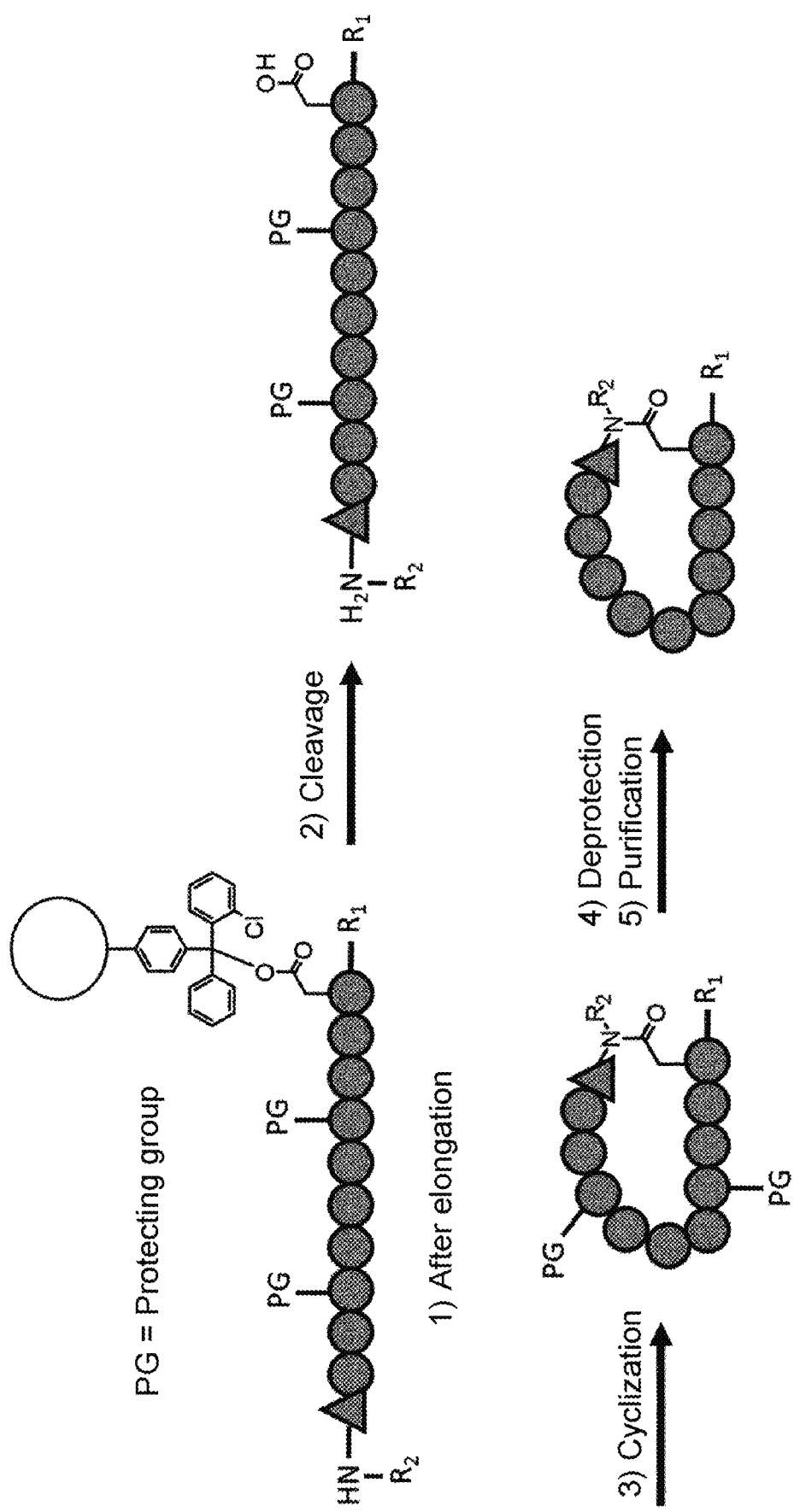
FIG. 5 shows a synthetic route for the peptide synthesis by the Fmoc method described in WO2013/100132 or WO 2018/225864.

Example 3: Example in which MeAib was Introduced and a Peptide was Synthesized by the Method of the Present Invention Peptide elongation was performed through the following basic route according to the peptide synthesis method by the Fmoc method described in WO 2013/100132 or WO 2018/225864, specifically, by the following five steps:

1) peptide elongation reaction by the Fmoc method from the N-terminal amino acid of a peptide in which the Asp side-chain carboxylic acid or the peptide main-chain carboxylic acid has been loaded onto a 2-chlorotrityl resin;

2) process of cleaving the peptide from the 2-chlorotrityl resin;

3) amide cyclization by condensation between the Asp side-chain carboxylic acid or peptide main-chain carboxylic acid resulting from release from the 2-chlorotrityl resin by the cleaving process and the amino group at the peptide chain N-terminus (triangle unit);

4) deprotection of the protecting group of a side-chain functional group contained in the peptide chain, as necessary; and 5) purification of the compound by preparative HPLC. See FIG. 5. In the present Examples, peptide compounds were synthesized through this basic route unless specified otherwise.

Example 3-1: Synthesis of (5S, 8S, 11 S, 15R, 18S, 23aS, 29S, 35S, 37aS)-8,11-di((S)-sec-butyl)-29-(3-chloro-4-(trifluoromethyl)phenethyl)-35-(cyclohexvlmethyl)-18-isopropyl-5,6,12,15,16,19,21,21, 22,33,36-undecamethyltetracosahydro-2H-azeto[2,1-u]pyrrolo[2,1-i][1,4,7,10,13,16,19,22,25,28,31] undecaazacyclotetratriacontyne-4,7,10,13,17,20,23, 28,31,34,37(14H)-undecaone (Compound 3-1)

Compound 3 - 1

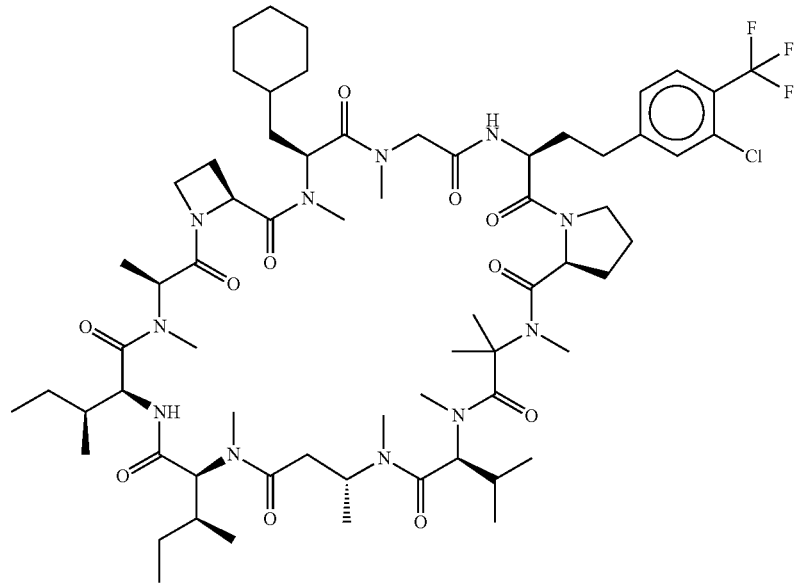

Compound 3-1 was synthesized from Compound 1-2-4 according to the following scheme.
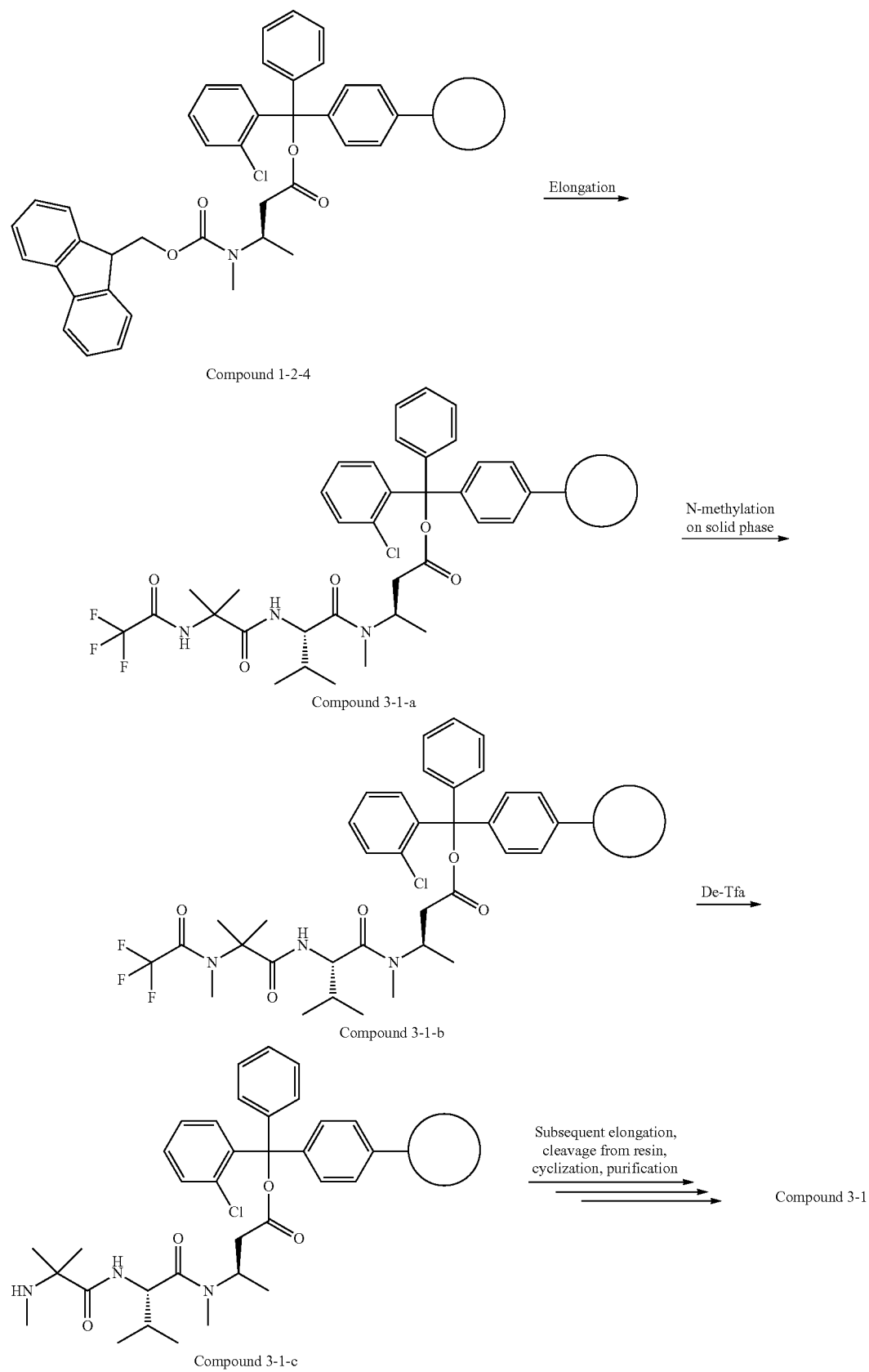

Using (3R)-3-[9H-fluoren-9-ylmethoxycarbonyl(methyl)amino]butanoic acid-2-chlorotrityl resin (Fmoc-D-3-MeAbu-O-Trt(2-Cl) resin) (Compound 1-2-4, 100 mg, 0.343 mmol/g, 0.0343 mmol) as a raw material, elongation of Fmoc-MeVal-OH was performed by the peptide elongation method described in Examples 1-2-2 in a filter-equipped reaction vessel, and then elongation of Tfa-Aib-OH (2-methyl-2-(2,2,2-trifluoroacetamide)propanoic acid) (Compound 1-3-1) was performed in the same manner as in Example 2-1-1 to give Compound 3-1-a.

The resulting Compound 3-1-a was swollen with DCM (I mL) and then washed 4 times with DMF (1 mL). A DMF solution (180 μL) of phosphazene base P1-tBu (38 μL, 0.150 mmol) and a DMF solution (180 μL) of methyl iodide (62 μL, 1 mmol) were added, and the vessel was shaken at 40° C. for 30 minutes while being hermetically closed. After the reaction solution was removed, the resin was washed 4 times with DMF (1 mL) and further washed 4 times with DCM (1 mL) to give Compound 3-1-b. A part of the resulting resin was removed with TFE/DCM (1/1 (v/v)), and LCMS analysis confirmed production of Compound 3-1-b*.

Compound 3 - 1 - b *

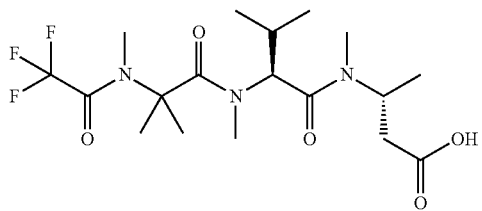

LCMS (ESI) m/z=424 (M−H)−

Retention time: 0.57 min (Analysis condition SQDFA05)

Sodium borohydride (NaBH₄) (758 mg, 20 mmol) was placed in a flask, pumped up, then brought into a nitrogen atmosphere, and dissolved in triglyme (10 mL) to give Solution A. Compound 3-1-b obtained above was swollen with DCM (1 mL) and then washed 4 times with THF (0.7 mL). THF (0.5 mL), methanol (0.25 mL), and Solution A (0.25 mL) were added to the resin, and the mixture was shaken in an open system at room temperature for 40 minutes. After the reaction solution was removed, a washing operation of adding methanol (0.7 mL) and discarding the liquid after 1 minute was repeated 4 times and, further, washing with DCM (0.7 mL) was similarly performed 4 times to give Compound 3-1-c. A part of the resulting resin was cleaved with TFE/DCM (1/1 (v/v)) and analyzed by LCMS, and thus production of Compound 3-1-c* was confirmed.

Compound 3 - 1 - c *

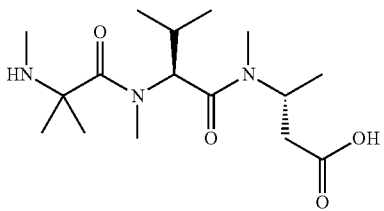

LCMS (ESI) m/z=330 (M+H)+

Retention time: 0.33 min (Analysis condition SQDFA05)

The steps of peptide elongation, cyclization, and purification after preparation of Compound 3-1-c were performed according to the following synthesis method.

As in Example 1-2-2, Compound 3-1-c (100 mg per column), an NMP solution (Solution 1) of various Fmoc-amino acids (Fmoc-Pro-OH, Fmoc-Hph(4-CF3-3-Cl)-OH (Compound AA2-001), Fmoc-MeGly-OH, Fmoc-McCha-OH, Fmoc-Aze(2)-OH, Fmoc-MeAla-OH, Fmoc-Ile-OH, Fmoc-MeLeu-OH) (0.3 to 0.6 mol/L) and HOAt or oxyma or HOOBt (0.375 mol/L), and a N,N-dimethylformamide (DMF) solution of diisopropylcarbodiimide (DIC) (10% v/v, Solution 2) were placed in a peptide synthesizer.

Solution 1 and Solution 2 after being mixed in the mixing vial of the synthesizer were added to the resin to perform a condensation reaction between the amino group on the resin and the Fmoc amino acid.

Synthesis was performed using a DMF solution (2% v/v) of diazabicycloundecene (DBU) as an Fmoc deprotecting solution. After the resin was washed with DMF, a cycle consisting of Fmoc deprotection and then a condensing reaction of Fmoc amino acid was repeatedly performed to elongate a peptide on the resin surface. After completion of peptide elongation, the Fmoc group at the N-terminus of the resin was removed in the peptide synthesizer, and then the resin was washed with DMF.

After DCM was added to the resulting linear peptide loaded on the solid phase to swell the resin again, 2,2,2-trifluoroethanol (TFE)/DCM (1/1 (v/v), 2 mL) was added to the resin, and the mixture was shaken at room temperature for 2 hours. Then, the resin was removed by filtering the solution in the tube through a synthesis column, and the remaining resin was further washed twice with 2,2,2-trifluoroethanol (TFE)/DCM (1/1 (v/v), 1 mL). All the resulting cleaved solutions were mixed and concentrated under reduced pressure.

The residue concentrated under reduced pressure after cleaving was dissolved in DMF/DCM (1/1 (v/v), 8 mL). A 0.5 M O-(7-aza-1H-benzotriazol-1-yl)-N,N,N,N-tetramethyluronium hexafluorophosphate (HATU)/DMF solution (a volume of 1.5 eq of the molar number on the resin used (loading amount (mmol/g) multiplied by the amount of the resin used (usually 0.10 g)) and DIPEA (1.8 eq of the molar number on the resin used) were added, and the mixture was shaken at room temperature for 2 hours. Then, the solvent was removed under reduced pressure. Production of the cyclic peptide of interest was confirmed by LCMS measurement.

Then, after the solvent was removed under reduced pressure, DMF or DMSO was added, insoluble matter was removed by filtration, then preparative HPLC purification was performed to give Compound 3-1 ((5S, 8S, 11S, 15R, 18S, 23aS, 29S, 35S, 37aS)-8,11-di((S)-sec-butyl)-29-(3-chloro-4-(trifluoromethyl)phenethyl)-35-(cyclohexylmethyl)-18-isopropyl-5,6,12,15,16,19,21,21,22,33,36-undecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone) (4.1 mg, 9%).

The results of LCMS analysis are provided in Table 12.

Example 3-2: Example in which peptide synthesis was performed in the same manner as in Example 3-1

Compound 3-2 to Compound 3-9 were also similarly synthesized by the method shown in Example 3-1. The relationship between the formal name, structure, and abbreviation of each amino acid residue constituting the cyclic peptides shown with respect to Compound 3-1 to Compound 3-9 (which structural formulae are provided in Table 13) can be understood from Tables 3 to 5 above and Table 11 below.

The results of LCMS analysis are provided in Table 12.

TABLE 11

| Abbreviation | Amino acid structural formula A | Name |
| --- | --- | --- |
| MeAib | | 2-Methyl-2-(methylamino)propanoic acid |
| MecLeu | | 1-(Methylamino)cyclopentanecarboxylic acid |
| Me(Me)Phe | | (2S)-2-Methyl-2-(methylamino)-3-phenyl-propanoic acid |
| Me(Me)Abu | | (S)-2-Methyl-2-(methylamino)butanoic acid |
| Me(Me)Leu | | (S)-2,4-Dimethyl-2-(methylamino)pentanoic acid |
| Me(Me)Ser(Me) | | (S)-3-Methoxy-2-methyl-2-(methylamino)propanoic acid |
| Me(Me)Phe | | (2S)-2-Methyl-2-(methylamino)-3-phenyl-propanoic acid |

TABLE 11-continued

| Abbreviation | Amino acid structural formula A | Name |
|---|---|---|
| Me(Me)Cha | | (S)-3-Cylohexyl-2-methyl-2-(methylamino)propanoic acid |
| Me(Me)Val | | (S)-2,3-Dimethyl-2-(methylamino)butanoic acid |
| EtAib | | 2-(Ethylamino)-2-methylpropanoic acid |
| nPrAib | | 2-Methyl-2-(propylamino)propanoic acid |
| AllylAib | | 2-(Allylamino)-2-methylpropanoic acid |
| BnAib | | 2-(Benzylamino)-2-methylpropanoic acid |
| MeAla | | (2S)-2-(Methylamino)propanoic acid |
| MeLeu | | (2S)-4-Methyl-2-(methylamino)pentanoic acid |

TABLE 11-continued

| Abbreviation | Amino acid structural formula A | Name |
|---|---|---|
| MeCha | | (2S)-3-Cyclohexyl-2-(methylamino)propanoic acid |
| MeVal | | (2S)-3-Methyl-2-(methylamino)butanoic acid |
| MeAla(cPent) | | (2S)-3-Cyclopentyl-2-(methylamino)propanoic acid |
| MeAla(cBu) | | (2S)-3-Cyclobutyl-2-(methylamino)propanoic acid |
| MeAla(cPr) | | (2S)-3-Cyclopropyl-2-(methylamino)propanoic acid |
| MeChg | | (2S)-2-Cyclohexyl-2-(methylamino)acetic acid |
| MeGly(cPent) | | (2S)-2-Cyclopentyl-2-(methylamino)acetic acid |
| MeGly(cBu) | | (2S)-2-Cyclobutyl-2-(methylamino)acetic acid |
| MeGly(cPr) | | (2S)-2-Cyclopropyl-2-(methylamnino)acetic acid |

TABLE 11-continued

| Abbreviation | Amino acid structural formula A | Name |
|---|---|---|
| MeAbu | | (2S)-2-(Methylamino)butanoic acid |
| MeNva | | (2S)-2-(Methylamino)pentanoic acid |
| MeNle | | (2S)-2-(Methylamino)hexanoic acid |
| MeNva(5-F2) | | (2S)-5,5-Difluoro-2-(methylamino)pentanoic acid |
| MeHle | | (2S)-5-Methyl-2-(methylamino)hexanoic acid |
| MeIle | | (2S,4S)-4-Methyl-2-(methylamino)hexanoic acid |
| MeSer(nPr) | | (2S)-2-(Methylamino)-3-propoxy-propanoic acid |
| MeSer(cPr) | | (2S)-3-(Cyclopropoxy)-2-(methylamino)propanoic acid |

TABLE 11-continued

| Abbreviation | Amino acid structural formula A | Name |
|---|---|---|
| MeHnl | | (2S)-2-(Methylamino)heptanoic acid |
| MeHnl(7-F2) | | (2S)-7,7-Difluoro-2-(methylamino) heptanoic acid |
| MePRA | | (2S)-2-(Methylamino)pent-4-ynoic acid |
| MeSer(Me) | | (2S)-3-Methoxy-2-(methylamino)propanoic acid |
| MeThr | | (2S,3R)-3-Hydroxy-2-(methylamino) butanoic acid |
| MeSer(cBu) | | (2S)-3-(Cyclobutoxy)-2-(methylamino) propanoic acid |
| MeSer(Tfe) | | (2S)-2-(Methylamino)-3-(2,2,2-trifluoroethoxy)propanoic acid |
| MeThr(Me) | | (2S,3R)-3-Methoxy-2-(methylamino) butanoic acid |

TABLE 11-continued

| Abbreviation | Amino acid structural formula A | Name |
|---|---|---|
| MeHse(Me) | | (2S)-4-Methoxy-2-(methylamino)butanoic acid |
| MeMet(O2) | | (2S)-2-(Methylamino)-4-methylsulfonyl-butanoic acid |
| EtVal | | (2S)-2-(Methylamino)-3-methylbutanoic acid |
| nPrVal | | (2S)-3-Methyl-2-(propylamino)butanoic acid |
| MeSer(tBuOH) | | (2S)-3-(2-Hydroxy-2-methyl-propoxy)-2-(methylamino)propanoic acid |
| bAla | | 3-Aminopropanoic acid |
| bMeAla | | 3-(Methylamino)propanoic acid |
| MeGly | | 2-(Methylamino)acetic acid |

TABLE 11-continued

| Abbreviation | Amino acid structural formula A | Name |
|---|---|---|
| MePhe | | (2S)-2-(Methylamino)-3-phenyl-propanoic acid |
| MePhe(3-F) | | (2S)-3-(3-Fluorophenyl)-2-(methylamino) propanoic acid |
| MePhe(4-F) | | (2S)-3-(4-Fluorophenyl)-2-(methylamino) propanoic acid |
| D-MePhe | | (2R)-2-(Methylamino)-3-phenyl-propanoic acid |
| 2-ACHxC | | (1R,2R)-2-Aminocyclohexanecarboxylic acid |
| 2-ACPnC | | (1R,2R)-2-Aminocyclopentanecarboxylic acid |
| 3-CF3-bAla | | (3R)-3-Amino-4,4,4-trifluoro-butanoic acid |
| Asp-mor | | (3S)-3-Amino-4-morpholino-4-oxo-butanoic acid |

TABLE 11-continued

| Abbreviation | Amino acid structural formula A | Name |
|---|---|---|
| Asp-mor(26-bicyc) | | (3S)-3-Amino-4-(3-oxa-8-azabicyclo[3,2,1]octan-8-yl)-4-oxo-butanoic acid |
| Asp-mor(SO2) | | (3S)-3-Amino-4-(1,1-dioxo-1,4-thiadinan-4-yl)-4-oxo-butanoic acid |
| Asp-NMe2 | | (3S)-3-Amino-4-(dimethylamino)-4-oxo-butanoic acid |
| Asp-oxz | | (3S)-3-Amino-4-oxazolidin-3-yl-4-oxo-butanoic acid |
| Asp-pip | | (3S)-3-Amino-4-oxo-4-(1-pyperidyl)butanoic acid |
| Asp-pip(345-F6) | | (3S)-3-Amino-4-(3,3,4,4,5,5-hexafluoro-1-pyperidyl)-4-oxo-butanoic acid |
| Asp-pip-(4-Me) | | (3S)-3-Amino-4-(4-methyl-1-pyperidyl)-4-oxo-butanoic acid |

TABLE 11-continued

| Abbreviation | Amino acid structural formula A | Name |
|---|---|---|
| Asp-pip-tBu | | (3S)-3-Amino-4-(4-tert-butyl-1-pyperidyl)-4-oxo-butanoic acid |
| Asp-piz(oxe) | | (3S)-3-Amino-4-[4-(oxetan-3-yl)pyperadin-1-yl]-4-oxo-butanoic acid |
| Asp-pyrro | | (3S)-3-Amino-4-oxo-4-pyrolidin-1-yl-butanoic acid |
| Asp-pyrro(34-F4) | | (3S)-3-Amino-4-oxo-4-(3,3,4,4-tetrafluoropyrolidin-1-yl)butanoic acid |
| Asp-pyrro(3-Me2) | | (3S)-3-Amino-4-(3,3-dimethylpyrolidin-1-yl)-4-oxo-butanoic acid |
| D-(Propargyl)Gly-(C#CH2) | | (3R)-3-Aminohexa-5-ynoic acid |

TABLE 11-continued

| Abbreviation | Amino acid structural formula A | Name |
|---|---|---|
| D-3-Abu | | (3R)-3-Aminobutanoic acid |
| D-3-MeAbu | | (3R)-3-(Methylamino)butanoic acid |
| D-Gly(Allyl)-(C#CH2) | | (3R)-3-Aminohexa-5-enoic acid |
| D-Hph-(C#CH2) | | (3R)-3-Amino-5-phenyl-pentanoic acid |
| D-Leu-(C#CH2) | | (3R)-3-Amino-5-methyl-hexanoic acid |
| D-MeAsp-pyrro | | (3R)-3-(Methylamino)-4-oxo-4-pyrolidin-1-yl-butanoic acid |
| D-MeLeu-(C#CH2) | | (3R)-5-Methyl-3-(methylamino)hexanoic acid |
| D-Pic(2)-(C#CH2) | | 2-[(2R)-2-Piperidyl]acetic acid |
| D-Pro-(C#CH2) | | 2-[(2R)-Pyrrolidin-2-yl]acetic acid |

TABLE 11-continued

| Abbreviation | Amino acid structural formula A | Name |
|---|---|---|
| D-Ser(iPen)-(C#CH2) | | (3S)-3-Amino-4-isopentyloxy-butanoic acid |
| D-Ser(NtBu-Aca)-(C#CH2) | | (3S)-3-Amino-4-[2-(tert-butylamino)-2-oxo-ethoxy]butanoic acid |
| EtAsp-pip | | (3S)-3-(Ethylamino)-4-oxo-4-(1-piperidyl)butanoic acid |
| MeAsp-aze | | (3S)-4-(Azetidin-1-yl)-3-(methylamino)-4-oxo-butanoic acid |
| MeAsp-mor | | (3S)-3-(Methylamino)-4-morpholino-4-oxo-butanoic acid |
| MeAsp-mor(26-bicyc) | | (3S)-3-(Methylamino)-4-(3-oxa-8-azabicyclo[3.2.1]octan-8-yl)-4-oxo-butanoic acid |
| MeAsp-mor(SO2) | | (3S)-4-(1,1-Dioxo-1,4-thiadinan-4-yl)-3-(methylamino)-4-oxo-butanoic acid |

TABLE 11-continued

| Abbreviation | Amino acid structural formula A | Name |
|---|---|---|
| MeAsp-NMe2 | 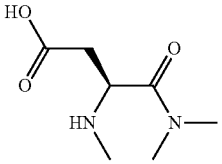 | (3S)-4-(Dimethylamino)-3-(methylamino)-4-oxo-butanoic acid |
| MeAsp-oxz | 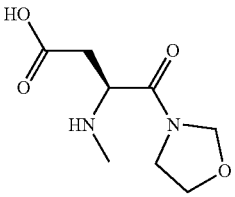 | (3S)-3-(Methylamino)-4-oxazolidin-3-yl-4-oxo-butanoic acid |
| MeAsp-pip | 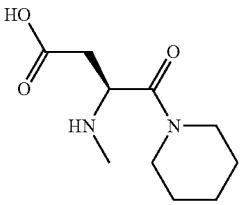 | (3S)-3-(Methylamino)-4-oxo-4-(1-pyperidyl)butanoic acid |
| MeAsp-pip-(345-F6) | 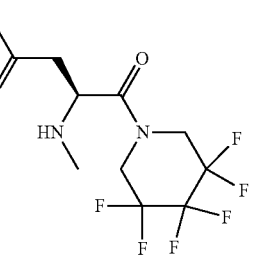 | (3S)-4-(3,3,4,4,5,5-Hexafluoro-1-pyperidyl)-3-(methylamino)-4-oxo-butanoic acid |
| MeAsp-pip(3-F2) | 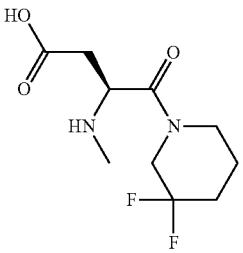 [SMILES: CN[C@@H](CC(=O)O)C(=O)N1CCCC(F)(F)C1] | (3S)-4-(3,3-Difluoro-1-pyperidyl)-3-(methylamino)-4-oxo-butanoic acid |
| MeAsp-pip(4-F2) | 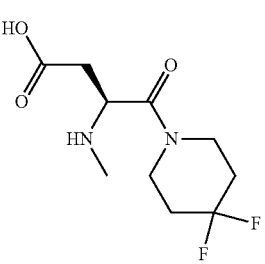 [SMILES: CN[C@@H](CC(=O)O)C(=O)N1CCC(F)(F)CC1] | (3S)-4-(4,4-Difluoro-1-pyperidyl)-3-(methylamino)-4-oxo-butanoic acid |

TABLE 11-continued

| Abbreviation | Amino acid structural formula A | Name |
|---|---|---|
| MeAsp-pip(4-Me) | | (3S)-3-(Methylamino)-4-(4-methyl-1-pyperidyl)-4-oxo-butanoic acid |
| MeAsp-piz(oxe) | | (3S)-3-(Methylamino)-4-[4-(oxetan-3-yl)pyperadin-1-yl]-4-oxo-butanoic acid |
| MeAsp-pyrro | | (3S)-3-(Methylamino)-4-oxo-4-pyrolidin-1-yl-butanoic acid |
| MeAsp-pyrro(34-F4) | | (3S)-3-(Methylamino)-4-oxo-4-(3,3,4,4-tetrafluoropyrrolidin-1-yl)butanoic acid |
| MeAsp-pyrro(3-Me2) | | (3S)-4-(3,3-Dimethylpyrrolidin-1-yl)-3-(methylamino)-4-oxo-butanoic acid |
| nPrAsp-pip | | (3S)-4-oxo-4-(1-pyperidyl)-3-(propylamino)butanoic acid |

TABLE 12

| Compound number | LCMS condition | Retention time (min) | LCMS(ESI) m/z | MS polarity |
|---|---|---|---|---|
| Compound 3-1 | SSC-A-AF-01 | 7.513 | 1318.6 | (M + H)+ |
| Compound 3-2 | SSC-A-FA-01 | 5.337 | 1302.6 | (M + H)+ |
| Compound 3-3 | SSC-A-AF-01 | 7.408 | 1288.7 | (M − H)− |
| Compound 3-4 | SSC-A-FA-01 | 4.595 | 1262.5 | (M + H)+ |
| Compound 3-5 | SSC-A-AF-01 | 7.603 | 1314.9 | (M − H)− |

TABLE 12-continued

| Compound number | LCMS condition | Retention time (min) | LCMS(ESI) m/z | MS polarity |
|---|---|---|---|---|
| Compound 3-6 | SSC-A-FA-01 | 5.383 | 1300.7 | (M − H)− |
| Compound 3-7 | SSC-A-AF-01 | 7.243 | 1286.9 | (M − H)− |
| Compound 3-8 | SSC-A-FA-01 | 5.564 | 1316.6 | (M + H)+ |
| Compound 3-9 | SSC-A-FA-01 | 5.204 | 1290.6 | (M + H)+ |

TABLE 13

| Compound number | Structural formula | Chemical name |
|---|---|---|
| Compound 3-1 | | (5S,8S,11S,15R,18S,23aS,29S,35S,37aS)-8,11-Di((S)-sec-butyl)-29-(3-chloro-4-(trifluoromethyl)phenethyl)-35-(cyclohexylmethyl)-18-isopropyl-5,6,12,15,16,19,21,21,22,33,36-undecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |
| Compound 3-2 | | (5S,8S,11S,15R,18S,23aS,29S,35S,37aS)-8-((S)-sec-Butyl)-29-(3-chloro-4-(trifluoromethyl)phenethyl)-18-(cyclobutylmethyl)-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |

TABLE 13-continued

| Compound number | Structural formula | Chemical name |
|---|---|---|
| Compound 3-3 | | (5S,8S,11S,15R,18S,23aS,29S,35S, 37aS)-8,18-di((S)-sec-butyl)-29-(3-chloro-4-(trifluoromethyl)phenethyl)-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |
| Compound 3-4 | | (5S,8S,11S,15R,18S,23aS,29S,35S, 37aS)-8-((S)-sec-Butyl)-29-(3-chloro-4-(trifluoromethyl)phenethyl)-35-(cyclohexylmethyl)-18-ethyl-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |
| Compound 3-5 | | (5S,8S,11S,15R,18S,23aS,29S,35S, 37aS)-8-((S)-sec-Butyl)-29-(3-chloro-4-(trifluoromethyl)phenethyl)-18-(cyclohexyl)-35-(cyclohexylmethyl)-5,6,11,12,15,16,19,21,21 22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |

TABLE 13-continued

| Compound number | Structural formula | Chemical name |
| --- | --- | --- |
| Compound 3-6 | | (5S,8S,11S,15R,18S,23aS,29S,35S,37aS)-8-((S)-sec-Butyl)-29-(3-chloro-4-(trifluoromethyl)phenethyl)-35-(cyclohexylmethyl)-18-cyclopentyl-5,6,11,12,15,16,19,21,21 22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |
| Compound 3-7 | | (5S,8S,11S,15R,18S,23aS,29S,35S,37aS)-8-((S)-sec-Butyl)-29-(3-chloro-4-(trifluoromethyl)phenethyl)-18-cyclobutyl-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecaone |
| Compound 3-8 | | (5S,8S,11S,15R,18S,23aS,29S,35S,37aS)-8-((S)-sec-Butyl)-29-(3-chloro-4-(trifluoromethyl)phenethyl)-35-(cyclohexylmethyl)-18-(cyclopentylmethyl)-5,6,11,12,15,16,19,21,21,22,33,36-dodecamethyltetracosahydro-2H-azeto[2,1-u]pyrrolo[2,1-i]1,4,7,10,13,16,19,22,25,28,31]undecaazacyclotetratriacontyne-4,7,10,13,17,20,23,28,31,34,37(14H)-undecaone |

TABLE 13-continued

| Compound number | Structural formula | Chemical name |
|---|---|---|
| Compound 3-9 | 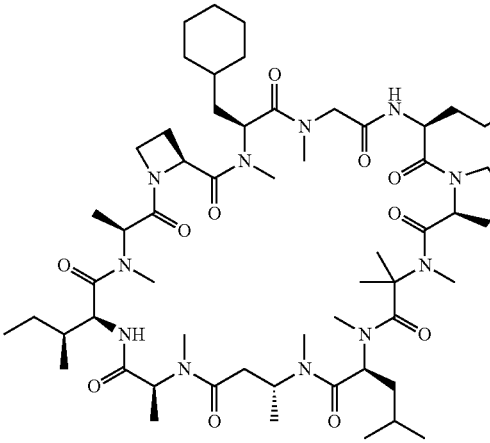 | (5S,8S,11S,15R,18S,23aS,29S,35S,37aS)-8-((S)-sec-Butyl)-29-(3-chloro-4-(trifluoromethyl)phenethyl)-35-(cyclohexylmethyl)-18-isobutyl-5,6,11,12,15,16,19,21,21,22,33,36-dodecamethyltetracosahydro-2H-azeto[2,1-u]pyrrolo[2,1-][1,4,7,10,13,16,19,22,25,28,31]undecaazacyclotetratriacontyne-4,7,10,13,17,20,23,28,31,34,37(14H)-undecaone |

Comparative Example 1: N-Methylation by Mitsunobu reaction on the Tfa amide moiety of Tfa-Aib-MeVal-Asp(O-Trt(2-Cl)-resin)-pyrro (Compound 2-1)

As a comparative example to the present invention, a known method involving a Mitsunobu reaction (Org. Lett. 2013, 15, 5012-5015) was attempted as a method for selective N-methylation at the trifluoroacetamide moiety.

In a filter-equipped reaction vessel, dichloromethane (1 mL) was added to Tfa-Aib-MeVal-Asp(O-Trt(2-Cl)-resin)-pyrro (Compound 2-1-2) (0.473 mmol/g, 100 mg) prepared in Example 2-1-2, and the mixture was shaken at room temperature for 15 minutes to swell the resin. After dichloromethane was removed through a filter, the resin was washed 4 times with THF (0.7 mL).

A triphenylphosphine (66.0 mg)/THF (0.7 mL) solution, methanol (20 µL), and DIAD (49 µL) were added to the resulting resin, and the mixture was shaken at 40° C. for 30 minutes. After the liquid phase was removed through a filter, a triphenylphosphine (66.0 mg)/THF (0.7 mL) solution, methanol (20 µL), and DIAD (49 µL) were added again, and the mixture was shaken at 40° C. for 1 hour. After the liquid phase was removed through a filter, the resin was washed 4 times with THF (0.7 mL) and 4 times with dichloromethane (0.7 mL).

Figure 2:
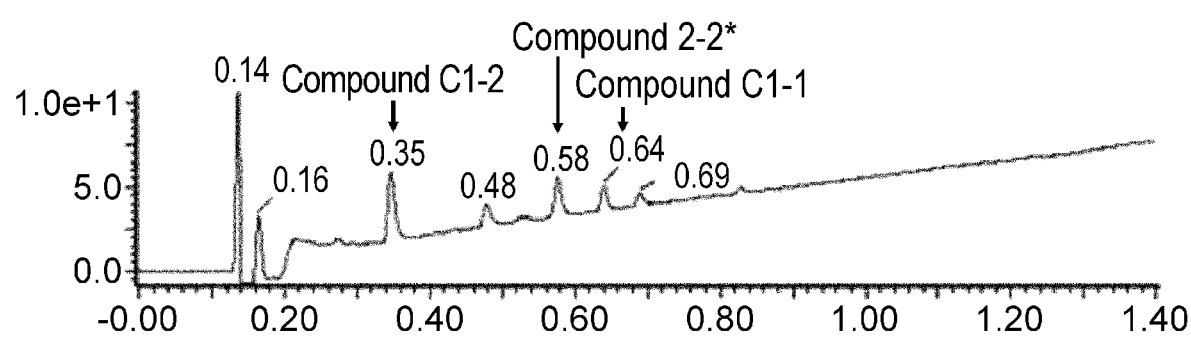
FIG. 2 shows the results of LCMS analysis (analysis condition: SQDFA05) on the reaction mixture of Comparative Example 1 detected at the maximum absorption wavelength using a photodiode array detector.

The resulting resin was subjected to peptide cleavage with a TFE/DCM solution (1/1 (v/v)), and LCMS analysis of the cleaved solution detected a product that was O-methylated at the Tfa amide moiety (Compound $C_1$-1) and H-Aib-MeVal-Asp-pyrro (Compound $C_{1-2}$) obtained through hydrolysis therefrom, in addition to production of the peptide of interest Tfa-MeAib-MeVal-Asp-pyrro (Compound 2-2*). The LC chart is as provided in FIG. 2.

Peptide of interest Tfa-MeAib-MeVal-Asp-pyrro (Compound 2-2*)

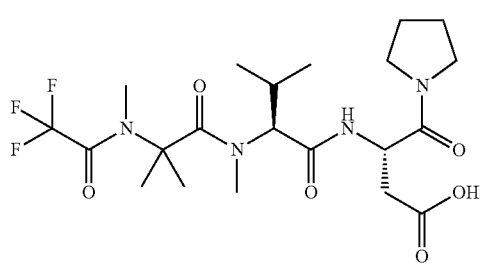

Compound 2 - 2 *

LCMS (ESI) m/z=495.26 (M+H)+

Retention time: 0.58 min (Analysis condition SQDFA05)

Product O-methylated at the Tfa amide moiety (Compound $C_1$-1)

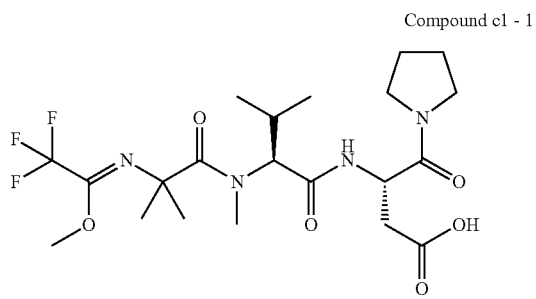 [SMILES: CO/C(=N\C(C)(C)C(=O)N(C)[C@H](C(=O)N[C@@H](CC(=O)O)C(=O)N1CCCC1)C(C)C)C(F)(F)F]

Compound c1 - 1

LCMS (ESI) m/z=495.26 (M+H)+

Retention time: 0.64 min (Analysis condition SQDFA05)

H-Aib-MeVal-Asp-pyrro (Compound $C_{1-2}$) obtained through hydrolysis from Compound $C_1$-1

Compound c1-2

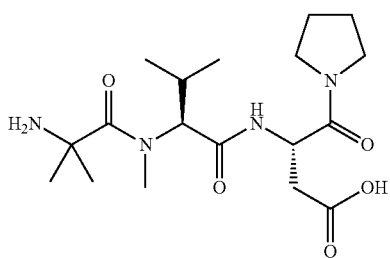

LCMS (ESI) m/z=385.26 (M+H)+

Retention time: 0.35 min (Analysis condition SQDFA05)

It was confirmed from this result that, unlike the literature (Org. Lett. 2013, 15, 5012-5015), when the N-terminus is an α,α-dialkylamino acid, O-methylation in addition to N-methylation significantly progresses at the same time, resulting in a decrease in yield and purity. This result is in contrast to the result of N-selective methylation shown in Example 2-2 and Example 2-3.

Comparative Example 2: Experiment Attempting to Introduce MeAib by Performing. After Elongation of Fmoc-Aib-OH Subsequent to an N-Methylamino Acid by a Conventional Solid-Phase Synthesis Method. Switching from Fmoc Protection to Ns Protection. N-Methylation of the N-Terminus on Resin. And Denosylation As a comparative example to the present invention, an attempt to introduce MeAib was made according to the same method as described in the literature (Nature Protocols 2012, 7, 3, 432-444) by performing, after elongation of Fmoc-Aib-OH subsequent to an N-methylamino acid by a solid-phase synthesis method, switching from Fmoc protection to Ns protection, N-methylation of the N-terminus on the resin, and denosylation.

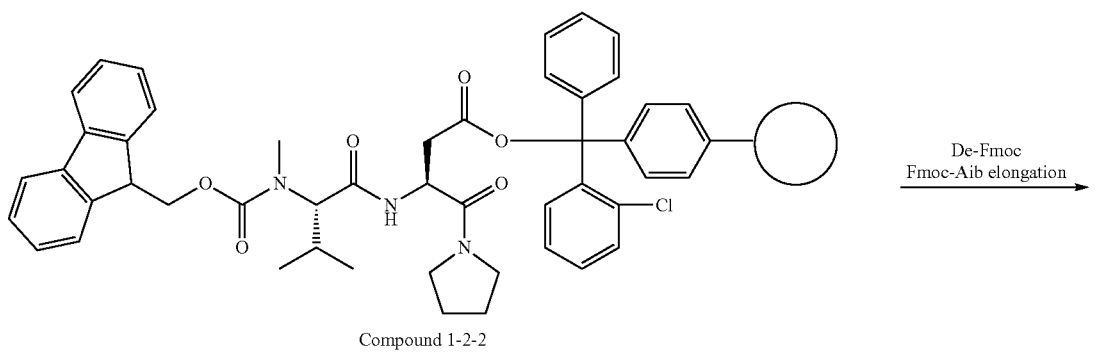

Compound 1-2-2

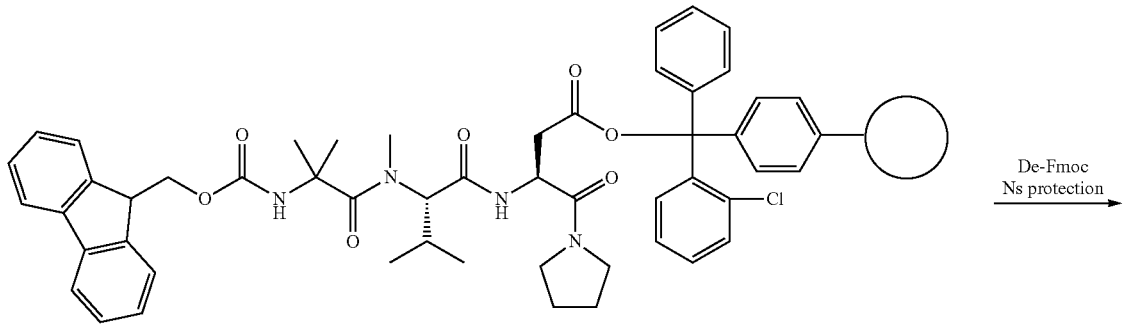

Compound c2-1

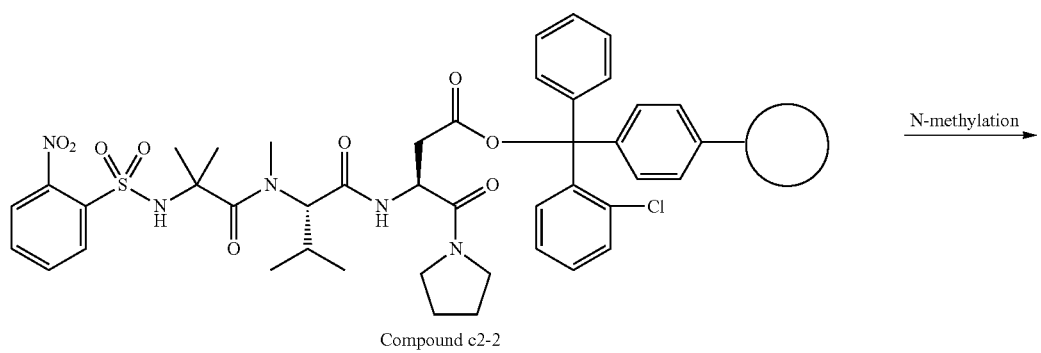

Compound c2-2

-continued

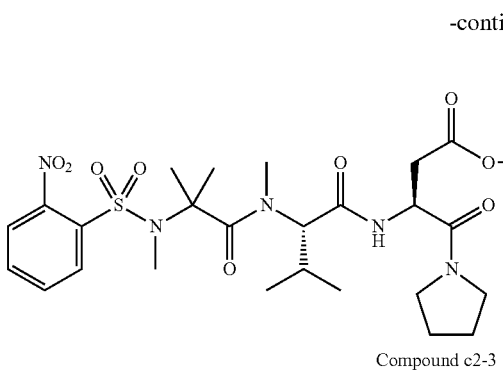

Compound c2-3

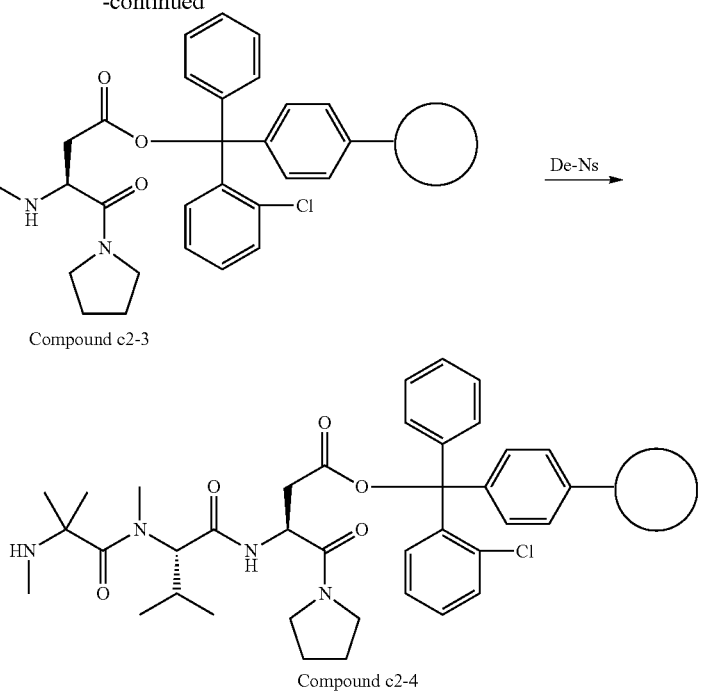

Compound c2-4

Comparative Example 2-1. Fmoc-Aib-OH elongation reaction in a solid phase on Fmoc-MeVal-Asp (O-Trt(2-Cl)-resin)-pyrro (Compound 1-2-2)

Fmoc-MeVal-Asp(0-Trt(2-Cl)-resin)-pyrro (Compound 1-2-2) (0.464 mmol/g, 100 mg) prepared in Example 1-2-2 was placed in a filter-equipped reaction vessel, dichloromethane (1 mL) was added, and the mixture was shaken at room temperature for 30 minutes to swell the resin. After dichloromethane was removed through a filter, the resin was washed twice with DMF (1 mL). Subsequently, a 2% DBU/DMF solution (de-Fmoc solution: 0.7 mL) was added to the resin, and the mixture was shaken at room temperature for 10 minutes to remove Fmoc. After the de-Fmoc solution was removed, the resin was washed 4 times with DMF (0.7 mL).

An Fmoc-Aib-OH elongation reaction was performed on the resulting resin.

The elongation reaction was performed by adding a solution obtained by mixing a 0.6 M Fmoc-Aib-OH/0.375 M oxyma/NMP solution (0.3 mL) and a 10% DIC/DMF solution (0.36 mL) to the resin and shaking the mixture at 50° C. for 15 hours.

This elongation reaction was repeated 2 more times. (Conditions of the second elongation: 50° C. 24 hours, and conditions of the third elongation: 50° C. 20 hours.)

After the liquid phase of the elongation reaction was removed through a filter, the resin was washed 4 times with DMF (0.7 mL) and 4 times with dichloromethane (0.7 mL).

To confirm the progression of elongation, a part (about 5 mg) of the resulting resin was removed, and the unreacted point was capped with Fmoc-Gly-OH.

Capping was performed by adding a solution obtained by mixing a 0.6 M Fmoc-Gly-OH/0.375 M HOAt/NMP solution (0.3 mL) and a 10% DIC/DMF solution (0.36 mL) to the resin and shaking the mixture at 40° C. for 45 minutes.

After the liquid phase of the elongation reaction was removed through a filter, the resin was washed 4 times with DMF (0.7 mL) and 4 times with dichloromethane (0.7 mL).

Peptide cleavage was conducted with a TFE/DCM solution (1/1 (v/v)), and LCMS analysis of the cleaved solution confirmed production of 60.4% of the peptide of interest Fmoc-Aib-MeVal-Asp-pyrro (Compound C2-1*).

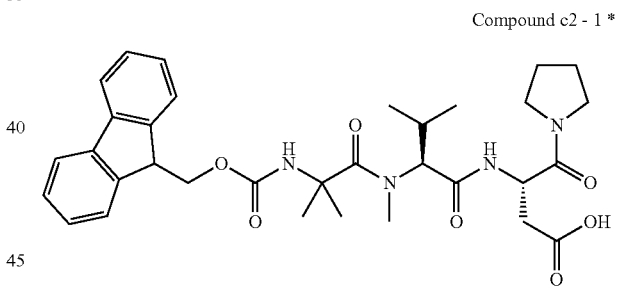

Compound c2-1*

LCMS (ESI) m/z=605.52 (M−H)−
Retention time: 2.16 min (Analysis condition SQDFA05 long)

The unreacted point of the resulting resin was capped with Z-Gly-OH (N-α-carbobenzoxyglycine, CAS: 1138-80-3) purchased from a commercial supplier.

Capping was performed by adding a solution obtained by mixing a 0.6 M Z-Gly-OH/0.375 M HOAt/NMP solution (0.3 mL) and a 10% DIC/DMF solution (0.36 mL) to the resin and shaking the mixture at 40° C. for 2 hours.

After the liquid phase of the capping reaction was removed through a filter, the resin was washed 4 times with DMF (0.7 mL) and 4 times with dichloromethane (0.7 mL) to give Compound C2-1.

Comparative Example 2-2: De-Fmoc and N-terminal nosylation of Fmoc-Aib-MeVal-Asp(O-Trt(2-Cl)-resin)-pyrro (Compound C2-1)

Fmoc-Aib-MeVal-Asp(O-Trt(2-Cl)-resin)-pyrro (Compound C2-1) (0.464 mmol/g, 100 mg) prepared in Comparative Example 2-1 was placed in a filter-equipped reaction vessel, dichloromethane (1 mL) was added, and the mixture was shaken at room temperature for 30 minutes to swell the resin. After dichloromethane was removed through a filter, the resin was washed twice with DMF (1 mL). Subsequently, a 2% DBU/DMF solution (de-Fmoc solution: 0.7 mL) was added to the resin, and the mixture was shaken at room temperature for 10 minutes to remove Fmoc. After the de-Fmoc solution was removed, the resin was washed 3 times with DMF (1 mL) and then 4 times with THF (1 mL).

A THF solution (0.35 mL) of 2,4,6-trimethylpyridine (0.062 mL, 0.464 mmol) and a THF solution (0.35 mL) of 2-nitrobenzenesulfonyl chloride (0.041 g, 0.186 mmol) were added to the resulting resin, and the mixture was shaken at 40° C. for 2 hours.

After the liquid phase was removed through a filter, the resin was washed 3 times with THF (1 mL) and 4 times with dichloromethane (I mL).

The above nosylation with 2-nitrobenzenesulfonyl chloride was repeated 2 more times (second time: shaking at 40° C. for 16 hours, third time: shaking at 40° C. for 21 hours).

To confirm the progression of elongation, a part (about 5 mg) of the resulting resin was removed, peptide cleavage was conducted with a TFFJDCM solution (1/1 (v/v)), and LCMS to analysis of the cleaved solution confirmed production of 64.9% of the peptide of interest Ns-Aib-MeVal-Asp-pyrro (Compound C2-2*).

The unreacted point of the resulting resin was capped with Z-Gly-OH.

Capping was performed by adding a solution obtained by mixing a 0.6 M Z-Gly-OH/NMP solution (0.3 mL) and a 10% DIC/DMF solution (0.36 mL) to the resin and shaking the mixture at 40° C. for 2 hours.

After the liquid phase of the elongation reaction was removed through a filter, the resin was washed 4 times with DMF (0.7 mL) and 4 times with dichloromethane (0.7 mL) to give Ns-Aib-MeVal-Asp(0-Trt(2-Cl)-resin)-pyrro (Compound C2-2).

Compound C2 - 2*

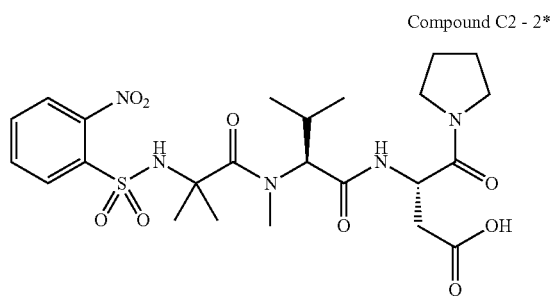 [SMILES: CC(C)[C@@H](C(=O)N[C@@H](CC(=O)O)C(=O)N1CCCC1)N(C)C(=O)C(C)(C)NS(=O)(=O)c1ccccc1[N+](=O)[O-]]

LCMS (ESI) m/z=568.45 (M–H)–
Retention time: 0.59 min (Analysis condition SQDFA05)

Comparative Example 2-3: N-Methylation by Mitsunobu reaction on the Ns amide moiety of Ns-Aib-MeVal-Asp(O-Trt(2-Cl)-resin)-pyrro (Compound C2-2)

In a filter-equipped reaction vessel, dichloromethane (1 mL) was added to Ns-Aib-MeVal-Asp(O-Trt(2-Cl)-resin)-pyrro (Compound C2-2) (0.464 mmol/g, 100 mg) prepared in Comparative Example 2-2, and the mixture was shaken at room temperature for 20 minutes to swell the resin. After dichloromethane was removed through a filter, the resin was washed 4 times with THF (1 mL).

A THF (0.7 mL) solution of triphenylphosphine (61.0 mg, 0.232 mmol) and methanol (19 µL, 0.464 mmol) was added to the resulting resin, and then DIAD (45 µL, 0.232 mmol) was added, and the mixture was shaken at 40° C. for 30 minutes. After the liquid phase was removed through a filter, the resin was washed 4 times with THF (1 mL) and 4 times with dichloromethane (1 mL).

A part (about 5 mg) of the resulting resin was subjected to peptide cleavage conducted with a TFE/DCM solution (1/1 (v/v)), and LCMS analysis of the cleaved solution confirmed production of the peptide of interest Ns-MeAib-MeVal-Asp-pyrro (Compound C2-3*) (the conversion ratio from Compound C2-2 was 96%). The remaining Ns-MeAib-MeVal-Asp(O-Trt(2-Cl)-resin)-pyrro (Compound C2-3) was used in the next step.

Compound C2 - 3*

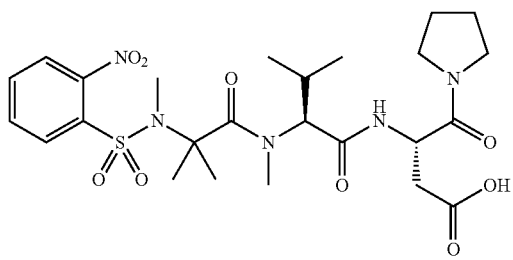

LCMS (ESI) m/z=582.47 (M–H)–
Retention time: 0.63 min (Analysis condition SQDFA05)

Comparative Example 2-4: Denosylation of Ns-MeAib-MeVal-Asp-pyrro resin (Compound C2-3)

In a filter-equipped reaction vessel, dichloromethane (0.5 mL) was added to Ns-MeAib-MeVal-Asp(O-Trt(2-Cl)-resin)-pyrro (Compound C2-3) (0.464 mmol/g, 50 mg) prepared in Comparative Example 2-3, and the mixture was shaken at room temperature for 20 minutes to swell the resin. After dichloromethane was removed through a filter, the resin was washed 4 times with NMP (0.5 mL).

A DBU (17 µL, 0.115 mmol)/NMP solution (0.35 mL) and a 2-mercaptoethanol (16 µL, 0.230 mmol)/NMP solution (0.30 mL) were added to the resulting resin, and the mixture was shaken at room temperature for 1 hour. After the liquid phase was removed through a filter, the resin was washed 4 times with NMP (0.5 mL) and 4 times with dichloromethane (0.5 mL).

Figure 3:
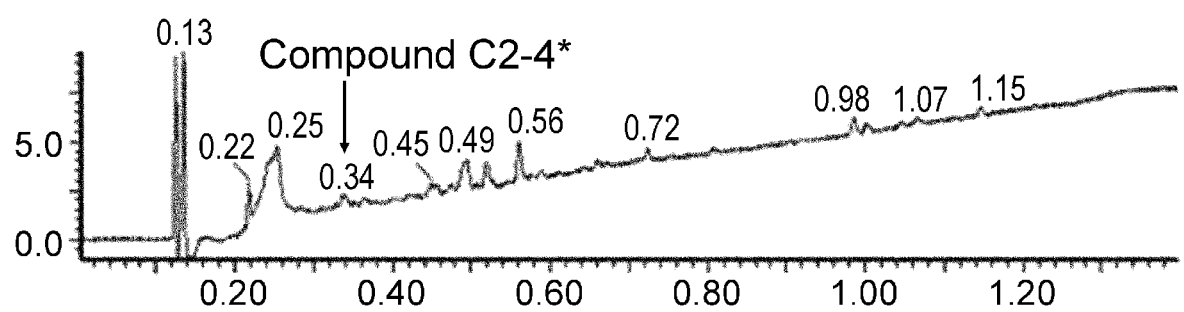
FIG. 3 shows the results of LCMS analysis (analysis condition: SQDFA05) on the reaction mixture of Comparative Example 2-4 detected at the maximum absorption wavelength using a photodiode array detector.

A part (about 5 mg) of the resulting resin was cleaved from the resin with a TFE/DCM solution (1/1 (v/v)), and LCMS analysis of the cleaved solution confirmed production of the peptide of interest H-MeAib-MeVal-Asp-pyrro (Compound C2-4*) with progressed denosylation as shown in FIG. 3.

Compound C2 - 4 *

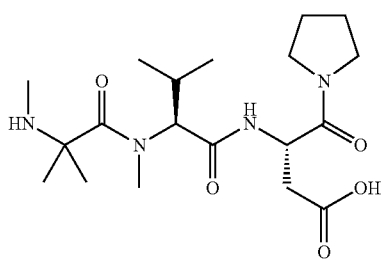

LCMS (ESI) m/z=399.29 (M+H)+
Retention time: 0.34 min (Analysis condition SQDFA05)

Comparative Example 2-5: Denosylation of Ns-MeAib-MePhe-Asp(O-Trt(2-Cl)-resin)-pyrro In a filter-equipped reaction vessel, dichloromethane (0.5 mL) was added to Ns-MeAib-MePhe-Asp(O-Trt(2-Cl)-resin)-pyrro (Compound C2-5-1) (0.464 mmol/g, 50 mg) prepared by the same operation as in Comparative Example 2-1 to Comparative Example 2-3 in place of Compound 1-2-3 (100 mg) prepared in Example 1-2-3, and the mixture was shaken at room temperature for 20 minutes to swell the resin. After dichloromethane was removed through a filter, the resin was washed 4 times with NMP (0.5 mL).

A DBU (17 µL, 0.115 mmol)/NMP solution (0.35 mL) and a 2-mercaptoethanol (16 µL, 0.230 mmol)/NMP solution (0.30 mL) were added to the resulting resin, and the mixture was shaken at room temperature for 1 hour. After

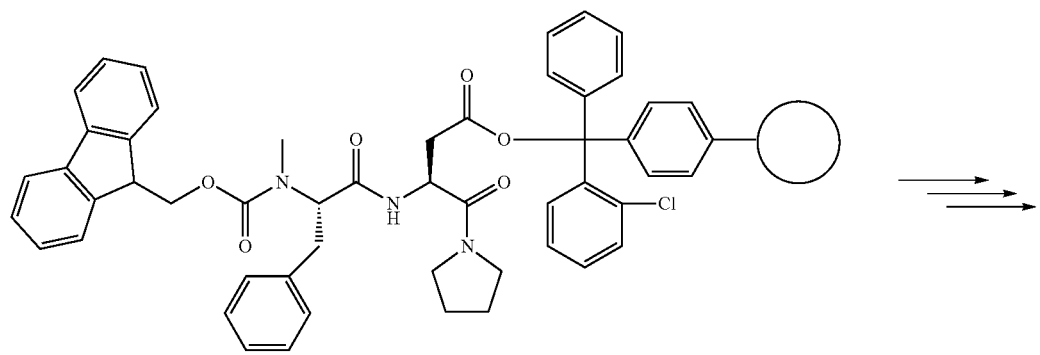

Compound 1-2-3

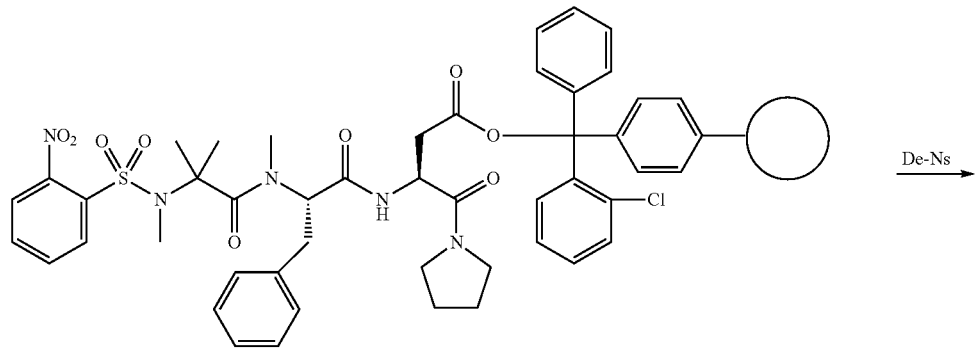

Compound c2-5-1

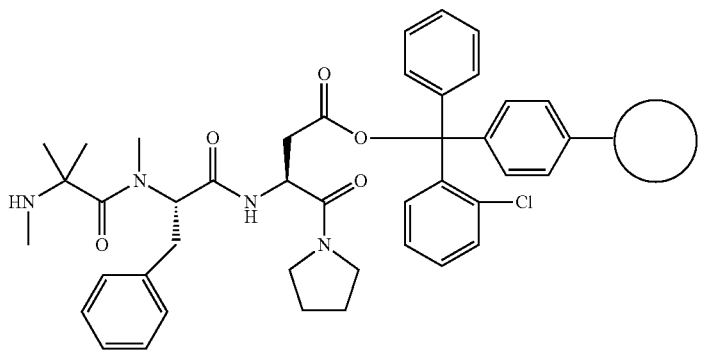

Compound c2-5-2 the liquid phase was removed through a filter, the resin was washed 4 times with NMP (0.5 mL) and 4 times with dichloromethane (0.5 mL).

Figure 4:
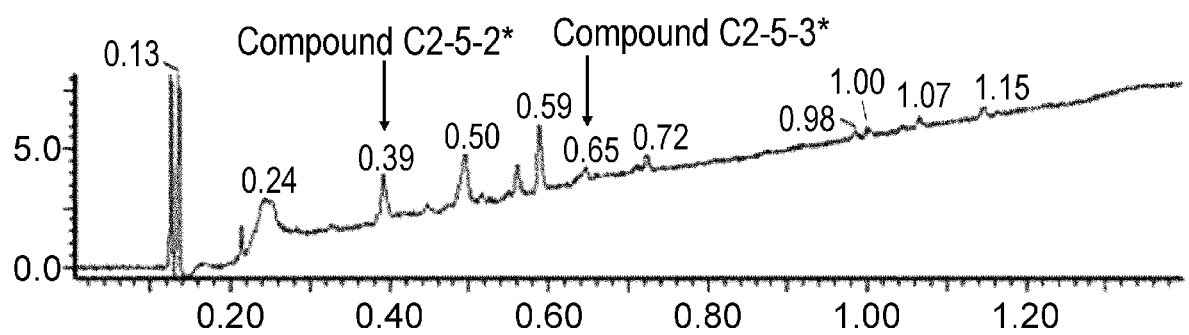
FIG. 4 shows the results of LCMS analysis (analysis condition: SQDFA05) on the reaction mixture of Comparative Example 2-5 detected at the maximum absorption wavelength using a photodiode array detector.

A part (about 5 mg) of the resulting resin was cleaved from the resin with a TFE/DCM solution (1/1 (v/v)), and LCMS analysis of the cleaved solution detected an impurity presumed to be obtained by ipso-substitution of 2-mercaptoethanol for the Ns-protected nitro group (Compound C2-5-3*) in addition to production of the peptide of interest H-MeAib-MePhe-Asp-pyrro (Compound C2-5-2*) with progressed denosylation as shown in FIG. 4.

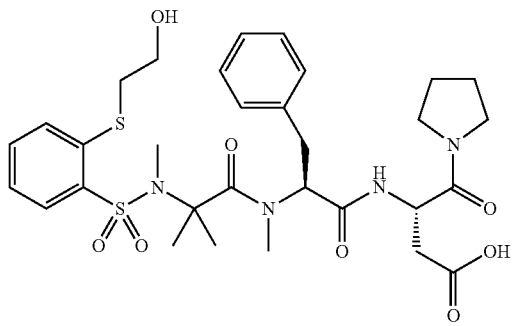

Compound C2-5-3*

LCMS (ESI) m/z=661.74 (M–H)–
Retention time: 0.65 min (Analysis condition SQDFA05)

It was confirmed from these results of Comparative Example 2 that, while a bulky N-methyl-α,α-dialkylamino acid (MeAib in this example) can be introduced to the N-terminus of a bulky N-methylamino acid, a series of steps including elongation of Fmoc-Aib and switching of the protecting group with a Ns group results in low purity and low yield. Also, it was found that a side reaction on the Ns-protecting group at the denosylation stage causes a reduction in to purity. It was confirmed that it is difficult to introduce a bulky N-methyl-α,α-dialkylamino acid to the N-terminus of a bulky N-methylamino acid at high purity and high yield under the known conditions described in the literature.

Reference Example: Attempt to Elongate Fmoc-MeAib-OH Following an N-Methylamino Acid by a Conventional Solid-Phase Synthesis Method

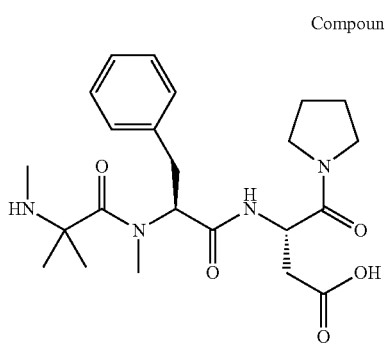

Compound C2-5-2*

LCMS (ESI) m/z=447.31 (M+H)+
Retention time: 0.39 min (Analysis condition SQDFA05)

Reference Example 1: Fmoc-MeAib-OH Elongation Reaction on Fmoc-MeVal-Asp(O-Trt(2-C)-Resin)-Pyrro (Compound 1-2-2) in a Solid Phase

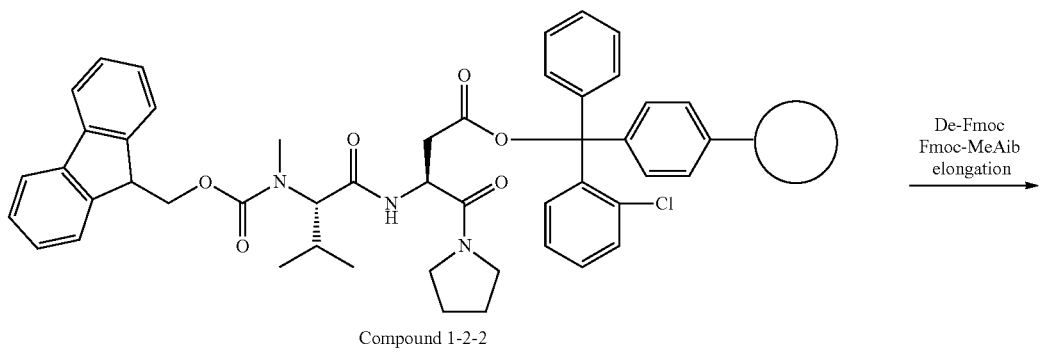

Compound 1-2-2

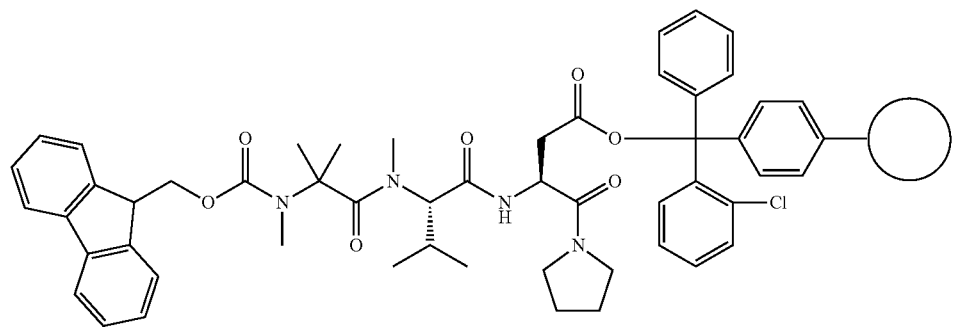

Compound R1

An attempt to elongate Fmoc-MeAib-OH was made by placing Fmoc-MeVal-Asp(O-Trt(2-Cl)-resin)-pyrro (Compound 1-2-2) (0.464 mmol/g, 100 mg) prepared in Example 1-2-2 in a filter-equipped reaction vessel, and performing the same operations as in Comparative Example 2-1.

The elongation reaction was performed by adding a solution obtained by mixing a 0.6 M Fmoc-MeAib-OH/ 0.375 M oxyma/NMP solution (0.3 mL) and a 10% DIC/ DMF solution (0.36 mL) to the resin, shaking the mixture at 40° C. for 21 hours, discarding the reaction solution, and then repeating the same operation one more time (for 21.5 hours at 40° C.).

After the elongation reaction, washing the resin, capping the unreacted point with Fmoc-Gly-OH, and cleaving the peptide from the resin were suitably performed through the same operations as in Comparative Example 2-1, but LCMS analysis of the cleaved solution did not detect the peptide of interest Fmoc-MeAib-MeVal-Asp-pyrro (Compound R1*).

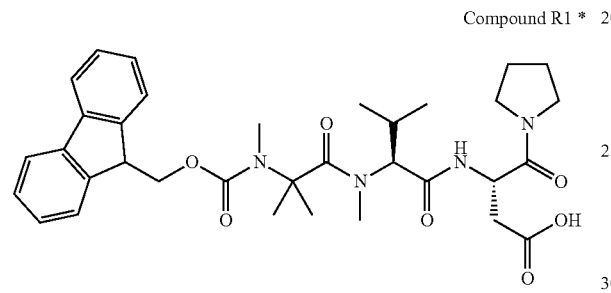

Compound R1*

Reference Example 2: Fmoc-MeAib-OH Elongation Reaction on Fmoc-MePhe-Asp(0-Trt(2-Cl)-Resin)-Pyrro (Compound 1-2-3) in a Solid Phase An attempt to elongate Fmoc-MeAib was made by placing Fmoc-MePhe-Asp(O-Trt(2-Cl)-resin)-pyrro (Compound 1-2-3) (0.464 mmol/g, 100 mg) prepared in Example 1-2-3 in a filter-equipped reaction vessel, and performing the same operations as in Reference Example 1. The elongation reaction was performed at 40° C. for 15 hours.

Thereafter, washing the resin, capping the unreacted point with Fmoc-Gly-OH, and cleaving the peptide from the resin were suitably performed through the same operations as in Reference Example 1, but when the cleaved solution was analyzed by LCMS, production of the peptide of interest Fmoc-MeAib-MePhe-Asp-pyrro (Compound R2*) remained at 3.1%.

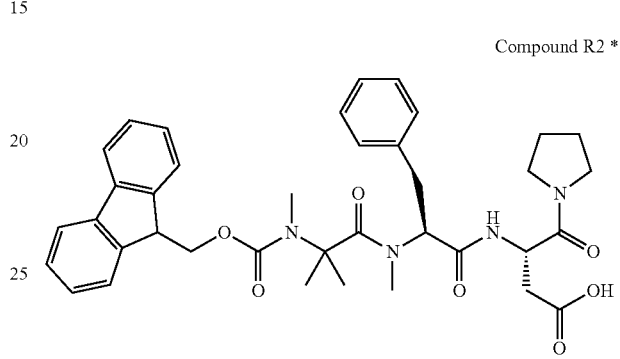

Compound R2*

LCMS (ESI) m/z=669.43 (M+H)+
Retention time: 0.88 min (Analysis condition SQDFA05)

Thus, it was confirmed from the results of the reference examples that elongation of Fmoc-MeAib-OH (i.e., an N-substituted-α,α-disubstituted amino acid) subsequent to

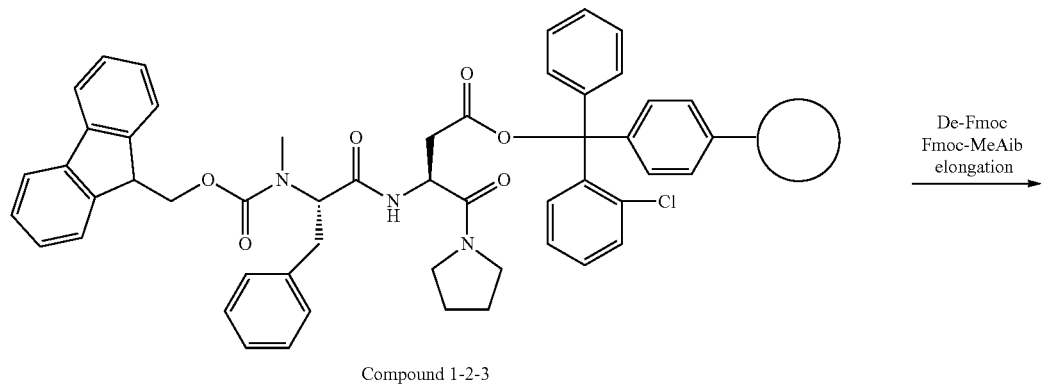

Compound 1-2-3

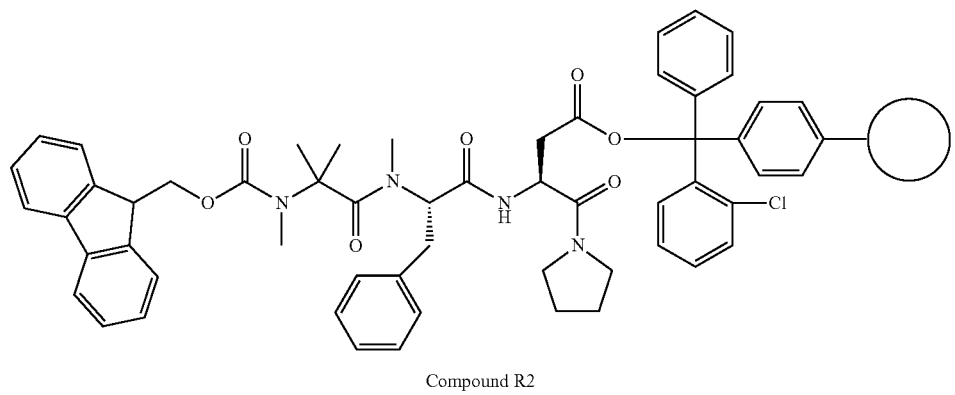

Compound R2

N-methylamino acid (i.e., an N-substituted amino acid) by a conventional solid-phase synthesis method (Fmoc method) is very difficult, and that there are also cases where the peptide of interest cannot be obtained.

Industrial Applicability

According to the present invention, it was found that, in the production of peptide compounds using a solid-phase method, it is possible to efficiently produce peptide compounds comprising a dipeptide residue in which an N-substituted-α,α-disubstituted amino acid residue is linked to an N-substituted amino acid residue. The present invention is useful in the field of peptide synthesis.

The invention claimed is:

1. A method for producing a peptide compound having an N-substituted-α,α-disubstituted amino acid residue at the N-terminus and comprising a dipeptide residue in which the N-substituted-α,α-disubstituted amino acid residue is linked to an N-substituted amino acid residue, a salt thereof, or a solvate of these, the method comprising the following steps of:

Step A: reacting (1) an N-substituted amino acid, a salt thereof, or a solvate of these, or a peptide compound having an N-substituted amino acid residue at the N-terminus, a salt thereof, or a solvate of these, wherein the main-chain amino group of the N-substituted amino acid or the N-substituted amino acid residue is represented by —NHR, wherein R is optionally substituted alkyl, optionally substituted alkenyl, optionally substituted alkynyl, optionally substituted aryl, optionally substituted heteroaryl, optionally substituted aralkyl, and optionally substituted cycloalkyl, or R represents a carbon chain bonded to the N atom, which together with the carbon atom at the α-position form an optionally substituted ring, with (2) an α,α-disubstituted amino acid having an amino group protected with an electron-withdrawing protecting group, a salt thereof, a dehydrated product thereof, or a solvate of these, wherein the amino group is the amino group on the main chain of the α,α-disubstituted amino acid and is represented by the formula —NHR', wherein R' is the electron-withdrawing protecting group, wherein the electron-withdrawing protecting group is a protecting group with which the pKa in water of the NH group to which the protecting group is bonded is 6 to 11, in the presence or absence of a condensing reagent to obtain a peptide compound having an α,α-disubstituted amino acid residue having an amino group protected with an electron-withdrawing protecting group at the N-terminus and comprising a dipeptide residue in which the α,α-disubstituted amino acid residue is linked to an N-substituted amino acid residue, a salt thereof, or a solvate of these; and Step B: introducing a substituent to the amino group of the α,α-disubstituted amino acid residue protected with the electron-withdrawing protecting group at the N-terminus in the presence of a base and a substituent-introducing agent to obtain a peptide compound having an α,α-disubstituted amino acid residue having an amino group on the main chain of the α,α-disubstituted amino acid substituted with the substituent and protected with the electron-withdrawing protecting group at the N-terminus and comprising a dipeptide residue in which the α,α-disubstituted amino acid residue is linked to the N-substituted amino acid residue, a salt thereof, or a solvate of these.

2. The method of claim 1, wherein the pKa in acetonitrile of the conjugate acid of the base is 18 to 31.

3. The method of claim 1, wherein the N-substituted amino acid or the peptide compound having an N-substituted amino acid residue at the N-terminus is loaded on a resin for solid-phase synthesis.

4. The method of claim 1, wherein the N-substituted amino acid or the peptide compound having an N-substituted amino acid residue at the N-terminus is represented by formula (2):

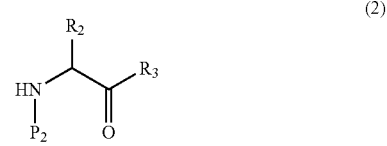

wherein $P_2$ is $C_1$-$C_6$ alkyl, $C_2$-$C_6$ alkenyl, or $C_7$-$C_{14}$ aralkyl;

$R_2$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl;

$R_3$ is hydroxy, O-$PG_2$, an arbitrary amino acid residue, or an arbitrary peptide residue; and $PG_2$ is a protecting group for a carboxyl group.

5. The method of claim 1, wherein the α,α-disubstituted amino acid having an amino group protected with an electron-withdrawing protecting group is represented by formula (3):

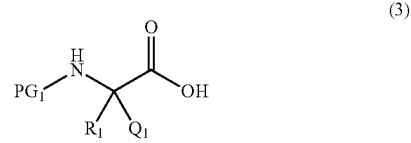

wherein $PG_1$ is the electron-withdrawing protecting group; and $R_1$ and $Q_1$ are independently selected from $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, and optionally substituted $C_7$-$C_{14}$ aralkyl, or $R_1$ and $Q_1$ together with the carbon atom to which they are bonded form a 3- to 8-membered alicyclic ring or a 4- to 7-membered saturated heterocyclic ring.

6. The method of claim 1, wherein the peptide compound obtained in step A is represented by formula (4):

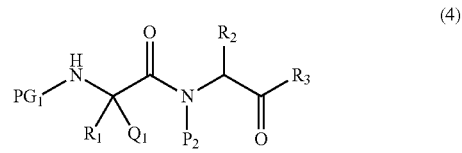

wherein
PG$_1$ is the electron-withdrawing protecting group;
R$_1$ and Q$_1$ are independently selected from C$_1$-C$_6$ alkyl, C$_2$-C$_6$ alkenyl, C$_1$-C$_6$ alkoxyC$_1$-C$_6$ alkyl, C$_3$-C$_8$ cycloalkylC$_1$-C$_6$ alkyl, and optionally substituted C$_7$-C$_{14}$ aralkyl, or
R$_1$ and Q$_1$ together with the carbon atom to which they are bonded form a 3- to 8-membered alicyclic ring or a 4- to 7-membered saturated heterocyclic ring;
P$_2$ is C$_1$-C$_6$ alkyl, C$_2$-C$_6$ alkenyl, or C$_7$-C$_{14}$ aralkyl;
R$_2$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_2$-C$_6$ alkynyl, C$_1$-C$_6$, alkoxyC$_1$-C$_6$ alkyl optionally substituted with one or more halogens, C$_3$-C$_8$ cycloalkyl, C$_3$-C$_8$ cycloalkylC$_1$-C$_6$ alkyl, C$_3$-C$_8$ cycloalkoxyC$_1$-C$_6$ alkyl, or C$_7$-C$_{14}$ aralkyl; and
R$_3$ is hydroxy, O-PG$_2$, an arbitrary amino acid residue, or an arbitrary peptide residue, wherein PG$_2$ is a protecting group for a carboxyl group.

7. The method of claim 6, wherein the substituent-introducing agent in step B is P$_1$X, wherein P$_1$ is the same as P$_1$ in formula (1), and X is a leaving group, and the peptide compound obtained in step B is represented by formula (1):

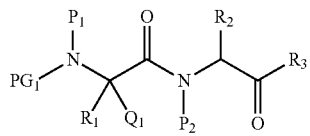

(1)

wherein
P$_1$ is C$_1$-C$_6$ alkyl, C$_2$-C$_6$ alkenyl, or C$_7$-C$_{14}$ aralkyl; and
PG$_1$, R$_1$, Q$_1$, P$_2$, R$_2$, and R$_3$ are the same as PG$_1$, R$_1$, Q$_1$, P$_2$, R$_2$, and R$_3$ in formula (4), respectively.

8. A method for producing a peptide compound comprising a structure in which two amino acid residues are connected as represented by formula (1), a salt thereof, or a solvate of these:

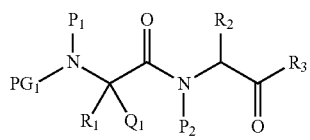

(1)

wherein
PG$_1$ is a protecting group for an amino group;
P$_1$ is C$_1$-C$_6$ alkyl, C$_2$-C$_6$ alkenyl, or C$_7$-C$_{14}$ aralkyl;
R$_1$ and Q$_1$ am independently selected from C$_1$-C$_6$ alkyl, C$_2$-C$_6$ alkenyl, C$_1$-C$_6$ alkoxyC$_1$-C$_6$ alkyl, C$_3$-C$_8$ cycloalkylC$_1$-C$_6$ alkyl, and optionally substituted C$_7$-C$_{14}$ aralkyl, or
R$_1$ and Q$_1$ together with the carbon atom to which they are bonded form a 3- to 8-membered alicyclic ring or a 4- to 7-membered saturated heterocyclic ring;
P$_2$ is C$_1$-C$_6$ alkyl, C$_2$-C$_6$ alkenyl, or C$_7$-C$_{14}$ aralkyl;
R$_2$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_2$-C$_6$ alkynyl, C$_1$-C$_6$ alkoxyC$_1$-C$_6$ alkyl optionally substituted with one or more halogens, C$_3$-C$_8$ cycloalkyl, C$_3$-C$_8$ cycloalkylC$_1$-C$_6$ alkyl, C$_3$-C$_8$ cycloalkoxyC$_1$-C$_6$ alkyl, or C$_7$-C$_{14}$ aralkyl;

R$_3$ is hydroxy, O-PG$_2$, an arbitrary amino acid residue, or an arbitrary peptide residue; and
PG$_2$ is a protecting group for a carboxyl group,
the method comprising the following steps of:
Step A: reacting a compound represented by formula (2):

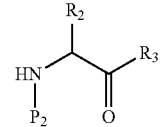

(2)

wherein P$_2$, R$_2$, and R$_3$ are the same as P$_2$, R$_2$, and R$_3$ in formula (1), respectively,
a salt thereof, or a solvate of these and a compound represented by formula (3):

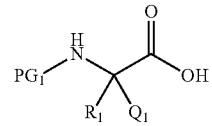

(3)

wherein PG$_1$, Q$_1$, and R$_1$ are the same as PG$_1$, Q$_1$, and R$_1$ in formula (1), respectively,
a salt thereof, a dehydrated product thereof, or a solvate of these with a condensing reagent, or reacting the compound represented by formula (2), a salt thereof, or a solvate of these with a dehydrated product of the compound represented by formula (3), a salt thereof, or a solvate of these to obtain a compound represented by formula (4):

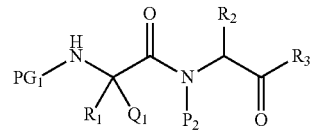

(4)

wherein PG$_1$, P$_2$, Q$_1$, and R$_1$ to R$_3$ are the same as PG$_1$, P$_2$, Q$_1$, and R$_1$ to R$_3$ in formula (1), respectively,
wherein the pKa in water of the NH group to which PG$_1$ is bonded in formula (3) and/or formula (4) is 11 or less,
a salt thereof, or a solvate of these; and
Step B: reacting the compound represented by formula (4), a salt thereof, or a solvate of these with a P$_1$-introducing reagent comprising a base to obtain the peptide compound represented by formula (1), a salt thereof, or a solvate of these.

9. The method of claim 5, wherein
R$_1$ and Q$_1$ together with the carbon atom to which they are bonded form a cyclopropane ring, a cyclobutane ring, a cyclopentane ring, a cyclohexane ring, or a tetrahydropyran ring; or
R$_1$ and Q$_1$ are independently selected from methyl, ethyl, 2-methylpropyl, allyl, methoxymethyl, cyclohexylmethyl, optionally substituted benzyl, or optionally substituted phenethyl.

10. The method of claim 8, wherein the pKa in water of the NH group to which $PG_1$ is bonded in formula (3) and/or formula (4) is 6 to 11.

11. The method of claim 5, wherein $PG_1$ is $C_2$-$C_6$ haloacyl.

12. The method of claim 11, wherein $C_2$-$C_6$ haloacyl is trifluoroacetyl, trichloroacetyl, pentafluoropropionyl, 2,3,3,3-tetrafluoro-2-(trifluoromethyl)propionyl, or 3,3,3-trifluoro-2-(trifluoromethyl)propionyl.

13. The method of claim 1, wherein the dehydrated product is represented by the following formula:

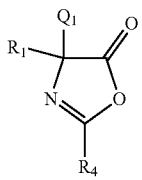

(3′)

wherein $R_1$ and $Q_1$ are independently selected from $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, and optionally substituted $C_7$-$C_{14}$ aralkyl, or $R_1$ and $Q_1$ together with the carbon atom to which they are bonded form a 3- to 8-membered alicyclic ring or a 4- to 7-membered saturated heterocyclic ring; and $R_4$ is $C_1$-$C_5$ haloalkyl.

14. The method of claim 13, wherein $R_1$ and $Q_1$ together with the carbon atom to which they are bonded form a 3- to 8-membered alicyclic ring.

15. The method of claim 13, wherein $R_4$ is trifluoromethyl, trichloromethyl, pentafluoroethyl, 1,2,2,2-tetrafluoro-1-(trifluoromethyl)ethyl, or 2,2,2-trifluoro-1-(trifluoromethyl)ethyl.

16. The method of claim 7, wherein $P_1$ is methyl, ethyl, n-propyl, i-propyl, allyl, benzyl, or phenethyl.

17. The method of claim 4, wherein $P_2$ is methyl, ethyl, n-propyl, i-propyl, allyl, benzyl, or phenethyl.

18. The method of claim 4, wherein $R_3$ is an arbitrary amino acid residue or an arbitrary peptide residue loaded on a resin for solid-phase synthesis.

19. The method of claim 3, wherein the resin for solid-phase synthesis is CTC resin, Wang resin, or SASRIN resin.

20. The method of claim 1, wherein the condensing reagent is either DIC or EDCI·HCl, or a combination of DIC and Oxyma.

21. The method of claim 8, wherein the $P_1$-introducing reagent is a combination of $P_1X$, wherein $P_1$ is the same as $P_1$ in formula (1), and X is a leaving group, and the base.

22. The method of claim 21, wherein pKa in acetonitrile of a conjugate acid of the base is 18 to 31.

23. The method of claim 2, wherein the base is selected from the group consisting of:

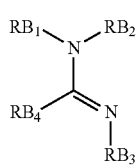

(B1)

wherein
$RB_1$ and $RB_4$ are each independently $C_1$-$C_4$ alkyl, or $RB_1$ and $RB_4$ together with the nitrogen atom to which $RB_1$ is bonded and the carbon atom to which $RB_4$ is bonded form a 5- to 8-membered ring; and
$RB_2$ and $RB_3$ are each independently $C_1$-$C_4$ alkyl, or $RB_2$ and $RB_3$ together with the nitrogen atom to which $RB_2$ is bonded, the nitrogen atom to which $RB_3$ is bonded, and the carbon atom to which the nitrogen atoms are bonded form a 5- to 8-membered ring;

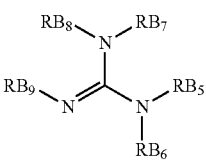

(B2)

wherein
$RB_6$ is hydrogen or $C_1$-$C_4$ alkyl;
$RB_5$ and $RB_7$ are each independently $C_1$-$C_4$ alkyl or, together with the respective nitrogen atoms to which they are bonded and the carbon atom to which the respective nitrogen atoms are bonded, form a 5- to 8-membered ring;
$RB_8$ is $C_1$-$C_4$ alkyl and $RB_9$ is $C_1$-$C_4$ alkyl or phenyl, or $RB_8$ and $RB_9$ together with the respective nitrogen atoms to which they are bonded and the carbon atom to which the respective nitrogen atoms are bonded, form a 5- to 8-membered ring; and
wherein, when $RB_9$ is phenyl, two benzene rings of the phenyl groups in two B2 may be condensed to form naphthalene;

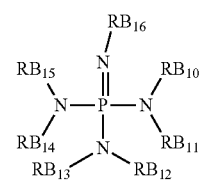

(B3)

wherein
$RB_{10}$ is $C_1$-$C_4$ alkyl, or $RB_{10}$ and $RB_{11}$ together with the nitrogen atom to which they are bonded form a 5- to 8-membered ring;
$RB_{11}$ except when $RB_{10}$ and $RB_{11}$ form a 5- to 8-membered ring is $C_1$-$C_4$ alkyl, or $RB_{11}$ and $RB_{12}$ together with the respective nitrogen atoms to which they are bonded and the phosphorus atom to which the respective nitrogen atoms are bonded form a 5- to 8-membered ring;
$RB_{12}$ except when $RB_{11}$ and $RB_{12}$ form a 5- to 8-membered ring is $C_1$-$C_4$ alkyl, or $RB_{12}$ and $RB_{13}$ together with the nitrogen atom to which they are bonded form a 5- to 8-membered ring;
$RB_{13}$ except when $RB_{12}$ and $RB_{13}$ form a 5- to 8-membered ring is $C_1$-$C_4$ alkyl, or $RB_{13}$ and $RB_{14}$ together with the respective nitrogen atoms to which they are bonded and the phosphorus atom to which the respective nitrogen atoms are bonded form a 5- to 8-membered ring;
$RB_{14}$ except when $RB_{13}$ and $RB_{14}$ form a 5- to 8-membered ring is $C_1$-$C_4$ alkyl, or $RB_{14}$ and $RB_{15}$ together with the nitrogen atom to which they are bonded form a 5- to 8-membered ring;

$RB_{15}$ except when $RB_{14}$ and $RB_{15}$ form a 5- to 8-membered ring is $C_1$-$C_4$ alkyl; and $RB_{16}$ is hydrogen, $C_1$-$C_5$ alkyl, or $C_6$-$C_{10}$ aryl; and (B4)

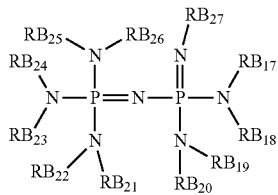

wherein $RB_{17}$ is independently $C_1$-$C_4$ alkyl, or $RB_{17}$ and $RB_{15}$ together with the nitrogen atom to which they are bonded form a 5- to 8-membered ring;

$RB_{15}$ except when $RB_{17}$ and $RB_{15}$ form a 5- to 8-membered ring is $C_1$-$C_4$ alkyl, or $RB_{15}$ and $RB_{19}$ together with the respective nitrogen atoms to which they are bonded and the phosphorus atom to which the respective nitrogen atoms are bonded form a 5- to 8-membered ring;

$RB_{19}$ except when $RB_{15}$ and $RB_{19}$ form a 5- to 8-membered ring is $C_1$-$C_4$ alkyl, or $RB_{19}$ and $RB_{20}$ together with the nitrogen atom to which they are bonded form a 5- to 8-membered ring;

$RB_{20}$ except when $RB_{19}$ and $RB_{20}$ form a 5- to 8-membered ring is $C_1$-$C_4$ alkyl;

$RB_{21}$ is $C_1$-$C_4$ alkyl, or $RB_{21}$ and $RB_{22}$ together with the nitrogen atom to which they are bonded form a 5- to 8-membered ring;

$RB_{22}$ except when $RB_{21}$ and $RB_{22}$ form a 5- to 8-membered ring is $C_1$-$C_4$ alkyl, or $RB_{22}$ and $RB_2$ together with the respective nitrogen atoms to which they are bonded and the phosphorus atom to which the respective nitrogen atoms are bonded form a 5- to 8-membered ring;

$RB_2$ except when $RB_{22}$ and $RB_2$ form a 5- to 8-membered ring is $C_1$-$C_4$ alkyl, or $RB_2$ and $RB_{24}$ together with the nitrogen atom to which they are bonded form a 5- to 8-membered ring;

$RB_{24}$ except when $RB_{23}$ and $RB_{24}$ form a 5- to 8-membered ring is $C_1$-$C_4$ alkyl, or $RB_{24}$ and $RB_{25}$ together with the respective nitrogen atoms to which they are bonded and the phosphorus atom to which the respective nitrogen atoms are bonded form a 5- to 8-membered ring;

$RB_{25}$ except when $RB_{24}$ and $RB_{25}$ form a 5- to 8-membered ring is $C_1$-$C_4$ alkyl, or $RB_{25}$ and $RB_{26}$ together with the nitrogen atom to which they are bonded form a 5- to 8-membered ring;

$RB_{26}$ except when $RB_{25}$ and $RB_{26}$ form a 5- to 8-membered ring is $C_1$-$C_4$ alkyl; and $RB_{27}$ is $C_1$-$C_4$ alkyl or $C_6$-$C_{10}$ aryl.

24. The method of claim 2, wherein the base is selected from the group consisting of 1,8-diazabicyclo[5.4.0]undec-7-ene (DBU), 1,5-diazabicyclo[4.3.0]non-5-ene (DBN), 1,8-bis(tetramethylguanidino)naphthalene (TMGN), 7-methyl-1,5,7-triazabicyclo[4.4.0]dec-5-ene (MTBD), 2-tert-butyl-1,1,3,3-tetramethylguanidine (BTMG), 1,5,7-triazabicyclo[4.4.0]dec-5-ene (TBD), tert-butylimino-tris(dimethylamino)phosphorane ($P_1$-tBu), tert-butylimino-tri(pyrrolidino)phosphorane ($P_1$-t-Bu-tris(tetramethylene), BTPP), 2-tert-butylimino-2-diethylamino-1,3-dimethylperhydro-1,3,2-diazaphosphorine (BEMP), tert-octylimino-tris(dimethylamino)phosphorane ($P_1$-t-Oct), imino-tris(dimethylamino)phosphorane (HP1(dma)), 1-tert-butyl-2,2,4,4,4-pentakis(dimethylamino)-$2\lambda^5,4\lambda^5$-catenadi(phosphazene) ($P_2$-t-Bu), and 1-ethyl-2,2,4,4,4-pentakis(dimethylamino)-$2\lambda^5,4\lambda^5$-catenadi(phosphazene) ($P_2$-Et).

25. The method of claim 1, wherein step B is carried out in a solvent selected from the group consisting of DMF, NMP, DMI, tetrahydrofuran, 2-methyltetrahydrofuran, and acetonitrile.

26. A method for producing a peptide compound comprising a dipeptide residue in which an N-substituted-α,α-disubstituted amino acid residue is linked to an N-substituted amino acid residue, a salt thereof, or a solvate of these, the method comprising the method of claim 1, and further comprising deprotecting an N-terminal protecting group from a peptide compound, a salt thereof, or a solvate of these produced by the method of claim 1.

27. A method for producing a cyclic peptide compound, a salt thereof, or a solvate of these, the method comprising the steps of:
  deprotecting an N-terminal protecting group from a peptide compound, a salt thereof, or a solvate of these produced by the method of claim 1;
  optionally, elongating a peptide chain; and
  cyclizing a group on the C-terminal side and a group on the N-terminal side to form a cyclic moiety,
  wherein the cyclic peptide compound comprises 8 to 15 amino acid residues, at least 3 N-substituted amino acid residues, and at least 1 N-unsubstituted amino acid residue, and the cyclic moiety comprises at least 8 amino acid residues.

* * * * *